US007632828B2

(12) United States Patent
Choi et al.

(10) Patent No.: US 7,632,828 B2
(45) Date of Patent: Dec. 15, 2009

(54) GRAM-POSITIVE CARBAPENEM ANTIBACTERIALS AND PROCESSES FOR THEIR PREPARATION

(75) Inventors: Woo-Baeg Choi, Atlanta, GA (US); David S. Menaldino, Atlanta, GA (US); Deog-Il Kim, Suwannee, GA (US); Martin Bouygues, Atlanta, GA (US); Michael W. Hager, Lilburn, GA (US)

(73) Assignee: FOB Synthesis, Inc., Kennesaw, GA (US)

( * ) Notice: Subject to any disclaimer, the term of this patent is extended or adjusted under 35 U.S.C. 154(b) by 0 days.

(21) Appl. No.: 11/150,522

(22) Filed: Jun. 10, 2005

(65) Prior Publication Data

US 2006/0074070 A1 Apr. 6, 2006

Related U.S. Application Data

(60) Provisional application No. 60/578,632, filed on Jun. 10, 2004.

(51) Int. Cl.

| | |
|---|---|
| ***C07D 477/12*** | (2006.01) |
| ***A61K 31/407*** | (2006.01) |
| ***A61P 31/04*** | (2006.01) |
| ***A61K 31/5377*** | (2006.01) |
| *A61K 31/426* | (2006.01) |
| *A61K 31/4439* | (2006.01) |
| *A61K 31/4995* | (2006.01) |
| *A61K 31/496* | (2006.01) |
| *A61K 31/4178* | (2006.01) |

(52) U.S. Cl. .................. 514/210.09; 540/302; 548/204; 546/334

(58) Field of Classification Search ................. 540/302; 514/210.09

See application file for complete search history.

(56) References Cited

U.S. PATENT DOCUMENTS

| | | | | |
|---|---|---|---|---|
| 3,950,357 | A | 4/1976 | Kahan et al. | |
| 4,866,171 | A | 9/1989 | Kumagai et al. | |
| 4,933,333 | A | 6/1990 | Sunagawa et al. | |
| 4,943,569 | A | 7/1990 | Sunagawa | |
| 4,962,103 | A | 10/1990 | Sunagawa et al. | |
| 5,011,832 | A | 4/1991 | DiNinno et al. | |
| 5,034,384 | A | 7/1991 | Greenlee et al. | |
| 5,068,232 | A * | 11/1991 | Ziegler et al. | 514/63 |
| 5,122,604 | A | 6/1992 | Sunagawa et al. | |
| 5,607,928 | A * | 3/1997 | Arnould | 514/210.09 |
| 6,255,300 | B1 | 7/2001 | DiNinno et al. | |
| 6,277,843 | B1 * | 8/2001 | Dininno et al. | 514/210.09 |
| 6,310,055 | B2 | 10/2001 | DiNinno et al. | |
| 6,399,597 | B1 | 6/2002 | Cama et al. | |
| 2006/0069081 | A1 * | 3/2006 | Choi et al. | 514/210.09 |

FOREIGN PATENT DOCUMENTS

| | | | | |
|---|---|---|---|---|
| EP | 0 292 191 | A1 | | 11/1988 |
| GB | 2092147 | A | * | 8/1982 |
| JP | 59036677 | A | | 2/1984 |
| WO | WO 99/12928 | A1 | | 3/1999 |

OTHER PUBLICATIONS

Arnould et al., Bioorganic & Medicinal Chemistry Letters vol. 6, Issue 20 , Oct. 22, 1996, pp. 2449-2454.*

Bersier et al., Electroanalysis vol. 2, Issue 5, pp. 373-381 (1990).*

Aldridge, K. E., "Ertapenem (MK-0826), a new carbapenem: comparative in vitro activity against clinically significant anaerobes" *Diagn. Microbiol. Infect. Dis.*, 44(2):181-6 (Oct. 2002).

Ambler, R.P., et al., "A standard numbering scheme for the class A beta-lactamases," *Biochem. J.*, 276 (pt. 1):269-270 (May 15, 1991).

Arnould, J.C., et al., "Synthesis and antibacterial activity of lipophilic carbapenems with anti-MRSA activity," *Bioorg. Med. Chem. Lett.*, 6(20):2449-2454 (Oct. 22, 1996).

Bouffard, F.A., et al., "Thienamycin total synthesis. 1. Synthesis of azetidinone precursors of (±)-thienamycin and its stereoisomers," *J. Org. Chem.*, 45(6), 1130-1142 (1980).

(Continued)

*Primary Examiner*—Mark L Berch
(74) *Attorney, Agent, or Firm*—King & Spalding

(57) ABSTRACT

The present invention provides β-methyl carbapenem compounds and pharmaceutical compositions useful in the treatment of bacterial infections and methods for treating such infections using such compounds and/or compositions, wherein the compounds are generally of the Formulae

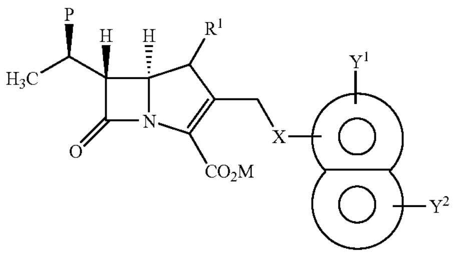

or

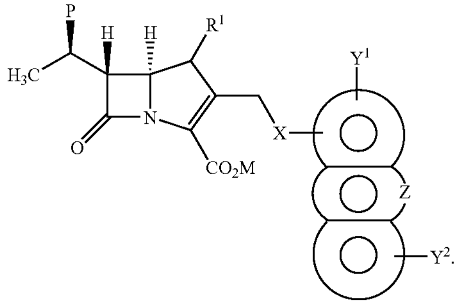

The invention includes administering an effective amount of a carbapenem compound or salt and/or prodrug thereof to a host in need of such a treatment. The present invention is also in the field of synthetic organic chemistry and is specifically provides an improved method of synthesis of ÿ-methyl carbapenems which are useful as antibacterial agents.

85 Claims, 13 Drawing Sheets

OTHER PUBLICATIONS

Cunha, B.A., "Ertapenem. A review of its microbiologic, pharmacokinetic and clinical aspects," *Drugs Today* (*Barc.*), 38(3):195-213 (Mar. 2002).

Edwards, J.R., et al., "In vitro antibacterial activity of SM-7338, a carbapenem antibiotic with sta-bility to dehydropeptidase I," *Antimicrob. Agents Chemother.*, 33(2):215-222 (Feb. 1989).

Hazumi, N., "Mechanism of enhanced antipseudomonal activity of BO-2727, a new injectable 1-beta-methyl carbapenem," et al., *Antimicrob. Agents Chemother.*, 39(3):702-706 (Mar. 1995).

Inoue, K., et al., "In vitro antibacterial activity and beta-lactamase stability of a new carbapenem, BO-2727," *Antimicrob. Agents Chemother.*, 39(10):2331-2336 (Oct. 1995).

Johnston, D.B.R., et al., "Total synthesis of (±)-thienamycin," *J. Am. Chem. Soc.*, 100(1):313-315 (1978).

Kahan, J.S., et al., "Thienamycin, a new beta-lactam antibiotic. I. Discovery, taxonomy, isolation and physical properties," *J. Antibiot.* (Tokyo), 32(1):1-12 (Jan. 1979).

Leanza, W.J., et al., "N-Acetimidoyl- and N-formimidoylthienamycin derivatives: antipseudomonal beta-lactam antibiotics," *J. Med. Chem.*, 22(12):1435-1436 (Dec. 1979).

Lin, W., et al., "Reduction of azides to amines or amides with zinc and ammonium chloride as reducing agent," *Synthetic Communications*, 32:3279-3284 (2002).

Nakagawa, S., et al., "In vitro activity of a new carbapenem antibiotic, BO-2727, with potent antipseudomonal activity," *Antimicrob. Agents Chemother.*, 37(12):2756-2759 (Dec. 1993).

Neu, H.C., et al., "In vitro activity and beta-lactamase stability of a new carbapenem, SM-7338," *Antimicrob. Agents Chemother.*, 33(7):1009-1018 (Jul. 1989).

Odenholt, I., et al., "Comparative in vitro pharmacodynamics of BO-2727, meropenem and imipenem against Gram-positive and Gram-negative bacteria," *Clin. Microbiol. Infect.*, 3(1):73-81 (Feb. 1997).

Salzmann, T.N., et al., "A stereocontrolled synthesis of (+)-thienamycin," *J. Am. Chem. Soc.* 102(19):6161-6163 (1980).

Shah, P.M., and Isaacs, R.D., "Ertapenem, the first of a new group of carbapenems," *J. Antimicrob. Chemother.*, 52(4):538-542 (Oct. 2003) (published electronically Sep. 1, 2003).

Shimada, J., and Kawahara, Y., "Overview of a new carbapenem, panipenem/betamipron," *Drugs Exp Clin Res.*, 20(6):241-245 (1994).

Weaver, S.S., et al., "Thienamycin: new beta-lactam antibiotic with potent broad-spectrum activity," *Antimicrob. Agents Chemother.*, 15:518-521 (1979).

Arnould, J. et al., "New Applications of the Mitsunobu Reaction in the Synthesis of C-2 N-Methyl Carbapenems," *Tetrahedron Letters*, 1992, vol. 33, No. 47, pp. 7133-7136.

Chung, J. et al., "Sequential Nitromethane Conjugate Addition/Elimination-Pd-Catalyzed Allylation of β-Trifloxy Acrylates. Application to Carbapenem Synthesis," *Organic Letters*, 1999, vol. 1, No. 11, pp. 1783-1785.

Imuta, M. et al., "Carbapenem and Penem Antibiotics. VI. Synthesis and Antibacterial Activity of 2-Heteroaromatic-Thiomethyl and 2-Carbamoyloxymethyl 1-Methylcarbapenems," *Chemical and Pharmaceutical Bulletin*, 1991, vol. 39, No. 3, pp. 663-671.

Uyeo, S. et al., "Practical, Stereocontrolled Synthesis of 2-Functionalized-methyl-1β-methylcarbapenems," *Tetrahedron Letter*, 1994, vol. 35, No. 25, pp. 4377-4378.

Wilkening, R. et al., "Synthesis and Activity of 2-(Sulfonamido)methylcarbapenems: Discovery of a Novel, Anti-MRSA 1,8-Naphthosultam Pharmacophore," *Bioorganic & Medicinal Chemistry Letters*, 1999, vol. 9, No. 5, pp. 673-678.

Ziegler, C. et al., "An Intramolecular Addition-Elimination Strategy for the Synthesis of Carbapenems," *Tetrahedron*, 1994, vol. 50, No. 42, pp. 12085-12096.

* cited by examiner

Thienamycin

Imipenem

Meropenem

Panipenem

Biapenem

LJC 10627

Lenapenem

BO 2727

L-786 392

Faropenem

CS 834

Sanfetrinem cilexetil

GV 118819

22 ,

24 ,

26 ,

28 ,

30 ,

32 ,

34 ,

36 ,

39 ,

41 ,

43 ,

45,

47,

49,

51,

53a,

55,

57,

59,

61,

63,

65,

67,

69 ,

71 ,

73 ,

75 ,

77 ,

79 ,

81 ,

83 ,

85 ,

87 ,

89 ,

91 ,

93 ,

95 ,

97 ,

100

,

148

,

152

,

157

,

162

,

167

,

171

,

175

,

180

,

183

,

188

,

191

,

,

194

, and

197

FIGURE 4 - TABLE 1: MIC (*IN VITRO* SUSCEPTIBILITY) DATA FOR 5-ALKYL-SUBSTITUTED-1-NAPHTHOL CP ANALOGS

In Vitro Susceptibility Results

| NO | Genus | Species | Resistance | 22 | 24 | 26 | 28 | 30 | 32 | 34 | 36 | 39 | 41 | Vancomycin | Linezolid |
|---|---|---|---|---|---|---|---|---|---|---|---|---|---|---|---|
| 1 | Staphylococcus | aureus | | 0.016 | <=0.008 | <=0.008 | 0.016 | <=0.008 | 0.016 | 0.016 | 0.031 | 0.016 | 0.016 | 1 | 2 |
| 2 | Staphylococcus | aureus | HR-MRSA | 4 | 1 | 1 | 2 | 2 | 2 | 8 | 4 | 4 | 4 | 0.5 | 2 |
| 3 | Staphylococcus | aureus | HR-MRSA | 2 | 0.5 | 0.5 | 1 | 1 | 1 | 4 | 4 | 4 | 2 | 1 | 2 |
| 4 | Staphylococcus | aureus | Qui-R-MRSA | 0.13 | 0.031 | 0.031 | 0.063 | 0.063 | 0.063 | 0.063 | 0.13 | 0.13 | 0.13 | 1 | 2 |
| 5 | Staphylococcus | aureus | Van-I-MRSA | 2 | 0.5 | 0.5 | 1 | 1 | 1 | 4 | 2 | 4 | 2 | 4 | 1 |
| 6 | Staphylococcus | aureus | Van-I-MRSA | 1 | 0.25 | 0.25 | 0.5 | 0.5 | 0.5 | 2 | 1 | 2 | 1 | 2 | 1 |
| 7 | Staphylococcus | aureus | Van-I-MRSA | 0.063 | 0.016 | 0.031 | 0.031 | 0.031 | 0.031 | 0.063 | 0.063 | 0.063 | 0.063 | 4 | 1 |
| 8 | Staphylococcus | aureus | LR-MRSA | 2 | 0.5 | 0.5 | 1 | 1 | 1 | 4 | 2 | 4 | 2 | 1 | 64 |
| 9 | Staphylococcus | epidermidis | | 0.031 | 0.016 | 0.016 | 0.031 | 0.031 | 0.031 | 0.031 | 0.063 | 0.031 | 0.031 | 1 | 2 |
| 10 | Staphylococcus | epidermidis | MRSE | 1 | 0.25 | 0.25 | 0.5 | 0.5 | 0.5 | 2 | 1 | 1 | 1 | 1 | 1 |
| 11 | Staphylococcus | epidermidis | Qui-R-MRSA | 0.13 | 0.063 | 0.063 | 0.063 | 0.063 | 0.063 | 0.13 | 0.13 | 0.13 | 0.13 | 1 | 2 |
| 12 | Staphylococcus | epidermidis | Van-I-MRSE | 0.13 | 0.063 | 0.13 | 0.063 | 0.063 | 0.063 | 0.13 | 0.13 | 0.13 | 0.13 | 4 | 1 |
| 13 | Staphylococcus | saprophyticus | MRSS | 0.016 | <=0.008 | <=0.008 | <=0.008 | <=0.008 | <=0.008 | 0.031 | 0.031 | 0.016 | 0.016 | 1 | 2 |
| 14 | Staphylococcus | haemolyticus | MRSH | <=0.008 | <=0.008 | <=0.008 | <=0.008 | 0.063 | <=0.008 | <=0.008 | <=0.008 | <=0.008 | <=0.008 | 1 | 1 |
| 15 | Staphylococcus | haemolyticus | Van-I-MRSH | 0.13 | 0.031 | 0.031 | 0.031 | 0.063 | 0.031 | 0.13 | 0.13 | 0.063 | 0.25 | 4 | 2 |
| 16 | Streptococcus | pyogenes | | <=0.008 | <=0.008 | <=0.008 | <=0.008 | <=0.008 | <=0.008 | <=0.008 | <=0.008 | <=0.008 | <=0.008 | 0.5 | 1 |
| 17 | Streptococcus | agalactiae | | <=0.008 | <=0.008 | <=0.008 | <=0.008 | 0.25 | <=0.008 | <=0.008 | <=0.008 | <=0.008 | <=0.008 | 0.5 | 2 |
| 18 | Enrterococcus | faecalis | | 1 | 0.25 | 0.25 | 0.25 | 0.25 | 0.25 | 0.5 | 0.5 | 1 | 0.5 | 2 | 2 |
| 19 | Enrterococcus | faecalis | Van-R | 1 | 0.5 | 0.5 | 0.5 | 0.5 | 0.5 | 1 | 0.5 | 1 | 1 | >64 | 2 |
| 20 | Enrterococcus | faecalis | Van-R | 2 | 1 | 2 | 1 | 2 | 2 | 4 | 4 | 2 | 4 | >64 | 2 |
| 21 | Enrterococcus | faecium | | 8 | 2 | 4 | 4 | 4 | 4 | 8 | 8 | 8 | 8 | 0.5 | 2 |
| 22 | Enrterococcus | faecium | Van-R | 16 | 4 | 8 | 8 | 8 | 8 | 16 | 16 | 16 | 16 | >64 | 2 |
| 23 | Enrterococcus | faecium | Van-R | 8 | 4 | 4 | 4 | 8 | 8 | 8 | 8 | 8 | 8 | >64 | 2 |
| 24 | Haemophilus | Influenzae | | <=0.008 | <=0.008 | <=0.008 | <=0.008 | <=0.008 | <=0.008 | <=0.008 | <=0.008 | <=0.008 | <=0.008 | 1 | 2 |
| 25 | Haemophilus | Influenzae | | 0.063 | 0.031 | 0.063 | 0.031 | 0.031 | 0.031 | 0.031 | 0.016 | 0.125 | 0.063 | >16 | 16 |
| 26 | Streptococcus | pneumoniae | | <=0.008 | <=0.008 | <=0.008 | <=0.008 | <=0.008 | <=0.008 | <=0.008 | <=0.008 | <=0.008 | <=0.008 | 0.5 | 2 |
| 27 | Streptococcus | pneumoniae | Pen-R | 0.25 | 0.125 | 0.125 | <=0.008 | 0.125 | 0.016 | 0.125 | 0.031 | 0.25 | 0.25 | 0.125 | 0.5 |

FIGURE 4 - TABLE 1: CONTINUED

| NO | Genus | Species | Resistance | 43 | 45 | 47 | 49 | 51 | 53a | 55 | 57 | 59 | 61 | Vancomycin | Linezolid |
|---|---|---|---|---|---|---|---|---|---|---|---|---|---|---|---|
| 1 | Staphylococcus | aureus | | <=0.008 | 0.031 | 0.016 | 0.031 | 0.016 | <0.008 | 0.031 | 0.031 | <=0.008 | 0.016 | 1 | 2 |
| 2 | Staphylococcus | aureus | HR-MRSA | 2 | 8 | 4 | 4 | 4 | 2 | 16 | 4 | 2 | 8 | 0.5 | 2 |
| 3 | Staphylococcus | aureus | HR-MRSA | 1 | 8 | 2 | 4 | 4 | 1 | 16 | 2 | 2 | 8 | 1 | 2 |
| 4 | Staphylococcus | aureus | Qui-R-MRSA | 0.063 | 0.063 | 0.063 | 0.13 | 0.063 | 0.031 | 0.13 | 0.063 | 0.031 | 0.063 | 1 | 2 |
| 5 | Staphylococcus | aureus | Van-I-MRSA | 1 | 2 | 2 | 4 | 2 | 1 | 8 | 1 | 2 | 4 | 4 | 1 |
| 6 | Staphylococcus | aureus | Van-I-MRSA | 0.5 | 1 | 1 | 2 | 1 | 0.5 | 2 | 0.5 | 0.5 | 2 | 2 | 1 |
| 7 | Staphylococcus | aureus | Van-I-MRSA | 0.031 | 0.063 | 0.031 | 0.063 | 0.063 | 0.031 | 0.13 | 0.063 | 0.031 | 0.063 | 4 | 1 |
| 8 | Staphylococcus | aureus | LR-MRSA | 1 | 2 | 2 | 2 | 2 | 1 | 8 | 1 | 2 | 4 | 1 | 64 |
| 9 | Staphylococcus | epidermidis | | 0.016 | 0.031 | 0.016 | 0.063 | 0.031 | 0.016 | 0.063 | 0.031 | 0.016 | 0.031 | 1 | 2 |
| 10 | Staphylococcus | epidermidis | MRSE | 0.5 | 2 | 1 | 2 | 1 | 0.5 | 4 | 0.5 | 1 | 4 | 1 | 1 |
| 11 | Staphylococcus | epidermidis | Qui-R-MRSA | 0.063 | 0.13 | 0.063 | 0.25 | 0.063 | 0.063 | 0.25 | 0.13 | 0.063 | 0.063 | 1 | 2 |
| 12 | Staphylococcus | epidermidis | Van-I-MRSE | 0.063 | 0.25 | 0.063 | 0.25 | 0.13 | 0.063 | 0.25 | 0.13 | 0.063 | 0.13 | 4 | 1 |
| 13 | Staphylococcus | saprophyticus | MRSS | <=0.008 | 0.031 | 0.016 | 0.031 | 0.031 | <0.008 | 0.063 | 0.031 | 0.031 | 0.031 | 1 | 2 |
| 14 | Staphylococcus | haemolyticus | MRSH | <=0.008 | <=0.008 | <=0.008 | <=0.008 | <=0.008 | <0.008 | 0.031 | 0.016 | <=0.008 | 0.016 | 1 | 1 |
| 15 | Staphylococcus | haemolyticus | Van-I-MRSH | 0.031 | 0.13 | 0.063 | 0.25 | 0.13 | 0.063 | 0.25 | 0.063 | 0.063 | 0.25 | 4 | 2 |
| 16 | Streptococcus | pyogenes | | <=0.008 | <=0.008 | <=0.008 | <=0.008 | <=0.008 | <0.008 | <=0.008 | <=0.008 | <=0.008 | <=0.008 | 0.5 | 1 |
| 17 | Streptococcus | agalactiae | | <=0.008 | <=0.008 | <=0.008 | <=0.008 | <=0.008 | <0.008 | <=0.008 | <=0.008 | <=0.008 | <=0.008 | 0.5 | 2 |
| 18 | Enrterococcus | faecalis | | 0.25 | 1 | 0.5 | 1 | 0.5 | 0.25 | 1 | 0.5 | 0.5 | 1 | 2 | 2 |
| 19 | Enrterococcus | faecalis | Van-R | 0.5 | 1 | 0.5 | 1 | 0.5 | 0.25 | 1 | 0.5 | 0.5 | 1 | >64 | 2 |
| 20 | Enrterococcus | faecalis | Van-R | 1 | 2 | 2 | 4 | 2 | 1 | 8 | 2 | 4 | 4 | >64 | 2 |
| 21 | Enrterococcus | faecium | | 4 | 8 | 4 | 8 | 8 | 2 | 32 | 8 | 8 | 16 | 0.5 | 2 |
| 22 | Enrterococcus | faecium | Van-R | 8 | 16 | 8 | 16 | 16 | 4 | >32 | 16 | 32 | 32 | >64 | 2 |
| 23 | Enrterococcus | faecium | Van-R | 4 | 8 | 4 | 8 | 8 | 4 | 32 | 8 | 8 | 16 | >64 | 2 |
| 24 | Haemophilus | Influenzae | | <=0.008 | <=0.008 | <=0.008 | <=0.008 | <=0.008 | <0.008 | <=0.008 | <=0.008 | <=0.008 | <=0.008 | 1 | 2 |
| 25 | Haemophilus | Influenzae | | 0.031 | 1 | 0.031 | 0.063 | 0.031 | 0.016 | 0.125 | <=0.008 | 0.063 | 0.13 | >16 | 16 |
| 26 | Streptococcus | pneumoniae | | <=0.008 | <=0.008 | <=0.008 | <=0.008 | <=0.008 | <0.008 | <=0.008 | <=0.008 | <=0.008 | <=0.008 | 0.5 | 2 |
| 27 | Streptococcus | pneumoniae | Pen-R | 0.125 | 0.25 | 0.13 | 0.25 | 0.125 | 0.063 | 0.125 | <=0.008 | 0.25 | 0.13 | 0.125 | 0.5 |

FIGURE 4 - TABLE 1: CONTINUED

| | | | | | | | | | | | | | | | |
|---|---|---|---|---|---|---|---|---|---|---|---|---|---|---|---|
| 27 | Streptococcus | pneumoniae | Pen-R | 0.125 | 0.25 | 0.13 | 0.25 | 0.125 | 0.5 | 0.125 | <=0.008 | 0.25 | 0.13 | *0.125* | *0.5* |
| **NO** | **Genus** | **Species** | **Resistance** | **63** | **65** | **67** | **69** | **71** | **73** | **75** | **77** | **79** | **81** | *Vancomycin* | *Linezolid* |
| 1 | Staphylococcus | aureus | | <=0.008 | 0.031 | 0.063 | <=0.008 | 0.031 | 0.031 | 0.031 | 0.031 | 0.016 | 0.016 | *1* | 2 |
| 2 | Staphylococcus | aureus | HR-MRSA | 2 | 8 | 4 | 1 | 4 | 8 | 4 | 4 | 2 | 4 | *0.5* | 2 |
| 3 | Staphylococcus | aureus | HR-MRSA | 2 | 4 | 2 | 1 | 4 | 4 | 2 | 4 | 1 | 2 | *1* | 2 |
| 4 | Staphylococcus | aureus | Qui-R-MRSA | 0.063 | 0.063 | 0.25 | 0.063 | 0.13 | 0.25 | 0.13 | 0.13 | 0.063 | 0.13 | *1* | 2 |
| 5 | Staphylococcus | aureus | Van-I-MRSA | 2 | 4 | 4 | 1 | 2 | 4 | 2 | 4 | 1 | 2 | *4* | *1* |
| 6 | Staphylococcus | aureus | Van-I-MRSA | 0.5 | 1 | 1 | 0.5 | 1 | 1 | 1 | 2 | 0.5 | 1 | *2* | *1* |
| 7 | Staphylococcus | aureus | Van-I-MRSA | 0.031 | 0.063 | 0.13 | 0.031 | 0.063 | 0.13 | 0.063 | 0.13 | 0.031 | 0.063 | *4* | *1* |
| 8 | Staphylococcus | aureus | LR-MRSA | 2 | 4 | 2 | 0.5 | 2 | 2 | 2 | 4 | 1 | 2 | *1* | *64* |
| 9 | Staphylococcus | epidermidis | | 0.031 | 0.031 | 0.13 | 0.031 | 0.063 | 0.063 | .063 | 0.063 | 0.031 | 0.031 | *1* | 2 |
| 10 | Staphylococcus | epidermidis | MRSE | 1 | 1 | 2 | 0.25 | 1 | 2 | 1 | 2 | 0.5 | 1 | *1* | *1* |
| 11 | Staphylococcus | epidermidis | Qui-R-MRSA | 0.063 | 0.13 | 0.5 | 0.063 | 0.13 | 0.13 | 0.13 | 0.25 | 0.13 | 0.13 | *1* | 2 |
| 12 | Staphylococcus | epidermidis | Van-I-MRSE | 0.13 | 0.25 | 0.5 | 0.031 | 0.25 | 0.25 | 0.13 | 0.25 | 0.063 | 0.13 | *4* | *1* |
| 13 | Staphylococcus | saprophyticus | MRSS | 0.016 | 0.063 | 0.031 | <=0.008 | 0.031 | 0.031 | 0.031 | 0.063 | <=0.008 | <=0.008 | *1* | 2 |
| 14 | Staphylococcus | haemolyticus | MRSH | <=0.008 | 0.031 | 0.031 | <=0.008 | 0.016 | 0.016 | 0.016 | 0.016 | <=0.008 | <=0.008 | *1* | *1* |
| 15 | Staphylococcus | haemolyticus | Van-I-MRSH | 0.063 | 0.063 | 0.25 | 0.031 | 0.25 | 0.25 | 0.25 | 0.25 | 0.13 | 0.13 | *4* | 2 |
| 16 | Streptococcus | pyogenes | | <=0.008 | <=0.008 | <=0.008 | <=0.008 | <=0.008 | <=0.008 | <=0.008 | <=0.008 | <=0.008 | <=0.008 | *0.5* | *1* |
| 17 | Streptococcus | agalactiae | | <=0.008 | <=0.008 | <=0.008 | <=0.008 | <=0.008 | <=0.008 | <=0.008 | <=0.008 | <=0.008 | <=0.008 | *0.5* | 2 |
| 18 | Enrterococcus | faecalis | | 0.5 | 1 | 2 | 0.25 | 0.5 | 0.5 | 1 | 1 | 0.5 | 0.5 | *2* | 2 |
| 19 | Enrterococcus | faecalis | Van-R | 1 | 2 | 2 | 0.5 | 1 | 1 | 1 | 1 | 0.5 | 1 | *>64* | 2 |
| 20 | Enrterococcus | faecalis | Van-R | 2 | 8 | 4 | 1 | 2 | 4 | 4 | 4 | 2 | 2 | *>64* | 2 |
| 21 | Enrterococcus | faecium | | 4 | 32 | 16 | 4 | 8 | 8 | 16 | 16 | 4 | 8 | *0.5* | 2 |
| 22 | Enrterococcus | faecium | Van-R | 8 | >32 | 32 | 8 | 16 | 32 | 8 | 32 | 8 | 16 | *>64* | 2 |
| 23 | Enrterococcus | faecium | Van-R | 8 | 32 | 16 | 4 | 8 | 8 | 8 | 8 | 4 | 8 | *>64* | 2 |
| 24 | Haemophilus | Influenzae | | <=0.008 | 0.016 | <=0.008 | <=0.008 | <=0.008 | <=0.008 | 0.031 | <=0.008 | <=0.008 | <=0.008 | *1* | 2 |
| 25 | Haemophilus | Influenzae | | 1 | 0.063 | 0.125 | <=0.008 | 0.063 | 0.063 | 0.063 | 0.063 | 2 | 0.063 | *>16* | *16* |
| 26 | Streptococcus | pneumoniae | | <=0.008 | <=0.008 | <=0.008 | <=0.008 | <=0.008 | <=0.008 | <=0.008 | 0.016 | <=0.008 | <=0.008 | *0.5* | 2 |

Figure 4 - Table 1: continued

| NO | Genus | Species | Resistance | 83 | 85 | 87 | 89 | 91 | 93 | 95 | 97 | 100 | Vancomycin | Linezolid |
|---|---|---|---|---|---|---|---|---|---|---|---|---|---|---|
| 1 | Staphylococcus | aureus | | 0.031 | 0.031 | 0.016 | 0.031 | 0.031 | 0.063 | 0.25 | 0.016 | 0.016 | 1 | 2 |
| 2 | Staphylococcus | aureus | HR-MRSA | 4 | 2 | 8 | 8 | 8 | 16 | 32 | 4 | 4 | 0.5 | 2 |
| 3 | Staphylococcus | aureus | HR-MRSA | 4 | 2 | 8 | 4 | 4 | 16 | 16 | 2 | 4 | 1 | 2 |
| 4 | Staphylococcus | aureus | Qui-R-MRSA | 0.13 | 0.063 | 0.031 | 0.063 | 0.125 | 0.25 | 0.5 | 0.13 | 0.063 | 1 | 2 |
| 5 | Staphylococcus | aureus | Van-I-MRSA | 4 | 1 | 2 | 4 | NA | NA | NA | 2 | 1 | 4 | 1 |
| 6 | Staphylococcus | aureus | Van-I-MRSA | 2 | 0.5 | 1 | 1 | NA | NA | NA | 1 | 0.5 | 2 | 1 |
| 7 | Staphylococcus | aureus | Van-I-MRSA | 0.063 | 0.031 | 0.031 | 0.063 | NA | NA | NA | 0.031 | 0.031 | 4 | 1 |
| 8 | Staphylococcus | aureus | LR-MRSA | 4 | 1 | 4 | 4 | NA | NA | NA | 2 | 2 | 1 | 64 |
| 9 | Staphylococcus | epidermidis | | 0.063 | 0.031 | 0.031 | 0.031 | 0.031 | 0.063 | 0.25 | 0.031 | 0.016 | 1 | 2 |
| 10 | Staphylococcus | epidermidis | MRSE | 2 | 0.5 | 2 | 1 | 4 | 4 | 8 | 1 | 0.5 | 1 | 1 |
| 11 | Staphylococcus | epidermidis | Qui-R-MRSA | 0.13 | 0.063 | 0.063 | 0.13 | NA | 0.25 | 0.5 | 0.13 | 0.13 | 1 | 2 |
| 12 | Staphylococcus | epidermidis | Van-I-MRSE | 0.13 | 0.063 | 0.13 | 0.25 | 0.125 | NA | NA | 0.063 | 0.13 | 4 | 1 |
| 13 | Staphylococcus | saprophyticus | MRSS | 0.031 | 0.016 | 0.031 | 0.063 | 0.031 | 0.063 | 0.13 | 0.016 | 0.016 | 1 | 2 |
| 14 | Staphylococcus | haemolyticus | MRSH | <=0.008 | 0.016 | 0.016 | 0.031 | 0.016 | 0.063 | 0.13 | <=0.008 | <=0.008 | 1 | 1 |
| 15 | Staphylococcus | haemolyticus | Van-I-MRSH | 0.13 | 0.063 | 0.063 | 0.063 | NA | NA | NA | 0.063 | 0.063 | 4 | 2 |
| 16 | Streptococcus | pyogenes | | <=0.008 | <=0.008 | <=0.008 | <=0.008 | <=0.008 | 0.016 | 0.031 | <=0.008 | <=0.008 | 0.5 | 1 |
| 17 | Streptococcus | agalactiae | | 0.016 | <=0.008 | <=0.008 | <=0.008 | <=0.008 | 0.016 | 0.031 | <=0.008 | <=0.008 | 0.5 | 2 |
| 18 | Enrterococcus | faecalis | | 0.5 | 0.5 | 0.5 | 1 | 0.5 | 1 | 2 | 0.5 | 1 | 2 | 2 |
| 19 | Enrterococcus | faecalis | Van-R | 0.5 | 0.5 | 0.5 | 2 | 1 | 2 | 4 | 1 | 1 | >64 | 2 |
| 20 | Enrterococcus | faecalis | Van-R | 2 | 1 | 4 | 8 | 4 | 8 | 16 | 2 | 2 | >64 | 2 |
| 21 | Enrterococcus | faecium | | 8 | 4 | 16 | 32 | 32 | >32 | >32 | 8 | 8 | 0.5 | 2 |
| 22 | Enrterococcus | faecium | Van-R | 16 | 8 | 32 | >32 | 16 | 32 | >32 | 16 | 16 | >64 | 2 |
| 23 | Enrterococcus | faecium | Van-R | 8 | 4 | 16 | 32 | 16 | 16 | >32 | 8 | 8 | >64 | 2 |
| 24 | Haemophilus | Influenzae | | <=0.008 | <=0.008 | <=0.008 | 0.016 | <=0.008 | 0.031 | <=0.008 | <=0.008 | <=0.008 | 1 | 2 |
| 25 | Haemophilus | Influenzae | | 0.125 | 0.016 | 0.25 | 0.063 | 0.25 | 0.25 | 2 | 0.031 | 0.25 | >16 | 16 |
| 26 | Streptococcus | pneumoniae | | <=0.008 | <=0.008 | <=0.008 | <=0.008 | <=0.008 | 0.016 | <=0.008 | <=0.008 | <=0.008 | 0.5 | 2 |
| 27 | Streptococcus | pneumoniae | Pen-R | 0.125 | 0.031 | 0.063 | 0.25 | 0.25 | 0.5 | 1 | 0.125 | 0.25 | 0.125 | 0.5 |

Figure 5 - Table 2: MIC (*in vitro* Susceptibility) Data for Aminonaphthol CP Analogs

| CP Analog | 148 | 152 | 157 | 162 | 167 | 171 | 175 | 180 | 183 | 188 | 191 | 194 | 197 | Imipenem |
|---|---|---|---|---|---|---|---|---|---|---|---|---|---|---|
| *S.aureus* | 0.063 | 0.016 | 0.031 | 0.016 | 0.063 | ≤0.008 | 0.031 | 0.016 | 0.031 | 0.031 | 0.031 | 0.016 | 0.016 | 0.016 |
| *S.aureus* | 0.031 | ≤0.008 | 0.031 | 0.016 | 0.063 | ≤0.008 | 0.016 | 0.016 | 0.031 | 0.016 | 0.016 | 0.016 | 0.016 | ≤0.008 |
| *S.aureus* | 0.063 | 0.016 | 0.031 | 0.016 | 0.063 | ≤0.008 | 0.031 | 0.031 | 0.031 | 0.031 | 0.031 | 0.016 | 0.031 | 0.016 |
| *S.aureus* $^{MR}$ | 4 | 1 | 2 | 1 | 4 | 0.5 | 4 | 4 | 2 | 2 | 2 | 0.25 | 1 | 2 |
| *S.aureus* $^{MR}$ | 1 | 0.25 | 0.5 | 0.25 | 0.5 | 0.13 | 0.25 | 0.25 | 0.5 | 0.25 | 0.25 | 0.25 | 0.5 | 2 |
| *S.aureus* $^{MR}$ | 16 | 8 | 8 | 8 | >64 | 16 | 32 | 64 | 16 | 8 | 8 | 32 | 8 | 64 |
| *S.aureus* $^{MR}$ | 16 | 8 | 16 | 8 | >64 | 16 | 32 | 64 | 16 | 8 | 8 | 32 | 8 | 64 |
| *S.aureus* $^{MR}$ | 8 | 4 | 4 | 4 | 64 | 8 | 16 | 16 | 8 | 4 | 4 | 16 | 4 | 32 |
| *S.aureus* $^{MR}$ | 8 | 4 | 8 | 4 | 64 | 8 | 16 | 32 | 8 | 4 | 4 | 16 | 4 | 64 |
| *S.aureus* $^{MR}$ | 16 | 8 | 8 | 8 | >64 | 16 | 32 | 32 | 16 | 8 | 8 | 16 | 8 | 64 |
| *S.aureus* $^{MR}$ | 16 | 8 | 8 | 4 | >64 | 16 | 32 | 32 | 16 | 8 | 8 | 16 | 8 | 64 |
| *S.epidermidis* $^{MR}$ | 0.5 | 0.25 | 0.25 | 0.5 | 1 | 0.13 | 0.5 | 0.5 | 0.5 | 0.25 | 0.25 | 0.5 | 0.5 | 0.5 |
| *S.epidermidis* | 0.063 | 0.016 | 0.031 | 0.016 | 0.063 | ≤0.008 | 0.016 | 0.016 | 0.031 | 0.031 | 0.031 | 0.016 | 0.031 | ≤0.008 |
| *E.faecalis* | 2 | 0.5 | 1 | 0.5 | 2 | 0.25 | 2 | 1 | 2 | 1 | 1 | 0.5 | 0.5 | 1 |
| *E. faecalis* $^{Van A}$ | 2 | 0.5 | 1 | 1 | 4 | 0.25 | 2 | 1 | 2 | 1 | 1 | 0.5 | 1 | 1 |
| *E. faecalis Van* | 2 | 0.5 | 1 | 1 | 4 | 0.25 | 2 | 1 | NA | 1 | 1 | 0.5 | 1 | 1 |
| *E. faecium* $^{Van A}$ | 32 | 16 | 32 | 16 | >64 | 32 | 64 | 64 | >32 | 32 | 32 | >32 | 32 | >64 |
| *E. faecium* $^{Van B}$ | 32 | 16 | 32 | 32 | >64 | 64 | 64 | 64 | >32 | 32 | 32 | >32 | 32 | >64 |
| *E. faecium* | 16 | 8 | 8 | 8 | 64 | 16 | 32 | 32 | 16 | 16 | 8 | 32 | 16 | >64 |

GRAM-POSITIVE CARBAPENEM ANTIBACTERIALS AND PROCESSES FOR THEIR PREPARATION

CROSS REFERENCE TO RELATED APPLICATIONS

This application claims priority to U.S. Provisional Application No. 60/578,632, filed Jun. 10, 2004.

FIELD OF THE INVENTION

This invention provides novel carbapenem compounds and their salts and prodrugs, methods of treatment of gram-positive bacterial infections with an effective amount of the compounds and pharmaceutical compositions including the compounds.

DESCRIPTION OF RELATED ART

The worldwide exploitation of antibiotics to treat infectious diseases has grown dramatically over the last forty years. In 1954, two million pounds of antibiotics were produced in the United States. Today, the figure exceeds 50 million pounds. According to the Centers Disease Control (CDC), humans consume 235 million doses of antibiotics annually.

Widespread misuse or overuse of antibiotics has fostered the spread of antibiotic resistance and has contributed to the development of a serious public health problem. Antibiotic resistance occurs when bacteria that cause infection are not killed by the antibiotics taken to stop the infection. The bacteria survive and continue to multiply, causing more harm. For example, the bacterium *Staphylococous aureus* is a major cause of hospital acquired infections that, historically, responded satisfactorily to the antibiotic vancomycin. Recently, however, many strains of *S. aureus* have been found to be resistant to vancomycin. Moreover, the death rate for some communicable diseases such as tuberculosis has started to rise again, in part because of increases in bacterial resistance to antibiotics.

Antibiotics are used therapeutically to treat bacterial infections. Several types of antibiotics, classified according to their mechanism of action, are currently employed. The known types of antibiotics include, e.g. cell wall synthesis inhibitors, cell membrane inhibitors, protein synthesis inhibitors and inhibitors that bind to or affect the synthesis of DNA or RNA. Numerous antibiotic agents, suitable for use in the treatment of bacteria-related diseases and disorders, are known and disclosed, e.g. in *The Physician's Desk Reference* (*PDR*), Medical Economics Company (Montvale, N.J.), ($53^{rd}$ Ed.), 1999; *Mayo Medical Center Formulary, Unabridged Version*, Mayo Clinic (Rochester, Minn.), January 1998; *Merck Index: An Encyclopedia of Chemicals, Drugs and Biologicals*, ($11^{th}$ Ed.), Merck & Co., Inc. (Rahway, N.J.), 1989; *University of Wisconsin Antimicrobial Use Guide*, http://www.med-sch.wisc.edu/clinsci/5amcg/amcg.html; *Introduction on the Use of the Antibiotics Guideline, of Specific Antibiotic Classes*, Thomas Jefferson University, http://jeffiine.tju.edu/CWIS/OAC/antibiotics_guide/intro.html; and references cited therein.

The first carbapenem to be isolated was thienamycin, shown below, which was isolated from *Streptomyces cattleya* (U.S. Pat. No. 3,950,357) and is active against *Pseudomonas* spp. and has β-lactamase stability (Kahan, J. S., et al., *J. Antibiot.*, 32, pp. 1-12 (1979); Bodey, G. P., et al., *Antimicrob. Agents Chemother.*, 15, pp. 518-521 (1979). The racemic synthesis of thienamycin was reported shortly thereafter by Merck (Johnston, D. B. R., et al., *J. Am. Chem. Soc.*, 100, pp. 313-315 (1978); Bouffard, F. A., et al., *J. Org. Chem.*, 45, 1130-1142 (1980)), as well as an asymmetric total synthesis (Salzmann, T. N., et al., *J. Am. Chem. Soc.* 102, pp. 6161-6163 (1980)).

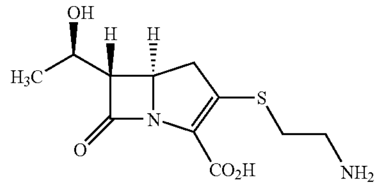

However, this molecule is chemically unstable due to its lactam nucleus and amino acid configuration. Chemical stability issues associated with the intermolecular aminolysis of the azetidinone (β-lactam) ring of one molecule of thienamycin by the primary amine in the cysteamine side chain of another thienamycin molecule, resulted in abandonement of thienamycin as a drug candidate.

As a result of the problems associated with thienamycin, N-formimidoyl thienamycin, known as imipenem, was synthesized (Leanza, W. J., et al., *J. Med. Chem.*, 22, pp. 1435-1436 (1979)). This compound bears a more basic amidine functionality on the 2' side chain, which is protonated at physiological pH, preventing the compound from initiating a nucleophilic attack on another imipenem molecule. However, poor urinary tract recovery from test subjects revealed instability of this compound to the mammalian β-lactamase renal dehydropeptidase-I (DHP-I) (Shimada, J., et al., *Drugs Exp Clin Res.*, 20, pp. 241-245 (1994)). Consequently, the compound cilastatin was developed for use in co-administration in order to prevent hydrolysis and degradation by DHP-I; this combination therapy is currently prescribed under the name Primaxin® (Merck Frosst Std).

In response to the problem of carbapenems to degradation by renal dehydropeptidase-1, the carbapenem antibiotic meropenem (SM7338) (shown below), was developed (see, Edwards, J. R., et al., *Antimicrob. Agents Chemother.*, 33, pp. 215-222 (1989); Neu, H. C., et al., *Antimicrob. Agents Chemother.*, 33, pp. 1009-1018 (1989)).

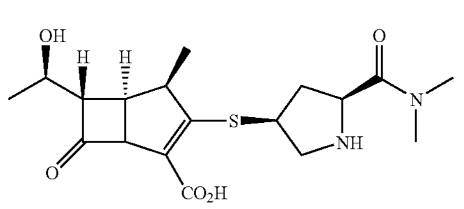

This compound was shown to be active against a large number of Gram-negative bacteria. Meropenem is currently prescribed for intravenous use (Merrem® IV; AstraZeneca) in the treatment of intra-abdominal infections and bacterial meningitis.

The carbapenem ertapenem (shown below; formerly MK-0826; Cunha, B. A., *Drugs of Today*, 38, pp. 195-213 (2002)) is potentially useful as a long-acting, parenteral carbapenem (Shah, P. M., et al., *J. Antimicrob. Chemother.*, 52, pp. 538-542 (2003); Aldridge, K. E., *Diagn. Microbiol. Infect. Dis.*, 44(2), pp. 181-6 (2002)).

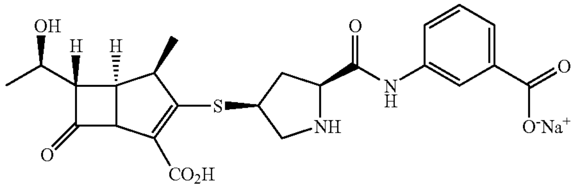

Ertapenem has received regulatory approval in both the United States (November, 2001) and the European Union (April, 2002).

A carbapenem having a fused pyrazole ring system (see below; also known as L-627; Biapenem) was developed by Lederle Ltd. (Japan), and introduced a methyl radical at the 1-β position of the carbapenem skeleton (see, U.S. Pat. No. 4,866,171). This structural modification reportedly gave biapenem stability against hydrolysis by kidney dehydropeptidase, and exhibits potency across a wide bacterial spectrum.

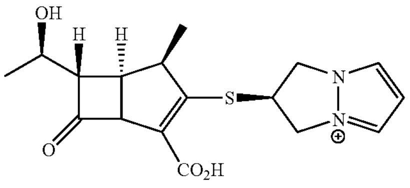

A 1-β-methyl carbapenem antibiotic having an (R)-1-hydroxymethyl-methylaminopropyl group exhibiting both broad spectrum antibacterial activity (BO-2727) and antipseudomonal activity has been reported (Nakagawa, S., et al., *Antimicrob. Agents Chemother.,* 37, pp. 2756-2759 (1993); Hazumi, N., et al., *Antimicrob. Agents Chemother.,* 39, pp. 702-706 (1995)).

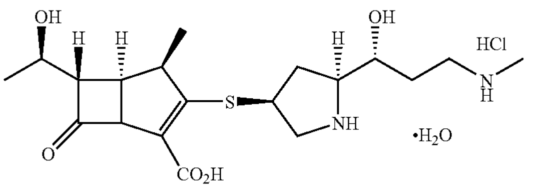

This compound has been shown to have a prophylactic efficacy against both Gram-positive and Gram-negative bacterial systemic infections similar to that of imipenem and biapenem (Odenholdt, I., et al., *Clin. Microbiol. Infect.,* 3, pp. 73-81 (1997); Inoue, K., et al., *Antimicrob. Agents Chemother.,* 39, pp. 2331-2336 (1995)).

U.S. Pat. No. 6,255,300 to Merck & Co. describes certain carbapenem antibacterial agents in which the carbapenem nucleus is substituted with an iodo-phenyl linked through a methyl-oxygen lincage. The patent states that these compounds are useful against gram positive bacterial infections. Similarly, U.S. Pat. No. 6,310,055 provides carbapenem compounds with aromatic side chains that are halogen substituted, linked therough an alkoxy unsaturated group.

European Publication No. 0 292 191 to Merck & Co. describes certain 2-(substituted methyl)-1-alkylcarbapenem compounds useful as antibiotic agents.

U.S. Pat. No. 6,399,597, also to Merck & Co. describes certain napthosultam compounds that are allegedly useful in the treatment of certain drug resistant bacterial infections.

Since the discovery of thienamycin having a potential antimicrobial activity against Gram-negative and Gram-positive bacteria, studies on the syntheses of carbapenem derivatives which are analogous to thienamycin have been widely developed. As a result, it was found that carbapenem derivatives having, as their 2-side chain, a substituent derived from 4-hydroxy-proline, i.e. an optionally substituted pyrrolidinyl group substituted on its 2-position, for example a carbonyl group substituted with various substituents, exhibit a potential antimicrobial activity and are useful as medicines or as intermediates for compounds possessing antimicrobial activity.

1-β-methyl carbapenem antibiotics, are particularly well known for treating a broad spectrum of gram-negative and gram-positive bacterial infections. See for example U.S. Pat. Nos. 4,962,103; 4,933,333; 4,943,569; 5,122,604; 5,034,384 and 5,011,832.

Because of the difficulty in developing effective carbapenem compounds due to hydrolysis of the β-lactam ring and low recovery, compounds with superior anti-bacterial activity have not been developed.

The development of new drugs is an essential component to strategies designed to reverse the problem of bacterial resistance, particularly in treating infectious diseases (e.g. bacterial infections). Accordingly, there is a need to identify additional compounds to treat infectious diseases (e.g. bacterial infections).

There is an increasing need for agents effective against drug-resistant pathogens, including methicillin resistant *Staphylococcus aureus* (MRSA), methicillin resistant *Staphylococcus epidermidis* (MRSE), methicillin resistant coagulase negative Staphylococci (MRCNS), vancomycin resistant *Enterococcus faecalis*, and/or vancomycin resistant *Enterococcus faecium*, which are optionally relatively free from undesirable side effects.

Therefore, it is one object of the present invention to provide novel compounds that are effective antimicrobial agents.

It is another object of the present invention to provide methods for the treatment of gram-positive bacteria that can be drug-resistant and/or multi-drug resistant.

SUMMARY OF THE INVENTION

In one embodiment, a carbapenem is provided, of the formula (I), (II), (III) or (IV):

(I)

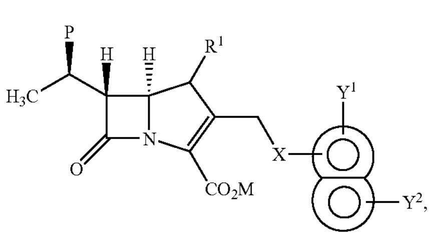

-continued (II)

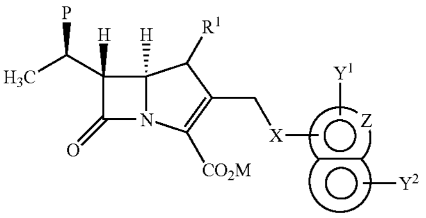

(III)

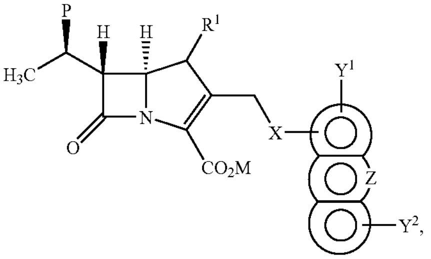

(IV)

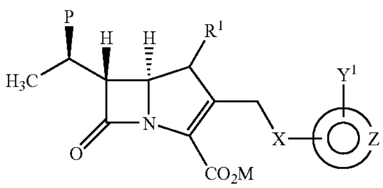

or a pharmaceutically acceptable salt and/or prodrug thereof, wherein $R^1$ is H or alkyl, such as a lower alkyl such as $CH_3$;

$CO_2M$ represents a carboxylic acid, a carboxylate anion, a pharmaceutically acceptable ester group or a carboxylic acid protected by a protecting group;

P represents hydrogen, hydroxyl, F or hydroxyl protected by a hydroxyl-protecting group;

X is O, S, $S(O)_x$, with x equal to 0, 1 or 2, phosphate, carbonyl, thiocarbonyl, iminyl, $P(O)_2$, $P(O)_3$, C(O), C(O)O, OC(O), C(O)NH, C(O)NR, NHC(O), NRC(O), amine, NH, or NR;

each R is independently H or alkyl, for example a lower alkyl such as $CH_3$;

each

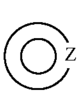 and 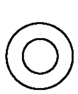

is independently a 5- or 6-membered monocyclic aromatic or heteroaromatic ring;

Z is present or absent, and when present, represents members selected from the group consisting of: C═$CR_2$, C═$CY^1$, O, S, carbonyl, thiocarbonyl, iminyl, C(O), C(O)O, OC(O), C(O)NH, C(O)NR, NHC(O), NRC(O), N(A-$(CH_2)_n$-Q)C(O), CON(A-$(CH_2)_n$-Q), C(═NH), C(═NR), C(—N-A-$(CH_2)_n$-Q), amine, NH, NR, or N(A-$(CH_2)_n$-Q);

each $Y^1$ and $Y^2$ is independently selected from: hydrogen; halo; —CN; —$NO_2$; —$NR^aR^b$; —$OR^c$; —$SR^c$; —C(O)$NR^aR^b$; —C(O)$OR^h$; S(O)$R^c$; —$SO_2R^c$; —$SO_2NR^aR^b$; —$NR^aSO_2R^b$; —C(O)$R^a$; —OC(O)$R^a$; OC(O)$NR^aR^b$; —$NR^a$C(O)$NR^bR^c$; —$NR^aCO_2R^h$; —$OCO_2R^h$; $NR^a$C(O)$R^b$; —$C_{1-6}$ straight- or branched-chain alkyl, —$C_{2-6}$ straight- or branched-chain alkenyl, or —$C_{2-6}$ straight- or branched-chain alkynyl, unsubstituted or substituted with one to four $R^d$ groups; -A-$(CH_2)_n$-Q; —$(CH_2)_n$A-Q; —$[(CH_2)_nA]_m(CH_2)_p$-Q; —$CH_2$N-Q; and —$C_{3-7}$ cycloalkyl, unsubstituted or substituted with one to four $R^d$ groups;

A represents O, S, NH, $NCH_3$, NR, or —$CH_2$—;

each m, n, and p independently represents an integer 0, 1, 2 or 3;

each $R^a$, $R^b$ and $R^c$ independently represents hydrogen, —$C_6$ straight- or branched-chain alkyl, unsubstituted or substituted with one to four $R^d$ groups, or $C_{3-7}$ cycloalkyl, unsubstituted or substituted with one to four $R^d$ groups;

or $R^a$ and $R^b$ taken together with any intervening atoms represent a 4-6 membered saturated ring optionally interrupted by one or more of O, S, $NR^c$, with $R^c$ as defined above, or —C(O)—, said ring being unsubstituted or substituted with one to four $R^i$ groups;

or $R^b$ and $R^c$ taken together with any intervening atoms represent a 4-6 membered saturated ring optionally interrupted by one to three of O, S, $NR^a$, with $R^a$ as defined above, or —C(O)—, said ring being unsubstituted or substituted with one to four $R^i$ groups;

each $R^d$ independently represents halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; $NR^e$-$CONR^fR^g$; —$NR^eCO_2R^h$; —$OCO_2R^h$; —C($NR^e$)$NR^fR^g$; $NR^e$C(NH)$NR^fR^g$ or —$NR^e$C($NR^f$)$R^g$;

each $R^e$, $R^f$ and $R^g$ independently represents hydrogen; —R; —$C_{1-6}$ straight- or branched-chain alkyl unsubstituted or substituted with one to four $R^i$ groups;

or $R^e$ and $R^f$ taken together with any intervening atoms represent a 4-6 membered saturated ring optionally interrupted by one to three of O, S, —C(O)— or $NR^g$ with $R^g$ as defined above, said ring being unsubstituted or substituted with one to four $R^i$ groups;

each $R^i$ independently represents halo; —CN; —$NO_2$; phenyl; —$NHSO_2R^h$; —$OR^h$, —$SR^h$; —$N(R^h)_2$; —$N^+(R^h)3$; —C(O)$N(R^h)_2$; $SO_2N(R^h)2$; heteroaryl; heteroarylium; —$CO_2R^h$; —C(O)$R^h$; —$OCOR^h$; $NHCOR^h$; guanidinyl; carbamimidoyl or ureido;

each $R^h$ independently represents hydrogen, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4-6 membered saturated ring, optionally interrupted by one or two of O, S, $SO_2$, —C(O)—, NH and $NCH_3$;

each Q is selected from the group consisting of:

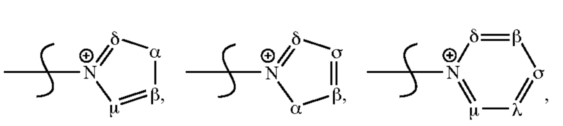

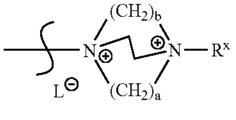 and 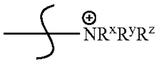

wherein:

a and b are independently 1, 2 or 3;

$L^-$ is a pharmaceutically acceptable counterion;

α represents O, S or $NR^s$;

β, δ, λ, μ, and σ represent $CR^t$, N or $N^+R^s$, provided that no more than one of β, δ, λ, μ, and σ is $N^+R^s$;

each $R^s$ independently represents hydrogen; phenyl or $C_{1-6}$ straight- or branched-chain alkyl, unsubstituted or substituted with one to four $R^i$ groups;

each $R^t$ independently represents hydrogen; halo; phenyl; —CN; —$NO_2$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;

each $R^u$ and $R^v$ represent hydrogen or —$C_{1-6}$ straight- or branched-chain alkyl, unsubstituted or substituted with one to four $R^i$ groups;

or $R^u$ and $R^v$ together with any intervening atoms represent a 4-6 membered saturated ring optionally interrupted by one or more of O, S, $NR^w$ or —C(O)—, said ring being unsubstituted or substituted with one to four $R^i$ groups;

each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1-4 $R^i$ groups; or $R^h$ and $R^w$ taken together with any intervening atoms represent a 5-6 membered saturated ring, optionally interrupted by one or two of O, S, $SO_2$, NH or $NCH_3$;

$R^x$ represents hydrogen or a $C_{1-8}$ straight- or branched chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR_hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

Each $R^y$ and $R^z$ independently represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—;

or $R^x$ and $R^y$ together with any intervening atoms represent a 4-6 membered saturated ring optionally interrupted by O, S, $SO_2$, $NR^w$, $N^+R^hR^w$ or —C(O)—, unsubstituted or substituted with 1-4 $R^i$ groups, and when $R^x$ and $R^y$ together represent a 4-6 membered ring as defined above, $R^z$ is as defined above or $R^z$ represents an additional saturated 4-6 membered ring fused to the ring represented by $R^x$ and $R^y$ taken together, optionally interrupted by O, S, $NR^w$ or —C(O)—, said rings being unsubstituted or substituted with one to four $R^i$ groups;

wherein if the compound is of formula (III), X is O and R is $CH_3$, then the substituent

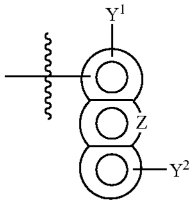

is not

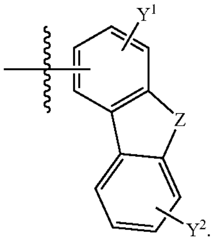

In one embodiment, at least one of $Y^1$ and $Y^2$ is not hydrogen.

In one subembodiment of the present invention, the carbapenem is of the formula (V):

(V)

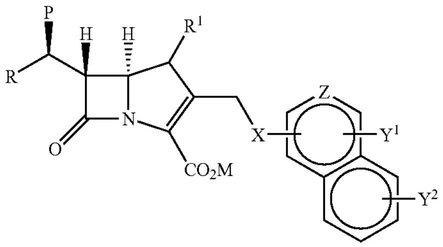

or a pharmaceutically acceptable salt and/or prodrug thereof, wherein R, P, $R^1$, $CO_2M$, X, Z, $Y^1$ and $Y^2$ are as defined above.

In another particular subembodiment of the present invention, the carbapenem of the formula (Va):

(Va)

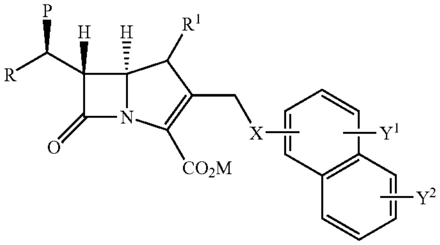

or a pharmaceutically acceptable salt and/or prodrug thereof wherein R, P, $R^1$, $CO_2M$, X, $Y^1$ and $Y^2$ are as defined above.

In one embodiment of the present invention, the carbapenem is of the formula (Va) and at least one of $Y^1$ and $Y^2$ is not hydrogen.

In a further embodiment of the present invention, the carbapenem is of the formula (Va) and $Y^1$ is hydrogen and $Y^2$ is not hydrogen.

In another particular subembodiment of the present invention, the carbapenem is of the formula (Vb):

(Vb)

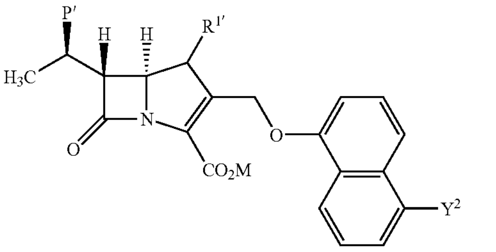

or a pharmaceutically acceptable salt and/or prodrug thereof, wherein:

P' is hydrogen or hydroxyl;

$R^{1'}$ is hydrogen or methyl; and $CO_2M$ and $Y^2$ are as defined above.

In another particular embodiment of the present invention, the carbapenem is of the formula (Vc):

(Vc)

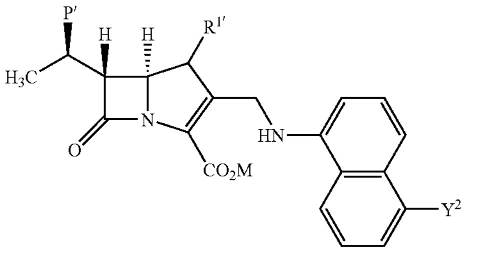

or a pharmaceutically acceptable salt and/or prodrug thereof; wherein

P' is hydrogen or hydroxyl;

$R^{1'}$ is hydrogen or methyl; and $CO_2M$ and $Y^2$ are as defined above.

In another embodiment of the present invention, the carbapenem is of the formula (VI):

(VI)

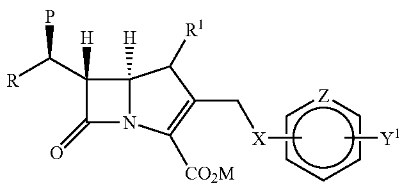

or a pharmaceutically acceptable salt and/or prodrug thereof, wherein:

X is O or NH;

$Y^1$ is $-(CH_2)_n$-Q wherein n=1-3 and Q is selected from the group consisting of $-NH-C(=NR^3)-N(R^3)_2$, $-S-C(=NR^3)-N(R^3)_2$ and $-S-O_2-N(R^3)_2$, wherein $R^3$ is independently $C_1$-$C_4$ alkyl or H; and R, P, $R^1$, $CO_2M$ and Z are as defined above.

The present invention also provides a pharmaceutical composition comprising a compound of the invention, or a pharmaceutically acceptable salt and/or prodrug therein, alone or, optionally, in combination with one or more other antimicrobial agents, optionally with a pharmaceutically acceptable carrier or diluent.

The present invention also provides a method of preventing or treating a bacterial infection, in a host, such as an animal, and typically a human, including administering to the host a therapeutic amount of a compound of the present invention, or a pharmaceutically acceptable salt and/or prodrug therein, optionally in a pharmaceutically acceptable carrier or diluent where the bacterial infection is due to a gram-positive bacteria.

In one embdodiment, the bacterial infection is from a drug resistant and/or multiple-drug resistant bacterium. In specific embodiments, the bacteria is at least one of methicillin resistant *Staphylococcus aureus* (MRSA), methicillin resistant *Staphylococcus epidermidis* (MRSE), methicillin resistant coagulase negative Staphylococci (MRCNS), vancomycin resistant *Enterococcus faecalis*, and/or vancomycin resistant *Enterococcus faecium*.

The present invention also provides a method of preventing or treating a bacterial infection, in a host, such as an animal, and typically a human, including administering to the host a therapeutic amount of a compound of the present invention, or a pharmaceutically acceptable salt and/or prodrug therein, in combination or alternation with one or more other antimicrobial agents, optionally in a pharmaceutically acceptable carrier or diluent where the bacterial infection is due to a gram-positive bacteria. In one embdodiment, the bacterial infection is from a drug resistant and/or multiple-drug resistant bacterium.

The invention also provides the use of a therapeutically effective amount of a compound of the present invention, alone or, optionally, in combination with another agent, optionally in a pharmaceutically acceptable carrier in the prevention or treatment or preparation of a medicament for the prevention or treatment of a gram-postitive bacterial infection in a host. The bacteria can be drug resistant and/or multiple-drug resistant. In some embodiments, the other agent is another antimicrobial agent that can be effective against gram positive bacterial infections.

The carbapenems of the present invention can be synthesized using any method known in the art. In one embodiment, a process for synthesizing a compound represented by formula I, II, III, or IV, or a pharmaceutically acceptable salt and/or prodrug thereof, is provided.

The present invention also is directed to methods of efficient synthesis of β-methyl carbapenems from available precursors with the option of introducing functionality as needed. Therefore, in one embodiment, the carbapenems are synthesized using the process described herein.

The invention also provides intermediates disclosed herein that are useful in the preparation of compounds of the present invention as well as synthetic methods for preparing the compounds of the invention.

DESCRIPTION OF THE FIGURES

FIG. 4 is a table of MIC (in vitro susceptibility) data for 5-alkyl-substituted-1-naphthol CP analogs.

FIG. 5 is a table of MIC (in vitro Susceptibility) data for aminonaphthol CP analogs.

DETAILED DESCRIPTION OF THE INVENTION

Figure 1:
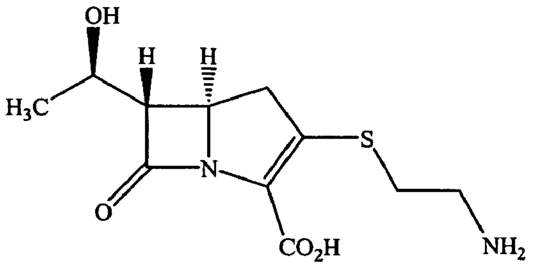
FIG. 1 shows a nonlimiting illustrative example of known carbapenems.
Figure 1:
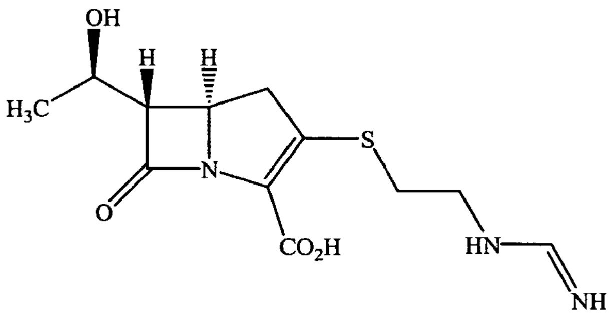
Figure 1:
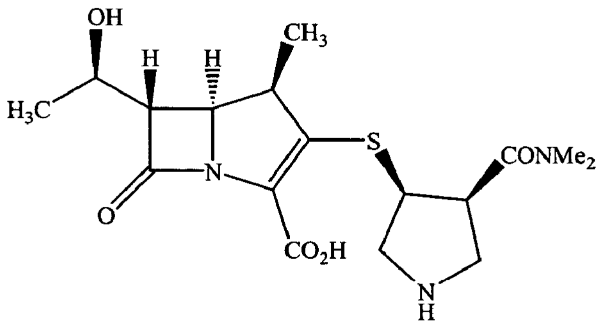
Figure 1:
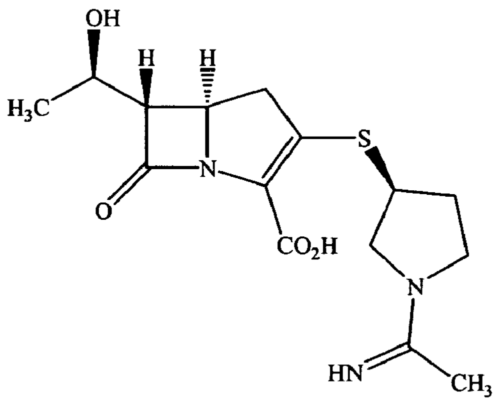
Figure 1:
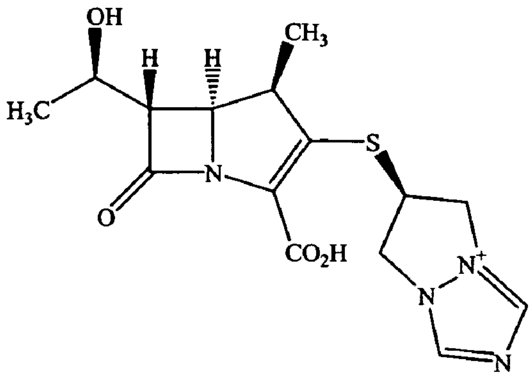
Figure 1:
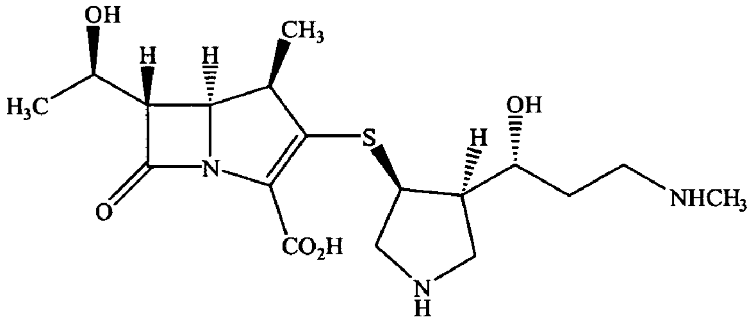
Figure 1:
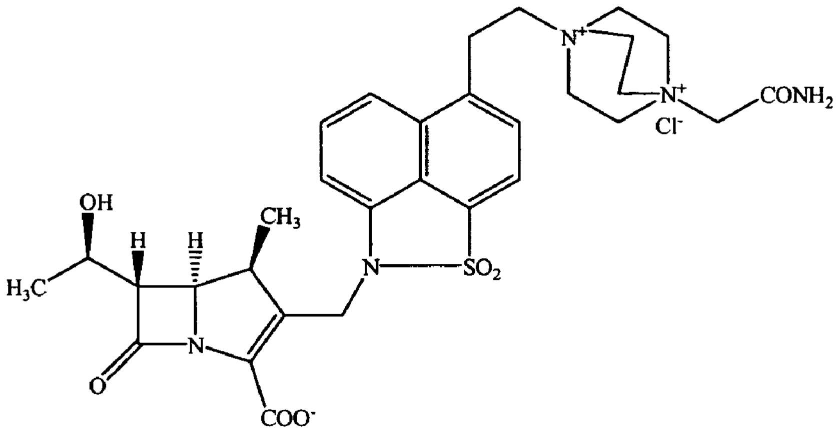
Figure 1:
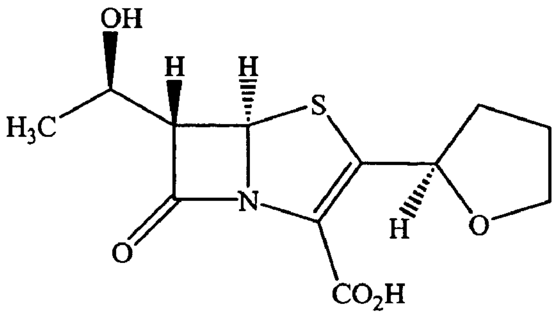
Figure 1:
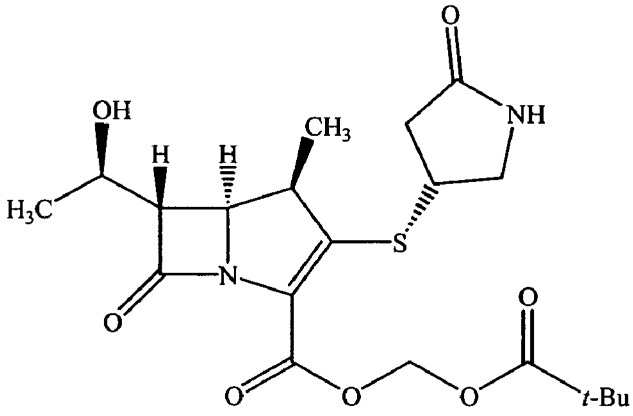
Figure 1:
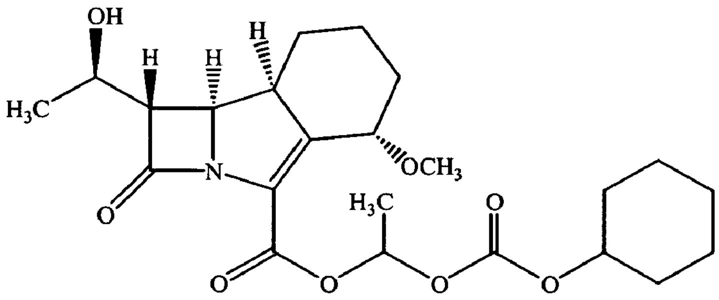

The invention provides carbapenem compounds or their pharmaceutically acceptable salts or prodrugs, pharmaceutical compositions containing these compounds and methods of their use in the treatment or prevention of gram-positive bacterial infections.

Definitions

The numbering system for the carbapenem compounds used in this specification is set out below, wherein the numbering of the carbapenem nucleus is in accordance with standards in the art (see, Tiraby, G., et al., *Biochem J,* 276 (pt. 1), pp. 269-270 (1991)).

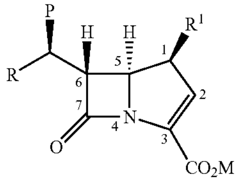

Whenever a range is presented herein it should be understood to include each element of the range. For example, the range "$C_1$ to $C_4$" alkyl independently includes $C_1$, $C_2$, $C_3$ and $C_4$ alkyl groups. When such a range is stated, each element has been contemplated and the range is used merely for convenience.

Generally, while the compounds, compositions and methods are described in terms of "comprising" various components or steps, the compounds, compositions and methods can also "consist essentially of" or "consist of" the various components and steps.

The term "alkyl", as used herein, unless otherwise specified, includes a saturated straight, branched, or cyclic, primary, secondary, or tertiary hydrocarbon of $C_1$ to $C_{10}$. The term includes both substituted and unsubstituted alkyl groups. Moieties with which the alkyl group can be substituted are selected from the group consisting of hydroxyl, halo (F, Cl, Br, I), amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. When the alkyl group is said to be substituted with an alkyl group, this is used interchangeably with "branched alkyl group". Specific examples of alkyls and/or substituted alkyls includes, but are not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl.

The term "lower alkyl", as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is typical. Similarly, when alkyl or lower alkyl is a suitable moiety, unsubstituted alkyl or lower alkyl is typical.

Cycloalkyl is a species of alkyl containing from 3 to 15 carbon atoms, without alternating or resonating double bonds between carbon atoms. It may contain from 1 to 4 rings which are fused.

The term "alkenyl" includes a hydrocarbon radical straight, branched or cyclic containing from 2 to 10 carbon atoms and at least one carbon to carbon double bond. Examples of alkenyl groups include ethenyl, propenyl, butenyl and cyclohexenyl.

The term "alkynyl" refers to a hydrocarbon radical straight or branched, containing from 2 to 10 carbon atoms and at least one carbon to carbon triple bond. Examples of alkynyl groups include ethynyl, propynyl and butynyl.

"Alkoxy" includes $C_1$-$C_4$ alkyl-O—, with the alkyl group optionally substituted as described herein.

The term "alkylamino" or "arylamino" refers to an amino group that has one or two alkyl or aryl substituents, respectively.

"Aryl" refers to aromatic rings e.g., phenyl, substituted phenyl, biphenyl, and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The typical aryl groups are phenyl, naphthyl and phenanthrenyl. The term includes both substituted and unsubstituted moieties. The aryl group can be substituted with one or more moieties selected from the group consisting of bromo, chloro, fluoro, iodo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991. Typical substituted aryls include phenyl and naphthyl.

The term "alkaryl" or "alkylaryl" refers to an alkyl group with an aryl substituent. The term "aralkyl" or "arylalkyl" refers to an aryl group with an alkyl substituent.

The term "heteroaryl" or "heteroaromatic", as used herein, refers to an aromatic group that includes at least one sulfur, oxygen, nitrogen or phosphorus in the aromatic ring. Heteroaryl or heteroaromatic compounds include monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one, two or three additional carbon atoms are optionally replaced by a heteroatom selected from oxygen, sulfur or nitrogen heteroatom. Examples of this type are pyrrole, pyridine, oxazole, thiazole and oxazine. Additional nitrogen atoms may be present together with the first nitrogen and oxygen or sulfur, giving, e.g., thiadiazole. Examples include the following.

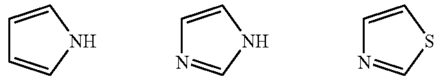

pyrrole (pyrrolyl) imidazole (imidazolyl) thiazole (thiazolyl)

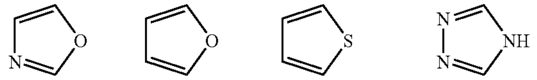

oxazole (oxazolyl) furan (furyl) thiophene (thienyl) triazole (triazolyl)

-continued

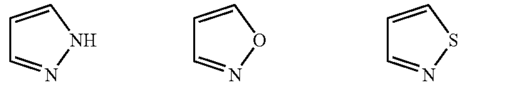

pyrazole (pyrazolyl) isoxazole (isoxazolyl) isothiazole (isothiazolyl)

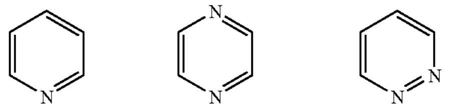

pyridine (pyridinyl) pyrazine (pyrazinyl) pyridazine (pyridazinyl)

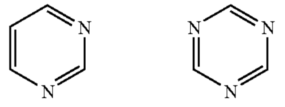

pyrimidine (pyrimidinyl) triazine (triazinyl)

The heteroaryl or heteroaromatic group can be optionally substituted with one or more substituent selected from halogen, haloalkyl, alkyl, alkoxy, hydroxy, carboxyl derivatives, amido, amino, alkylamino, dialkylamino. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyl-diphenylsilyl, trityl or substituted trityl, alkyl groups, acyl groups such as acetyl and propionyl, methanesulfonyl, and p-toluenylsulfonyl.

"Heteroarylium" refers to heteroaryl groups bearing a quaternary nitrogen atom and thus a positive charge. Examples include the following.

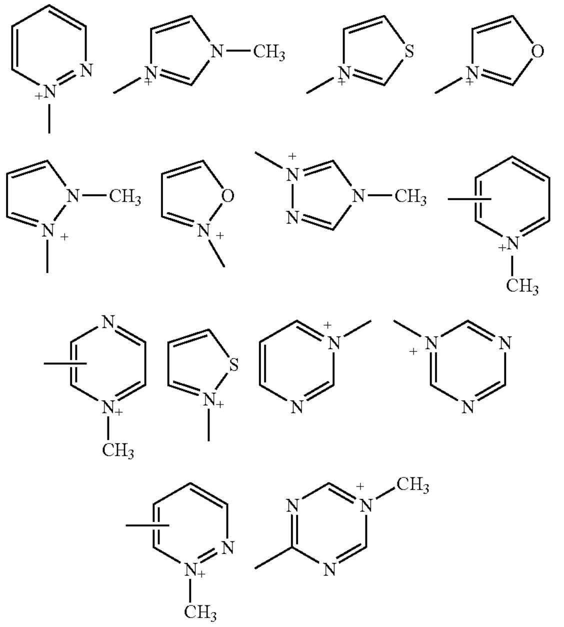

When a charge is shown on a particular nitrogen atom in a ring which contains one or more additional nitrogen atoms, it is understood that the charge may reside on a different nitrogen atom in the ring by virtue of charge resonance that occurs.

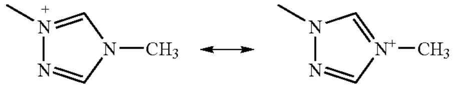

and

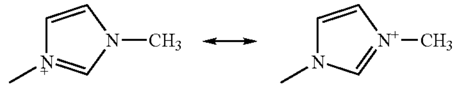

The term "heterocycloalkyl" refers to a cycloalkyl group (nonaromatic) in which one of the carbon atoms in the ring is replaced by a heteroatom selected from O, S or N, and in which up to three additional carbon atoms may b e replaced by heteroatoms.

The terms "quaternary nitrogen" and "positive charge" refer to tetravalent, positively charged nitrogen atoms including, e.g., the positively charged nitrogen in a tetraalkylammonium group (e.g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" refers to oxygen, sulfur, nitrogen, phosphorus, and selenium, selected on an independent basis.

Halogen and "halo", as used herein, includes bromine, chlorine, fluorine and iodine.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters typically include a phenyl group. The term "lower acyl" refers to an acyl group in which the non-carbonyl moiety is lower alkyl.

"Carboxylate anion" refers to a negatively charged group —COO.

"Guanidinyl" refers to the group: $H_2NC(NH)NH$—.

"Carbamimidoyl" refers to the group: $H_2NC(NH)$—.

"Ureido" refers to the group: $H_2NC(O)NH$—.

When a group is "optionally interrupted", this includes one or more of the interrupting moieties in combination, as well as said moieties located at either or both ends of the chain. Thus, it includes terminating the group as well.

When a group is termed "substituted", unless otherwise indicated, this means that the group contains from 1 to 4 substituents thereon. With respect to R, $R^a$, $R^b$ and $R^c$, the substituents available on alkyl groups are selected from the values of $R^d$. Many of the variable groups are optionally substituted with up to four $R^i$ groups. With respect to $R^e$, $R^f$ and $R^g$, when these variables represent substituted alkyl, the substituents available thereon are selected from the values of $R^i$.

When a functional group is termed "protected", this means that the group is in modified form to preclude undesired side reactions at the protected site, and unless otherwise defined refers to a group that is added to an oxygen, nitrogen, or phosphorus atom to prevent its further reaction or for other purposes. In some of the carbapenem compounds of the present invention, M is a readily removable carboxyl protecting group, and/or P represents a hydroxyl which is protected by a hydroxyl protecting group. Such protecting groups are used to protectively block the hydroxyl or carboxyl group during the synthesis procedures and are readily removable by procedures that will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

A wide variety of oxygen and nitrogen protecting groups are known to those skilled in the art of organic synthesis. Suitable protecting groups for the compounds of the present invention will be recognized from the present application taking into account the level of skill in the art, and with reference to standard textbooks, such as Greene, T. W. and Wuts, P. M., *Protective Groups in Organic Synthesis,* 3rd Ed., Wiley, N.Y. (1991). Examples of carboxyl protecting groups include allyl, benzhydryl, 2-naphthylmethyl, benzyl (Bn), silyl such as t-butyldimethylsilyl (TBDMS), phenacyl, p-methoxybenzyl, o-nitrobenzyl, p-methoxyphenyl, p-nitrobenzyl, 4-pyridylmethyl and t-butyl. Examples of suitable C-6 hydroxyethyl protecting groups include triethylsilyl (TES), t-butyldimethylsilyl (TBDMS), o-nitrobenzyloxycarbonyl (ONB), p-nitrobenzyloxycarbonyl (PNB), benzyloxycarbonyl (CBz), allyloxycarbonyl (Alloc), t-butyloxycarbonyl (Boc), 2,2,2-trichloroethyloxycarbonyl (Troc), and the like.

The phrase "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, such as palatability, absorption, distribution, metabolism and excretion. Other factors that are also important in the selection are cost of the raw materials, ease of crystallization, yield, stability, solubility, hygroscopicity and flowability of the resulting bulk drug.

"Pharmaceutically acceptable salts" include salts that retain the desired biological activity of the parent compound and do not impart undesired toxicological effects. These salts can take the form —COOM, where M is a negative charge, which is balanced by a counterion. These include salts formed with cations such as sodium, potassium, $NH_4^+$, magnesium, zinc, ammonium, or alkylammonium cations such as tetramethylammonium, tetrabutylammonium, choline, triethylhydroammonium, meglumine, triethanolhydroammonium, calcium, and calcium polyamines such as spermine and spermidine. These can also include salts formed from elemental anions such as chloride, bromide, and iodide. They can also include acid addition salts, for example, salts derived from inorganic or organic acids. Included among such salts are the following: acetate, adipate, alginate, ascorbic acid, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconic acid, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitric acid, oxalate, palmitic acid, pamoate, pectinate, persulfate, 3-phenylpropionate, phosphoric acid, picrate, pivalate, polygalacturonic acid; polyglutamic acid, propionate, p-toluenesulfonic acid, succinate, sulfuric acid, tannic acid, tartrate, thiocyanate, tosylate and undecanoate.

The term "prodrug" includes a compound that, when administered to an animal, is converted under physiological conditions to a compound of the invention, for example a pharmaceutically acceptable ester.

The pharmaceutically acceptable esters are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl. These are also referred to as "biolabile esters", which are biologically hydrolysable. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties.: acetoxymethyl, 1-acetoxyethyl, 1-acetoxypropyl, pivaloyloxymethyl, 1isopropyloxycarbonyloxyethyl, 1-cyclohexyloxycarbonyloxyethyl, phthalidyl and (2-oxo methyl-1,3-dioxolenyl)methyl.

The term "host", as used herein, refers to a unicellular or multicellular organism in which the bacteria can replicate, including cell lines and animals. Alternatively, the host can be carrying a part of the bacterial particles, whose replication and/or function can be altered by the compounds of the present invention. The term host refers to infected cells, cells transfected with all or part of the bacteria and animals, such as, primates (including chimpanzees) and, in one embodiment, the host is a human. Veterinary applications are also encompassed by the present invention.

The term "treatment" as used herein, includes an approach for obtaining beneficial or desired results including clinical results, including alleviation of symptoms, diminishment of extent of disease, stabilization (i.e., not worsening) state of disease, preventing spread of disease, preventing or reducing occurrence or recurrence of disease, delay or slowing of disease progression, and reduction of incidence of disease or symptoms. As used herein, the phrase "anti-bacterially effective amount" means an amount effective for treating the bacterial infection.

Compounds of the Invention

In one embodiment, a carbapenem is provided, of the formula (I), (II), (III) or (IV):

(I)

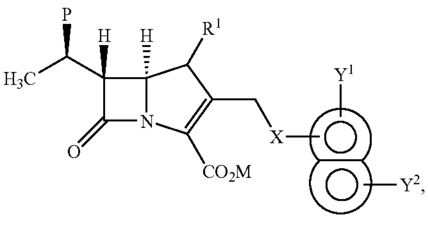

(II)

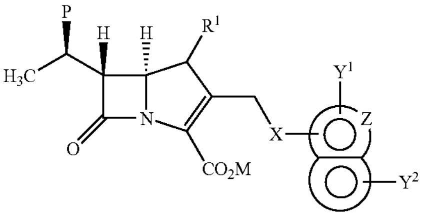

-continued (III)

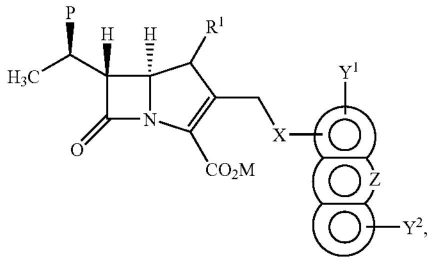

(IV)

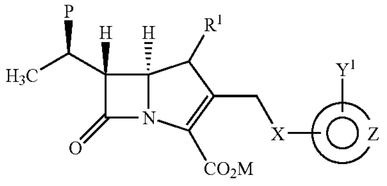

or a pharmaceutically acceptable salt and/or prodrug thereof, wherein $R^1$ is H or alkyl, typically a lower alkyl such as $CH_3$;

$CO_2M$ represents a carboxylic acid, a carboxylate anion, a pharmaceutically acceptable ester group or a carboxylic acid protected by a protecting group;

P represents hydrogen, hydroxyl, F or hydroxyl protected by a hydroxyl-protecting group;

X is selected from the group consisting of O, S, $S(O)_x$, with x equal to 0, 1 or 2, phosphate, carbonyl, thiocarbonyl, iminyl, $P(O)_2$, $P(O)_3$, C(O), C(O)O, OC(O), C(O)NH, C(O)NR, NHC(O), NRC(O), amine, NH and NR;

each R is independently H or alkyl, typically a lower alkyl such as $CH_3$;

each

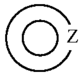 and 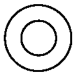

is independently a 5- or 6-membered monocyclic aromatic or heteroaromatic ring;

Z is present or absent, and when present, represents members selected from the group consisting of C═$CR_2$, C═$CY^1$, O, S, carbonyl, thiocarbonyl, iminyl, C(O), C(O)O, OC(O), C(O)NH, C(O)NR, NHC(O), NRC(O), N(A-$(CH_2)_n$-Q)C(O), CON(A-$(CH_2)_n$-Q), C(═NH), C(═NR), C(═N-A-$(CH_2)_n$-Q), amine, NH, NR and N(A-$(CH_2)_n$-Q);

each $Y^1$ and $Y^2$ is independently selected from the group consisting of hydrogen; halo; —CN; —$NO_2$; —$NR^aR^b$; —$OR^c$; —$SR^c$; —C(O)$NR^aR^b$; —C(O)$OR^h$; S(O)$R^c$; —$SO_2R^c$; —$SO_2NR^aR^b$; —$NR^aSO_2R^b$; —C(O)$R^a$; —OC(O)$R^a$; OC(O)$NR^aR^b$; —$NR^a$C(O)$NR^bR^c$; —$NR^aCO_2R^h$; —$OCO_2R^h$; $NR^a$C(O)$R^b$; —$C_{1-6}$ straight- or branched-chain alkyl, —$C_{2-6}$ straight- or branched-chain alkenyl, or —$C_{2-6}$ straight- or branched-chain alkynyl, unsubstituted or substituted with one to four $R^d$ groups; -A-$(CH_2)_n$-Q; —$(CH_2)_n$A-Q; —$[(CH_2)_nA]_m(CH_2)_p$-Q; —$CH_2$N-Q; and —$C_{3-7}$ cycloalkyl, unsubstituted or substituted with one to four $R^d$ groups;

A is selected from the group consisting of O, S, NH, $NCH_3$, NR, and —$CH_2$—;

n is an integer 0, 1, 2, or 3;

each $R^a$, $R^b$ and $R^c$ is independently selected from the group consisting of hydrogen, —$C_{1-6}$ straight- or branched-chain alkyl, unsubstituted or substituted with one to four $R^d$ groups, and —$C_{3-7}$ cycloalkyl, unsubstituted or substituted with one to four $R^d$ groups;

or $R^a$ and $R^b$ taken together with any intervening atoms is a 4-6 membered saturated ring optionally interrupted by one or more of O, S, $NR^c$, with $R^c$ as defined above, or —C(O)—, wherein the ring is unsubstituted or substituted with one to four $R^i$ groups;

or $R^b$ and $R^c$ taken together with any intervening atoms is a 4-6 membered saturated ring optionally interrupted by one to three of O, S, $NR^a$, with $R^a$ as defined above, or —C(O)—, wherein the ring is unsubstituted or substituted with one to four $R^i$ groups;

each $R^d$ is independently selected from the group consisting of halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; $NR^eCONR^fR^g$; —$NR^eCO_2R^h$; —$OCO_2R^h$; —C($NR^e$)$NR^fR^g$; $NR^e$C(NH)$NR^fR^g$ and —$NR^e$C($NR^f$)$R^g$;

each $R^e$, $R^f$ and $R^g$ are independently selected from the group consisting of H, —R and —$C_{1-6}$ straight- or branched-chain alkyl, unsubstituted or substituted with 1-4 $R^i$ groups;

or $R^e$ and $R^f$ taken together with any intervening atoms is a 4-6 membered saturated ring optionally interrupted by one to three of O, S, —C(O)— or $NR^g$ with $R^g$ as defined above, wherein the ring is unsubstituted or substituted with one to four $R^i$ groups;

each $R^i$ independently represents halo; —CN; —$NO_2$; phenyl; —$NHSO_2R^h$; —$OR^h$, —$SR^h$; —$N(R^h)_2$; —$N^+(R^h)3$; —C(O)$N(R^h)_2$; $SO_2N(R^h)2$; heteroaryl; heteroarylium; —$CO_2R^h$; —C(O)$R^h$; —$OCOR^h$; $NHCOR^h$; guanidinyl; carbamimidoyl or ureido;

each $R^h$ is independently selected from the group consisting of H, a —$C_{1-6}$ straight or branched-chain alkyl group, a —$C_3$-$C_6$ cycloalkyl group or phenyl, or, when two $R^h$ groups are present, the $R^h$ groups may be taken in combination and be a 4-6 membered saturated ring, optionally interrupted by one or two of O, S, $SO_2$, —C(O)—, NH and $NCH_3$;

each Q is selected from the group consisting of:

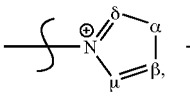 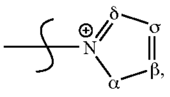 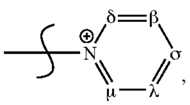,

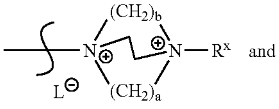 and 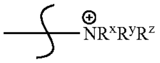

wherein:

a and b are 1, 2 or 3;

$L^-$ is a pharmaceutically acceptable counterion;

α is selected from O, S or $NR^s$;

β, δ, λ, μ, and σ are selected from $CR^t$, N or $N^+R^s$, provided that no more than one of β, δ, λ, μ, and σ is $N^+R^s$;

each $R^s$ independently represents hydrogen; phenyl or $C_{1-6}$ straight- or branched-chain alkyl, unsubstituted or substituted with one to four $R^i$ groups;

each $R^t$ independently represents hydrogen; halo; phenyl; —CN; —$NO_2$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;

each $R^u$ and $R^v$ represent hydrogen or —$C_{1-6}$ straight- or branched-chain alkyl, unsubstituted or substituted with one to four $R^i$ groups;

or $R^u$ and $R^v$ together with any intervening atoms represent a 4-6 membered saturated ring optionally interrupted by one or more of O, S, NRW or —C(O)—, said ring being unsubstituted or substituted with one to four $R^i$ groups;

each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1-4 $R^i$ groups; or $R^h$ and $R^w$ taken together with any intervening atoms represent a 5-6 membered saturated ring, optionally interrupted by one or two of O, S, $SO_2$, NH or $NCH_3$;

$R^x$ represents hydrogen or a $C_{1-8}$ straight- or branched chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SOR^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

each $R^y$ and $R^z$ independently represents hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—;

or $R^x$ and $R^y$ together with any intervening atoms represent a 4-6 membered saturated ring optionally interrupted by O, S, $SO_2$, $NR^w$, $N^+R^hR^w$ or —C(O)—, unsubstituted or substituted with 1-4 $R^i$ groups, and when $R^x$ and $R^y$ together represent a 4-6 membered ring as defined above, $R^z$ is as defined above or $R^z$ represents an additional saturated 4-6 membered ring fused to the ring represented by $R^x$ and $R^y$ taken together, optionally interrupted by O, S, $NR^w$ or —C(O)—, said rings being unsubstituted or substituted with one to four $R^i$ groups;

wherein if the compound is of formula (III), X is O and R is $CH_3$, then the substituent

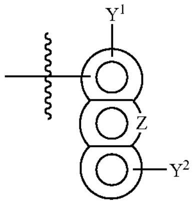

is not

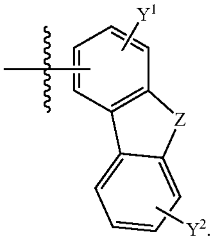

In one embodiment, $R^1$ is methyl.

In another embodiment, P is hydroxyl or hydroxyl protected by hydroxyl-protecting group.

In one embodiment, n is 0 or 1.

In another embodiment, at least one of $Y^1$ and $Y^2$ is not hydrogen.

In another embodiment, at least one of $Y^1$ and $Y^2$ attached to the aromatic ring system contains a positively charged moiety. In a more particular embodiment, one of $Y^1$ and $Y^2$ represents -A-$(CH_2)_n$-Q, and the remaining $Y^1$ or $Y^2$ is hydrogen or a group other than -A-$(CH_2)_n$-Q. In a particular embodiment, one of $Y^1$ and $Y^2$ is -A-$(CH_2)_n$-Q, and A represents —$CH_2$—.

In one embodiment of Formula I or II, $R^1$ is lower alkyl;

P is hydroxyl or hydroxyl protected by a hydroxyl-protecting group;

X is O, S or NH;

each R is independently H or alkyl;

each $Y^1$ and $Y^2$ is independently selected from the group consisting of —$NR^aR^b$; —$OR^c$; —$C_{1-6}$ straight- or branched-chain alkyl, —$C_{2-6}$ straight- or branched-chain alkenyl, or —$C_{2-6}$ straight- or branched-chain alkynyl, unsubstituted or substituted with one to four $R^d$ groups; -A-$(CH_2)_n$-Q; or —$(CH_2)_n$A-Q; unsubstituted or substituted with one to four $R^d$ groups;

A is selected from the group consisting of O, S, NH, $NCH_3$, NR, and —$CH_2$—;

n is an integer 0, 1, 2, or 3;

each $R^a$, $R^b$ and $R^c$ is independently selected from the group consisting of hydrogen, —$C_{1-6}$ straight- or branched-chain alkyl, unsubstituted or substituted with one to four $R^d$ groups, and —$C_{3-7}$ cycloalkyl, unsubstituted or substituted with one to four $R^d$ groups;

or $R^a$ and $R^b$ or $R^b$ and $R^c$ taken together with any intervening atoms is a 4-6 membered saturated ring optionally interrupted by one or more of O, S, $NR^c$, with $R^c$ as defined above, wherein the ring is unsubstituted or substituted with one to four $R^i$ groups;

each $R^d$ is independently selected from the group consisting of halo; —CN; —$NO_2$; —$NR^eR^f$; —$C(NR^e)NR^fR^g$; $NR^eC(NH)NR^fR^g$ and —$NR^eC(NR^f)R^g$;

each $R^e$, $R^f$ and $R^g$ are independently selected from the group consisting of H, —R and —$C_{1-6}$ straight- or branched-chain alkyl, unsubstituted or substituted with 1-4 $R^i$ groups;

each $R^i$ independently represents halo; —CN; —$NO_2$; phenyl; —$N(R^h)_2$; —$N^+(R^h)3$; heteroaryl;

each $R^h$ is independently selected from the group consisting of H, a —$C_{1-6}$ straight or branched-chain alkyl group, or a —$C_3$-$C_6$ cycloalkyl group or phenyl;

each Q is selected from the group consisting of:

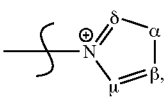 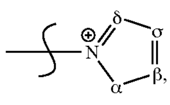 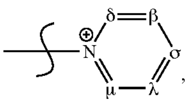 ,

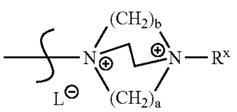 and 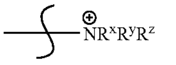

wherein:

α is selected from O, S or $NR^s$;

β, δ, λ, μ, and σ are selected from $CR^t$, N or $N^+R^s$, provided that no more than one of β, δ, λ, μ, and σ is $N^+R^s$;

each $R^s$ independently represents hydrogen; phenyl or $C_{1-6}$ straight- or branched-chain alkyl, unsubstituted or substituted with one to four $R^i$ groups;

each $R^t$ independently represents hydrogen; halo; phenyl; —CN; —$NO_2$; —$NR^uR^v$; —$OR^u$; —$CONR^uR^v$; —$COOR^h$; —$COR^u$; —$NR^uCOR^v$; —$NR^uCO_2R^v$; —$C_{1-6}$ straight- or branched-chain alkyl, unsubstituted or substituted with one to four $R^i$ groups;

each $R^u$ and $R^v$ represent hydrogen or —$C_{1-6}$ straight- or branched-chain alkyl, unsubstituted or substituted with one to four $R^i$ groups;

or $R^u$ and $R^v$ together with any intervening atoms represent a 4-6 membered saturated ring optionally substituted with one to four $R^i$ groups.

In another embodiment, one of $Y^1$ and $Y^2$ is -A-$(CH_2)_n$-Q, and Q is

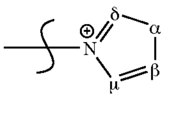 or 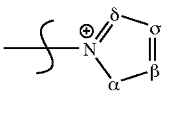

wherein:

α is O, S or $NR^s$; and

β, δ, λ, μ, and σ are independently $CR^t$, N or $N^+R^s$, provided that no more than one of β, δ, λ, μ, and σ is $N^+R^s$, balanced by $L^-$, which is a pharmaceutically acceptable counterion, and $R^s$ is as originally defined.

In another embodiment, one of $Y^1$ and $Y^2$ is -A-$(CH_2)_n$-Q, and Q is either

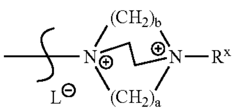 or 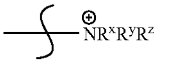

a and b are 2;

$L^-$ is a pharmaceutically acceptable counterion; and $R^x$, $R^y$ and $R^z$ are as originally defined.

In a particular embodiment, one of $Y^1$ and $Y^2$ is -A-$(CH_2)_n$ -Q, and Q is

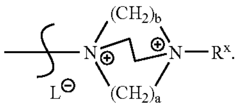

In another embodiment, one of $Y^1$ and $Y^2$ is -A-$(CH_2)_n$-Q, and Q is

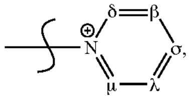

wherein

α is O, S or $NR^s$; and

β, δ, λ, μ, and σ are independently $CR^t$, N or $N^+R^s$, provided that no more than one of β, δ, λ, μ, and σ is $N^+R^s$, balanced by $L^-$, which is a pharmaceutically acceptable counterion, and $R^s$ is as originally defined or as defined in one of the previous embodiments.

In another embodiment, —$CO_2M$ is a carboxylic acid or a carboxylate anion. In this embodiment, M is a negative charge which will be balanced by a positively charged group, such as in the positively charged R group. If the positively charged R group contains more than one positive charge, a negatively charged counterion can be present which in combination with the carboxylate anion, provides overall charge neutrality.

In one subembodiment of the present invention, the carbapenem is of the formula (V):

(V)

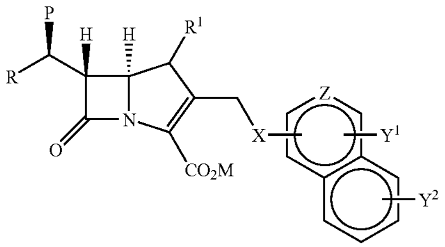

or a pharmaceutically acceptable salt and/or prodrug thereof, wherein R, P, $R^1$, $CO_2M$, X, Z, $Y^1$ and $Y^2$ are as defined above.

In another particular subembodiment of the present invention, the carbapenem of the formula (Va):

(Va)

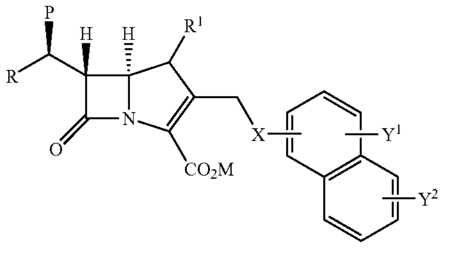

or a pharmaceutically acceptable salt and/or prodrug thereof, wherein R, P, $R^1$, $CO_2M$, X, $Y^1$ and $Y^2$ are as defined above.

In one subembodiment of formula (Va), X is either O or NH and $Y^1$ and $Y^2$ are independently —$NR^aR^b$ or —$OR^c$, wherein $R^a$, $R^b$ and $R^c$ are as defined above.

In one sub-embodiment of formula (Va), at least one of $Y^1$ and $Y^2$ is not hydrogen. In a particular subembodiment, $Y^1$ is hydrogen and $Y^2$ is not hydrogen.

In another embodiment of (Va), one of $Y^1$ and $Y^2$ is -A-$(CH_2)_n$-Q, and Q is

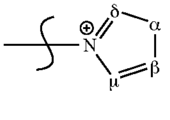 or 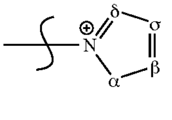 wherein:

α is O, S or $NR^s$; and

β, δ, λ, μ, and σ are independently $CR^t$, N or $N^+R^s$, provided that no more than one of β, δ, λ, μ, and σ is $N^+R^s$, balanced by $L^-$, which is a pharmaceutically acceptable counterion, and $R^s$ is as originally defined.

In another embodiment of (Va), one of $Y^1$ and $Y^2$ is -A-$(CH_2)_n$-Q, and Q is either

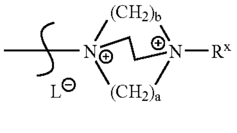 or 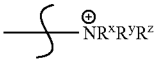

a and b are 2;

$L^-$ is a pharmaceutically acceptable counterion; and $R^x$, $R^y$ and $R^z$ are as originally defined.

In a particular embodiment of (Va), one of $Y^1$ and $Y^2$ is -A-$(CH_2)_n$-Q, and Q is

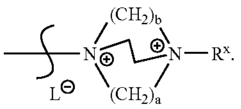

In another embodiment of (Va), one of $Y^1$ and $Y^2$ is -A-$(CH_2)_n$-Q, and Q is

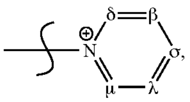, wherein

α is O, S or $NR^s$; and

β, δ, λ, μ, and σ are independently $CR^t$, N or $N^+R^s$, provided that no more than one of β, δ, λ, μ, and σ is $N^+R^s$, balanced by $L^-$, which is a pharmaceutically acceptable counterion, and $R^s$ is as originally defined.

In another particular embodiment of the present invention, the carbapenem is of the formula (Vb):

(Vb)

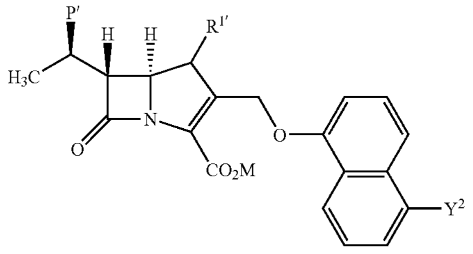

or a pharmaceutically acceptable salt and/or prodrug thereof; wherein

P' is hydrogen or hydroxyl;

$R^{1'}$ is hydrogen or methyl; and $Y^2$ is —$(CH_2)_{n1}$-A-$(CH_2)_{n2}$-Q, wherein $n_1$ and $n_2$ are independently 0-4, A is selected from the group consisting of O, S, NH, $NHR^2$ and $N(R^2)_2$, wherein $R^2$ is independently $C_1$-$C_4$ alkyl and Q is either —NH—C(=$NR^3$)—$N(R^3)_2$, —S—C(=$NR^3$)—$N(R^3)_2$, or —$NR^3$—$SO_2$—$N(R^3)_2$, wherein $R^3$ is independently $C_1$-$C_4$ alkyl or H.

In a particular subembodiment of the present invention, the carbapenem is of the formula (Vc):

(Vc)

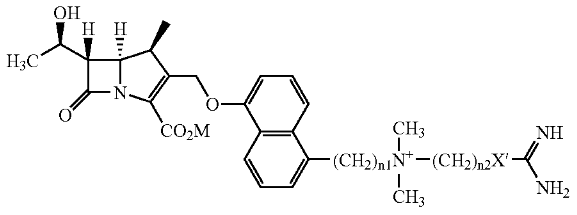

or a pharmaceutically acceptable salt and/or prodrug thereof; wherein $CO_2M$ is as defined above;

$n_1$ is either 1 or 2;

$n_2$ is either 1, 2, or 3; and

X' is selected from S or NH.

In another particular embodiment of the present invention, the carbapenem is of the formula (Vd):

(Vd)

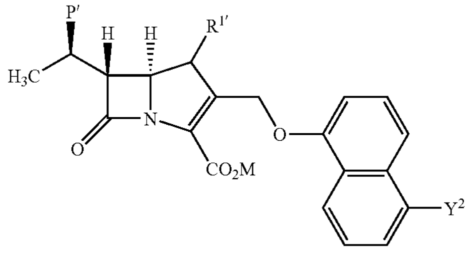

or a pharmaceutically acceptable salt and/or prodrug thereof, wherein:

P' is hydrogen or hydroxyl;

$R^{1'}$ is hydrogen or methyl; and $Y^2$ is —$(CH_2)_n$-Q, wherein n is 0, 1, 2, 3 or 4, and Q is either —NH—C(=$NR^3$)—$N(R^3)_2$, —S—C(=$NR^3$)—$N(R^3)_2$, or $NR^3$—$SO_2$—$N(R^3)_2$, wherein $R^3$ is independently $C_1$-$C_4$ alkyl or H.

In a particular embodiment of Formula (Vd), P' is hydroxyl, $R^1$ is methyl, and $Y^2$ is $—(CH_2)_n—X''—C(=NH)—NH_2$, wherein n=1 or 2 and X''=S or NH.

In another particular embodiment of the present invention, the carbapenem is of the formula (Ve):

(Ve)

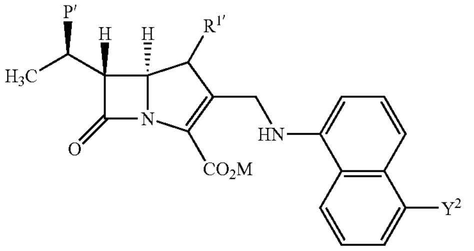

or a pharmaceutically acceptable salt and/or prodrug thereof; wherein

P' is hydrogen or hydroxyl;

$R^{1''}$ is hydrogen or methyl; and $Y^2$ is $—(CH_2)_{n1}$-A-$(CH_2)_{n2}$-Q, wherein $n_1$ and $n_2$ are independently 0-4, A is selected from the group consisting of O, S, NH, $NHR^2$ and $N(R^2)_2$, wherein $R^2$ is independently $C_1$-$C_4$ alkyl, and Q is either $—NH—C(=NR^3)—N(R^3)_2$ or $—S—C(=NR^3)—N(3)_2$, wherein $R^3$ is independently $C_1$-$C_4$ alkyl or H.

In another particular embodiment of the present invention, the carbapenem is of the formula (Vf):

(Vf)

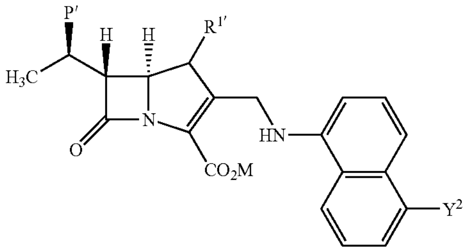

or a pharmaceutically acceptable salt and/or prodrug thereof; wherein

P' is hydrogen or hydroxyl;

$R^{1'}$ is hydrogen or methyl; and $Y^2$ is $—(CH_2)_n$-Q wherein n is 0, 1, 2, 3 or 4 and Q is either $—NH—C(=NR^3)—N(R^3)_2$ or $—S—C(=NR^3)—N(R^3)_2$, wherein $R^3$ is independently $C_1$-$C_4$ alkyl or H.

In another embodiment of the present invention, the carbapenem is of the formula (VI):

(VI)

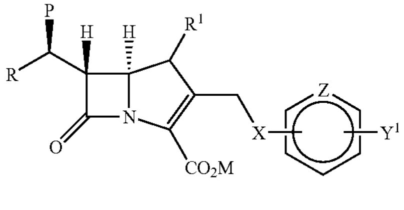

or a pharmaceutically acceptable salt and/or prodrug thereof, wherein R, P, $R^1$, $CO_2M$, X, Z and $Y^1$ are as defined above.

In a subembodiment of the carbapenem of formula (VI), X is O or NH, $Y^1$ is $—(CH_2)_n$-Q, wherein n is 1-3, Q is selected from the group consisting of $—NH—C(=NR^3)—N(R^3)_2$, $—S—C(=NR^3)—N(R^3)_2$ and $—S—O_2—N(R^3)_2$, wherein $R^3$ is independently $C_1$-$C_4$ alkyl or H; and R, P, $R^1$, $CO_2M$ and Z are as defined above.

The group $—CO_2M$, which is typically attached to the carbapenem nucleus at position 3 represents a carboxylic acid group (M represents H), a carboxylate anion (M represents a negative charge), a pharmaceutically acceptable ester (M represents an ester forming group) or a carboxylic acid protected by a protecting group (M represents a carboxyl protecting group).

$L^-$ can be present or absent as necessary to maintain the appropriate charge balance. When present, $L^-$ represents a pharmaceutically acceptable counterion. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate and tosylate. Other suitable anionic species will be apparent to the ordinarily skilled chemist. When $L^-$ represents a species with more than one negative charge, such as malonate, tartrate or ethylenediaminetetraacetate (EDTA), an appropriate number of carbapenem molecules can be found in association therewith to maintain the overall charge balance and neutrality.

When the side chain is neutral and the 3-carboxylate is in the form of an anion, the molecule is charge balanced by the presence of an appropriately charged group, such as $L^-$. Suitable positively charged groups include cations, such as sodium, potassium, calcium, magnesium and the like. Protonated moieties are also acceptable, such as tetraalkylammonium and the like.

Figure 2:
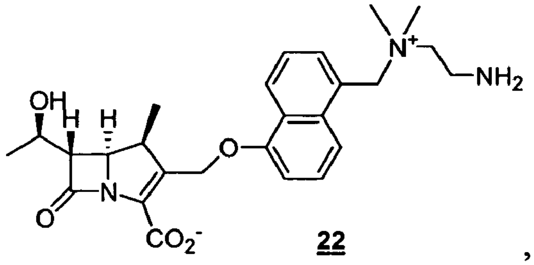
FIG. 2 shows a nonlimiting illustrative example of the structure of carbapenem analogs of the present invention possessing Gram-positive biological activity.
Figure 2:
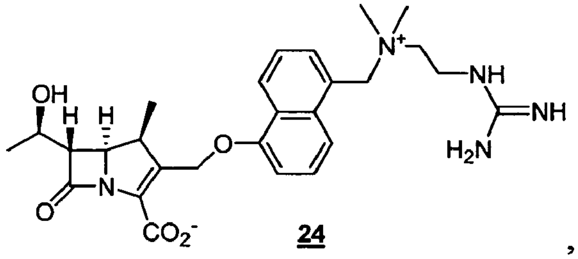
Figure 2:
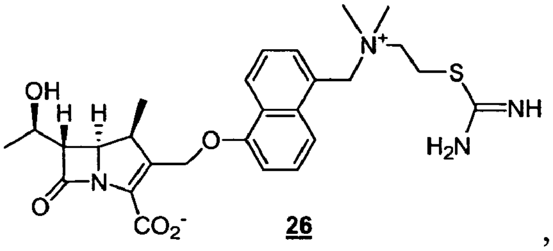
Figure 2:
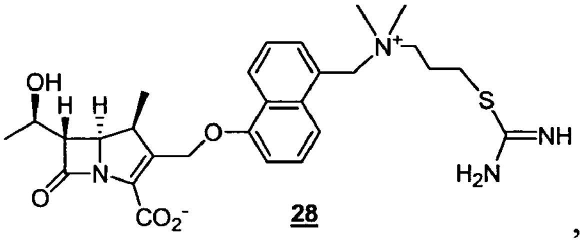
Figure 2:
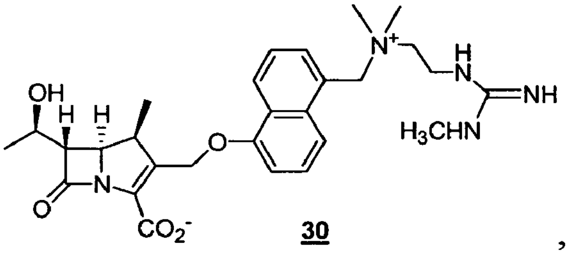
Figure 2:
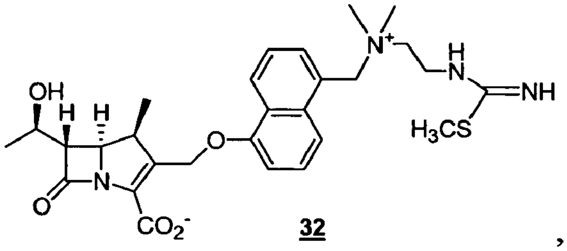
Figure 2:
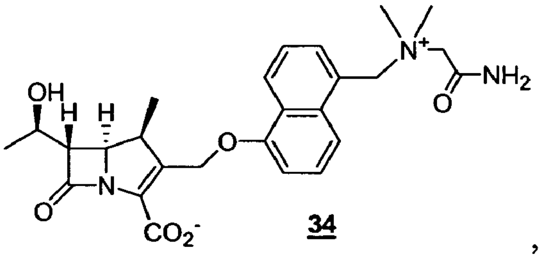
Figure 2:
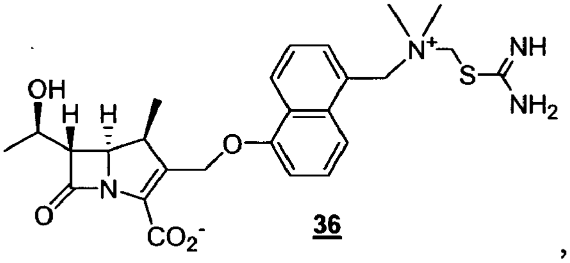
Figure 2:
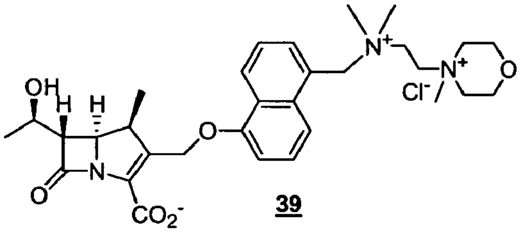
Figure 2:
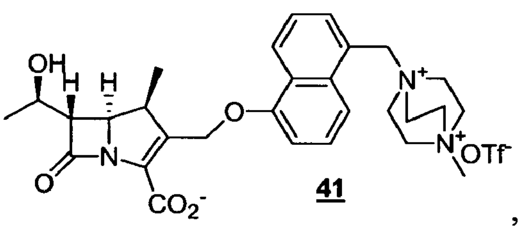
Figure 2:
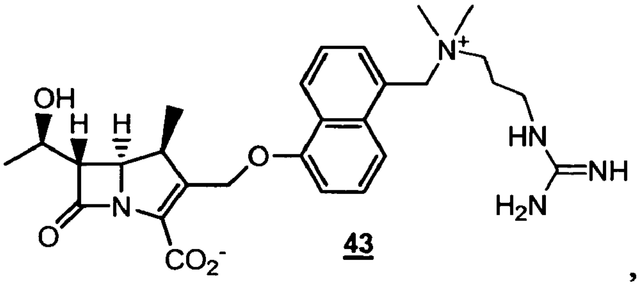
Figure 2:
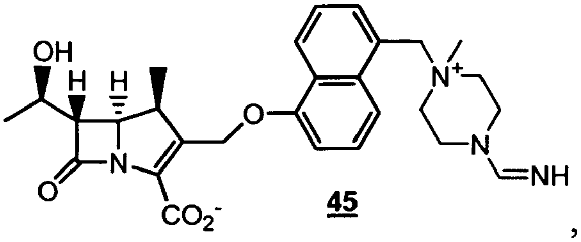
Figure 2:
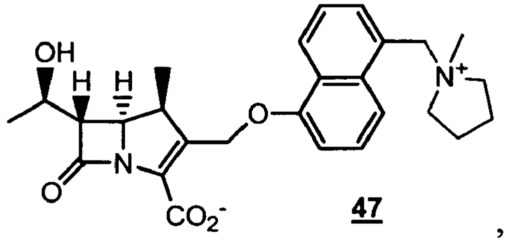
Figure 2:
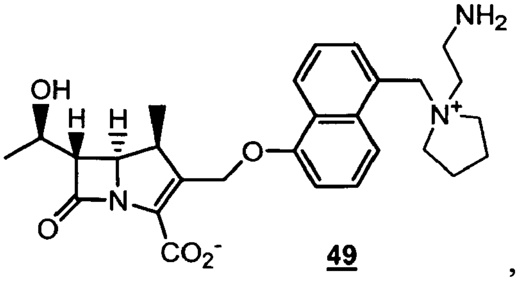
Figure 2:
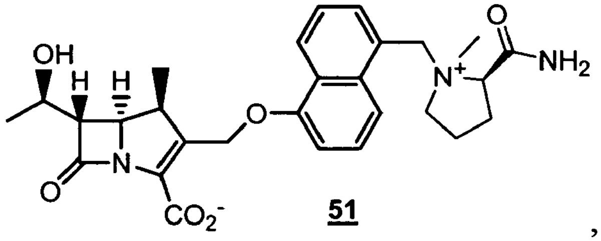
Figure 2:
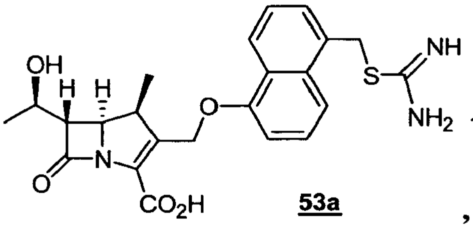
Figure 2:
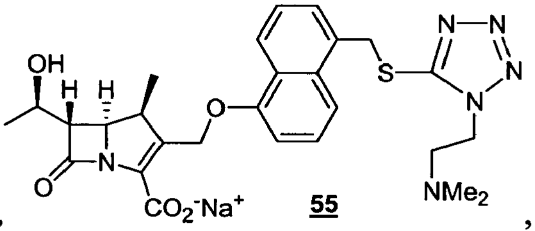
Figure 2:
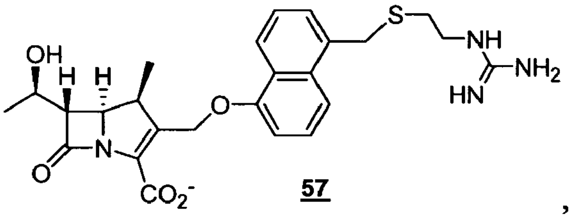
Figure 2:
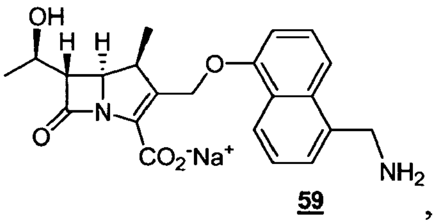
Figure 2:
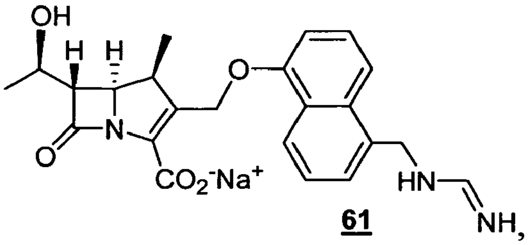
Figure 2:
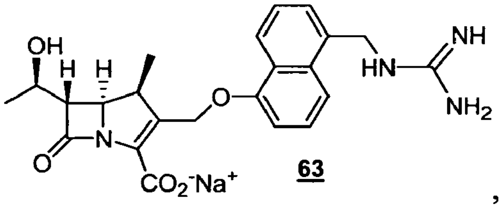
Figure 2:
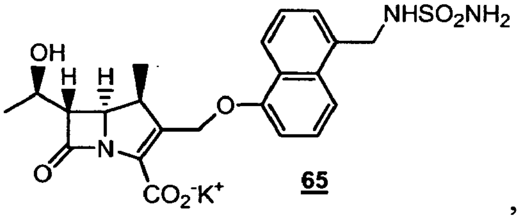
Figure 2:
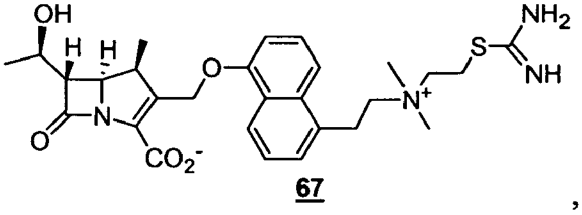
Figure 2:
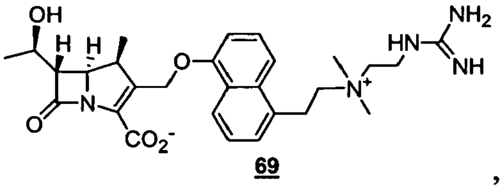
Figure 2:
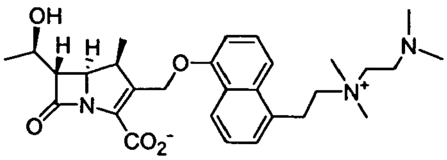
Figure 2:
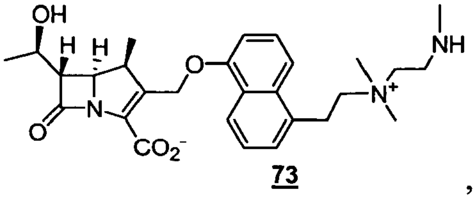
Figure 2:
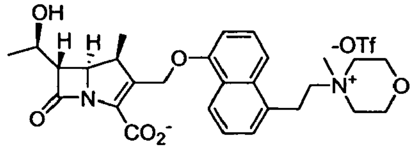
Figure 2:
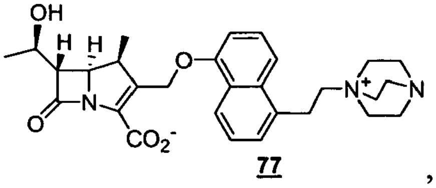
Figure 2:
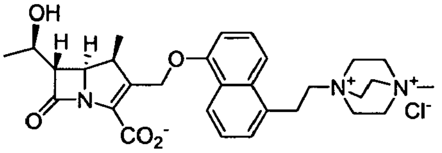
Figure 2:
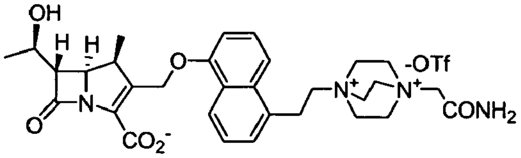
Figure 2:
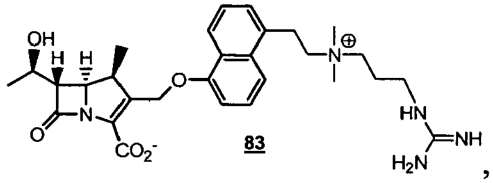
Figure 2:
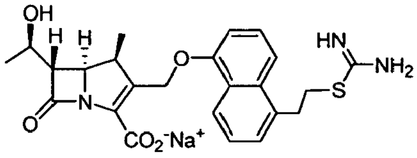
Figure 2:
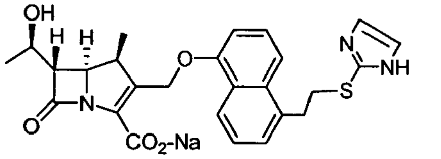
Figure 2:
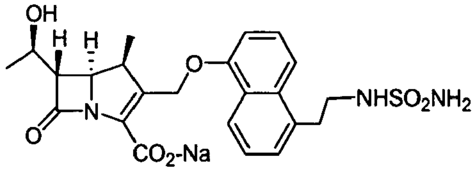
Figure 2:
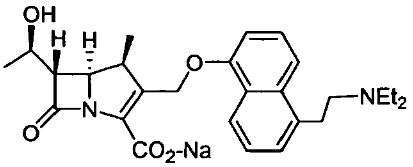
Figure 2:
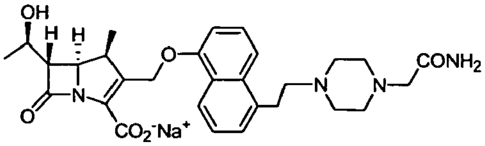
Figure 2:
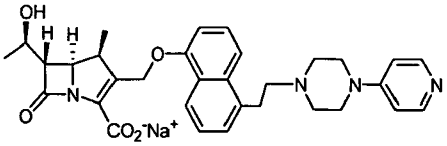
Figure 2:
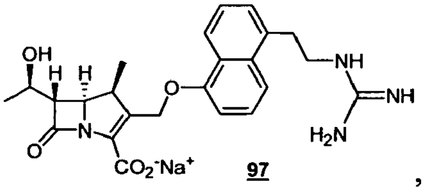
Figure 2:
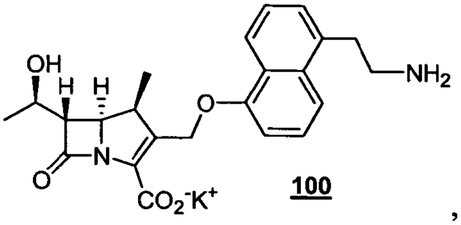
Figure 2:
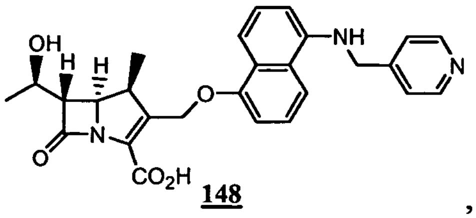
Figure 2:
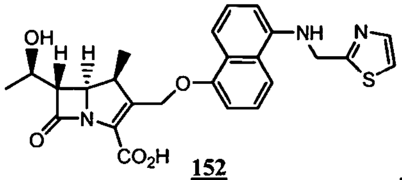
Figure 2:
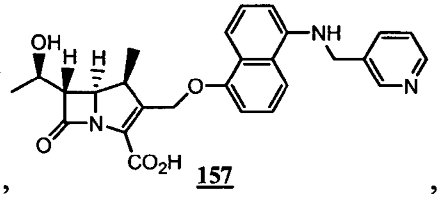
Figure 2:
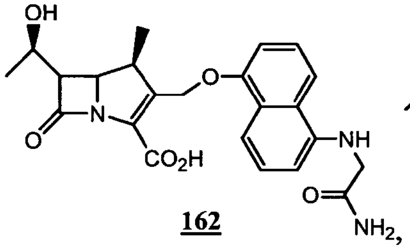
Figure 2:
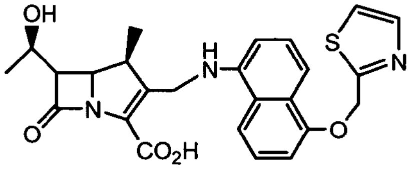
Figure 2:
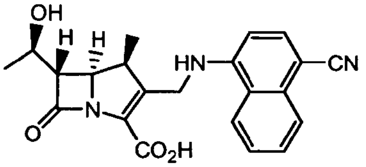
Figure 2:
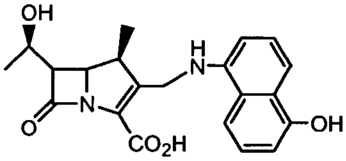
Figure 2:
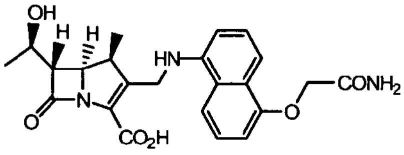
Figure 2:
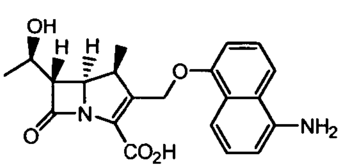
Figure 2:
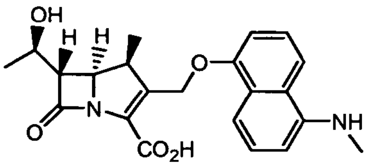
Figure 2:
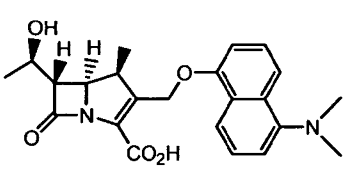
Figure 2:
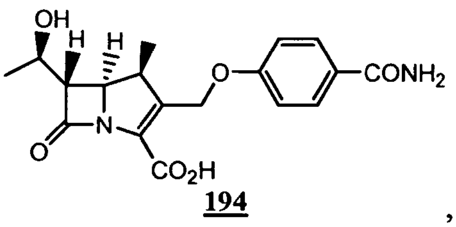
Figure 2:
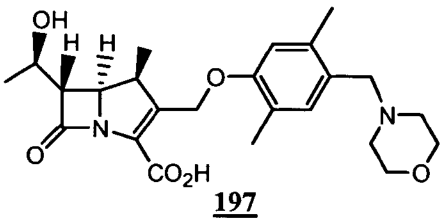

The compounds of the present invention having the formula I, II, III, IV, V or VI specifically include those compounds shown in FIG. 2.

Process of Making Compounds

Figure 3:
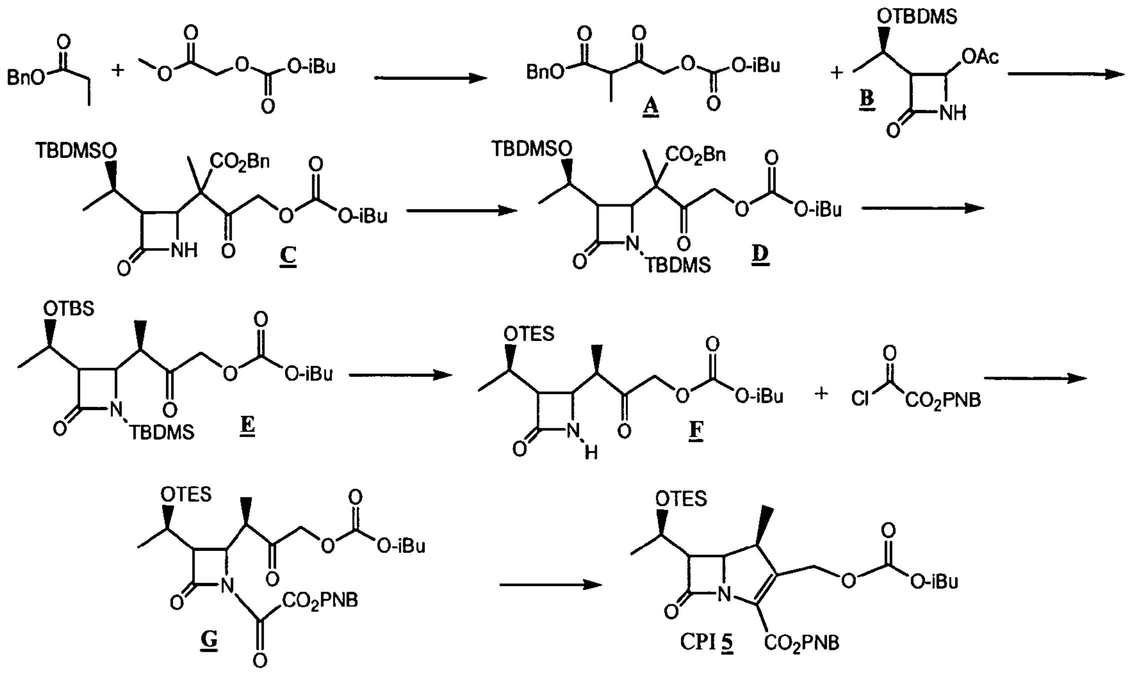
FIG. 3 shows the synthetic process of preparing Carbapenem Intermediate (CPI) 5.

The compounds of the present invention can be prepared using the general process outlined in scheme 1, above, such as from CPI 5 illustrated in FIG. 3. Reagents and substrates used herein can be either purchased, or synthesized according to known procedures.

In one embodiment of the invention, the carbapenem intermediate is synthesized using Scheme 1, which is shown in greater detail in FIG. 3.

SCHEME 1

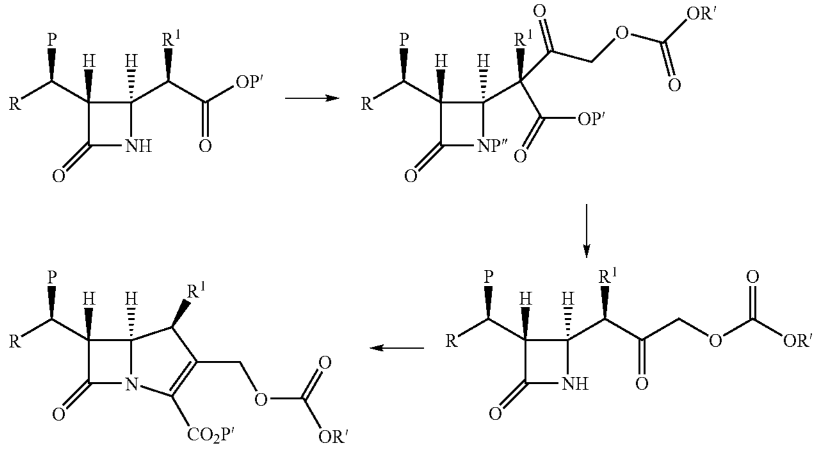

(A)

This carbapenem intermediate, containing an activated —$O(CO)_2R'$, wherein R' is an alkyl, such as —$O(CO)_2$(i-Bu), to achieve coupling of the carbapenem to the heteroaromatic side chain, including a oxygen or nitrogen moiety, to produce a β-methyl carbapenem.

Briefly, the method for preparing β-methyl carbapenems includes:

a) preparing or obtaining a carbapenem intermediate of the structure (A), for example using the process of Scheme 1

(A)

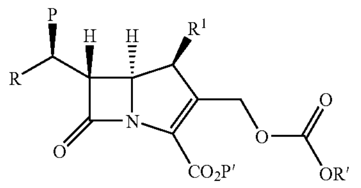

wherein

P, R and $R^1$ are as defined above;

P' is a suitable carboxyl protecting group; and

R' is an alkyl or substituted alkyl; and then b) coupling the compound of structure (A) with a moiety with a free hydroxyl, such as an aromatic alcohol or a heteroaromatic alcohol, or a mono- or di-substituted amine, such as a aromatic amine or heteroaromatic amine, to obtain an β-methyl carbapenem; and then c) optionally deprotecting the β-methyl carbapenem, if necessary.

In one illustrative embodiment, the carbapenem intermediate (A), is the following compound (A*).

(A*)

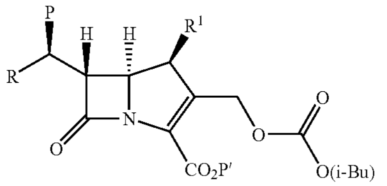

The selection of reaction conditions should take into account the ease of substitution of the —$O(CO_2)R$ in the carbapenem intermediate to form the desired carbapenem. Some combinations of protecting groups, leaving groups, and solvent systems may result in the formation of the undesired elimination product.

The process of synthesis is applicable to a wide range of oxygen and nitrogen linkers, as well as other heteroatom linkers, such as sulfur and phosphorus. The carbapenems made according to the present invention can also be used as synthetic intermediates in the preparation of a variety of other β-methyl carbapenem analogs, as well as additional derivatives obtained by subsequent functional group manipulations.

The process of preparing the compounds of the invention includes coupling a napthol in the presence of $Pd_2dba_3$*$CHCl_3$ as a catalyst in a nonpolar solvent. In one embodiment, the reaction is carried out at room temperature. In a particular embodiment, triethyl phosphite is also included as a ligand in the reaction. In one embodiment, the palladium is at 1-5 mole percent. In another embodiment, the concentration of starting material is between 10 and 50 mmol/liter, for example about 10, about 15, about 20, about 25, about 30, about 35, about 40, about 45 or about 50 mmol/liter. In another particular embodiment, the reaction does not contain an acid or a base.

Suitable solvents for carrying out the processes of the present disclosure are inert organic solvents, including but are not limited to, alcohols, aldehydes, amides, ethers, esters, halogenated solvents, hydrocarbons, glycols and glycol ethers, ketones, nitriles, and numerous other solvents common in chemical processes, as well as mixtures of such solvents. These inert solvents can be used alone or in combination, and can be miscible or immiscible with each other, with the proviso only that the compounds of interest are at least partially soluble in the solvent or solvents used. In the instance of using an immiscible, or 2-phase, solvent system, the process can also include the addition of a phase-transfer agent. Suitable phase-transfer agents are known in the art, such as those described in Sasson, et al., *Handbook of Phase Transfer Catalysis*, Kluwer Academic Publishers, 1997.

For the purpose of the present invention, the inert organic solvents suitable for use in preparing the compounds described and claimed herein include but are not limited to aromatic solvents, such as benzene, toluene, chloro benzene, styrene, tetraline, biphenyl, and xylenes; ether solvents, such as diethyl ether, n-butyl ether, methyl tert-butyl ether, tetrahydrofuran (THF), and 1,4-dioxane; halogenated solvents, such as chloroform, bromoform, carbon tetrachloride, dichloromethane (DCM), dichloroethane, trichloroethane, dichlorobenzne, and chlorobenzene; alcohols, including $C_1$-$C_{10}$ alkanols, which can be linear, branched, or cyclic, and may be saturated or unsaturated, including methanol, ethanol, 2-propanol, butanol and hexanol; $C_1$-$C_{10}$ hydrocarbon solvents, which can be linear, branched, or cyclic, and may be saturated or unsatured, including hexane, heptane, cyclohexane, cyclohexene, and pentane; ester and ketone solvents, such as acetone, ethyl acetate, isopropyl acetate, methylbutyl ketone (2-hexanone), methyl ethyl ketone (MEK), methylisobutyl ketone (MIBK), methyl n-butyl ketone (MBK), methyl isopropyl ketone, and cyclohexanone; and nitrogen-containing solvents, including acetonitrile, nitromethane, N,N-dimethylformamide (DMF), dimethylacetamide (DMA), hexamethylphosphoramide (HMPA), N-methylpyrrolidinone (NMP), N,N'-dimethylpropylene urea (DMPU), 1,3-dimethyl-2-oxohexahydropyrimidine, and N-ethylpyrrolidinone.

In one embodiment, a non-polar, aprotic solvent is used. In this embodiment, the process produces less than 10% of a β-lactam-compromised (ring-opened) by-product. In subembodiments, the solvent is toluene. In one subembodiment, at least 70%, 80%, 90%, 95%, 98%, 99% or 100% toluene is used. In another embodiment, up to 5%, 10%, 15% or 20% or more THF or up to 5%, or 10% or more DMF in toluene is used, particularly in the preparation of compounds with polar sidechains. In one embodiment, the sidechain is dissolved in a minimal amount of THF or DMF (for example 2-3 mL per 100 mg sidechain) and then added to the reaction flask containing a solution of all other reagents in toluene (for example 40-80 mL).

Bases suitable for use in conducting certain of the synthetic transformations described and claimed herein include but are not limited to carbonates, including alkali metal carbonates and bicarbonates, such as sodium carbonate, sodium bicarbonate, potassium carbonate, rubidium carbonate, and cesium carbonate; alkaline earth metal carbonates, such as magnesium carbonate, calcium carbonate, and strontium carbonate; hydroxides, such as sodium hydroxide and potassium hydroxide; and transition metal bases, such as zinc hydroxide. Also suitable for use as bases in the transformations described herein are organic bases, including but not limited to triethylamine (TEA); diethylamine; diisopropylamine; N,N-diisopropylethylamine (DIPEA or DIEA, also known as Hunig's base); dimethylamine; benzylamine; 4-dimethylaminopyridine (DMAP); ureas, such as tetramethylurea (TMU); pyridine; 2,6-lutidine; imidazole; pyrrole; diphenylamine; tri-n-propylamine; cyclohexylamine; triphenylamine; pyrrolidine; ureas, such as tetramethylurea (TMU); and piperidine.

As defined above, when a functional group is termed to be "protected" with a "protecting group" (herein represented by the letter designation, P), this means that the group is chemically modified to preclude undesired side reactions at the protected site. Suitable compounds for use with the compounds of the present invention will be recognized from the present application, and include those included in such standard reference texts known to those of skill in the art as Greene, T. W. and Wuts, P. G. M., "Protective Groups in Organic Synthesis, Third Edition", Wiley Interscience, New York (1999). Examples of suitable protecting groups include but are not limited to silyl protecting groups, including tri-$C_{1-6}$ alkyl silyl groups (e.g., trimethylsilyl and triethylsilyl), diphenyl siloxy groups (e.g., t-butyldiphenylsilyl (TBDPS)), $C_{1-6}$ alkyl silyloxy groups (e.g., tert-butyldimethylsilyl (TBDMS)), substituted and unsubstituted benzyl groups (e.g., benzyl, benzyloxycarbonyl, o-nitrobenzyloxycarbonyl, p-nitrobenzyloxycarbonyl), carbonyls, such as 2,2,2-trichloroethyloxycarbonyl (Troc), allyloxycarbonyl (Alloc), and fluorenylmethyloxycarbonyl (Fmoc).

The processes of preparing the compounds of the present invention are suitably conducted at a temperature in a range of from about −78° C. to the boiling point of the reaction medium or solvent (e.g., from about −78° C. to about 200° C.), and are typically conducted at a temperature in a range of from about −50° C. to the boiling point of the reaction medium or solvent. In one embodiment, the temperature is in a range of from about −20° C. to the boiling point of the reaction medium or solvent. In another embodiment, the temperature is in the range of from about −10° C. to the boiling point of the reaction medium or solvent.

The reactants used in the presently disclosed process can be added to the reaction vessel (also referred to herein as the reaction "pot", or "round bottom") concurrently, either together or separately, or they can be added sequentially in either order.

Method of Treatment

The present invention also provides a method of preventing or treating a bacterial infection, in a host, for example an animal, and typically a human, including administering a therapeutic amount of a compound of the present invention, or a pharmaceutically acceptable salt and/or prodrug therein, optionally in a pharmaceutically acceptable carrier or diluent where the bacterial infection is due to a gram-positive bacteria.

In one embodiment, a method of preventing or treating an infection by a gram positive bacteria, in a host, is provided comprising administering to the host a therapeutic amount of a compound of Formula Vc, optionally in a pharmaceutically acceptable carrier.

In one embodiment, the bacterial infection is a drug resistant and/or multiple-drug resistant bacterial infection. In specific embodiments, the infection is from at least one of methicillin resistant *Staphylococcus aureus* (MRSA), methicillin resistant *Staphylococcus epidermidis* (MRSE), methicillin resistant coagulase negative *Staphylococci* (MRCNS), vancomycin resistant *Enterococcus faecalis*, and/or vancomycin resistant *Enterococcus faecium.*

The invention also provides a compound of the present invention for use in medical therapy.

The present invention also provides a use of a therapeutic amount of a compound of the present invention, or a pharmaceutically acceptable salt and/or prodrug therein, optionally in a pharmaceutically acceptable carrier or diluent, for preventing or treating a gram-positive bacterial infection, in a host, such as an animal, and typically a human.

Gram positive bacteria are generally characterised by having as part of their cell wall structure peptidoglycan as well as polysaccharides and/or teichoic acids. The peptidoglycans which are sometimes also called murein are heteropolymers of glycan strands, which are cross-linked through short peptides. Generally, gram-positive bacteria are the endospore formers and typically (though certainly not always) are the exotoxin releasers.

Gram Positive cocci include, for example, *Streptococcus* (e.g. *Streptococcus pneumoniae*), *Staphylococcus* (e.g. *Staphylococcus aureus*), and *Enterococcus*. Gram Positive Rods include, for example, *Corynebacteria* (i.e. *Corynebacterium diphtheriae*), *Listeria monocytogenes, Bacillus anthracis* (i.e. anthrax) and *Erysipelothrix rhusiopathiae*. Gram Positive Branching Organisms include, for example, Actinomycetes. Gram positive bacteria include: *Bacillus anthracis; Bacillus subtilis; Clostridium botulinum; Clostridium perfringens; Clostridium tetani; Corynebacterium diphtheriae; Lactobacillus* spp.; *Listeria monocytogenes; Mycobacterium leprae; Mycobacterium tuberculosis; Mycoplasma pneumoniae; Staphylococcus aureus; Streptococcus* spp. *Mycobacterium* stain acid-fast but phylogentically are more closely related to the gram-positives than they are to the gram-negatives. *Mycoplasma* stain gram-negative but phylogentically are more closely related to the gram-positives than they are to the gram-negatives (it is their lack of a cell wall which leads to this confusing state). Additional gram positive bacteria are listed, for example, in volume 2 of Bergey's Manual, which contains six sections covering all gram-positive bacteria except the actinomycetes. Bacteria are distributed among these sections on the basis of their shape, the ability to form endospores, acid fastness, oxygen relationships, the ability to temporarily form mycelia, and other properties.

The present invention also provides a use of a therapeutic amount of a compound of the present invention, or a pharmaceutically acceptable salt and/or prodrug therein, optionally in a pharmaceutically acceptable carrier or diluent, for preventing or treating a methicillin resistant *Staphylococcus aureus* (MRSA), methicillin resistant *Staphylococcus epidermidis* (MRSE), methicillin resistant coagulase negative *Staphylococci* (MRCNS), vancomycin resistant *Enterococcus faecalis*, and/or vancomycin resistant *Enterococcus faecium* infection in a host, such as an animal, and typically a human.

The present invention also provides a use of a therapeutic amount of a compound of the present invention, or a pharmaceutically acceptable salt and/or prodrug therein, optionally in a pharmaceutically acceptable carrier or diluent, in the manufacture of a medicament for preventing or treating a gram-positive bacterial infection, in a host, such as an animal, and typically a human.

The invention also includes methods of inhibiting bacterial infection in a host. Inhibition of bacterial replication or treatment of an infection in a cell can be measured by showing a reduction in bacterial replication in a cell to a level lower than the level in an otherwise identical cell, which was not administered the compound of the invention. The reduction can be by about 80%, 85%, 90%, 95%, about 99.9% or more. The level of bacterial replication in a cell can be assessed by any known methods. For example, the level of bacterial replication in a cell can be assessed by evaluating the number of bacterial particles or amount of a bacterial component, such as a bacterial protein, a bacterial enzyme, or bacterial nucleic acid, in the cell or in fluid or debris associated with the cell. The number of infectious bacteria in a cell can be evaluated, for example, in a plaque assay. The level of a bacterial component such as a bacterial protein or enzyme in a cell can be evaluated using standard analytical techniques of protein biochemistry, such as, for example, using an activity assay for a bacterial enzyme, or using Western blotting or quantitative gel electrophoresis for a bacterial protein. Bacterial nucleic acid levels in a cell can be evaluated using standard analytical techniques such as Northern blotting and Southern Blotting or quantitation by polymerase chain reaction (PCR).

Combination and Alternation Therapies

In one embodiment of the invention, one or more therapeutic agents, including particularly antimicrobial agents such as antibiotic agents that are effective against gram positive bacteria, can be used in combination and/or alternation with the compound/composition of the present invention to achieve a additive and/or synergistic therapeutic effect.

The active compounds can be administered in combination, alternation or sequential steps with another anti-bacterial agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. In some embodiments, an anti-bacterial agent that exhibits an $EC_{50}$ of 10-15 μM or less, or typically less than 1-5 μM, is desirable.

It is possible that drug-resistant variants of bacteria can emerge after prolonged treatment with an anti-bacterial agent. The efficacy of a drug against the bacterial infection can be prolonged, augmented, or restored by administering the compound in combination or alternation with a second, and perhaps third, anti-bacterial agent, for example with a different site of activity than the principle drug. Alternatively, the pharmacokinetics, biodistribution or other parameter of the drug can be altered by such combination or alternation therapy. In general, combination therapy is typical because it induces multiple simultaneous stresses on the bacteria.

Suitable antibiotic agents are disclosed, e.g. in Physician's Desk 30 Reference (PDR), Medical Economics Company (Montvale, N.J.), (53rd Ed.), 1999; Mayo Medical Center Formulary, Unabridged Version, Mayo Clinic (Rochester, Minn.), January 1998; Merck Index An Encyclopedia of Chemicals, Drugs and Biologicals, (11th Ed.), Merck & Co., Inc. (Rahway, N.J.), 1989; University of Wisconsin Antimicrobial Use Guide, http://www.medsch.wisc.edu/clinsci/5amcg/amcg.html; Introduction on the Use of the Antibiotics Guideline, of Specific Antibiotic Classes, Thomas Jefferson University, http://jeffiine.tju.edu/CWIS/OAC/antibiotics_guide/intro.html; and references cited therein.

Nonlimiting examples of agents that can be used in combination or alternation with the compounds of the invention include: aminoglycosides, β-lactam antibiotics, cephalosporius, macrolides, miscellaneous antibiotics, penicillins, tetracyclines, antifungals, antimalarial agents, antituberculosis agents, antibacterials, leprostatics, miscellaneous anti-infectives, quinolones, sulfonamides, urinary anti-infectives, nasal antibiotics, opthalmic antibiotics, opthalmic antibacterials, opthalmicquinalones, opthalmic sulfonamides, skin and mucous membrane antibiotics, skin and mucous membrane antifungals, skin and mucous membrane antibacterials, skin and mucous membrane miscellaneous anti-infectives, skin and mucous membranescabicides and pedulicides, skin and mucous membrane antineoplasts, nitrofurans and oxazolidinones.

Specific compounds include, for example, Amikacin (amikacin sulfate); Craramyein (gentamicin sulfate); Nebcin (tobramycin sulfate); Netromycin (netilmicin sulfate); Streptomycin Sulfate; and TOBI (tobramycin), Azactam (aztreonam); Cefotan (cefotetan); Lorabid (loracarbef); Mefoxin (cefoxitin); Merrem (meropenem); and Primaxin (imipenem and cilastatin for injectable suspension); Ancef (cefazolin); Ceclor (cefaclor); Cedax (ceffibuten); Cefizox (ceffizoxime sodium); Cefobid (cefoperazone sodium); Ceftin (cefuroxime axetil); Cefzil (cefprozil); Ceptaz (ceftazidime); Claforan (cefotaxime); Duricef (cefadroxil monohydrate); Fortaz (ceftazidime); Keflex (cephalexin); Keftab (cephalexin HCl); Kefurox (cefuroxime); Kefzol (cefazolin); Mandol (cefamandole nafate); Maxipime (cefepime HCl); Monocid (cefonicidsodium); Omnicef (cefdinir); Rocephin (ceftriaxone); Suprax (cefixime); Tazicef (ceftazidime); Tazidime (ceftazidime); Vantin (cefpodoxime proxetil); and Zinacef5(cefuroxime); Biaxin (clarithromycin); Dynabac (dirithromycin); E.E.S. 200 (Erythromycin Ethylsuccinate); E.E.S. 400 (Erythromycin Ethylsuccinate); Ery-Ped 200 (Erythromycin Ethylsuccinate); EryPed 400 (Erythromycin Ethylsuccinate); Ery-Tab (Erythromycin delayed-release tablets); Erythrocin Stearate (Erythromycin stearate); Ilosone (erythromycinestolate); PCE Dispertab (erythromycin particles in tablets); Pediazole (erythromycin ethylsuccinate and sulfisoxazole acetyl for oral suspension); Tao (troleandomycin); Zithromax (azithromycin); and Erythromycin; Cleocin HCl (clindamycin hydrochloride); Cleotin Phosphate (elindamycin phosphate); Coly-Mycin M (colistimethate sodium); and Vancocin HCl (vancomycin hydrochloride); Amoxil (amoxicillin); Augmentin (amoxicillin/clavulanate potassium); Bicillin C-R 900/300 (Penicillin G benzathine and Penicillin G procaine suspension); Bicillin C-R (Penicillin G benzathine and Penicillin G procaine suspension); Bicillin L-A (Penicillin G benzathine suspension); Geoeillin (carbencillin indanyl sodium); Mezlin (sterile mezlocillinsodium); Omnipen (ampicillin); Pen-Vee K (penicillin V potassium); Pfizerpen (penicillin G potassium); Pipracil (piperacillin sodium); Speetrobid (bacampicillin-HCl); Ticar (tiearcillin disodium); Timentin (ticarcillin disodium and clavulanate potassium); Unasyn (ampicillin sodium/sulbactam sodium); Zosyn (piperacillin sodium and tazobactam sodium); and Dicloxacillin Sodium; Achromycin V (tetracycline HCl); Declomycin (demeclo-cycline HCl); Dynacin (minocylcine HCl); Minocin (minocycline hydrochloride); Monodox (Doxycycline monohydrate capsules); Terramycin (oxytetracyline); Vectrin (minocycline hydrochloride); Vibramycin Calcium (doxycycline sodium); Vibramycin Hyclate (doxycycline hyclate); Vibramycin Monohydrate (doxycycline monohydrate); Vibra-Tabs (doxycycline-hydrate); Declomycin (demeclocycline HCl); Vibramycin (doxycycline); Dynacin (Minocyline HCl); Terramycin (oxytetracycline HCl); Achromycin V capsules5 (tetracycline HCl); Linco-mycins; and Cleotin HCl (clindamycin HCl); Abelcet (amphotericin B lipid complex); AmBisome (amphotericin B); Amphotec (amphotericin B cholesterol sulfate-complex); Ancobon (flucytosine); Diflucan (fluconazole); Fulvicin P/Gamma (ultramicrosize griseofulvin); Fulvicin P/G 165 and 330 (ultramicrosize griseofulvin); Grifulvin V (griseofulvin); Gals-PEG (gxiseofulvin ultramicrosize); Lamisil (terbinafine hydrochloride); Nizoral (ketoconazole); Amphotericin B; Lotrimin (clotrimazole); Dapsone tablets (dapsone); Diflucan (fluconazole); Monistat-Derm cream (miconazole); Mycostalin Crc am (nystatin); and Sporanox (itraconazole); Aralen hydrochloride (chloroquine HCl); Aralen phosphate (chloroquine phosphate); Dataprim (pyrimethamine); Ladam (mefloquine HCl); and Plaquenil (hydroxychloroqnine sulfate); Capastat sulfate (capreomycin-sulfate); Myambutol (ethambutol hydrochloride); Mycobutin (rifabutin capsules); Nydrazid (isoniazid injection); Paser (aminosalicylic acid); Prifiin (rifapentine); Pyrazinamide tablets (pyrazinamide); Rifadin (rifampin capsules); Rifadin IV (rifampin for injection); Rifamate (rifampin and isoniazid); Rifater (rifampin, isoniazid and pyrazinamide); Seromycin (cycloserine capsules); Streptomycin-Sulfate; Tice BCG (BCG vaccine); Cycloserine (seromycin capsules); Urised (Methenamine); and Trecator-SC (ethionamide tablets); Alferon N (interferon alfa-n3); Crixivan (indinavir sulfate); Cytovene (ganciclovir); Cytovene-IV (ganciclovir sodium); Epivir (lamivudine); Famvir (famciclovir); Flumadine (rimantadine HCl); Foscavir (foscamet sodium); Hivid (zalcitabine); Intron A (interferon alfa-2b); Invirase (saquinavir mesylate); Norvir (ritonavir); Rebetron combination therapy, which contains Rebetrol (ribavirin) and Intron A (inteferon alfa-2b); Rescriptor (delavirdine mesylate); Retrovir (ziduvudine); Retrovir IV (ziduvudine); Symmetrel (amantadine HCl); Synagis (palivizumab); Valtrex (valacyclovir HCl); Videx (didanosine); Viracept (nelfinavir mesylate); Viramune (nevirapine); Virazole (ribavirin); Vistide (cidofovir); Zerit (stavudine (d4T)); Symmetrel Syrup (amantadine HCl); Combivir Tablets (lamiduvine); and Zovirax (acyclovir); Dapsone Tablets (dapsone); Daraprim (pyrimethamine); Flagyl 375 (metronidazole); Flagyl ER Tablets (metronidazole); Flagyl I.V. (metronidazole); Furoxone (furazolidone); Mepron (atovaquone); and Neutrexin (tfimetrexate glucuronate); Cipro (ciprofloxacin HCl); Floxin (ofloxacin); Levaquin (levofloxacin); Mazaquin (lomefioxacin HCl); Noroxin (norfloxacin); Penetrex (enoxacin); Raxar (grepafloxacin HCl); Trovan (trovafioxacin mesylate); and Zagam (sparfloxacin); Bactrim.(trimethoprim and sulfamethoxazole); Bactrim DS (Irimethoprim and sulfamethoxazole double strength); Pediazole (erythromycin ethylsuccinate and sulfisoxazole acetyl); Septra (trimethoprim and sulfamethoxazole); Septra DS (trimethoprim and sulfamethoxazole); Co-Trimoxazole, Sulfadiazine, Battrim I.V. Infusion (sulfamethoxazole); Sulfapyridine and Pediazole (erythromycin ethylsuccinate and sulfisoxazole acetyl); Furadantin (nitrofurantoin); Macrobid (nitrofurantoin monohydrate macrocrystals); Macrodantin (nitrofurantoin macrocrystals); Monurol Sachet (fosfomycin tromethamine); NegGram Caplets (nalidixic acid); Septra (trimethoprim and sulfamethoxazole); Septra DS (trimethoprim and sulfamethoxazole); Urised (a combination of the antisepticsmethenamine, methylene blue, phenyl salicylate, benzoic acid and parasympatholytics (atropine sulfate) hyoscyamine); (oxytetracycline HCl, sulfamethizole and phenazopyridine HCl); (methenamine mandelate); Bactroban (mupirocin); Chloromycetin opthalmic (chloramphenical); Cortisporin (neomycin and polymyxin [3 sulfates and hydrocortisone acetate cream); Ilotycin (erythromycin opthahnic ointment); NeoDecadron (neomycin sulfate—dexamethasone sodium phosphate); Polytrim (tfimethoprim and polythyxin [3 sulfate opthalmic solution); Terra-Cortril (oxytetracycline HCl and hydrocortisone acetate); Terramycin (oxytetracycline); and TobraDex (tobramycin and dexamethasone opthalmic suspension and ointment); Vita-A opthalmic ointment, (vidatabine); (norfloxacinopthalmic solution; Ciloxan opthalmic solution and ointment (Ciprofloxacin HCl); and Ocuflox opthalmic solution (ofioxacin), Blephamide opthalmicointment (sulfacetamide sodium and prednisolone acetate); and Blephamideopthalmic suspension (sulfacetamide sodium and predrdsolone acetate); A/T/S (erythromycin); Bactroban (mupirocin); Benzamycin (erythromycin-benzoyl peroxide topical gel); Betadine (povidone-odine); Cleotin T (clindamy cinphosphate topical solution); Clindets (clindamycin phosphate pledgets); Cortispofin (neomycin, polymyxin B sulfates and hydrocortisone acetate cream); Emgel (erythromycin); Erycette (erythromycin topical solution); Garamycin (gentamicin sulfate); Klaron (sodium sulfacetamide lotion); Mycostatin (nystatin cream); Theramycin Z (erythromycin topical solution); T-Stat (erythromycin); Chloromycetin (chloramphenicol opthalmic ointment); Cortisporin (neomycin and polymyxin B sulfates, bacitracin zinc and hydrocortisone opthalmic ointment); Ilotycin (erythromycin); NeoDeeadron (neomycin sulfate-dexamethasone sodium phosphate); Polytrim (trimethoprim and polymyxin B sulfate); Terra-Cortril (oxytetracycline HCl and hydrocortisone acetate); Terramycin (oxytetracycline); Exelderm (sulconazole nitrate); Fungizone (amphotericin B oral suspension); Lamisil (terbinafine hydrochloride cream); Loprox (ciclopiroxolamine); Lotrimin (clotrimazole); Lotrisone (clotrimazole and betamethasone diproprionate); Mentax (butenafine HCl); Monistat-Denn (miconazole nitrate); Mycelex (clotrimazole); Mycostatin (nystatin); Naffin (nattifine HCl); Nizoral Ocetoconazole); Nystop (nystatin); Oxistat (oxiconazole nitrate); Selsun Rx (2.5% selenium sulfide lotion); and Spectazole (econazole nitrate); Denavir (penciclovir cream); and Zovirax (acyclovir); Benzashave Coenzoyl peroxide); Betadine (povidone-iodine); Betasept (chlorhexidine gluconate); Cetaphil (soap substitute); Clorpactin WCS-90 (sodium oxychlorosene); Dapsone Tablets (dapsone); Desquam-E Coenzoyl peroxide); Desquam-X (benzoyl peroxide); Hibiclens (chlorhexidine gluconate); Hibistat (ehlorhexidine gluconate); Impregon (tetrachlorosalicylanilide 2%); MetroCream (metronidazole); MetroGel (metronidazole); Noritate (metronidazole); pHisoHex (hexachlorophene detergent cleanser); Sulfacet-R (sodium sulfacetamide 10% and sulfur 5%); Sulfamylon (materfide acetate); Tfiaz Coenzoyl peroxide); and Vanoxide-HC Coenzoyl peroxide hydrocortisone); Acticin (permethrin); Elimite (permethrin); Eurax (crotamiton); Efudex (fluoro-uracil); Fluoroplex.

Pharmaceutical Compositions

Hosts, including humans can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

An optional dose of the compound for treatment of a bacterial (such as a gram positive bacteria) infection is about 1 to 50 mg/kg, or 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

Optionally, the active ingredient should be administered to achieve peak plasma concentrations of the active compound of from about 0.2 to 70 M, e.g., about 1.0 to 10 uM. This may be achieved, for example, by the intravenous injection of a 0.1 to 5% solution of the active ingredient, optionally in saline, or administered as a bolus of the active ingredient. The concentration of active compound in the drug composition will depend on absorption, inactivation and excretion rates of the drug as well as other factors known to those of skill in the art. It is to be further understood that for any particular subject, specific dosage regimens should be adjusted according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

The compound is conveniently administered in unit any suitable dosage form, including but not limited to one containing 7 to 3000 mg, or 70 to 1400 mg of active ingredient per unit dosage form. A dosage of 50-1000 mg is optional.

The active compound can be administered in a pharmaceutically acceptable carrier available in the art, and can be administered by a chosen route of administration. Pharmaceutical compositions can be prepared, packaged, or sold in a variety of formulations which can be suitable for one or more routes of administration such as, for example, oral, intravenous, intramuscular, topical, subcutaneous, rectal, vaginal, parenteral, pulmonary, intranasal, buccal, ophthalmic, or another route of administration. The active materials can be administered in liquid or solid form. Other contemplated formulations include projected nanoparticles, liposomal preparations, resealed erythrocytes containing the active ingredient, and immunologically-based formulations.

The active compound may be administered intravenously or intraperitoneally by infusion or injection. Solutions of the active compound or its salts may be prepared in water or saline, optionally mixed with a non-toxic surfactant. Dispersions may be prepared in glycerol, liquid polyethylene glycols, triacetin, mixtures thereof, and in oils. Under ordinary conditions of storage and use, these preparations contain a preservative to prevent growth of microorganisms.

Pharmaceutical dosage forms suitable for injection or infusion may include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form is optionally sterile, fluid, and stable under conditions of manufacture and storage. The liquid carrier or vehicle may be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof.

For oral therapeutic administration, the active compound can be combined with one or more excipients and used in the form of ingestible tablets, buccal tablets, troches, capsules, elixirs, suspensions, syrups, wafers, and the like. Such compositions and preparations can contain at least 0.1% (w/w) of active compound. The percentage of the compositions and preparations can, of course, be varied, for example from about 0.1% to nearly 100% of the weight of a given unit dosage form. The amount of active compound in such therapeutically useful compositions is such that an effective dosage level will be obtained upon administration.

The tablets, troches, pills, capsules, and the like may also contain one or more of the following: binders, such as microcrystalline cellulose, gum tragacanth, acacia, corn starch, or gelatin; excipients, such as dicalcium phosphate, starch or lactose; a disintegrating agent, such as corn starch, potato starch, alginic acid, primogel, and the like; a lubricant, such as magnesium stearate or Sterotes; a glidant, such as colloidal silicon dixoide; a sweetening agent, such as sucrose, fructose, lactose, saccharin, or aspartame; a flavoring agent such as peppermint, methylsalicylate, oil of wintergreen, or cherry flavoring; and a peptide antibacterial agent, such as envuvirtide (Fuzeon™). When the unit dosage form is a capsule, it can contain, in addition to materials of the above type, a liquid carrier, such as a vegetable oil or a polyethylene glycol. Various other materials may be present as coatings or to otherwise modify the physical form of the solid unit dosage form.

In one embodiment, the active compounds are prepared with carriers that will protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylacetic acid. Methods for preparation of such formulations will be apparent to those skilled in the art. The materials may also be obtained commercially from Alza Corporation.

Other formulations can also be developed. For example, the compounds can be administered in liposomal suspensions (including liposomes targeted to infected cells with monoclonal antibodies to bacterial antigens). These may be prepared according to methods known to those skilled in the art, for example, as described in U.S. Pat. No. 4,522,811. For example, liposome formulations may be prepared in a variety of lipid(s) (such as stearoyl phosphatidyl ethanolamine, stearoyl phosphatidyl choline, arachadoyl phosphatidyl choline, and cholesterol).

A pharmaceutical composition of the invention may be prepared, packaged, or sold in a formulation suitable for rectal administration. Such a composition may be in the form of, for example, a suppository, a retention enema preparation, and a solution for rectal or colonic irrigation. A pharmaceutical composition of the invention may also be prepared, packaged, or sold in a formulation suitable for vaginal administration. Such a composition may be in the form of, for example, a suppository, an impregnated or coated vaginally-insertable material such as a tampon, a douche preparation, or a solution for vaginal irrigation.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration, which can include particles wherein at least 98% of the particles by weight have a diameter greater than 0.5 nanometers and at least 95% of the particles by number have a diameter less than 7 nanometers. Typically least 95% of the particles by weight have a diameter greater than 1 nanometer and at least 90% of the particles by number have a diameter less than 6 nanometers. The active ingredient can also be in the form of droplets of a solution or suspension, for example those that have an average diameter in the range from about 0.1 to about 200 nanometers.

The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers.

A pharmaceutical composition of the invention may be prepared, packaged, or sold in a formulation suitable for ophthalmic administration. For topical administration, the present compounds can be applied in pure form, i.e., as a liquid. However, typically, the compounds are administered to the skin as compositions or formulations, in combination with a dermatologically acceptable carrier. Useful solid carriers include finely divided solids such as talc, clay, microcrystalline cellulose, silica, alumina, and the like. Useful liquid carriers include water, alcohols, glycols, and blends of two or more of these, in which the present compounds can be dissolved or dispersed at effective levels, optionally with the aid of non-toxic surfactants. Adjuvants such as fragrances and additional antimicrobial agents can be added to optimize properties for a given use. The resulting liquid compositions can be applied using absorbent pads, used to impregnate bandages or other dressings, or sprayed onto the affected area using pump-type or aerosol sprayers.

The compounds/compositions of the present invention are optionally administered in a controlled release formulation, which can be a degradable or nondegradable polymer, hydrogel or ganogel or other physical construct that modifies the bioabsorption, half life or biodegradation of the active agent(s). The controlled release formulation can be a material that is painted or otherwise applied onto the afflicted site, either internally or externally. In one embodiment, the invention provides a biodegradable bolus or implant. The controlled release formulation with appropriated selected imaging agent can be used to coat a transplanted organ or tissue to prevent rejection. It can alternatively be implanted or otherwise applied near the site of potential infection.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

The compound or a pharmaceutically acceptable prodrug or salts thereof can also be mixed with other active materials that do not impair the desired action, or with materials that supplement the desired action, such as antibiotics, antifungals, anti-inflammatories, or other antibacterials, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antiacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposale syringes or multiple dose vials made of glass or plastic. If administered intravenously, useful carriers are physiological saline or phosphate buffered saline (PS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

The concentration of the compound(s) in a liquid composition, such as a lotion, will, for example, range from about 0.1% to about 95% by weight, or from about 0.5% to about 25% by weight. The concentration in a semi-solid or solid composition such as a gel or a powder will, for example, range from about 0.1% to 100% by weight, or about 0.5% to about 5% by weight. Single doses for intravenous injection, subcutaneous, intramuscular or topical administration, infusion, ingestion or suppository will generally be from about 0.001 to about 5000 mg, and be administered from about 1 to about 3 times daily, to yield levels of about 0.01 to about 500 mg/kg, for adults.

The invention also includes one or more compounds disclosed herein, or any combination thereof, or salt thereof, in an amount effective to inhibit bacterial (such as a gram positive bacteria) replication in a host. The compound can be useful for inhibiting bacterial replication in a cell or neutralization (i.e. inactivation) of extracellular bacteria.

As used herein, to inhibit bacterial replication in a host means to reduce the bacterial load in a host to a level which is lower than the level of the bacterial load in an otherwise identical host which was not administered the compound. Bacterial load in a mammal can be reduced by about 1 to 12 $\log_{10}$ or more relative to an otherwise identical mammal which was not administered the compound. Bacterial load in a mammal can be assessed by a number of methods known in the art such as, for example, obtaining a tissue or fluid sample from the mammal and assessing the amount of bacterial components in the mammal contained therein using technology which is either immunological, biochemical or molecular biological in nature and which is well known to the skilled artisan and which are described elsewhere herein. Inhibition of bacterial replication in a cell is assessed using similar or identical assays as those used to assess bacterial load in a mammal.

The invention also includes a kit for administering a compound of the invention, a pharmaceutically acceptable salt thereof, or a pharmaceutical composition, to a host for treatment of a bacterial (such as a gram positive bacteria) infection. Typically, the host is a human. The kit comprises one or more compounds of the invention, or a combination thereof, and optionally an instructional material, which describes adventitially administering the composition to the mammal by any of the routes of administration described herein. In another embodiment, this kit comprises a (typically sterile) solvent suitable for dissolving or suspending the composition of the invention prior to administering the compound to the mammal.

EXAMPLES

Melting points were determined on a Mel-temp II laboratory device and are uncorrected. Nuclear magnetic resonance spectra were obtained on a GE 300 Plus (300 MHz), a Varian INOVA 400 (400 MHz), and a Varian INOVA 600 (600 MHz) spectrometer; chemical shifts (δ) are reported in parts per million (ppm), and the signals are described as s (singlet), d (doublet), t (triplet), q (quartet), bs or brs (broad singlet), dd (doublet of doublet), and m (multiplet). UV spectra were obtained on a Beckman DU 650 spectrophotometer. Mass spectra were measured on a Micromass Inc. Autospec High Resolution double focussing sector (EBE) MS spectrometers. Infrared spectra were obtained on a Nicolet 510 FT-IR spectrometer. All reactions were monitored using thin layer chromatography on Analtech, 200 mm silica gel GF plates. Dry 1,2-dichloroethane, dichloromethane, acetonitrile, N,N-dimethylformamide, and THF were obtained by drying over 4 A molecular sieves.

Abbreviations

ACN: acetonitrile
DCE: 1,2-dichloroethane
DCM: dichloromethane
DDQ: dichlorodicyano quinone
DIEA: diisopropylethyl amine
DI $H_2O$: deionized water
DMAP: 4-N,N-dimethylamino pyridine
DMF: N,N-dimethyl formamide
LAH: lithiumaluminum hydride
LHMDS: lithium hexamethyldisilazide
Pd/C: palladium on carbon
PNB: para-nitrobenzyl
TBAF: tetrabutylammonium fluoride
TBDMS: t-butyldimethylsilyl
TEA: triethylamine
TES: triethylsilyl
TFA: trifluoroacetic acid
THF: tetrahydrofuran
TLC: thin layer chromatography
TBDPS: t-buthyldiphenylsilyl

Preparation of the Carbapenem Intermediate (CPI) 5

Carbapenem Intermediate (CPI) 5 was prepared according to the synthetic scheme shown in FIG. 3. In the first step of the process, benzyl propionate is reacted with isobutoxycarbonyloxy acetic acid methyl ester in a solvent at low temperature in the presence of LDA to form ketoester A. The ketoester A is then contacted with the acetoxyazetidinone B (prepared by any number of known, synthetic routes) in a solvent, and sodium carbonate is added. The reaction ages for a period of time at a temperature such that the reaction goes substantially to completion, generating the target lactam C.

The lactam C is dissolved in a solvent, such as DMF, to which a suitable base (such as DIEA) and TBSOTf are added, and the mixture allowed to age for a period of time at a temperature. Following workup, the bis-TBS-ketoester D is isolated.

The crude ketoester D is dissolved in ethyl acetate in an appropriate reaction vessel. Formic acid and a catalyst, such as Pd/C, are added to the reaction vessel, and the entire mixture is hydrogenated at an appropriate hydrogen pressure (40-50 psi) for a period of time such that the decarboxylation reaction proceeds to completion. The reaction mixture is filtered over a pad of Celite®, and the solvent is removed under vacuum. Product E is isolated following purification by column chromatography.

The bis-TBDMS ketolactam E is then de-silylated using 2 N HCl in ACN and the product is isolated after a standard aqueous workup. The crude product is dissolved in a solvent, such as DCM, and allowed to react with triethylsilyl chloride and imidazole for several hours (monitored by TLC) at rt. Following aqueous workup, O-TES ketolactam F was isolated and purified on silica gel.

N-PNB, O-TES ketolactam G is produced by reacting ketolactam F with p-nitrobenzyl oxalylchloride in a suitable solvent (DCM, for example) in the presence of a base (DIEA, for example). The mixture is allowed to age for a period of time (and at an appropriate temperature) to effect a substantially complete reaction as monitored by an appropriate means (e.g., TLC or HPLC). Following workup in a usual manner, intermediate G was isolated.

To a solution of compound G is a suitable solvent was added triethylphosphite, and the mixture heated to reflux until complete by TLC. Following workup and purification in the appropriate manner, CPI 5 was isolated.

Examples of 5-Alkyl-Substituted-1-Naphthol CP Analogs

Preparation of "1-Carbon" 5-Hydroxymethyl-1-Naphthol CPI 6

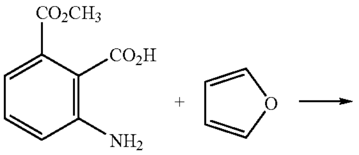

1

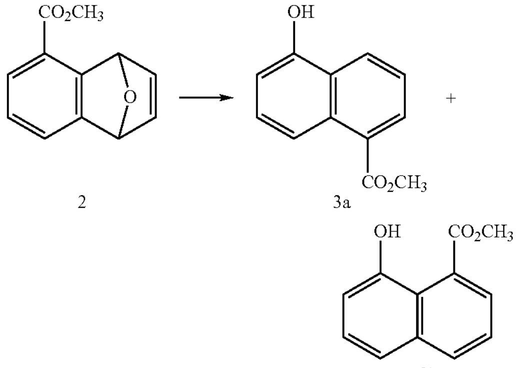

2 3a 3b

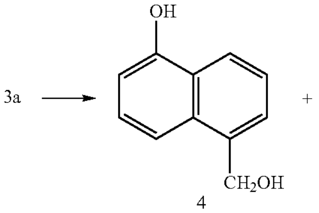

4

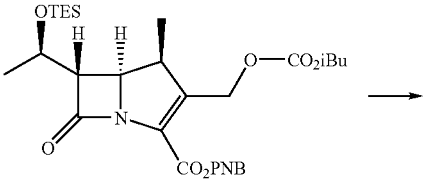

5

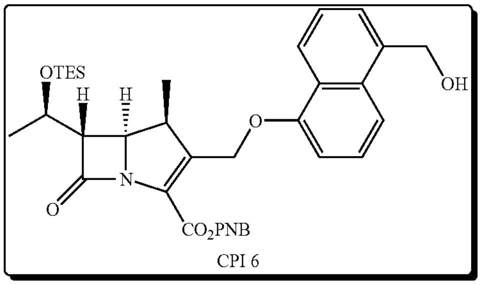

CPI 6

Discussion

2-Amino-6-(methoxycarbonyl) benzoic acid (1) was made from 3-nitrophthalic acid using the procedure first reported by Rogers and Averill (Rodgers, M. E. and Averill, B. A., *J. Org. Chem.,* 1986, 51, 3308) and then used immediately to make Diels Alder cycloadduct 2 via the 3-(methoxhycarbonyl)dehydrobenzene intermediate that is generated under aprotic diazotization reaction conditions (based on modified conditions first reported by Giles, R. G. F., Sargent, M. V., and Sianipar, H., *J. Chem. Soc. Perkin Trans I,* 1991, 1571). Treatment of cycloadduct 2 with TFA in refluxing methanol yielded a 1:2 mixture of regioisomeric naphthols 3a and 3b which were separated by column chromatography on silica gel. The 1,5-naphthol regioisomer (3a) was then reduced with LAH to produce 5-hydroxymethyl naphthol 4, which was then coupled to carbapenem intermediate 5 (CPI 5) with catalytic palladium to produce the 1-carbon naphthol coupled CPI 6.

Experimental

Preparation of Diels Alder Adduct 2

In a three neck round bottom flask equipped with two addition funnels, dry chloroform (300 mL) was added and heated to reflux. In one addition funnel was added a mixture of furan (35 mL, 480 mmol) and isoamyl nitrite (45 mL, 420 mmol). In the second addition funnel was added a solution of aniline 1 (50 g, 222 mmol) in dioxane/furan (200 mL/20 mL). The two reactants were then added dropwise simultaneously while at reflux. Upon completion of the addition, the mixture was heated for additional 2 h and then allowed to cool to rt. The mixture was concentrated under a reduced pressure and partitioned between ethyl acetate (300 mL), sodium bicarbonate solution (100 mL), and water (100 mL). The organic layer was washed with water (100 mL) and the solution was concentrated to dryness. Column chromatography using 10% ethyl acetate in hexanes afforded the cycloadduct 2 (31 g, 153 mmol, 69% yield).

$^1$H NMR ($CDCl_3$, 300 MHz) δ: 3.94 (s, 3H), 5.75 (s, 1H), 6.38 (s, 1H), 7.07 (m, 3H), 7.39 (d, 1H), 7.57 (d, 1H).

Rearrangement to 1,5-Naphthylesters 3a and 3b

The Diels Alder adduct 2 (31 g, 153 mmol) was dissolved in a mixture of acetic acid/TFA (50 mL/10 mL) and the resulting solution was heated to reflux for 2 h. The mixture was concentrated to dryness. Column chromatography using 10% ethyl acetate in hexanes yielded the 1,5-naphtholester 3a (19 g, 94 mmol, 61% yield) and the isomeric 1,8-naphtholactone 3b (5.0 g, 29.4 mmol, 19% yield).

$^1$H NMR ($CDCl_3$, 300 MHz): δ 4.00 (s, 3H), 5.38 (brs, 1H), 6.87 (d, 1H), 7.47 (m, 2H), 8.20 (d, 1H), 8.47 (d, 2H).

Reduction of Ester 3a to Diol 4

In a round bottom flask, ester 3a (10 g, 49.4 mmol) was dissolved in dry THF (300 mL) and the solution cooled to 0° C. In a separate flask, a solution of LAH (2.81 g, 74.2 mmol) was prepared in 50 mL of dry THF. The solution of hydride was added dropwise to the solution of ester 3a and the resulting mixture was warmed to rt and then aged for 3 hours. Rochelle salt solution (30 mL) was added to quench the reaction. The reaction mixture was filtered over celite and the solvent was concentrated to dryness. The organic residue was purified by flash column chromatography on silica gel using 30% ethyl acetate in hexanes to afford the alcohol 4 (6.29 g, 73% yield).

$^1H$ NMR ($CDCl_3$, 300 MHz): δ 4.80 (s, 2H), 6.85 (d, 1H), 7.30 (m, 2H), 7.55 (m 2H), 8.20 (d, 1H).

Preparation of 6 Via Palladium-Catalyzed Coupling Reaction

A mixture of toluene (450 mL) and THF (50 mL) was degassed at 0° C. (ice/water bath) with 3 nitrogen/vacuum cycles. After warming to ambient temperature, $Pd_2$ $dba_3$-$CHCl_3$ (tris(dibenylideneaceton)-dipalladium(0)-chloroform adduct) (876 mg, 0.847 mmol), and triethyl phosphite (0.874 mL, 2.54 mmol) were added and the solution was stirred for 1-2 h or until the solution became bright yellow. Naphthol 4 (3.09 g, 17.9 mmol) and CPI 5 (10 g, 16.9 mmol) were then simultaneously added to the solution as solids, the mixture degassed for several minutes, and the resulting mixture was aged for 4 h. The solvents were removed under reduced pressure and crude residue was purified by flash column chromatography with 7:3 Hex/EtOAc to afford the desired couple product 6 as a white solid (9.39 g, 86% yield).

$^1H$ NMR ($CDCl_3$, 300 MHz): δ 0.60 (q, J=7.8 Hz, 6H), 0.90 (t, J=7.8 Hz, 9H), 1.15 (d, J=6.1 Hz, 3H), 1.18 (d, J=7.4 Hz, 3H), 3.30 (d, 1H), 3.55 (m, 1H), 4.30 (m, 2H), 4.90 (d, 1H), 5.15 (brs, 2H), 5.30 (d, J=17.1 Hz, 1H), 5.50 (d, J=17.1 Hz, 1H), 5.65 (d, J=13.5 Hz, 1H), 6.90 (d, J=7.5 Hz, 1H), 7.40 (m, 2H), 7.60 (m, 1H), 7.75 (m, 3H), 8.20 (m, 3H).

Preparation of "2-Carbon" 5-Hydroxyethyl-1-Naphthol CPI 14

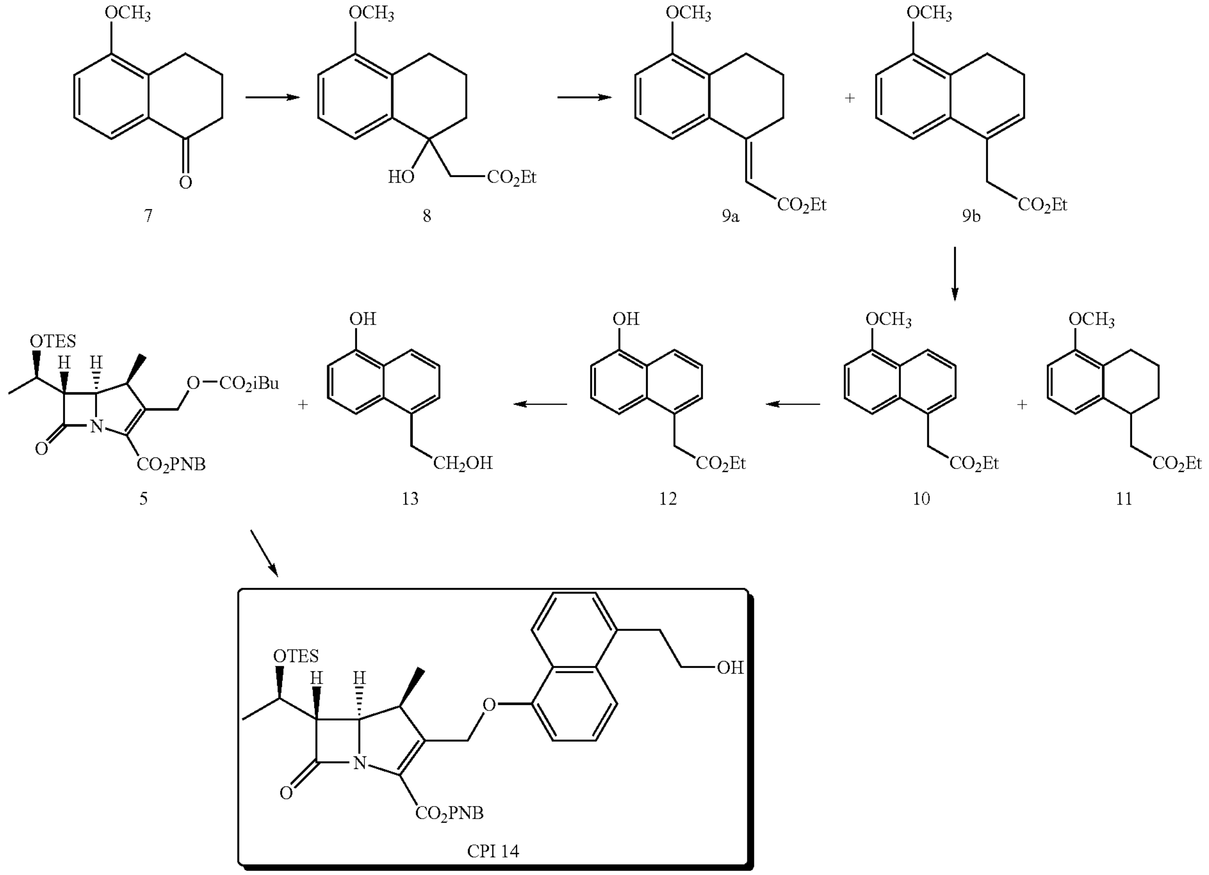

7 8 9a 9b 5 13 12 10 11 CPI 14

Discussion

5-Methoxy-1-tetralone (7) was converted into alcohol 8 by allowing it to react with the enolate generated from ethyl acetate. Treatment of alcohol 8 with TFA in refluxing toluene yielded a 1:2 mixture of olefins 9a and 9b. The mixture was then subjected to phase transfer catalysis reaction conditions with 10% Pd/C and cyclohexene/dioxane to produce a 1:1 mixture of the fully aromatic bicyclic adduct 10 and the monoaromatic bicyclic adduct 11. After further oxidation of the crude reaction mixture with DDQ, the fully aromatic product was isolated by column chromatography. Boron tribromide deprotection of methyl ether 10 followed by LAH reduction of ester 12 yielded the desired 2-carbon naphthol linker 13, which was coupled to CPI 5 using similar conditions as described earlier (see preparation of CPI 6).

Experimental

Preparation of Alcohol 8

Lithium hexamethyldisilazide (LHMDS) solution (1M in hexane, 280 mL, 280 mmol) and a dry THF (300 mL) were added to a dry 1-L round bottom flask and the solution was cooled to −78° C. Dry ethyl acetate (24.5 mL, 250 mmol) in THF (25 mL) was added to the base solution by syringe pump over 2 h while maintaining the internal temperature below −70° C. A solution of tetralone 7 (38 g, 216 mmol) in dry THF (50 mL) was added via syringe pump over 2 h while maintaining an internal temperature below −70° C. The resulting mixture was aged at −70° C. for 1 h, quenched with aq. HCl solution (50 mL conc HCl in 50 mL water), and allowed to warm up to rt. The mixture was extracted twice with ethyl acetate (200 mL, 100 mL) and the combined organic layers were washed with water (300 mL) and concentrated to dryness. Column chromatography using 10% ethyl acetate in hexanes afforded hydroxyester 8 (50 g, 189 mmol) in 88% yield.

$^1$H NMR ($CDCl_3$, 300 MHz): δ 1.25 (t, 3H), 1.75 (m, 1H), 1.85 (m, 2H), 2.10 (m, 1H), 2.70 (m, 4H), 3.80 (s, 3H), 4.2 (q, 2H), 6.75 (m, 1H), 7.2 (m, 2H).

Aromatization of Alcohol 8 to Ester 10

Hydroxyester 8 (33.5 g, 127 mmol) was dissolved in toluene/TFA (250 mL/5 mL) and the mixture was heated to reflux for 3 h. The mixture was then cooled to rt, diluted with ethyl acetate (100 mL), and washed with 1N NaOH aq solution (100 mL) and DI water (200 mL). The organic layer was concentrated to dryness to yield a 1:2 mixture of olefins 9a and 9b (32.5 g, 127 mmol, 100% yield) which was used directly in the next step.

$^1$H NMR ($CDCl_3$, 300 MHz): δ 1.20 (t, 2H), 1.25 (t, 1H), 1.85 (m, 0.5H), 2.30 (m, 1.5H), 2.80 (m, 2H), 3.20 (m, 0.5H), 3.40 (s, 1.5H), 3.80 (s, 3H), 4.20 (m, 2H), 6.00 (t, 0.7H), 6.35 (s, 0.3H), 6.80 (m, 1.5H), 7.15 (m, 1H), 7.25 (m, 0.5H).

A mixture of olefins 9a, 9b (36.5 g, 148 mmol) was dissolved in cyclohexene/dioxane (150 mL/50 mL). 10% Pd—C (2 g) was then added and the mixture heated to reflux for 16 h. The mixture was cooled to RT, filtered through a pad of celite, and the pad was washed with ethyl acetate (100 mL). The combined filtrates were concentrated to dryness to give a 1:3 mixture of 10 and 11 (41.4 g, 100% yield).

The above mixture was dissolved in toluene (500 mL). To this was added DDQ (33.6 g, 150 mmol), and the mixture heated at reflux for 2 h. Additional DDQ (20.5 g, 90 mmol) was added and the mixture was heated for an additional 2 h. The mixture was then cooled to rt, and the resulting solids were removed by filtration. The filtrate was concentrated to dryness and the product was purified by column chromatography using 15% ethyl acetate in hexanes to yield the desired naphthylester 10 (28.6 g, 117 mmol, 79% yield) and the reduced byproduct 11 (1.0 g, 4.1 mmol, 2.8% yield).

$^1$H NMR for 10 ($CDCl_3$, 300 MHz): δ 1.20 (t, 3H), 4.00 (s, 3H), 4.09 (s, 2H), 4.15 (q, 2H), 6.85 (d, 1H), 7.40 (m, 3H), 7.55 (m, 1H), 8.27 (t, 1H).

$^1$H NMR for 11 ($CDCL_3$, 300 MHz): δ 1.25 (t, 3H), 1.80 (m, 4H), 2.55 (m, 2H), 2.70 (m, 2H), 3.35 (m, 1H), 3.80 (s, 3H), 4.20 (q, 2H), 6.70 (d, 1H), 6.80 (d, 1H), 7.10 (t, 1H).

Demethylation of 10 to Naphthol 12

Naphthylether 10 (19.8 g, 81 mmol) was dissolved in a dry DCM (400 mL) and the solution cooled to −70° C. A solution of $BBr_3$ (1M in DCM, 160 mL, 160 mmol) was added dropwise while maintaining an internal temperature below −60° C. The mixture was aged at this temperature for an additional 30 min, then allowed to warm up to RT and aged for additional 2 h at rt. The mixture was then again cooled to −70° C., treated with absolute ethanol (20 mL), and the resulting mixture was aged at rt overnight. The solution was poured into a cold $NaHCO_3$ solution (500 mL, saturated aq) and vigorously stirred. The organic layer was washed with dilute HCl solution (0.1N, 200 mL) and with water (200 mL), and the solvent removed. Column chromatography of the resulting residue using 20% ethyl acetate in hexanes yielded the naphthylester 12 (17.6 g, 76.4 mmol) in 94% yield.

$^1$H NMR ($CDCl_3$, 300 MHz) δ: 1.25 (t, 3H), 4.10 (s, 2H), 4.20 (q, 2H), 6.00 (s, 1H), 6.65 (d, 1H), 7.25 (t, 1H), 7.40 (m, 2H), 7.50 (d, 1H), 8.15 (m, 1H).

Reduction of Ester 12 to Diol 13

In a round bottom flask, ester 12 (14.69 g, 63.7 mmol) was dissolved in dry THF (300 mL) and the solution was cooled to 0° C. In a separate flask, a solution of LAH (3.63 g, 95.6 mmol) was prepared in 50 mL of dry THF. The solution of hydride was added dropwise to the reaction. The reaction was the warmed to rt and aged for 3 h. Rochelle salt solution (30 mL) was added to quench the reaction and the resulting mixture was filtered over celite and concentrated to dryness. The organic residue was purified by flash column using 40% ethyl acetate in hexanes to afford alcohol 13 (11.47 g) in 95% yield.

$^1$H NMR for (CDCL3, 300 MHz) δ: 3.14 (t, 2H), 4.00 (t, 2H), 6.80 (d, 1H), 7.20 (m, 3H), 7.65 (d, 1H), 8.15 (d, 1H).

Preparation of 14 Via Palladium-Catalyzed Coupling Reaction

5-Ethylhydroxyl-1-naphthol (13, 1.5 g, 8 mmol) to was coupled to CPI 5 (4,72 g, 8 mmol) using a similar procedure described for the synthesis of CPI 6 and the desired coupled product 14 (4.84 g, 85% yield) was isolated after flash column chromatography using 7:3 Hex/EtOAc as pale yellow solid.

$^1$H NMR ($CDCl_3$, 300 MHz): δ 0.60 (q, J=7.8 Hz, 6H), 0.90 (t, J=7.8 Hz, 9H), 1.15 (d, J=6.1 Hz, 3H), 1.18 (d, J=7.4 Hz, 3H), 3.30 (m, 3H), 3.55 (m, 1H), 4.30 (m, 2H), 4.90 (d, 1H), 5.30 (d, J=17.1 Hz, 1H), 5.50 (d, J=17.1 Hz, 1H), 5.65 (d, J=13.5 Hz, 1H), 6.85 (d, J=7.5 Hz, 1H), 7.40 (m, 2H), 7.60 (m, 1H), 7.75 (m, 3H), 8.10 (m, 3H).

General Procedure for the Synthesis of "1-Carbon" Naphthol Analogs 17 trated. The crude mesylate was then dried to a light brown foam under high vacuum (approximately 30 minutes) and used immediately in the next step.

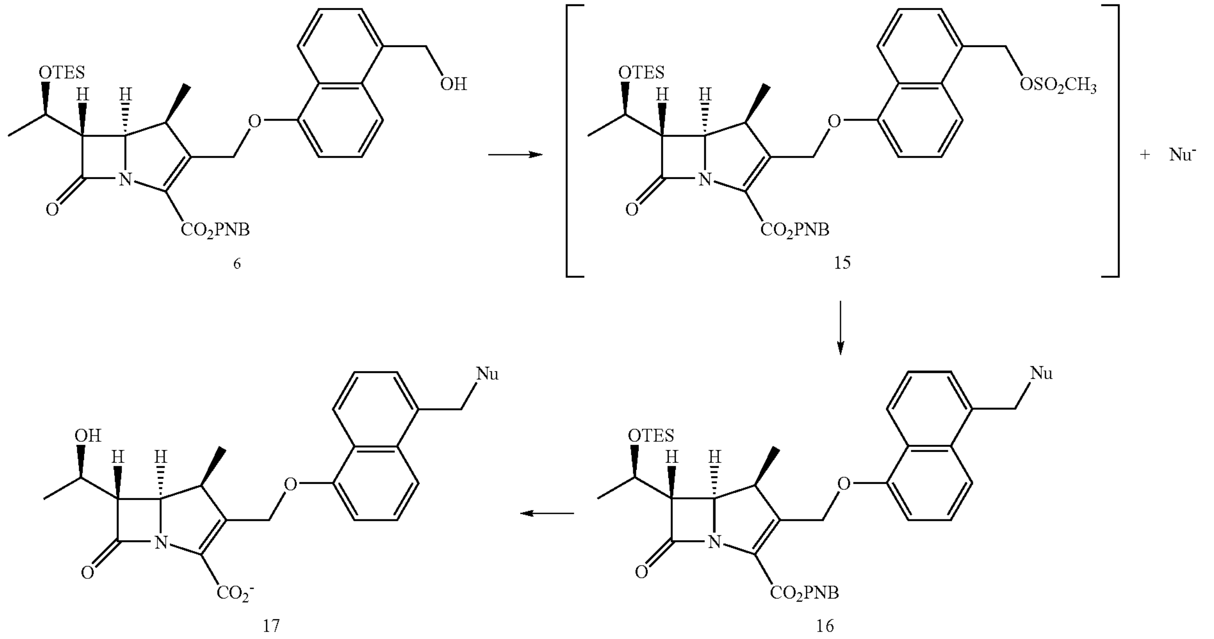

17

16

Nu = amines (1°, 2° and 3°), thioureas, sulfonamides, thiols, etc.

Discussion

The reaction scheme shown above represents the general synthetic route that was used to synthesize all of the 1-carbon naphthol ammonium salt analogs as well as some of the neutral sulfonamide, thiourea, thiol, amine, or ether containing analogs with the general structure of 17. First, CPI 6 was converted to its mesylate intermediate 15 with methanesulfonyl chloride and DIEA in DCM at 0° C. After aqueous work up, the crude mesylate was dried under high vacuum, re-dissolved in dry ACN or DMF, and allowed to react with a slight excess the nucleophile. Following careful purification of 16, a tandem 2-step, 1-pot deprotection procedure was then used to produce the final 1-carbon naphthol analogs (17). Purification of the final compounds was done on either SP-207 or HP-20 resin using gradient elusions of DI water/IPA or DI water/acetone.

Experimental

General Procedure for the Synthesis of Mesylate Intermediate 15

CPI 6 (0.46 mmol, 300 mg) was dissolved in dry DCM (60 mL) and the solution cooled to 0° C. under $N_2$ atmosphere. Methanesulfonyl chloride (0.71 mmol, 81 mg) was then added in one portion and the mixture aged 5 min at 0° C. DIEA (1.37 mmol, 180 mg) was then added in one portion and mixture aged for an additional 2-3 h at 0° C. The reaction was then quenched with chilled sat. aq $NaHCO_3$ solution (30 mL) and the resulting mixture was stirred for 5 minutes. The layers were then separated and the aqueous layer was re-extracted with DCM (50 mL). The combined organic layers were dried over anhydrous $Na_2SO_4$, filtered, and concen- $^1$H NMR ($CDCl_3$, 300 MHz); δ 8.33 (d, J=7.8 Hz, 1H), 8.21 (d, J=9.0 Hz, 2H), 7.67 (q, J=9.1 Hz, 4H), 7.50 (m, 2H), 6.91 (d, J=7.5 Hz, 1H), 5.70 (s, 2H), 5.67 (d, J=14.7 Hz, 1H), 5.50 (d, J=13.2 Hz, 1H), 5.29 (d, J=14.1 Hz, 1H), 4.95 (d, J=14.4 Hz, 1H), 4.31 (m, 2H), 3.56 (m, 1H), 3.34 (dd, J=5.2, 5.3 Hz, 1H), 2.85 (s, 3H), 1.32 (d, J=7.5 Hz, 3H), 1.26 (d, J=6.9 Hz, 3H), 0.95 (t, J=8 Hz, 9H), 0.61 (q, J=7.5 Hz, 6H).

General Procedure for the Nucleophilic Displacement of Mesylate 15

The crude mesylate 15 (0.46 mmol, 345 mg) was dissolved in dry ACN (100 mL) and stirred under $N_2$ atmosphere at rt. (Note: DMF and or THF could also be used as solvents or co-solvents). The nucleophile (1.0-1.2 eq) was then added and the resulting mixture aged for 24-72 h (until complete by TLC). The crude reaction mixture was concentrated to approximately 10 mL total volume, loaded onto a silica column, and purified with 1-5% water in ACN. Percent yields of 16: 40-86% (from CPI 6).

General Procedure for the Tandem 2-Step, 1-Pot Deprotection; Synthesis of 1-Carbon Naphthol Analogs (17)

TES-Protected intermediate 16 (300 mg) was placed in a 100 mL RBF equipped with a side arm, dissolved in THF/IPA (6 mL/6 mL), and cooled to 0° C. with stirring. 0.06N HCl solution (approximately 2-3 mL) was then added in 0.5 mL increments until the reaction pH=2.5-3.0 and then aged overnight at 0° C. The reaction mixture was then neutralized with 0.25 M sodium phosphate buffer (pH=7.0, approximately 2-3 mL). After adding 5% platinum on carbon catalyst to the mixture (0.5 mg catalyst/1.0 mg substrate), the flask was fitted with a hydrogen balloon, purged well with $H_2$, and allowed to age for 4-6 h at 0° C. The hydrogen source was then removed, the mixture diluted with EtOAc (20 mL) and DI water (20 mL), and the resulting mixture was stirred for 10 minutes at 0° C. The reaction mixture was then poured over a pad of celite, the celite pad washed well with DI water (25 mL) and EtOAc (25 mL), and the aqueous fraction lyophilized to a solid. Purification of the final products (17) was performed on either SP-207 or HP-20 resin.

General Procedure for the Synthesis of "2-Carbon" Naphthol Analogs 20

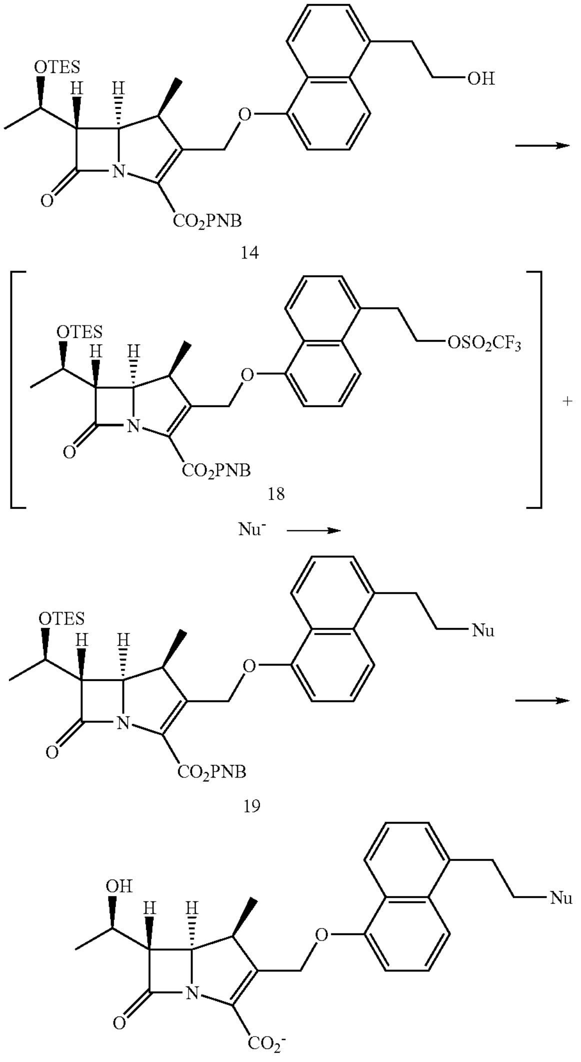

14

18

Nu⁻

19

20

Nu = amines (1°, 2° and 3°), thioureas, sulfonamides, thiols, etc.

All of the 2-carbon naphthol ammonium salt analogs as well as some of the neutral sulfonamide, thiourea, thiol, amine, or ether containing analogs with the general structure of 20 were synthesized from CPI 14. The three step procedure involves the generation and nucleophilic displacement of triflate intermediate 18 followed by the tandem 2-step, 1-pot deprotection sequence previously discussed in the general synthesis of 17. Purification of the final compounds was done on SP-207 or HP-20 resin using gradient elusions of DI water/IPA or DI water/acetone.

General Procedure for Formation and Nucleophilic Displacement of Triflate Intermediate 18

Alcohol 14 was dissolved in DCM and cooled down to −78° C. under nitrogen atmosphere. To the solution were added lutidine (2 eq.) and triflic anhydride (1.5 eq), respectively. After 30 min, a solution of the nucleophile in dry ACN was added, and the resulting mixture was gradually warmed to 0° C. and aged overnight at 0° C. The mixture was then concentrated undere vacuum and purified by a flash column chromatography on silica gel to afford a desired coupled intermediate 19.

General Procedure for the Tandem 2-Step, 1-Pot Deprotection; Synthesis of 2-Carbon Naphthol Analogs (20)

TES-Protected intermediate 19 (300 mg) was placed in a 100 mL RBF equipped with a side arm, dissolved in THF/IPA (6 mL/6 mL), and cooled to 0° C. with stirring. 0.06N HCl solution (approximately 2-3 mL) was then added in 0.5 mL increments until the reaction pH=2.5-3.0 and then aged overnight at 0° C. The reaction mixture was then neutralized with 0.25 M sodium phosphate buffer (pH=7.0, approximately 2-3 mL). After adding 5% platinum on carbon catalyst to the mixture (0.5 mg catalyst/1.0 mg substrate), the flask was fitted with a hydrogen balloon, purged well with $H_2$, and allowed to age for 4-6 h at 0° C. The hydrogen source was then removed, the mixture diluted with EtOAc (20 mL) and DI water (20 mL), and the resulting mixture was stirred for 10 minutes at 0° C. The reaction mixture was then poured over a pad of celite, the celite pad washed well with DI water (25 mL) and EtOAc (25 mL), and the aqueous fraction lyophilized to a solid. Purification of the final products (20) was performed on either SP-207 or HP-20 resin.

Examples of Charged (Cationic) 1-Carbon Naphthol CP Analogs

Example 1

TES-Protected N,N-Dimethylethylamine Intermediate 21

21

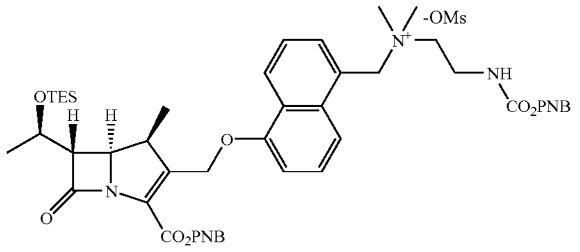

Percent yield; 98%: (yellow solid): $^1H$ NMR ($CDCl_3$, 300 MHz); δ 8.41 (d, J=7.8 Hz, 1H), 8.19 (J=8.1 Hz, 2H), 8.02 (d, J=8.4 Hz, 2H), 7.78 (m, 3H), 7.67 (d, J=8.7 Hz, 2H), 7.53 (m, 2H, 7.47 (m, 2H), 6.90 (d, J=7.8 Hz, 1H), 5.65 (d, J=13.5 Hz, 1H), 5.50 (d, J=13.5 Hz, 1H), 5.30 (d, J=14.4 Hz, 1H), 5.15

(m, 4H), 4.95 (d, J=13.2 Hz, 1H), 4.33 (m, 2H), 4.07 (m, 2H), 3.90 (m, 2H), 3.57 (m, 1H), 3.35 (dd, J=5.3, 3.8 Hz, 1H), 3.13 (bs, 6H), 2.86 (s, 3H), 1.33 (d, J=7.2 Hz, 3H), 1.26 (d, J=6.3 Hz, 3H), 0.95 (t, J=8.4 Hz, 9H), 0.61 (q, J=7.8 Hz, 6H).

N,N-Dimethylethylamine Analog 22

22

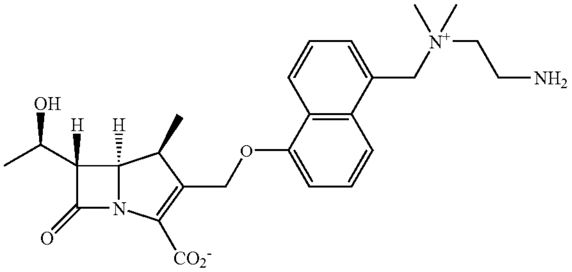

Percent yield; 31%: $^1$H NMR ($D_2O$+DMSO-d6, 300 MHz); δ 8.53 (d, J=7.8 Hz, 1H), 7.85 (m, 2H), 7.67 (m, 2H), 7.11 (d, J=8.1 Hz, 1H), 5.59 (d, J=6.3 Hz, 3H), 5.59 (d, J=15.0 Hz, 1H), 5.13 (s, 2H), 4.94 (d, J=15.0 Hz, 1H), 4.16 (m. 2H), 3.30 (m, 2H), 3.59 (m, 2H), 3.44 (m, 2H), 3.14 (s, 6H), 1.25 (d, J=7.5 Hz, 3H), 1.20 (d, J=6.0 Hz, 3H).

Example 2

TES-Protected N,N-Dimethylaminoethylene Guanidine Salt Intermediate 23

23

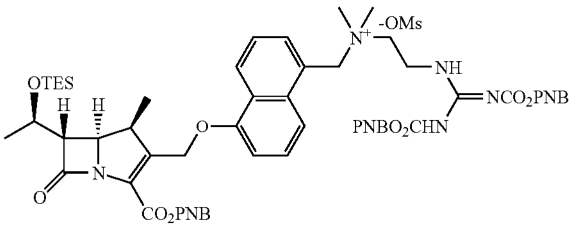

Percent yield; 84% (white solid): $^1$H NMR ($CDCl_3$, 300 MHz); δ 11.60 (bs, 1H), 9.01 (t, J=6 Hz, 1H), 8.36 (d, J=8 Hz, 1H), 8.15 (m, 6H), 7.93 (t, J=8.2 Hz, 2H), 7.66 (d, J=9 Hz, 2H), 7.46 (m, 6H), 6.86 (d, J=7.8 Hz, 1H), 5.60 (d, J=14.2 Hz, 1H), 5.49 (d, J=14.1 Hz, 1H), 5.28 (m, 4H), 5.23 (s, 2H), 4.93 (d, J=14 Hz, 1H), 4.32 (m, 2H), 4.24 (m. 2H), 4.15 (m, 2H), 3.55 (m, 1H), 3.35 (dd, J=6, 3 Hz, 1H), 3.22 (bs, 6H), 2.84 (s, 3H), 2.35 (bs, 1H), 1.30 (d, J=7.2 Hz, 3H), 1.26 (d, J=7.5 Hz, 3H), 0.94 (t, J=8.1 Hz, 9 J=6 Hz, H), 0.60 (q, J=7.8 Hz).

N,N-Dimethylaminoethylene Guanidine Salt Analog 24

24

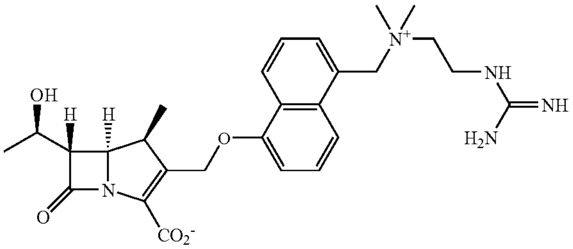

Percent yield; 46%: $^1$H NMR ($D_2O$, 400 MHz); δ 8.29 (d, J=8.4 Hz, 1H), 7.62 (d, J=8.4 Hz, 2H), 7.44 (m, 2H), 6.83 (d, J=7.2 Hz, 1H), 5.27 (d, J=14.4 Hz, 1H), 4.89 (q, J=13.8 Hz, 2H), 4.68 (d, J=14.4 Hz, 1H), 3.99 (t, J=6.6 Hz, 1H), 3.86 (d, J=10 Hz, 1H), 3.62 (m, 2H), 3.53 (m, 2H), 3.26 (m, 1H), 3.14 (m, 1H), 2.95 (s, 3H), 2.94 (s, 3H), 1.07 (d, J=6.4 Hz, 3H), 0.99 (d, J=8.0 Hz, 3H).

Example 3

TES-Protected N,N-Dimethylethylene Thioguanidine Salt Intermediate 25

25

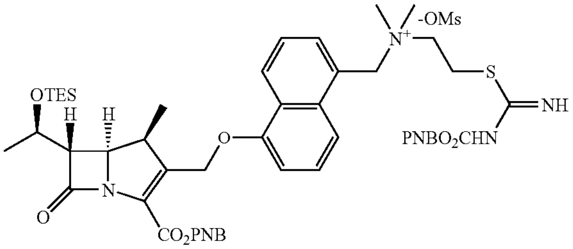

Percent yield; 48% (light yellow solid): $^1$H NMR ($CDCl_3$, 300 MHz); δ 8.96 (bs, 1H), 8.39 (d, J=7.8 Hz, 1H), 8.19 (d, J=9.0 Hz, 2H), 7.87 (d, J=6.3 Hz, 1H), 7.80 (s, 1H), 7.76 (d, J=7.5 Hz, 2H), 7.67 (d, J=8.4 Hz, 2H), 7.52 (t, J=8.1 Hz, 1H), 7.41 (t, J=8.1 Hz, 1H), 7.22 (d, J=8.1 Hz, 2H), 6.85 (d, J=8.7 Hz, 1H), 5.62 (d, J=14.4 Hz, 1H), 5.49 (d, J=14.1 Hz, 1H), 5.31 (bs, 2H), 5.30 (d, J=13.5 Hz, 1H), 5.02 (bs, 2H), 4.94 (d, J=14.4 Hz, 1H), 4.35 (m, 2H), 4.17 (m, 2H), 3.75 (m, 2H), 3.61 (m, 1H), 3.37 (dd, J=5.1, 6.0 Hz, 1H), 3.14 (bs, 6H), 2.75

(s, 3H), 1.34 (d, J=7.5 Hz, 3H), 1.27 J=6.9 Hz, 3H), 0.95 (t, J=7.5 Hz, 9H), 0.61 (q, J=7.5 Hz, 6H).

N,N-Dimethylethylene Thioguanidine Salt Analog 26

26

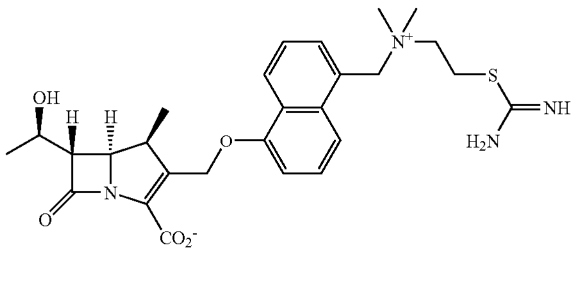

Percent yield; 25%: $^1$H NMR ($D_2O$+acetone-d6, 300 MHz); δ 8.35 (d, J=7.8 Hz, 1H), 7.72 (d, J=8.7 Hz, 2H), 7.50 (t, J=7.5 Hz, 2H), 6.99 (d, J=6.3 Hz, 1H), 5.51 (d, J=13.2 Hz, 1H), 4.99 (s, 2H), 4.79 (d, J=14.4 Hz, 1H), 4.04 (m, 2H), 3.73 (m, 2H), 3.60 (m, 2H), 3.25 (m, 2H), 3.04 (s, 6H), 1.12 (d, J=6.6 Hz, 3H), 1.08 (d, J=6.6 Hz, 3H).

Example 4

TES-Protected N,N-Dimethylpropyl Thioguanidine Salt Intermediate 27

27

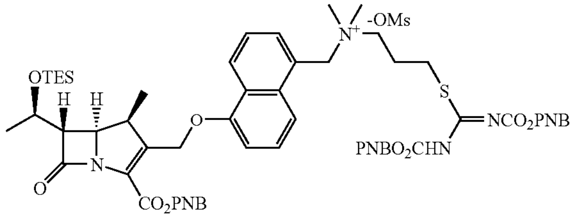

Percent yield; 56% (light yellow solid): 1H NMR (CDCl3, 300 MHz); δ 11.83 (bs, 1H), 8.35 (d, J=8.1 Hz, 1H), 8.19 (d, J=8.7 Hz, 4H), 8.02 (m, 2H), 7.91 (d, J=9.0 Hz, 1H), 7.85 (d, J=7.5 Hz, 1H), 7.67 (d, J=8.1 Hz, 2H), 7.48 (m, 6H), 6.88 (d, J=8.4 Hz, 1H), 5.63 (d, J=14.4 Hz, 1H), 5.49 (d, J=14.4 Hz, 1H), 5.29 (m, 4H), 5.22 (bs, 2H), 5.15 (bs, 2H), 4.94 (d, J=14.7 Hz, 1H), 4.34 (m, 2H), 3.88 (t, J=6.6 Hz, 2H), 3.58 (m, 1H), 3.36 (dd, J=4.6, 6.2 Hz, 1H), 3.16 (bs, 8H), 2.83 (s, 3H), 2.34 (m, 2H), 1.32 (d, J=7.2 Hz, 3H), 1.26 (d, J=5.4 Hz, 3H), 0.95 (t, J=8.1 Hz, 9H), 0.61 (q, J=7.7 Hz, 6H).

N,N-Dimethylpropyl Thioguanidine Salt Analog 28

28

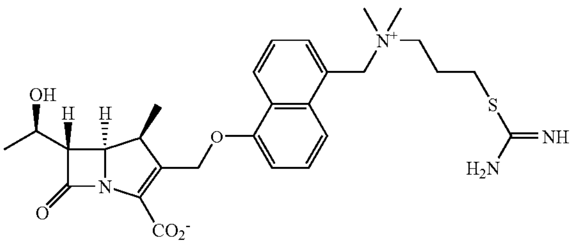

Percent yield; 19%: 1H NMR (D2O, 400 MHz); δ 8.40 (d, J=8.0 Hz, 1H), 7.74 (m, 2H), 7.56 (d, J=8.0 Hz, 2H), 6.98 (d, J=8.0 Hz, 1H), 5.46 (d, J=14.0 Hz, 1H), 4.16 (t, J=6.4 Hz, 1H), 4.03 (d, J=9.6 Hz, 1H), 3.48 (m, 2H), 3.41 (m, 1H), 3.31 (m, 1H), 3.12 (m, 2H), 3.05 (bs, 6H), 2.21 (m, 2H), 1.22 (d, J=6.0 Hz, 3H), 1.14 (d, J=6.8 Hz, 3H).

Example 5

TES-Protected N,N-Dimethylaminoethylene Guanidine Salt Intermediate 29

29

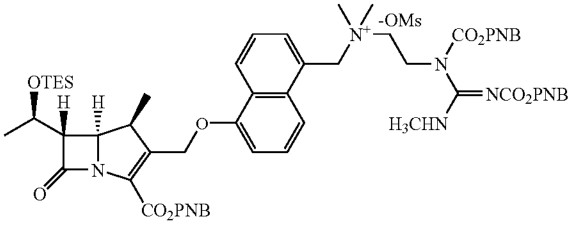

Percent yield; 55%: $^1$H NMR ($CDCl_3$, 300 MHz): δ 9.10 (br s, 1H), 8.43 (d, J=8.2 Hz, 1H), 8.20 (d, J=9.2 Hz, 2H), 8.12 (d, J=9.4 Hz, 2H), 8.09 (d, J=8.6 Hz, 2H), 7.82 (m, 2H), 7.68 (d, J=8.8 Hz, 2H), 7.52(m, 2H), 7.47 (d, J=8.5 Hz, 2H), 7.42 (d, J=7.9 Hz, 2H), 6.92 (d, J=8.1 Hz, 1H), 5.67(d, J=14.5 Hz, 1H), 5.52 (d, J=14.0, 1H), 5.32 (d, J=14.0, 1H), 5.21 (s, 2H), 5.13 (s, 2H), 5.06 (s, 2H), 4.97 (d, J=14 Hz, 1H), 4.33 (m, 2H), 4.26 (m, 2H), 4.13 (m, 2H), 3.56 (m, 1H), 3.36 (dd, J=2.9, 4.5 Hz, 1H), 3.12 (s, 6H), 3.01(d, J=3.7 Hz, 3H), 2.85 (s, 3H), 1.33 (d, J=7.5 Hz, 3H), 1.27 (d, J=6.1 Hz, 3H), 0.95 (t, J=7.8 Hz, 9H), 0.62 (q, J=7.8 Hz, 6H).

N,N-Dimethylaminoethylene Guanidine Salt Analog 30

30

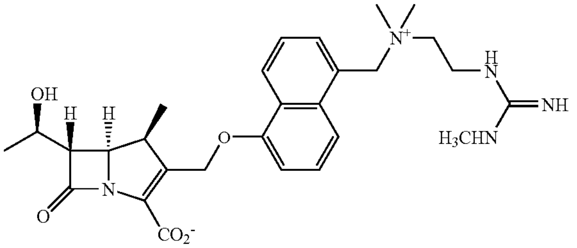

Percent yield; 37%: $^1H$ NMR ($D_2O$, 600 MHz): δ 8.38 (d, J=8.6, 1H), 7.76 (d, J=7.1 Hz, 1H), 7.74 (d, J=8.6 Hz, 1H), 7.58 (m, 1H), 7.55 (t, J=8.1 Hz, 1H), 6.93 (d, J=8.1 Hz, 1H), 5.35 (d, J=13.8 Hz, 1H), 5.09 (d, J=13.8 Hz, 1H), 4.99 (d, J=13.8 Hz, 1H), 4.13 (m, 1H), 3.99 (m, 1H), 3.76 (t, J=6.6 Hz, 2H), 3.68 (t, J=6.6 Hz, 2H), 3.39 (dd, J=2.9, 6.2 Hz, 1H), 3.28 (m, 1H), 3.11 (s, 3H), 3.08 (s, 3H), 2.80 (s, 3H), 1.24 (d, J=6.2, 3H), 1.11 (d, J=7.1, 3H).

Example 6

TES-Protected N,N-Dimethylpropyl Thioguanidine Salt Intermediate 31

31

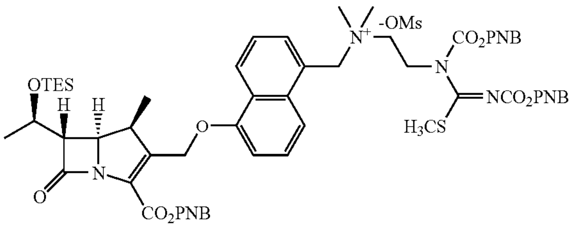

Percent yield; 65%: $^1H$ NMR ($CDCl_3$, 300 MHz): δ 8.39 (d, J=9.0 Hz, 1H), 8.19 (d, J=8.4 Hz, 2H), 8.12 (d, J=7.6 Hz, 2H), 8.07 (d, J=7.6 Hz, 2H), 7.97 (d, J=9.0 Hz, 1H), 7.91 (d, J=7.6 Hz, 1H), 7.68 (d, J=8.4 Hz, 2H), 7.51-7.41 (m, 6H), 6.89 (d, J=7.6 Hz, 1H), 5.64(d, J=12.7 Hz, 1H), 5.51 (d, J=14.1, 1H), 5.32 (m, 3H), 5.19 (s, 2H), 5.11 (s, 2H), 4.96 (d, J=14.1 Hz, 1H), 4.33 (m, 4H), 4.03 (m, 2H), 3.57 (m, 1H), 3.35 (m, 1H), 3.25 (s, 6H), 2.89 (s, 3H), 2.40 (s, 3H), 1.32 (d, J=7.2 Hz, 3H), 1.27 (d, J=5.4 Hz, 3H), 0.94 (t, J=7.8 Hz, 9H), 0.62 (q, J=7.8 Hz, 6H).

N,N-Dimethylpropyl Thioguanidine Salt Analog 32

32

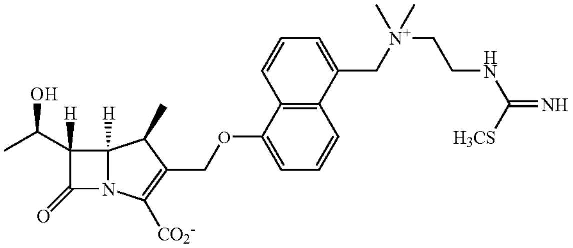

Percent yield; 13%: $^1H$ NMR ($D_2O$, 600 MHz): δ 8.47 (d, J=8.5, 1H), 7.78 (m, 2H), 7.60 (m, 2H), 7.03 (d, J=7.6 Hz, 1H), 5.55 (d, J=13.7 Hz, 1H), 5.05 (d, J=3.5 Hz, 2H), 4.92 (d, J=13.7 Hz, 1H), 4.17 (t, J=6.4 Hz, 1H), 4.07 (dd, J=2.8, 9.8 Hz, 1H), 3.80 (t, J=6.0 Hz, 2H), 3.69 (t, J=6.0 Hz, 2H), 3.43 (dd, J=2.8, 5.9 Hz, 1H), 3.32 (m, 1H), 3.09 (s, 6H), 2.44 (s, 3H), 1.24 (d, J=6.4, 3H), 1.19 (d, J=7.0, 3H).

Example 7

TES-Protected N,N-Dimethylacetamide Intermediate 33

33

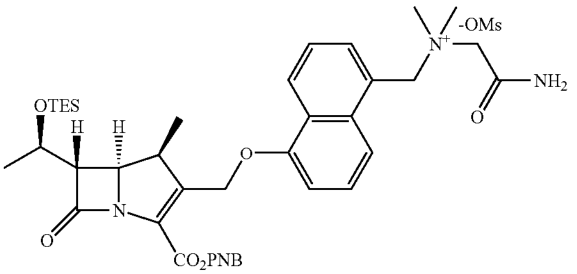

Percent yield; 52%: $^1H$ NMR (Acetone-$d_6$, 300 MHz); δ 8.68 (bs, 1H), 8.49 (d, J=8.1 Hz, 1H), 8.31 (d, J=9.0 Hz, 1H), 8.17 (d, J=7.8 Hz, 2H), 8.05 (d, J=7.2 Hz, 1H), 7.81 (d, J=9.0 Hz, 1H), 7.62-7.52 (m, 2H), 7.23 (bs, 1H), 7.04 (d, J=7.5 Hz, 1H), 5.62 (d, J=14.4 Hz, 1H), 5.58 (s, 2H), 5.54 (d, J=14.1 Hz, 1H), 5.35 (d, J=14.4 Hz, 1H), 5.07 (d, J=14.4 Hz, 1H), 4.89 (bs, 2H), 4.40-4.32 (m, 2H), 3.68 (m, 1H), 3.51 (m, 1H), 3.42

(s, 6H), 2.87 (s, 3H), 1.34 (d, J=7.5 Hz, 3H), 1.24 (d, J=6.9 Hz, 3H), 0.94 (t, J=8.4 Hz, 9H), 0.61 (q, J=7.8 Hz, 6H).

N,N-Dimethylacetamide Analog 34

34

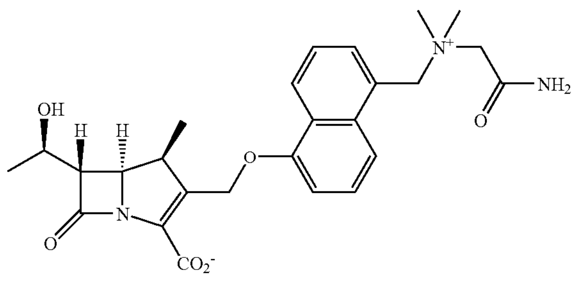

Percent yield; 37%: $^1$H NMR ($D_2O$, 300 MHz); δ 8.21 (d, J=8.1 Hz, 1H), 7.58 (bs, 2H), 7.41 (bs, 2H), 6.83 (d, J=6.3 Hz, 1H), 5.33 (d, J=14.4 Hz, 1H), 4.99 (s, 2H), 4.76 (d, J=14.4 Hz, 1H), 4.08 (s, 2H), 4.12-3.96 (m, 2H), 3.33 (m, 1H), 3.24 (m, 1H), 3.07 (s, 6H), 1.17 (d, J=6.0 Hz, 3H), 1.06 (d, J=6.0 Hz, 3H).

Example 8

TES-Protected N,N-Dimethyl Thioguanidine Salt Intermediate 35

35

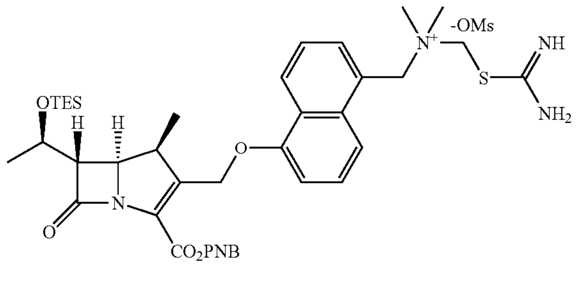

Percent yield; 22%: $^1$H NMR (Acetone-$d_6$, 300 MHz); δ 8.74 (bs, 1H), 8.17 (d, J=6.9 Hz, 1H), 8.14 (d, J=7.8 Hz, 2H), 7.76 (d, J=9.3 Hz, 2H), 7.68 (d, J=8.7 Hz, 1H), 7.55 (d, J=6.9 Hz, 1H), 7.41 (t, J=8.1 Hz, 1H), 7.35 (t, J=6.9 Hz, 1H), 6.91 (d, J=7.8 Hz, 1H), 5.55 (d, J=16.5 Hz, 1H), 5.50 (d, J=15.0 Hz, 1H), 5.30 (d, J=14.4 Hz, 1H), 5.06 (bs, 2H), 4.97 (d, J=13.5 Hz, 1H), 4.83 (bs, 2H), 4.65 (bs, 2H), 4.31 (m, 2H), 3.60 (m, 1H), 3.45 (m, 1H), 3.23 (s, 6H), 2.53 (s, 3H), 1.28 (d, J=7.2 Hz, 3H), 1.20 (d, J=5.7 Hz, 3H), 0.92 (t, J=7.8 Hz, 9H), 0.58 (q, J=8.7 Hz, 6H).

N,N-Dimethyl Thioguanidine Salt Analog 36

36

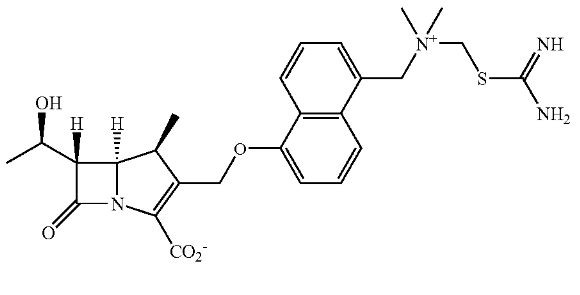

$^1$H NMR ($D_2O$, 400 MHz); δ 8.03 (d, J=8.4 Hz, 1H), 7.52 (d, J=9.2 Hz, 1H), 7.35-7.29 (m, 2H), 7.23 (t, J=8.0 Hz, 1H), 6.82 (d, J=7.6 Hz, 1H), 5.40 (d, J=13.2 Hz, 1H), 4.74 (d, J=13.6 Hz, 1H), 4.42 (s, 2H), 4.41 (s, 2H), 4.00 (p, J=6.0 Hz, 1H), 3.83 (dd, J=4.4, 8.8 Hz, 1H), 3.21 (dd, J=2.4, 4.4 Hz, 1H), 3.10 (m, 1H), 2.69 (s, 6H), 1.03 (d, J=6.4 Hz, 3H), 0.97 (d, J=6.8 Hz, 3H).

Example 9

TES-Protected N,N-Dimethyl Morpholine Intermediate 37

37

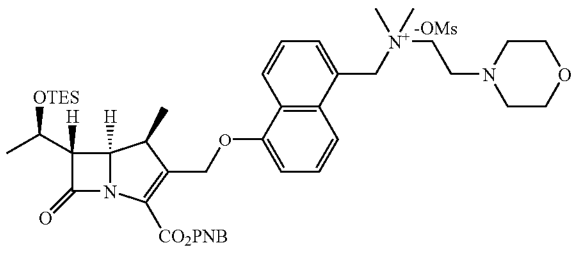

Percent yield; 92%: $^1$H NMR (Acetone-$d_6$, 300 MHz); δ 8.48 (d, J=8.7 Hz, 1H), 8.21 (d, J=8.7 Hz, 1H), 8.18 (d, J=8.7 Hz, 2H), 8.03 (d, J=7.2 Hz, 1H), 8.00 (d, J=8.4 Hz, 1H), 7.58 (t, J=7.5 Hz, 1H), 7.56 (t, J=7.5 Hz, 1H), 7.04 (d, J=7.8 Hz, 1H), 5.62 (d, J=14.4 Hz, 1H), 5.53 (d, J=13.8 Hz, 1H), 5.44 (s, 2H), 5.35 (d, J=14.1 Hz, 1H), 5.08 (d, J=13.5 Hz, 1H), 4.40-4.30 (m, 2H), 4.03 (m, 2H), 3.61 (t, J=4.5 Hz, 4H), 3.55 (m, 1H), 3.50 (m, 1H), 3.31 (s, 6H), 2.98 (t, J=4.5 Hz, 2H), 2.58

(bs, 4H), 2.46 (s, 3H), 1.35 (d, J=7.2 Hz, 3H), 1.26 (d, J=6.3 Hz, 3H), 0.94 (t, J=8.1 Hz, 9H), 0.61 (q, J=7.8 Hz, 6H).

TES-Protected N,N-Dimethyl Morpholine Salt Intermediate 38

38

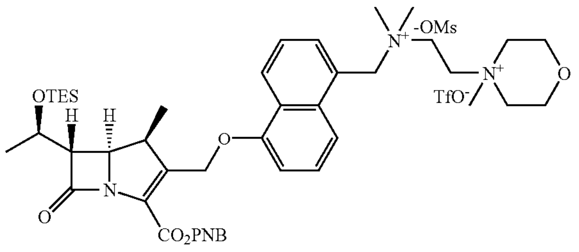

Percent yield; 85%: $^1$H NMR (Acetone-$d_6$, 300 MHz); δ 8.53 (d, J=8.4 Hz, 1H), 8.18 (d, J=9.0 Hz, 2H), 8.10 (d, J=9.0 Hz, 1H), 8.01 (d, J=6.6 Hz, 1H), 7.81 (d, J=8.7 Hz, 2H), 7.65-7.54 (m, 2H), 7.08 (d, J=7.8 Hz, 1H), 5.63 (d, J=13.8 Hz, 1H), 5.54 (d, J=14.7 Hz, 1H), 5.42 (bs, 2H), 5.36 (d, J=14.1 Hz, 1H), 4.62 (bs, 2H), 4.35 (m, 2H), 4.15 (m, 4H), 3.97-3.60 (m, 8H), 3.62 (s, 3H), 3.43 (s, 6H), 3.09 (s, 3H), 1.35 (d, J=6.5 Hz, 3H), 1.23 (d, J=6.0 Hz, 3H), 0.94 (t, J=8.4 Hz, 9H), 0.61 (q, J=7.8 Hz, 6H).

N,N-Dimethyl Morpholine Salt Analog 39

39

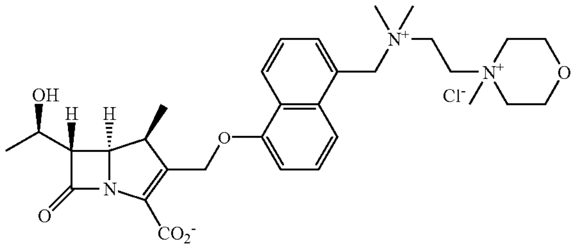

Percent yield; 23%: $^1$H NMR ($D_2O$, 400 MHz); δ 8.29 (d, J=8.0 Hz, 1H), 7.66 (d, J=7.2 Hz, 1H), 7.62 (d, J=8.0 Hz, 1H), 7.45 (q, J=7.2 Hz, 2H), 6.81 (d, J=7.6 Hz, 1H), 5.21 (d, J=14.0 Hz, 1H), 4.95 (m, 2H), 4.69 (d, J=13.6 Hz, 1H), 4.02-3.84 (m, 10H), 3.43 (m, 4H), 3.24 (dd, J=2.8, 4.4 Hz, 1H), 3.14 (s, 3H), 3.11 (m, 1H), 3.01 (s, 3H), 2.98 (s, 3H), 1.06 (d, J=6.4 Hz, 3H), 0.97 (d, J=7.6 Hz, 3H).

Example 10

TES-Protected N,N-Dimethyl DABCO Salt Intermediate 40

40

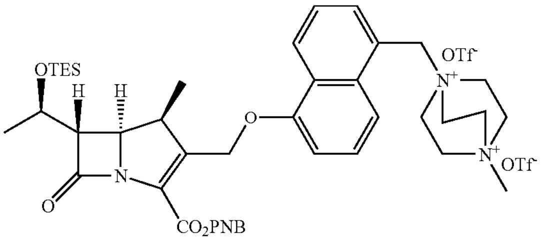

Percent yield; 51%: $^1$H NMR (Acetone-$d_6$, 300 MHz); δ 8.53 (d, J=8.7 Hz, 1H), 8.17 (d, J=7.8 Hz, 2H), 8.05 (d, J=8.7 Hz, 1H), 7.98 (d, J=6.6 Hz, 1H), 7.80 (d, J=8.1 Hz, 2H), 7.66-7.55 (m, 2H), 7.11 (d, J=7.5 Hz, 1H), 5.62 (d, J=14.1 Hz, 1H), 5.68 (s, 2H), 5.54 (d, J=14.1 Hz, 1H), 5.36 (d, J=14.8 Hz, 1H), 5.10 (d, J=13.8 Hz, 1H), 4.48-4.30 (m, 14H), 3.67 (m, 1H), 3.61 (s, 3H), 3.52 (m, 1H), 1.34 (d, J=7.2 Hz, 3H), 1.23 (d, J=5.7 Hz, 3H), 0.95 (t, J=7.5 Hz, 9H), 0.61 (q, J=8.1 Hz, 6H).

N,N-Dimethyl DABCO Salt Analog 41

41

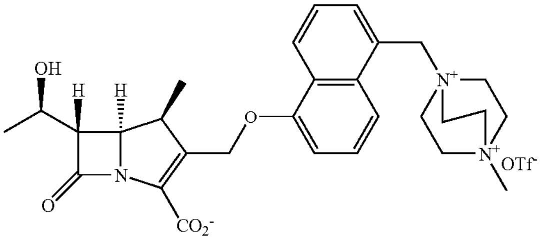

Percent yield; 13%: $^1$H NMR ($D_2O$, 400 MHz); δ 8.38 (d, J=8.8 Hz, 1H), 7.64-7.59 (m, 2H), 7.50-7.45 (m, 2H), 6.92 (d, J=7.2 Hz, 1H), 5.39 (d, J=14.0 Hz, 1H), 5.11 (m, 2H), 4.79 (d, J=14.0 Hz, 1H), 4.02 (t, J=6.4 Hz, 1H), 3.89 (m, 7H), 3.78 (m, 6H), 3.27 (dd, J=2.8, 4.4 Hz, 1H), 3.20 (m, 1H), 3.14 (s, 3H), 1.07 (d, J=6.4 Hz, 3H), 1.03 (d, J=7.2 Hz, 3H).

Example 11

TES-Protected N,N-Dimethylpropyl Guanidine Salt Intermediate 42

42

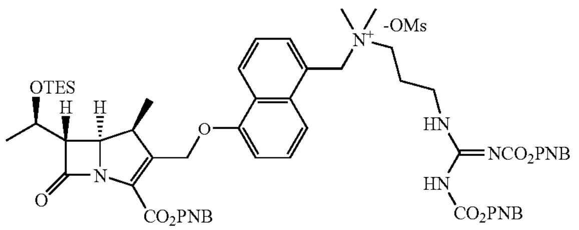

Percent yield: 75%; $^1$H NMR ($CDCl_3$/MeOD-d6, 300 MHz); δ 0.50 (q, J=8.1 Hz, 6H), 0.8 (t, J=8.4 Hz, 9H), 1.20 (d, J=6.0 Hz, 3H), 1.25 (d, J=7.5 Hz, 3H), 2.1 (m, 2H), 2.80 (s, 3H), 3.20 (s, 6H), 3.25 (m, 1H), 3.6 (m, 4H), 4.80 (m, 2H) 4.30 (m, 2H), 4.95 (d, 1H), 5.10 (s, 2H), 5.2 (s, 2H), 5.35 (d, 1H), 5.60 (d, 1H), 6.90 (d, 1H), 7.50 (m, 6H), 7.65 (m, 2H), 7.90 (m, 2H), 8.20 (m, 6H), 8.35 (t, 1H).

N,N-Dimethylpropyl Guanidine Salt Analog 43

43

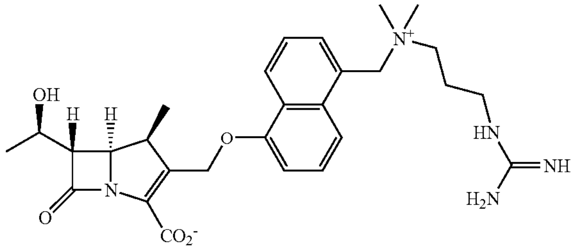

Percent yield: 30%; $^1$H NMR ($D_2O$, 400 MHz): δ 1.14 (d, J=7.3 Hz, 3H), 1.18 (d, J=7.7 Hz, 3H), 2.05 (m, 2H), 2.60 (m, 1H), 3.06 (s, 6H), 3.21 (m, 2H), 3.52 (m, 2H), 4.03 (M, 1H), 4.13 (m, 2H), 4.94 (d, 1H), 5.52 (d, 1H), 7.01 (d, 1H), 7.58 (m, 2H), 7.77 (m, 2H), 8.44 (d, 1H).

Example 12

TES-Protected Piperazine Guanidine Salt Intermediate 44

44

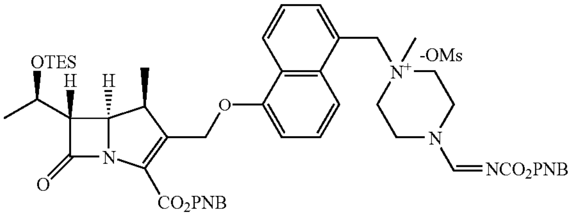

Percent yield: 62%; $^1$H NMR (acetone-$D_6$, 300 MHz): δ 0.50 (q, J=8.1 Hz, 6H), 0.8 (t, J=8.4 Hz, 9H), 1.20 (d, J=6.0 Hz, 3H), 1.25 (d, J=7.5 Hz, 3H), 2.45 (s, 3H), 2.80 (s, 3H), 3.50 (s, 4H), 3.65 (m, 1H), 3.90 (m, 2H), 4.20 (m, 2H), 4.35 (m, 2H), 4.60 (m, 1H), 5.10 (d, 1H), 5.20 (s, 2H), 5.35 (d, 1H), 5.50 (s, 2H), 5.57 (d, 1H), 5.60 (d, 1H), 7.00 (d, 1H), 7.60 (m, 4H), 7.80 (d, 2H), 8.10 (d, 1H), 8.20 (d, 4H), 8.25 (d, 1H), 8.45 (d, 1H), 8.50 (s, 1H).

Piperazine Guanidine Salt Analog 45

45

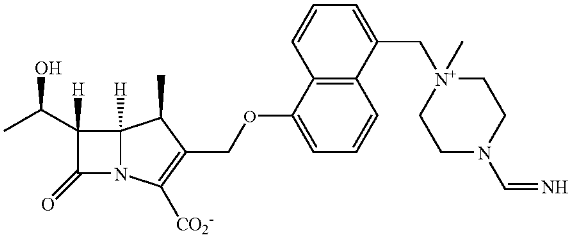

Percent yield: 30%; $^1$H NMR ($D_2O$, 400 MHz): δ 1.14 (d, J=7.3 Hz, 3H), 1.21 (d, J=7.7 Hz, 3H), 3.00 (s, 3H), 3.15 (M, 4H), 3.38 (m, 4H), 3.49 (m, 2H), 4.02 (m, 1H), 4.16 (m, 1H), 5.00 (d, 1H), 5.49 (d, 1H), 6.98 (d, 1H), 7.55 (m, 3H), 7.75 (m, 2H), 8.40 (d, 1H), 8.50 (s, 1H).

Example 13

TES-Protected Pyrrolidine Salt Intermediate 46

46

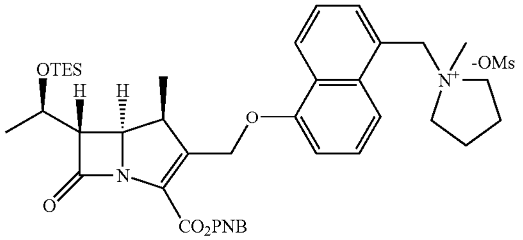

Percent yield: 78%; $^1$H NMR (acetone-$D_6$, 300 MHz): δ 0.50 (q, J=8.1 Hz, 6H), 0.8 (t, J=8.4 Hz, 9H), 1.20 (d, J=6.0 Hz, 3H), 1.25 (d, J=7.5 Hz, 3H), 2.45 (s, 3H), 2.30 (m, 4H), 2.50 (s, 3H), 2.90 (m, 2H), 3.15 (s, 3H), 3.50 (m, 1H), 3.65 (m, 3H), 4.00 (m, 2H), 4.35 (m, 2H), 5.05 (d, 1H), 5.40 (d, 1H), 5.50 (s, 2H), 5.55 (d, 1H), 5.60 (d, 1H), 7.00 (d, 1H), 7.50 (m, 2H) 7.75 (d, 2H), 8.15 (d, 1H), 8.20 (d, 2H), 8.35 (d, 1H), 8.45 (d, 1H).

Pyrrolidine Salt Analog 47

47

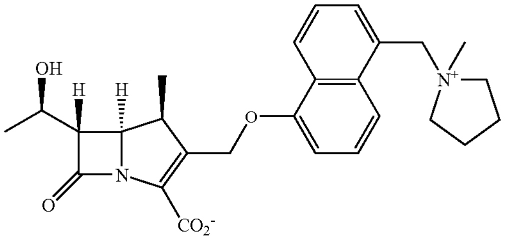

Percent yield: 31%; $^1$H NMR ($D_2O$, 400 MHz): δ 1.08 (d, J=7.3 Hz, 3H), 1.17 (d, J=7.7 Hz, 3H), 2.14 (brs, 4H), 2.86 (s, 3H), 3.26 (m, 1H), 3.35 (m, 3H), 3.35 (m, 2H), 3.98 (m, 1H), 4.15 (m, 1H), 4.88 (d, 1H), 5.41 (d, 1H), 6.90 (d, 1H), 7.47 (m, 2H), 7.69 (m, 2H), 8.28 (d, 1H).

Example 14

TES-Protected Pyrrolidine Salt Intermediate 48

48

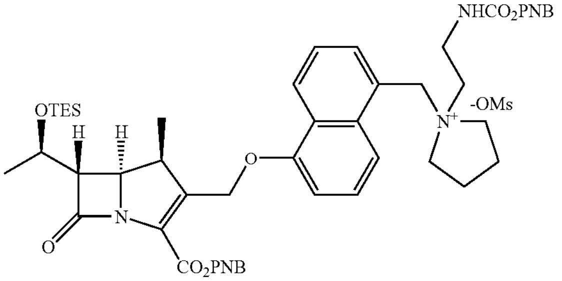

Percent yield: 93%; $^1$H NMR ($CDCL_3$, 300 MHz) δ 0.50 (q, J=8.1 Hz, 6H), 0.8 (t, J=8.4 Hz, 9H), 1.20 (d, J=6.0 Hz, 3H), 1.25 (d, J=7.5 Hz, 3H), 1.85 (m, 2H), 2.10 (m, 2H), 2.80 (s, 3H), 3.30 (m, 4H), 3.45 (m, 1H), 3.70 (m, 2H), 3.95 (m, 4H), 4.30 (m, 2H), 4.95 (d, 1H), 5.10 (s, 2H), 5.15 (s, 2H), 5.30 (d, 1H), 5.50 (d, 1H), 5.65 (d, 1H), 6.85 (d, 1H), 7.45 (m, 5H), 5.65 (m, 3H), 8.00 (d, 2H), 8.20 (d, 2H), 8.35 (d, 1H).

Pyrrolidine Salt Analog 49

49

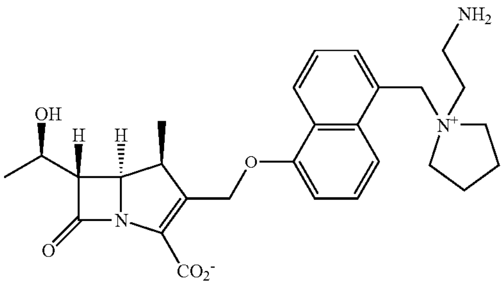

Percent yield: 20%; $^1$H NMR ($D_2O$, 400 MHz): δ 1.11 (d, J=7.3 Hz, 3H), 1.17 (d, J=7.7 Hz, 3H), 1.98 (m, 4H), 3.40 (m, 9H), 4.00 (m, 1H), 4.15 (m, 1H), 4.99 (d, 1H), 5.45 (d, 1H), 6.95 (d, 1H), 7.53 (m, 3H), 7.68 (m, 1H), 8.34 (d, 1H).

Example 15

TES-Protected Pyrrolidine Salt Intermediate 50

50

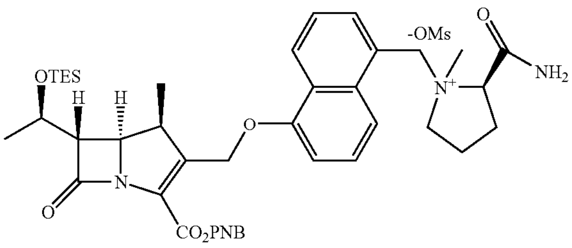

Percent yield: 66%; $^1$H NMR ($CDCL_3$, 300 MHz): δ 0.51 (q, J=8.1 Hz, 6H), 0.84 (t, J=8.4 Hz, 9H), 1.24 (d, J=6.0 Hz, 3H), 1.25 (d, J=7.5 Hz, 3H), 1.80 (m, 3H), 1.95 (m, 1H), 2.00 (s, 3H), 2.30 (m, 1H), 2.55 (m, 1H), 2.60 (s, 3H), 3.20 (m, 2H), 3.65 (m, 1H), 4.50 (m, 2H), 4.95 (d, 1H), 5.15 (brs, 1H), 5.30 (m, 3H), 5.50 (d, 1H), 5.60 (d, 1H), 6.85(d, 1H), 6.95 (brs, 1H), 7.45 (m, 4H), 7.80 (m, 3H), 8.15 (d, 2H).

Pyrrolidine Salt Analog 51

51

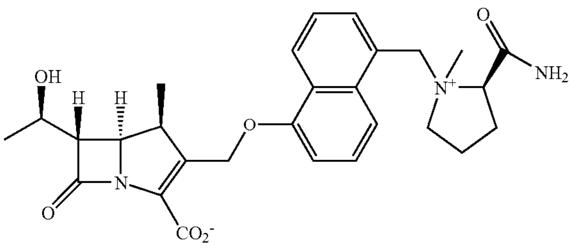

Percent yield: 30%; $^1$H NMR ($D_2O$, 400 MHz): δ 1.05 (d, J=7.3 Hz, 3H), 1.15 (d, J=7.7 Hz, 3H), 1.60 (m, 2H), 1.75 (m, 1H), 2.20 (m, 1H), 2.50 (m, 1H), 2.60 (s, 3H), 3.10 (m, 1H), 3.25 (m, 1H) 3.35 (m, 1H), 3.85 (d, 1H), 4.00 (d, 1H), 4.85 (d, 1H), 5.50 (d, 1H), 7.00 (d, 1H) 7.40 (m, 3H), 7.83 (d, 1H), 8.15 (d, 1H).

Examples of Uncharged (Neutral) 1-Carbon Naphthol CP Analogs

Example 16

TES-Protected Piperazine Intermediate 52

52

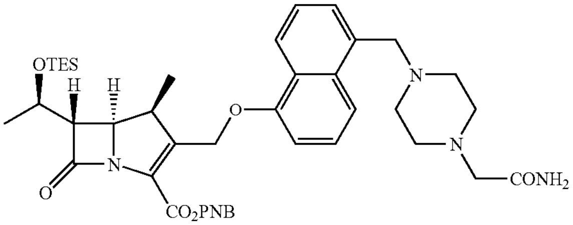

Percent yield: 65%; $^1$H NMR ($CDCl_3$, 300 MHz); δ 8.21 (d, J=8.4 Hz, 3H), 7.86 (d, J=9.3 Hz, 1H), 7.67 (d, J=8.4 Hz, 2H), 7.52 (q, J=6.9 Hz, 2H), 7.41 (m, 2H), 7.09 (bs, 1H), 6.84 (d, J=6.9 Hz, 1H), 5.64 (d, J=14.7 Hz, 1H), 5.50 (d, J=13.2 Hz, 2H), 5.29 (d, J=13.8 Hz, 1H), 4.93 (d, J=14.7 Hz, 1H), 4.30 (m, 2H), 3.92 (bs, 2H), 3.57 (m, 1H), 3.33 (dd, J=5.2, 2.6 Hz, 1H), 3.02 (s, 2H), 2.58 (bs, 8H), 1.31 (d, J=7.2 Hz, 3H), 1.26 (d, J=7.2 Hz, 3H), 0.95 (t, J=7.8 Hz, 9H), 0.61 (q, J=7.8 Hz, 6H).

Piperazine Analog 53

53

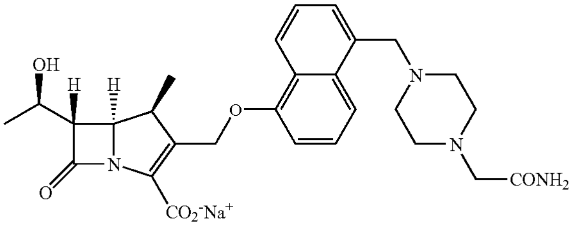

Percent yield: 32%; $^1$H NMR ($D_2O$, 400 MHz); δ 8.18 (d, J=8.4 Hz, 1H), 7.60 (d, J=8.0 Hz, 1H), 7.54 (d, J=7.6 Hz, 1H), 7.46 (t, J=7.7 Hz, 1H), 7.38 (m, 1H), 6.85 (d, J=8.0 Hz, 1H), 5.18 (d, J=12.8 Hz, 1H), 4.59 (d, J=13.6 Hz, 1H), 4.39 (s, 2H), 4.09 (m, 1H), 3.77 (d, J=8.8 Hz, 1H), 3.24 (m, 1H), 3.13 (m, 7H), 2.68 (s, 4H), 1.14 (d, J=5.2 Hz, 3H), 0.95 (d, J=7.2 Hz, 3H).

Example 16a

TES-Protected Thiourea Intermediate 52a

52a

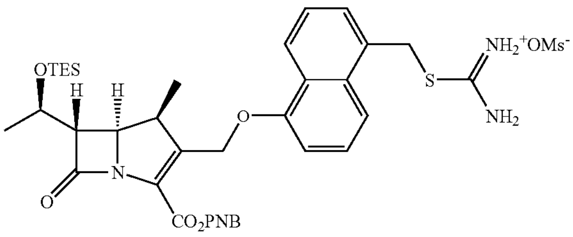

Percent yield: 67%; $^1$H NMR (acetone-$d_6$, 300 MHz): δ 9.46 (br s, 3H), 8.34 (d, J=8.7 Hz, 1H), 8.21 (d, J=8.6 Hz, 2H), 7.83 (m, 3H), 7.78 (d, J=7.2 Hz, 1H), 7.52 (t, J=8.7 Hz 1H), 7.49 (t, J=7.2 Hz, 1H), 7.04 (d, J=8.7 Hz, 1H), 5.66 (d, J=14.0 Hz, 1H), 5.56 (d, J=13.8 Hz, 1H), 5.37 (d, J=13.8, 1H), 5.06 (m, 3H), 4.39 (m, 2H), 3.65 (dq, J=10.6, 7.4 Hz, 1H), 3.50 (t, J=3.5 Hz, 1H), 2.56 (s, 3H), 1.35 (d, J=7.3 Hz, 3H), 1.24 (d, J=7.0 Hz, 3H), 0.94 (t, J=7.8 Hz, 9H), 0.62 (q, J=7.8 Hz, 6H).

Thiourea Analog 53a

53a

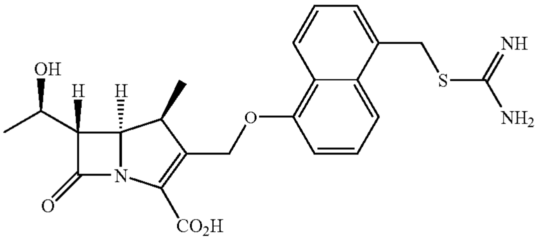

Percent yield: 17%; $^1$H NMR ($D_2O$/acetone-$d_6$, 300 MHz): δ 8.32 (d, J=8.6, 1H), 7.71 (d, J=8.6 Hz, 1H), 7.67 (d, J=6.7 Hz, 1H), 7.56 (t, J=8.6 Hz, 1H), 7.50 (t, J=7.6 Hz, 1H), 7.08 (d, J=7.6 Hz, 1H), 5.65 (d, J=13.4 Hz, 1H), 4.95 (d, J=13.4 Hz, 1H), 4.21 (quin., J=5.7 Hz, 1H), 4.12 (dd, J=10.5, 1.7 Hz, 1H), 3.42 (m, 2H), 1.26 (d, J=6.2, 3H), 1.22 (d, J=7.1 Hz, 3H).

Example 17

TES-Protected Thiotetrazole Intermediate 54

54

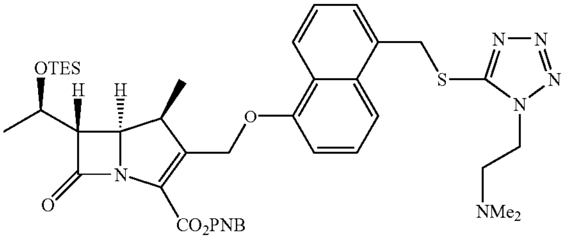

Percent yield: 48%; $^1$H NMR ($CDCl_3$, 300 MHz); δ 8.23 (d, J=7.2 Hz, 1H), 8.21 (d, J=8.4 Hz, 2H), 7.67 (d, J=7.8 Hz, 3H), 7.55 (d, J=6.0 Hz, 1H), 7.46 (t, J=8.1 Hz, 1H), 7.39 (t, J=8.1 Hz, 1H), 8.88 (d, J=8.7 Hz, 1H), 5.66 (d, J=14.1 Hz, 1H), 5.50 (d, J=14.4 Hz, 1H), 5.29 (d, J=13.5 Hz, 1H), 4.99 (s, 2H), 4.93 (d, J=14.7 Hz, 1H), 4.30 (m, 2H), 4.13 (t, J=7.2 Hz, 2H), 3.55 (m, 1H), 3.34 (dd, J=5.1, 3.0 Hz, 1H), 2.59 (t, J=6.4

Hz, 2H), 2.15 (s, 6H), 1.31 (d, J=7.2 Hz, 3H), 1.26 (d, J=6.3 Hz, 3H), 0.95 (t, J=7.6 Hz, 9H), 0.61 (q, J=8.0 Hz, 6H).

Thiotetrazole Analog 55

55

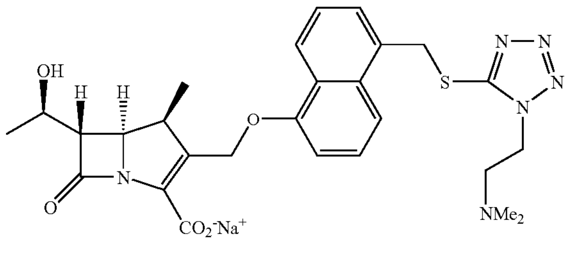

Percent yield: 26%; $^1$H NMR ($D_2O$, 400 MHz); δ 8.23 (d, J=8.4 Hz, 1H), 7.73 (d, J=8.4 Hz, 1H), 7.55 (t, J=8.0 Hz, 1H), 7.30 (t, J=8.0 Hz, 1H), 7.19 (d, J=7.6 Hz, 1H), 7.05 (d, J=8.0 Hz, 1H), 5.61 (d, J=14.0 Hz, 1H), 4.94 (d, J=13.6 Hz, 1H), 4.20 (t, J=6.0 Hz, 1H), 4.08 (d, J=8.0 Hz, 1H), 3.90 (t, J=7.0 Hz, 2H), 3.42 (m, 1H), 3.34 (m, 1H), 2.01 (t, J=7.0 Hz, 2H), 1.10 (d, J=6.4 Hz, 3H), 1.05 (d, J=6.8 Hz, 3H).

Example 18

TES-Protected Thioethyl Guanidine Intermediate 56

56

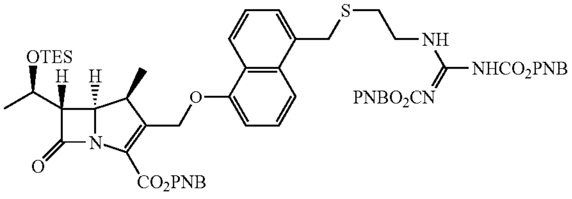

Percent yield; 68%: $^1$H NMR ($CDCl_3$, 300 MHz); δ 9.40 (bs, 1H), 9.19 (bs, 1H), 8.17 (d, J=8.4 Hz, 2H), 8.16 (d, J=8.1 Hz, 1H), 8.10 (d, J=9.0 Hz, 2H), 7.62 (d, J=7.5 Hz, 1H), 7.48 (d, J=8.7 Hz, 2H), 7.46 (d, J=8.4 Hz, 1H), 7.44 (d, J=8.4 Hz, 2H), 7.33-7.26 (m, 2H), 6.83 (d, J=6.9 Hz, 1H), 5.63 (d, J=14.1 Hz, 1H), 5.49 (d, J=14.1 Hz, 1H), 5.45 (d, J=15.0 Hz, 1H), 5.28 (s, 2H), 5.22 (s, 2H), 4.93 (d, J=14.4 Hz, 1H), 4.37-4.19 (m, 6H), 3.56 (m, 1H), 3.33 (dd, J=3.0, 5.1 Hz, 1H), 2.75 (t, J=7.2 Hz, 2H), 1.31 (d, J=7.8 Hz, 3H), 1.26 (d, J=6.0 Hz, 3H), 0.95 (t, J=7.2 Hz, 9H), 0.63 (q, J=7.2 Hz, 6H).

Thioethyl Guanidine Analog 57

57

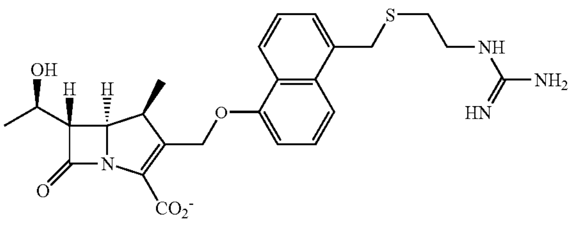

Percent yield; 38%: $^1$H NMR ($D_2O$+Acetone-$d_6$, 400 MHz); δ 8.20 (d, J=8.4 Hz, 1H), 7.69 (d, J=8.4 Hz, 1H), 7.50-7.40 (m, 3H), 7.06 (d, J=8.4 Hz, 1H), 5.70 (d, J=13.6 Hz, 1H), 4.91 (d, J=14.0 Hz, 1H), 4.22 (s, 2H), 4.19 (m, 1H), 4.13 (dd, J=2.8, 9.6 Hz, 1H), 3.41 (t, J=6.0 Hz, 2H), 3.40 (m, 1H), 3.34 (dd, J=2.8, 6.0 Hz, 1H), 2.74 (t, J=6.4 Hz, 2H), 1.24 (d, J=6.4 Hz, 3H), 1.21 (d, J=7.2 Hz, 3H).

Example 19

TES-Protected Aminomethyl Intermediate 58

58

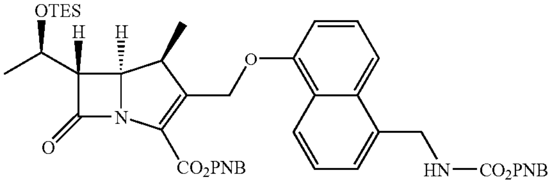

Percent yield: 75%; $^1$H NMR ($CDCl_3$, 300 MHz); δ 8.24 (s, 1H), 8.19 (dd, J=6.6, 8.3 Hz, 4H), 7.76 (d, J=8.7 Hz, 2H), 7.58 (d, J=13.5 Hz, 1H), 7.44 (m, 7H), 6.88 (d, J=7.8 Hz, 1H), 5.64 (d, J=14.1 Hz, 1H), 5.50 (d, J=13.5 Hz, 1H), 5.29 (d, J=13.8 Hz, 1H), 5.24 (bs, 2H), 5.18 (m, 1H), 4.94 (d, J=14.1 Hz, 1H), 4.84 (d, J=5.7 Hz, 2H), 4.30 (m, 2H), 3.76 (m, 2H), 3.56 *m, 1H), 3.34 (dd, J=4.7, 4.2 Hz, 12H), 1.31 (d, J=7.5 Hz, 3H), 1.26 (d, J=6.3 Hz, 3H), 0.95 (t, J=8.4 Hz, 9H), 0.61 (q, J=7.5 Hz, 6H).

Aminomethyl Analog 59

59

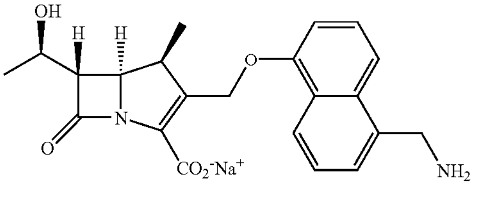

$^1$H NMR (DMSO-d6, 400 MHz); δ 8.12 (d, J=8.4 Hz, 1H), 7.59 (dd, J=8.0, 18 Hz, 2H), 7.44 (t, J=8.4 Hz, 1H), 7.38 (t,

J=8.4 Hz, 1H), 7.02 (d, J=7.6 Hz, 1H), 5.81 (d, J=12.8 Hz, 1H), 4.87 (m, 1H), 4.79 (d, J=12.8 Hz, 1H), 4.23 (s, 2H), 3.87 (dd, J=10.4, 2.8 Hz, 2H), 3.08 (m, 1H), 3.01 (dd, J=6.8, 2.8 Hz, 1H), 1.11 (d, J=6.4 Hz, 3H), 1.06 (d, J=6.8 Hz, 3H).

Example 20

TES-Protected Aminomethyl Amidine Intermediate 60

60

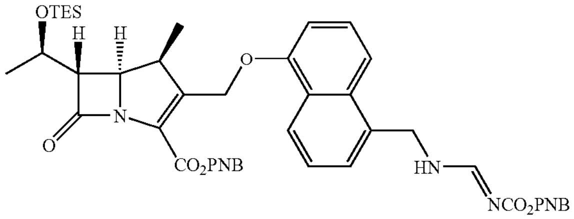

Percent yield: 64%; $^1$H NMR ($CDCl_3$, 300 MHz); δ 8.24 (s, 1H), 8.19 (dd, J=8.4, 6.3 Hz, 4H), 7.66 (d, J=8.4 Hz, 2H), 7.61 (d, J=8.4 Hz, 1H), 7.47 (m, 5H), 6.88 (d, J=7.2 Hz, 1H), 5.64 (d, J=15.0 Hz, 1H), 5.50 (d, J=13.2 Hz, 1H), 5.29 (d, J=13.8 Hz, 1H), 5.24 (s, 2H), 5.18 (m, 1H), 4.94 (d, J=13.8 Hz, 1H), 4.84 (d, J=4.8 Hz, 2H), 4.31 (m, 2H), 3.55 (m, 1H), 3.34 (dd, J=5.1, 4.2 Hz, 1H), 1.31 (d, J=7.2 Hz, 3H), 1.26 (d, J=6.6 Hz, 3H), 0.95 (t, J=8.1 Hz, 9H), 0.61 (q, J=7.7 Hz, 6H).

Aminomethyl Amidine Analog 61

61

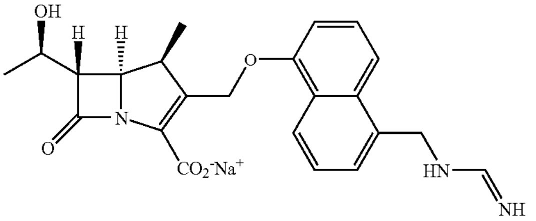

Percent yield: 22%; $^1$H NMR ($D_2O$, 400 MHz); δ 8.31 (d, J=8.4 Hz, 1H), 7.60 (m, 4H), 7.04 (d, J=6.4 Hz, 1H), 5.59 (d, J=12.8 Hz, 1H), δ 4.47 (s, 2H), 4.19 (m, 1H), 4.05 (m, 1H), 3.42 (m, 1H), 3.33 (m, 1H), 1.10 (d, J=6.2 Hz, 3H), 1.03 (d, J=7.2 Hz, 3H).

Example 21

TES-Protected Aminomethyl Guanidine Intermediate 62

62

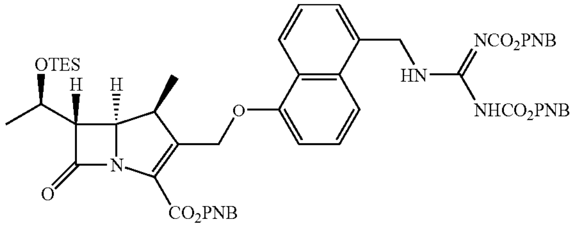

Percent yield: 68%; $^1$H NMR ($CDCl_3$, 300 MHz); δ 9.63 (bs, 1H), 9.46 (bs, 1H), 8.19 (t, J=8.1 Hz, 2H), 8.05 (d, J=8.7 Hz, 1H), 7.85 d, J=8.7 Hz, 2H), 7.69 (d, J=8.1 Hz, 2H), 7.43 (d, J=8.1 Hz, 1H), 7.37 (q, J=7.8 Hz, 3H), 7.08 (d, J=9.0 Hz, 1H), 6.83 d, J=8.1 Hz, 1H), 5.74 (bs, 1H), 5.66 (d, J=14.4 Hz, 1H), 5.51 (d, J=14.1 Hz, 1H), 5.31 (d, J=14.1 Hz, 1H), 5.14 (s, 3H), 4.97 (d, J=14.4 Hz, 1H), 4.35 (m, 2H), 3.64 (m, 1H), 3.37 (dd, J=5.4, 3.3 Hz, 1H), 1.30 (m, 6H), 0.93 (m, 9H), 0.62 (m, 6H).

Aminomethyl Guanidine Analog 63

63

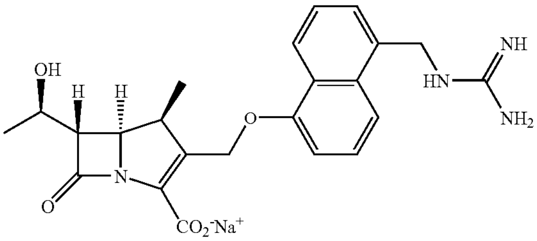

$^1$H NMR ($D_2O$+acetone-d6, 400 MHz); δ 8.36 (d, J=8.0 Hz, 1H), 7.62 (m, 4H), 7.18 (m, 1H), 5.76 (d, J=13.6 Hz, 1H), 5.01 (d, J=13.6 Hz, 1H), 4.95 (s, 2H), 4.29 (t, J=6.0 Hz, 1H), 4.22 (d, J=10.0 Hz, 1H), 3.48 (m, 2H), 1.34 (d, J=6.4 Hz, 3H), 1.31 d, J=6.8 Hz, 3H).

Example 22

TES-Protected Aminomethyl Sulfonamide Intermediate 64

64

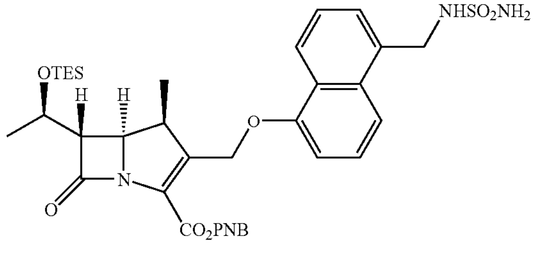

Percent yield: 28%; $^1$H NMR ($CDCl_3$, 300 MHz): δ 0.60 (q, J=7.8 Hz, 6H), 0.90 (t, J=7.8 Hz, 9H), 1.15 (d, J=6.1 Hz, 3H), 1.18 (d, J=7.4 Hz, 3H), 3.30 (d, 1H), 3.55 (m, 1H), 4.30

(m, 2H), 4.55 (s, 2H), 4.65 (s, 2H), 4.95 (d, 1H), 5.15 (d, 1H), 5.25 (d, 1H), 5.60 (d, 1H), 6.90 (d, 1H), 7.25 (m, 3H), 7.65 (m, 3H), 8.10 (m, 3H).

Aminomethyl Sulfonamide Analog 65

65

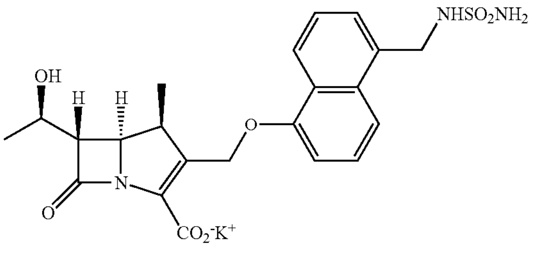

Percent yield: 33%; $^1$H NMR ($D_2O$, 400 MHz): δ 1.13 (d, J=7.3 Hz, 3H), 1.19 (d, J=7.7 Hz, 3H), 3.32 (m, 1H), 3.40 (2, 1H), 4.05 (d, 1H), 4.17 (m, 1H), 4.64 (s, 2H), 4.92 (d, 1H), 5.59 (d, 1H), 7.01 (d, 1H), 7.51 (m, 2H), 7.59 (d, 1H), 7.71 (d, 1H), 8.26 (m, 2H).

Examples of Cationic (Charged) 2-Carbon Naphthol CP Analogs

Example 23

TES-Protected N,N-Dimethylethylene Thioguanidine Salt Intermediate 66

66

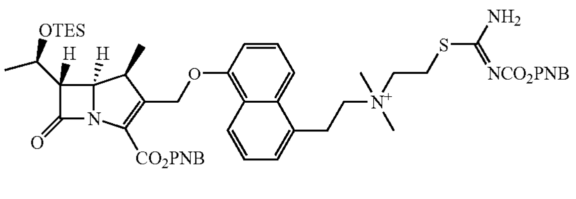

Percent Yield: 72%; $^1$H NMR ($CDCl_3$, 300 MHz,): δ 8.10 (d, J=8.4 Hz, 2H), 8.06 (d, J=9.0 Hz, 1H), 7.64 (d, J=9.0 Hz, 2H), 7.61 (d, J=9.6 Hz, 2H), 7.45 (d, J=9.3 Hz, 1H), 7.38 (t, J=7.8 Hz, 2H), 7.31 (d, J=8.4 Hz, 1H), 7.00 (d, J=9.3 Hz, 2H), 6.77 (d, J=8.1 Hz, 1H), 5.50 (d, J=13.2 Hz, 1H), 5.45 (d, J=13.5 Hz, 1H), 5.27 (d, J=14.4 Hz, 1H), 4.90 (d, J=14.4 Hz, 1H), 4.86 (s, 2H), 4.36 (dd, J=3.0, 10.2 Hz, 1H), 4.31 (p, J=3.0

Hz, 1H), 3.83 (br s, 2H), 3.64-3.35 (m, 8H), 3.29 (s, 6H), 1.33 (d, J=6.9 Hz, 3H), 1.27 (d, J=5.4 Hz, 3H), 0.95 (t, J=8.4 Hz, 9H), 0.61 (q, J=7.8 Hz, 6H).

N,N-Dimethylethylene Thioguanidine Salt Analog 67

67

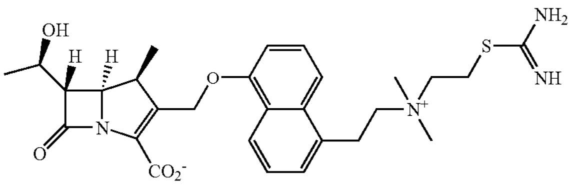

Percent yield: 14%; $^1$H NMR ($D_2O$, 400 MHz,): δ 8.21 (d, J=8.8 Hz, 1H), 7.64-7.46 (m, 4H), 7.09 (d, J=6.4 Hz, 1H), 5.72 (d, J=15.2 Hz, 1H), 4.93 (d, J=14.4 Hz, 1H), 4.22-4.13 (m, 2H), 3.85-3.59 (m, 4H), 3.53-3.20 (m, 8H), 2.91 (br s, 2H), 1.25 (d, J=6.8 Hz, 3H), 1.22 (d, J=6.4 Hz, 3H).

Example 24

TES-Protected N,N-Dimethylethylene Guanidine Salt Intermediate 68

68

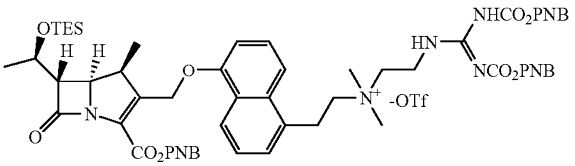

Percent yield: 63% yield; $^1$H NMR (Acetone-$d_6$, 300 MHz): δ 11.71 (s, 1H), 8.78 (t, J=6.3 Hz, 1H), 8.25 (d, J=8.7 Hz, 2H), 8.19 (d, J=8.4 Hz, 1H), 8.16 (d, J=7.8 Hz, 2H), 7.90 (d, J=9.0 Hz, 2H), 7.80 (d, J=8.4 Hz, 2H), 7.72 (d, J=8.1 Hz, 2H), 7.63 (m, 2H), 7.42 (m, 2H), 7.37 (d, J=8.4 Hz, 2H), 6.95 (d, J=7.5 Hz, 1H), 5.58 (d, J=13.2 Hz, 1H), 5.53 (d, J=15.0 Hz, 1H), 5.40 (s, 2H), 5.35 (d, J=13.8 Hz, 1H), 5.12 (s, 2H), 5.03 (d, J=13.8 Hz, 1H), 4.36 (dd, J=3.6, 9.9 Hz, 1H), 4.23 (m, 1H), 3.67-3.49 (m, 2H), 3.61 (s, 4H), 3.28 (s, 6H), 3.15 (br s, 2H), 2.88 (br s, 2H), 1.32 (d, J=7.2 Hz, 3H), 1.23 (d, J=6.0 Hz, 3H), 0.94 (t, J=7.8 Hz, 9H), 0.62 (q, J=7.5 Hz, 6H).

N,N-Dimethylethylene Guanidine Salt Analog 69

69

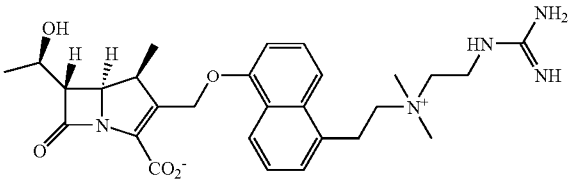

Percent yield: 39%; $^{1}$H NMR ($D_2O$+Acetone-$d_6$, 400 MHz,): δ 8.10 (d, J=8.8 Hz, 1H), 7.53-7.34 (m, 4H), 6.94 (d, J=7.6 Hz, 1H), 5.55 (d, J=13.2 Hz, 1H), 4.75 (d, J=14.0 Hz, 1H), 4.08 (t, J=6.0 Hz, 1H), 4.01 (d, J=9.6 Hz, 1H), 382 (m, 4H), 3.70 (m, 2H), 3.58 (m, 2H), 3.37 (s, 6H), 3.26 (t, J=8.4 Hz, 1H), 3.21 (m, 1H), 1.14 (d, J=6.8 Hz, 3H), 1.08 (d, J=7.2 Hz, 3H).

Example 25

TES-Protected N,N-Dimethylethylene Ethylenediamine Salt Intermediate 70

70

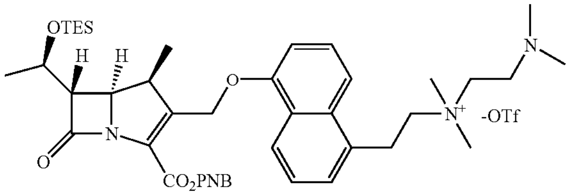

Percent yield: 78%; $^{1}$H NMR ($CDCl_3$, 300 MHz): δ 8.18 (d, J=8.7 Hz, 1H), 8.14 (d, J=9.0 Hz, 2H), 7.62 (d, J=9.0 Hz, 2H), 7.52 (t, J=8.4 Hz, 1H), 7.48-7.41 (m, 3H), 6.83 (d, J=7.5 Hz, 1H), 5.56 (d, J=14.4 Hz, 1H), 5.46 (d, J=13.5 Hz, 1H), 5.27 (d, J=13.8 Hz, 1H), 4.90 (d, J=13.2 Hz, 1H), 4.32 (dd, J=3.0, 6.9 Hz, 1H), 4.29 (p, J=3.0 Hz, 1H), 3.70-3.47 (m, 6H), 3.33 (s, 6H), 2.75 (t, J=5.1 Hz, 2H), 2.25 (s, 6H), 2.09 (br s, 2H), 1.29 (d, J=7.2 Hz, 3H), 1.25 (d, J=6.9 Hz, 3H), 0.95 (t, J=7.8 Hz, 9H), 0.61 (q, J=7.8 Hz, 6H).

N,N-Dimethylethylene Ethylenediamine Salt Analog 71

71

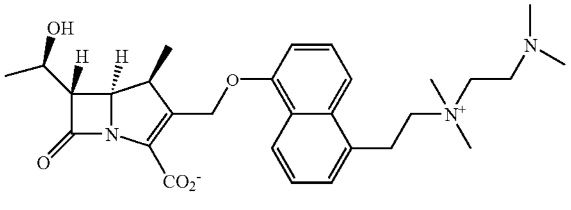

Percent yield: 25%; $^{1}$H NMR ($D_2O$, 300 MHz,): δ 8.16 (d, J=8.1 Hz, 1H), 7.53 (t, J=9.0 Hz, 1H), 7.49-7.41 (m, 3H), 6.94 (d, J=8.1 Hz, 1H), 5.46 (d, J=14.4 Hz, 1H), 4.81 (d, J=14.4 Hz, 1H), 4.12 (t, J=6.0 Hz, 1H), 3.94 (d, J=9.3 Hz, 1H), 3.53 (br s, 6H), 3.34 (m, 1H), 3.21 (s, 7H), 2.74 (m, 2H), 2.20 (s, 6H), 1.17 (d, J=6.0 Hz, 3H), 1.08 (d, J=7.2 Hz, 3H).

Example 26

TES-Protected N,N-Dimethylethylene Ethylenediamine Salt Intermediate 72

72

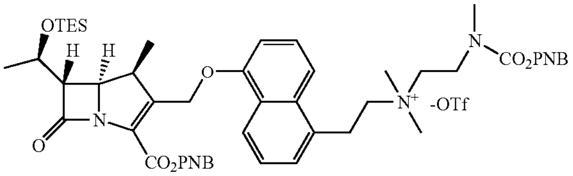

Percent yield: 58%; $^{1}$H NMR (Acetone-$d_6$, 300 MHz): δ 8.21 (m, 3H), 8.17 (d, J=9.3 Hz, 2H), 7.80 (d, J=7.8 Hz, 2H), 7.62 (m, 3H), 7.45 (m, 3H), 6.96 (d, J=7.5 Hz, 1H), 5.60 (d, J=13.8 Hz, 1H), 5.53 (d, J=13.8 Hz, 1H), 5.35 (d, J=14.4 Hz, 1H), 5.26 (s, 2H), 5.04 (d, J=14.1 Hz, 1H), 4.35 (m, 2H), 4.04-3.50 (m, 10H), 3.54 (s, 6H), 2.39 (s, 3H), 1.33 (d, J=7.2 Hz, 3H), 1.23 (d, J=5.7 Hz, 3H), 0.94 (t, J=7.8 Hz, 9H), 0.61 (q, J=7.5 Hz, 6H).

N,N-Dimethylethylene Ethylenediamine Salt Analog 73

73

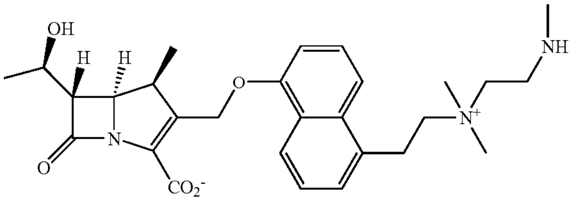

Percent yield; 32%; $^{1}$H NMR ($D_2O$+Acetone-$d_6$, 300 MHz,): δ 8.23 (d, J=9.3 Hz, 1H), 7.68 (d, J=7.2 Hz, 1H), 7.63-7.48 (m, 3H), 7.07 (d, J=7.8 Hz, 1H), 5.66 (d, J=13.2 Hz, 1H), 4.92 (d, J=12.6 Hz, 1H), 4.21 (p, J=3.0 Hz, 1H), 4.12 (d, J=9.3 Hz, 1H), 3.63 (m, 5H), 3.41-3.24 (m, 4H), 3.34 (s, 6H), 3.05 (m, 1H), 2.61 (s, 3H), 1.25 (d, J=6.3 Hz, 3H), 1.20 (d, J=7.2 Hz, 3H).

Example 27

TES-Protected Morpholine Salt Intermediate 74

74

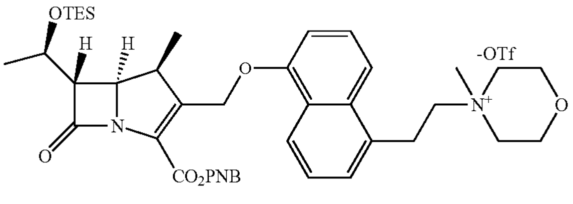

Percent yield; 78%; $^{1}$H NMR (Acetone-$d_6$, 300 MHz): δ 8.25 (d, J=8.4 Hz, 1H), 8.17 (d, J=8.4 Hz, 2H), 7.80 (d, J=8.4 Hz, 2H), 7.75 (d, J=9.3 Hz, 1H), 7.62 (d, J=6.9 Hz, 1H), 7.47 (t, J=8.4 Hz, 1H), 7.46 (t, J=8.4 Hz, 1H), 6.99 (d, J=8.1 Hz, 1H), 5.61 (d, J=13.8 Hz, 1H), 5.53 (d, J=14.1 Hz, 1H), 5.35 (d, J=14.4 Hz, 1H), 5.04 (d, J=13.8 Hz, 1H), 4.35 (m, 2H), 4.17

(m, 4H), 3.96 (m, 2H), 3.92-3.74 (m, 6H), 3.67 (s, 3H), 3.64 (m, 1H), 3.50 (p, J=3.6 Hz, 1H), 1.33 (d, J=7.5 Hz, 3H), 1.24 (d, J=6.6 Hz, 3H), 0.94 (t, J=8.4 Hz, 9H), 0.61 (q, J=8.7 Hz, 6H).

Morpholine Salt Analog 75

75

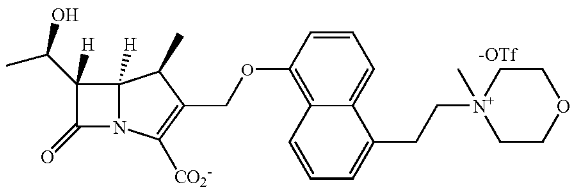

Percent yield; 66%; $^1$H NMR ($D_2O$+DMSO-$d_6$, 400 MHz,): δ 8.16 (d, J=7.6 Hz, 1H), 7.53-7.41 (m, 4H), 6.95 (d, J=8.0 Hz, 1H), 5.48 (d, J=14.0 Hz, 1H), 4.80 (d, J=12.8 Hz, 1H), 4.21 (p, J=6.0 Hz, 1H), 3.94 (br s, 5H), 3.60 (m, 2H), 3.48 (m, 6H), 3.26 (m, 5H), 1.10 (d, J=6.0 Hz, 3H), 1.07 (d, J=6.8 Hz, 3H).

Example 28

TES-Protected DABCO Salt Intermediate 76

76

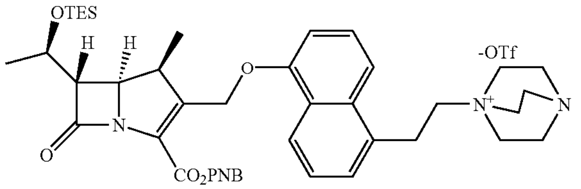

Percent yield; 87%; $^1$H NMR ($D_2O$+Acetone-$d_6$, 300 MHz): δ 8.17 (d, J=8.7 Hz, 1H), 8.05 (d, J=7.2 Hz, 2H), 7.67 (d, J=6.9 Hz, 2H), 7.59-7.45 (m, 4H), 6.94 (d, J=6.0 Hz, 1H), 5.47 (d, J=10.5 Hz, 1H), 5.43 (d, J=12.9 Hz, 1H), 5.27 (d, J=11.7 Hz, 1H), 4.97 (d, J=14.1 Hz, 1H), 4.33 (m, 2H), 3.81-3.58 (m, 10H), 3.47 (m, 1H), 3.40-3.27 (m, 7H), 1.28 (d, J=5.4 Hz, 3H), 1.21 (d, J=5.1 Hz, 3H), 0.92 (t, J=7.2 Hz, 9H), 0.58 (q, J=8.7 Hz, 6H).

DABCO Salt Analog 77

77

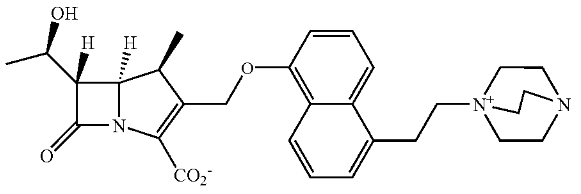

Percent yield; 37%; $^1$H NMR ($D_2O$+Acetone-$d_6$, 300 MHz,): δ 8.18 (d, J=8.7 Hz, 1H), 7.54-7.44 (m, 4H), 6.99 (d, J=6.0 Hz, 1H), 5.55 (d, J=14.4 Hz, 1H), 4.85 (d, J=14.4 Hz, 1H), 4.15 (p, J=6.0 Hz, 1H), 4.04 (d, J=8.4 Hz, 1H), 3.57 (m, 10H), 3.34 (m, 1H), 3.26 (m, 7H), 1.20 (d, J=5.4 Hz, 3H), 1.10 (d, J=8.1 Hz, 3H).

Example 29

TES-Protected DABCO Salt Intermediate 78

78

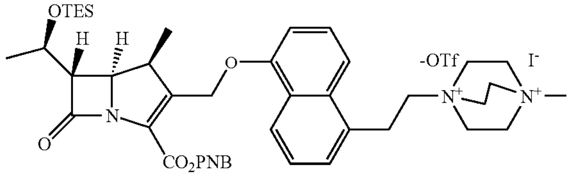

DABCO mono-salt 76 (240 mg, 0.261 mmole) was dissolved in acetonitrile at 0° C. and 33 μL of methyl iodide (0.52 mmole) was added to the solution. The mixture were stirred overnight, and then triturated with MTBE/diethyl ether to afford the product (78) as a white solid.

Percent yield; 90%; $^1$H NMR (Acetone-$d_6$, 300 MHz): δ 8.25 (d, J=8.7 Hz, 1H), 8.17 (d, J=9.0 Hz, 2H), 7.80 (d, J=9.0 Hz, 2H), 7.76 (d, J=9.6 Hz, 1H), 7.63 (d, J=6.6 Hz, 1H), 7.45 (m, 2H), 6.98 (d, J=8.1 Hz, 1H), 5.61 (d, J=14.1 Hz, 1H), 5.54 (d, J=14.4 Hz, 1H), 5.35 (d, J=14.7 Hz, 1H), 5.04 (d, J=14.1 Hz, 1H), 4.62 (m, 6H), 4.48 (m, 6H), 4.34 (m, 2H), 4.19 (m, 2H), 3.84 (m, 2H), 3.70 (s, 3H), 3.63 (m, 1H), 3.49 (m, 1H), 1.32 (d, J=7.5 Hz, 3H), 1.23 (d, J=6.3 Hz, 3H), 0.94 (t, J=7.8 Hz, 9H), 0.60 (q, J=8.4 Hz, 6H).

DABCO Salt Analog 79

79

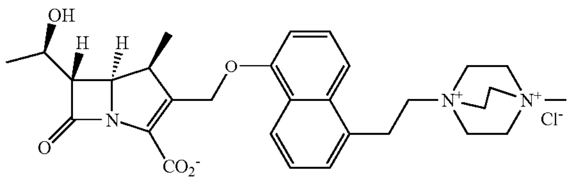

Percent yield; 41%; $^1$H NMR ($D_2O$, 400 MHz,): δ 8.10 (d, J=8.0 Hz, 1H), 7.38 (m, 4H), 6.84 (d, J=6.4 Hz, 1H), 5.33 (d, J=13.6 Hz, 1H), 4.72 (d, J=12.4 Hz, 1H), 4.00 (m, 6H), 3.94 (m, 6H), 3.82 (d, J=9.2 Hz, 1H), 3.75 (m, 1H), 3.56 (m, 2H), 3.49 (m, 1H), 3.24 (s, 3H), 3.21 (m, 1H), 3.11 (m, 1H), 1.06 (d, J=5.6 Hz, 3H), 0.98 (d, J=6.8 Hz, 3H).

Example 30

TES-Protected DABCO Salt Intermediate 80

80

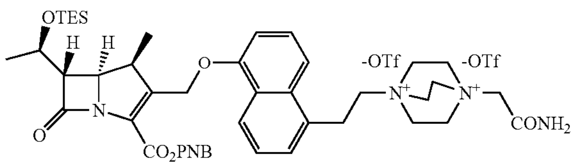

Percent yield: 89%; $^1$H NMR (Acetone-$d_6$, 300 MHz): δ 8.25 (d, J=7.5 Hz, 1H), 8.17 (d, J=8.7 Hz, 2H), 7.80 (d, J=8.7 Hz, 2H), 7.74 (d, J=9.6 Hz, 1H), 7.61 (d, J=6.9 Hz, 1H), 7.46 (m, 2H), 6.99 (d, J=8.4 Hz, 1H), 5.61 (d, J=14.1 Hz, 1H), 5.54 (d, J=14.4 Hz, 1H), 5.35 (d, J=13.8 Hz, 1H), 4.68 (s, 2H), 4.60 (br s, 12H), 4.38-4.31 (m, 2H), 4.19-4.13 (m, 2H), 3.91-3.80 (m, 2H), 3.63 (m, 1H), 3.50 (m, 1H), 1.33 (d, J=7.5 Hz, 3H), 1.23 (d, J=6.9 Hz, 3H), 0.94 (t, J=7.5 Hz, 9H), 0.60 (q, J=8.4 Hz, 6H).

DABCO Salt Analog 81

81

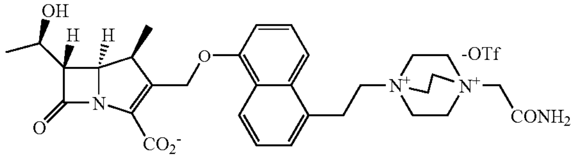

Percent yield: 39%; $^1$H NMR ($D_2O$, 400 MHz,): δ 8.07 (d, J=8.0 Hz, 1H), 7.38 (m, 4H), 6.79 (d, J=6.8 Hz, 1H), 5.20 (d, J=13.2 Hz, 1H), 4.68 (d, J=13.2 Hz, 1H), 4.20 (m, 6H), 4.18 (s, 2H), 4.10-3.96 (m, 8H), 3.76 (m, 2H), 3.49 (m, 2H), 3.21 (m, 1H), 3.06 (m, 1H), 1.06 (d, J=6.4 Hz, 3H), 0.92 (d, J=7.2 Hz, 3H).

Example 31

TES-Protected N,N-Dimethylpropyl Amidine Intermediate 82

Percent yield: 65%; $^1$H NMR ($CDCl_3$, 300 MHz): δ 0.50 (q, J=8.1 Hz, 6H), 0.8 (t, J=8.4 Hz, 9H), 1.20 (d, J=6.0 Hz, 3H), 1.25 (d, J=7.5 Hz, 3H), 2.1 (m, 2H), 2.70 (s, 6H), 3.30 (m, 2H), 3.6 (m, 6H), 4.30 (m, 2H) 5.00 (m, 3H), 5.10 (s, 2H), 5.25 (s, 2H), 5.45 (d, 1H), 5.60 (d, 1H), 6.90 (d, 1H), 7.40 (m, 4H), 7.60 (m, 6H), 8.20 (m, 6H), 8.6 (t, 1H).

N,N-Dimethylpropyl Amidine Analog 83

83

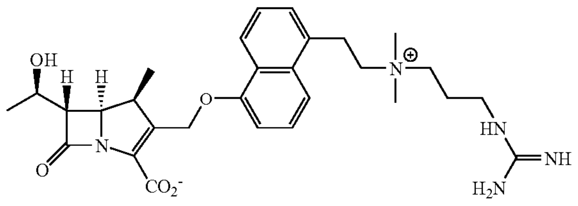

Percent yield: 25%; $^1$H NMR ($D_2O$, 400 MHz): δ 1.12 (d, J=7.3 Hz, 3H), 1.15 (d, J=7.7 Hz, 3H), 2.05 (m, 2H), 2.40 (s, 6H), 3.21 (m, 2H), 3.40 (m, 4H), 3.60 (m, 3H), 4.05 (m, 1H), 4.15 (m, 2H), 4.95 (d, 1H), 5.55 (d, 1H), 7.00 (d, 1H), 7.50 (m, 2H), 7.70 (m, 2H), 8.20 (d, 1H).

Examples of Uncharged (Neutral) 2-Carbon Naphthol CP Analogs

Example 32

TES-Protected Thiourea Intermediate 84

84

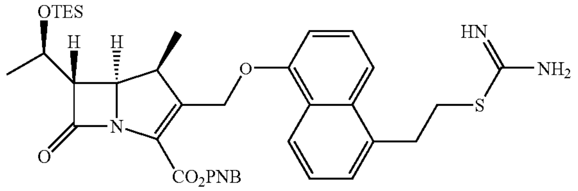

Percent yield: 89%; $^1$H NMR (Acetone-$d_6$, 300 MHz,): δ 8.21 (d, J=8.7 Hz, 1H), 8.15 (d, J=8.7 Hz, 2H), 7.77 (d, J=9.6 Hz, 2H), 7.67 (m, 1H), 7.50-7.40 (m, 2H), 7.13 (d, J=8.1 Hz, 1H), 6.95 (d, J=8.1 Hz, 1H), 5.58 (d, J=14.1 Hz, 1H), 5.51 (d, J=14.4 Hz, 1H), 5.32 (d, J=14.1 Hz, 1H), 5.02 (d, J=13.8 Hz,

82

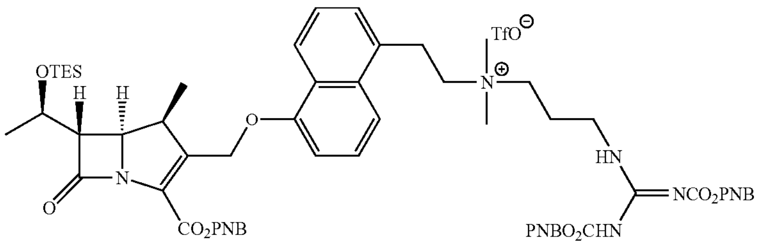

1H), 4.37-4.27 (m, 2H), 3.69-3.15 (m, 9H), 1.31 (d, J=7.5 Hz, 3H), 1.21 (d, J=5.4 Hz, 3H), 0.92 (t, J=7.8 Hz, 9H), 0.60 (q, J=7.8 Hz, 6H).

Thiourea Analog 85

85

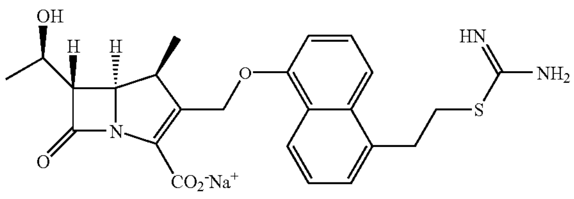

Percent yield: 36%; $^1$H NMR ($D_2O$+Acetone-$d_6$, 600 MHz,): δ 8.09 (t, J=4.8 Hz, 1H), 7.56 (d, J=8.4 Hz, 1H), 7.39 (t, J=7.8 Hz, 1H), 7.35 (m, 2H), 6.93 (d, J=7.8 Hz, 1H), 5.51 (d, J=13.8 Hz, 1H), 4.81 (d, J=12.6 Hz, 1H), 4.08 (p, J=6.0 Hz, 1H), 3.99 (d, J=10.2 Hz, 1H), 3.42 (t, J=6.0 Hz, 2H), 3.36 (t, J=6.0 Hz, 2H), 3.29 (m, 2H), 1.12 (d, J=6.6 Hz, 3H), 1.02 (d, J=7.2 Hz, 3H).

Example 33

TES-Protected Thioimidazole Intermediate 86

86

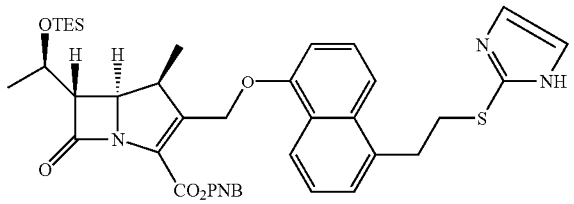

Percent yield: 98%; $^1$H NMR ($CDCl_3$, 300 MHz,): δ 8.18 (d, J=8.7 Hz, 2H), 8.11 (d, J=8.1 Hz, 1H), 7.65 (d, J=8.7 Hz, 2H), 7.53 (d, J=8.7 Hz, 1H), 7.47 (t, J=7.8 Hz, 1H), 7.43-7.31 (m, 2H), 7.12 (s, 2H), 6.96 (d, J=7.2 Hz, 2H), 6.79 (d, J=8.4 Hz, 1H), 5.61 (d, J=14.7 Hz, 1H), 5.47 (d, J=14.4 Hz, 1H), 5.27 (d, J=14.1 Hz, 1H), 4.91 (d, J=14.4 Hz, 1H), 4.28 (m, 2H), 3.56 (m, 1H), 3.33 (m, 5H), 1.29 (d, J=7.2 Hz, 3H), 1.25 (d, J=7.2 Hz, 3H), 0.95 (t, J=8.1 Hz, 9H), 0.60 (q, J=8.1 Hz, 6H).

Thioimidazole Analog 87

87

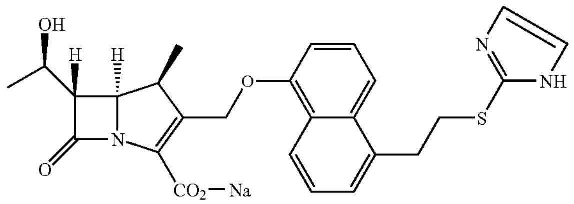

Percent yield: 28%; $^1$H NMR ($D_2O$+Acetone-$d_6$, 400 MHz,): δ 8.01 (d, J=8.4 Hz, 1H), 7.30-7.24 (m, 4H), 7.00 (s, 2H), 6.89 (d, J=8.4 Hz, 1H), 5.53 (d, J=14.4 Hz, 1H), 4.78 (d, J=13.6 Hz, 1H), 4.07 (p, J=6.8 Hz, 1H), 3.99 (dd, J=2.0, 9.2 Hz, 1H), 3.27 (m, 2H), 3.15 (br s, 4H), 1.12 (d, J=6.0 Hz, 3H), 1.08 (d, J=7.2 Hz, 3H).

Example 34

TES-Protected Sulfonamide Intermediate 88

88

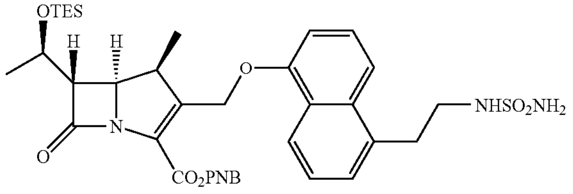

Percent yield: 26%; $^1$H NMR ($CDCl_3$, 300 MHz,): δ 8.22-8.15 (m, 3H), 7.71 (d, J=8.4 Hz, 1H), 7.67 (d, J=9.0 Hz, 1H), 7.47-7.36 (m, 3H), 6.85 (d, J=8.1 Hz, 1H), 5.65 (dd, J=2.7, 14.4 Hz, 1H), 5.50 (d, J=13.8 Hz, 1H), 5.29 (d, J=14.1 Hz, 1H), 4.93 (d, J=14.7 Hz, 1H), 4.28 (m, 2H), 4.00 (m, 1H), 3.66-3.54 (m, 2H), 3.38-3.26 (m, 3H), 1.31 (d, J=7.2 Hz, 3H), 1.26 (d, J=5.4 Hz, 3H), 0.95 (t, J=7.5 Hz, 9H), 0.61 (q, J=7.2 Hz, 6H).

Sulfonamide Analog 89

89

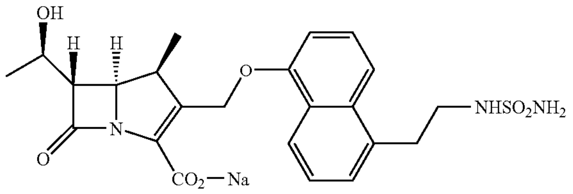

Percent yield: 67%; $^1$H NMR ($D_2O$, 400 MHz,): δ 8.05 (d, J=8.4 Hz, 1H), 7.57 (d, J=8.8 Hz, 1H), 7.34-7.27 (m, 3H), 6.86 (d, J=7.2 Hz, 1H), 5.47 (d, J=14.0 Hz, 1H), 4.79 (d, J=14.0 Hz, 1H), 4.02 (p, J=6.4 Hz, 1H), 3.90 (dd, J=2.4, 10.0

Hz, 1H), 3.40-3.34 (m, 2H), 3.26 (dd, J=2.8, 6.4 Hz, 1H), 3.17 (m, 2H), 3.09 (t, J=6.8 Hz, 1H), 1.07 (d, J=6.4 Hz, 3H), 1.04 (d, J=7.2 Hz, 3H).

Example 35

TES-Protected N,N-Diethylamine Intermediate 90

90

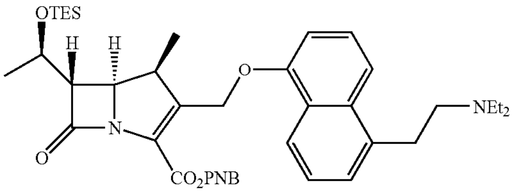

Percent yield: 88%; $^1$H NMR ($CDCl_3$, 300 MHz,): δ 8.22 (d, J=8.4 Hz, 2H), 8.15 (dd, J=3.0, 7.8 Hz, 1H), 7.67 (d, J=8.4 Hz, 2H), 7.53 (d, J=9.3 Hz, 1H), 7.40 (m, 3H), 6.84 (d, J=8.1 Hz, 1H), 5.65 (d, J=14.7 Hz, 1H), 5.50 (d, J=14.4 Hz, 1H), 5.30 (d, J=14.4 Hz, 1H), 4.93 (d, J=14.4 Hz, 1H), 4.28 (m, 2H), 3.56 (m, 1H), 3.31 (m, 3H), 2.92 (m, 2H), 2.83 (q, J=7.2 Hz, 4H), 1.31 (d, J=7.5 Hz, 3H), 1.26 (d, J=6.3 Hz, 3H), 1.18 (t, J=6.0 Hz, 6H), 0.95 (t, J=8.4 Hz, 9H), 0.62 (q, J=7.8 Hz, 6H).

N,N-Diethylamine Analog 91

91

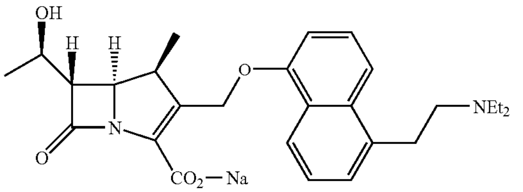

Percent yield: 12%; $^1$H NMR ($D_2O$, 400 MHz,): δ 8.00 (br s, 1H), 7.41-7.29 (m, 4H), 6.81 (d, J=7.6 Hz, 1H), 5.36 (d, J=14.0 Hz, 1H), 4.70 (d, J=13.6 Hz, 1H), 4.01 (br s, 1H), 3.85 (d, J=9.2 Hz, 1H), 3.32-3.08 (m, 10H), 1.12 (br s, 6H), 1.06 (d, J=4.0 Hz, 3H), 0.98 (d, J=7.6 Hz, 3H).

Example 36

TES-Protected Piperazine Intermediate 92

92

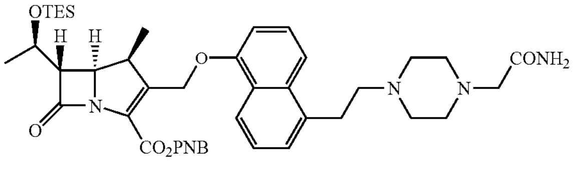

Percent yield: 30%; $^1$H NMR ($CDCl_3$, 300 MHz,): δ 8.21 (d, J=9.3 Hz, 2H), 8.06 (dd, J=2.4, 8.4 Hz, 1H), 7.52 (d, J=9.0 Hz, 1H), 7.42-7.29 (m, 3H), 7.06 (br s, 2H), 6.83 (d, J=8.4 Hz, 1H), 5.65 (d, J=14.4 Hz, 1H), 5.50 (d, J=13.8 Hz, 1H), 5.30 (d, J=13.8 Hz, 1H), 5.30 (s, 2H), 4.93 (d, J=14.7 Hz, 1H), 4.28 (m, 2H), 3.56 (m, 1H), 3.31 (m, 3H), 2.74-2.56 (m, 10H), 2.83 (q, J=7.2 Hz, 4H), 1.31 (d, J=7.5 Hz, 3H), 1.26 (d, J=6.9 Hz, 3H), 0.95 (t, J=7.5 Hz, 9H), 0.62 (q, J=8.4 Hz, 6H).

Piperazine Analog 93

93

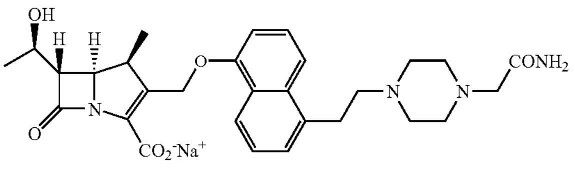

Percent yield: 48%; $^1$H NMR ($D_2O$, 400 MHz,): δ 7.99 (dd, J=3.2, 6.4 Hz, 1H), 7.43 (d, J=8.4 Hz, 1H), 7.32 (t, J=8.0 Hz, 1H), 7.25 (m, 2H), 6.80 (d, J=7.6 Hz, 1H), 5.35 (d, J=14.0 Hz, 1H), 4.70 (d, J=14.0 Hz, 1H), 4.69 (s, 2H), 4.00 (p, J=6.4 Hz, 1H), 3.83 (dd, J=3.2, 10.0 Hz, 1H), 3.21 (m, 2H), 3.12-2.98 (m, 10H), 2.66 (br s, 2H), 1.05 (d, J=6.4 Hz, 3H), 0.96 (d, J=7.6 Hz, 3H).

Example 37

TES-Protected Piperazine Intermediate 94

94

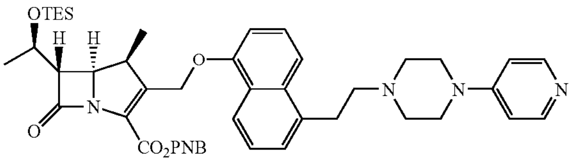

Percent yield: 41%; $^1$H NMR ($CDCl_3$, 300 MHz,): δ 8.24 (d, J=6.0 Hz, 2H), 8.20 (d, J=8.7 Hz, 2H), 8.15 (dd, J=2.4, 6.0 Hz, 1H), 7.66 (d, J=8.7 Hz, 2H), 7.40 (m, 3H), 6.83 (d, J=7.5 Hz, 1H), 6.75 (d, J=6.6 Hz, 2H), 5.64 (d, J=15.0 Hz, 1H), 5.49 (d, J=14.4 Hz, 1H), 5.29 (d, J=14.4 Hz, 1H), 4.93 (d, J=14.7 Hz, 1H), 4.28 (m, 2H), 3.59 (m, 1H), 3.48 (m, 3H), 3.35-3.15 (m, 4H), 2.80-2.65 (m, 6H), 1.31 (d, J=7.2 Hz, 3H), 1.25 (d, J=5.7 Hz, 3H), 0.95 (t, J=7.8 Hz, 9H), 0.61 (q, J=7.8 Hz, 6H).

Piperazine Analog 95

95

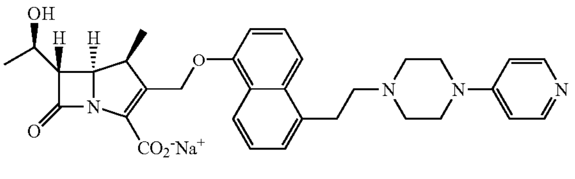

Percent Yield; 29% $^1$H NMR (DMSO, 300 MHz,): δ 8.16 (d, J=5.7 Hz, 2H), 8.06 (dd, J=3.0, 7.5 Hz, 1H), 7.62 (d, J=8.4 Hz, 1H), 7.42 (m, 3H), 6.94 (m, 3H), 5.55 (d, J=14.1 Hz, 1H), 4.91 (d, J=14.1 Hz, 1H), 4.10 (dd, J=3.0, 11.1 Hz, 1H), 3.92 (p, J=5.7 Hz, 1H), 3.66 (br s, 4H), 3.35 (m, 1H), 3.24 (m, 3H), 2.75 (br s, 6H), 1.12 (d, J=7.5 Hz, 3H), 1.09 (d, J=5.7 Hz, 3H).

Example 38

TES-Protected Guanidine Intermediate 96

96

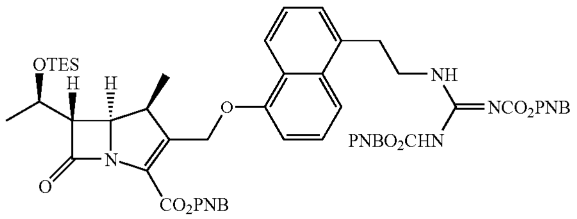

Percent yield: 50%; $^{1}H$ NMR ($CDCl_3$, 300 MHz); δ 11.76 (s, 1H), 8.38 (m, 1H), 8.22 (m, 8H), 7.78 (d, J=8.1 Hz, 1H), 7.67 (d, J=9.0 Hz, 2H), 7.54 (dd, J=8.4, 12.4 Hz, 4H), 7.37 (m, 4H), 6.84 (d, J=7.5 Hz, 1H), 5.64 (d, J=14.4 Hz, 1H), 5.50 (d, J=14.1 Hz, 1H), 5.31 (s, 1H), 5.29 (d, J=13.8 Hz, 1H), 5.25 (s, 2H), 5.23 (s, 2H), 4.93 (d, J=15.0 Hz, 1H), 4.30)m, 2H), 3.82 (m, 2H), 3.57 (m, 1H), 3.36 (m, 3H), 1.31 (d, J=7.2 Hz, 3H), 1.26 (d, J=6.6 Hz, 3H), 0.95 (t, J=8.1 Hz, 9H), 0.61 (q, J=7.7 Hz, 6H).

Guanidine Analog 97

97

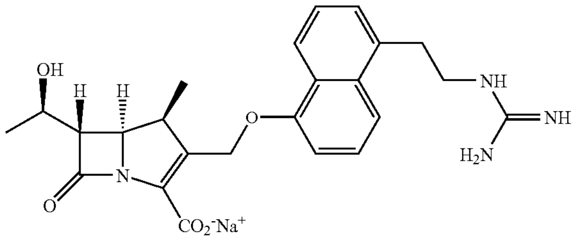

$^{1}H$ NMR ($D_2O$, 300 MHz); δ 8.08 (d, J=7.5 Hz, 1H), 7.57 (d, J=9.2 Hz, 1H), 7.34 (m, 3H), 6.89 (d, J=7.8 Hz, 1H), 5.49 (d, J=15.0 Hz, 1H), 4.90 (d, J=15.0 Hz, 1H), 4.06 (m, 1H), 3.95 (m, 1H), 3.52 (s, 2H), 3.44 (m, 2H), 3.19 (bs, 8H), 1.12 (d, J=6.6 Hz, 3H), 1.05 (d, J=8.1 Hz, 3H).

Example 39

TES-Protected Ethylamine Intermediate 98

98

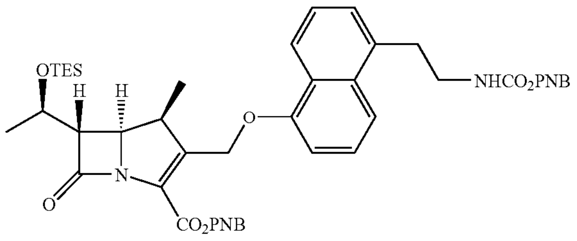

Percent yield: 87%; $^{1}H$ NMR ($CDCl_3$, 300 MHz): δ 0.60 (q, J=7.8 Hz, 6H), 0.90 (t, J=7.8 Hz, 9H), 1.15 (d, J=6.1 Hz, 3H), 1.18 (d, J=7.4 Hz, 3H), 3.30 (m, 3H), 3.65 (m, 3H), 4.50 (m, 1H), 4.95 (d, 1H), 5.20 (s, 2H), 5.25 (d, 1H), 5.50 (d, 1H), 5.65 (d, 1H), 6.85 (d, 1H), 7.40 (m, 5H), 7.65 (m, 2H), 8.20 (m. 5H).

Ethylamine Intermediate 99

99

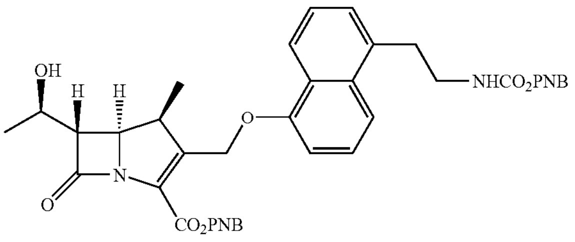

To a solution of 98 (245 mg, 0.296 mmol) in dry THF (25 mL) at 0° C. was added 1M solution TBAF in THF (1.18 mL, 1.18 mmol), and the mixture was aged for 2 hours at 0° C. Reaction was quenched with a addition of brine (15 mL) and extracted with EtOAc (75 mL), dried over $MgSO_4$, filtered and the solvent was concentrated under reduced pressure. The organic residue was purified by flash column 50% ethyl acetate in hexanes to afford the desired material 99.

Percent yield: 77%; $^{1}H$ NMR ($CDCL_3$, 300 MHz): δ 1.15 (d, J=6.1 Hz, 3H), 1.18 (d, J=7.4 Hz, 3H), 3.25 (m, 3H), 3.60 (m, 3H), 4.30 (m, 2H), 4.95 (d, 1H), 5.20 (s, 2H), 5.25 (d, 1H), 5.50 (d, 1H), 5.65 (d, 1H), 6.80 (d, 1H), 7.40 (m, 5H), 7.65 (m, 2H), 8.20 (m. 5H).

Ethylamine Analog 100

100

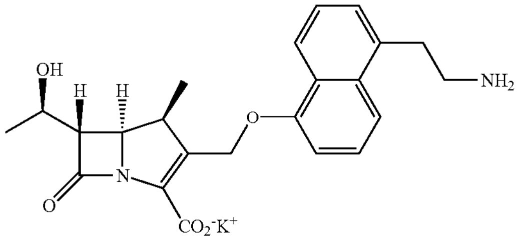

Percent yield: 20%; $^{1}H$ NMR ($D_2O$, 400 MHz): δ 1.08 (d, J=7.3 Hz, 3H), 1.15 (d, J=7.7 Hz, 3H), 3.30 (m, 1H), 3.93 (m, 3H), 4.13 (m, 1H), 5.46 (d, 1H), 6.92 (d, 1H), 740 (m, 2H), 7.60 (m, 2H), 8.14 (d, 1H)

Synthesis of the Nucleophile Intermediates and Supporting Reagents

Part I:

The following procedures were used to make the nucleophilic intermediates necessary for the synthesis of the cationic N,N-Dimethylamino-substituted analogs 22, 24, 26, 28, 34, 36, 43, 45, 49, 67, 69, 73, and 83.

Synthesis of bis-PNB-Protected Pyrazole Guanidation Reagent 101

101

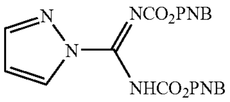

The bis-PNB-protected guanidation reagent (101) was synthesized from 1H-pyrazole-1-carboxamidine dihydrochloride using a modified procedure first reported by Bernatowicz, et al. (Bernatowicz, M. S., Wu, Y., and Matsueda, G. R., *Tetrahedron Letters,* 1993, 34, 3389. The only modification was the substitution of PNB for CBZ) in 69% overall yield and isolated as a white solid.

$^1$H NMR ($CDCl_3$+MeOD-d6, 300 MHz); δ 8.33 (d, J=2.1 Hz, 1H), 8.06 (d, J=8.4 Hz, 4H), 7.56 (s, 1H), 7.47 (d, J=8.4 Hz, 4H), 6.31 (t, J=2.1 Hz, 1H), 5.07 (s, 4H).

Synthesis of bis-PNB-Protected N,N-Dimethylethylene Guanidine Nucleophile 102

102

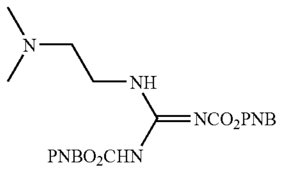

N,N-Dimethylethylene diamine (1.65 mmol, 145 mg) and bis-PNB pyrazole 101 were added to dry ACN (10 mL) and the resulting mixture was stirred at rt for 48 hrs (until complete by TLC) under inert atmosphere. After concentrating the mixture under reduced pressure, the reaction mixture was purified on a silica column using a DCM:MeOH:$NH_4$OH (79:20:1) solvent system and the product (102) isolated as a white solid in 82% yield.

$^1$H NMR ($CDCl_3$, 300 MHz); δ 11.76 (bs, 1H), 8.26 (m, 4H), 7.54 (m, 4H), 5.29 (s, 2H), 5.22 (s, 2H), 3.53 (q, J=5.4 Hz, 2H), 2.49 (t, J=5.4 Hz, 2H), 2.27 (s, 6H).

Synthesis of the N,N-Dimethylaminopropyl Guanidine Intermediate 103

103

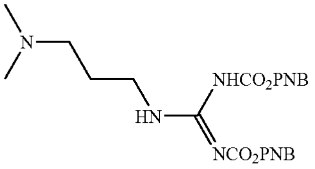

The same procedure was used as was described for the preparation of 102 except that N,N-dimethylpropylene diamine was substituted for N,N-dimethylethylene diamine.

Percent yield: 95%; $^1$H NMR ($CDCL_3$, 300 MHz): δ 1.70 (q, 2H), 2.20 (s, 6H), 2.38 (t, 2H), 3.5 (q, 2H), 5.20 (s, 2H), 5.30 (s, 2H), 7.55 (m, 4H), 8.20 (m, 4H), 9.15 (s, 1H).

Synthesis of mono-PNB-Protected Thioguanidine Nucleophile 104

104

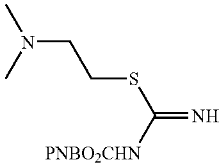

S-(2-Dimethylaminoethyl)isothiourea dihydrochloride (9.1 mmol., 2.0 g) was suspended in dry DCM (100 mL) and the mixture cooled to 0° C. under $N_2$ atm. DIEA (31.8 mmol, 4.2 g) was then added via syringe over 10 minutes and the mixture stirred until it became homogenous. A solution of 4-nitrobenzyl chloroformate (10.9 mmol, 2.35 g) in DCM (50 mL) was then added over 1 hr. via an addition funnel and the resulting mixture aged overnight at 0° C. The reaction mixture was then transferred to a separatory funnel, washed with water, dried over anhydrous $Na_2SO_4$, filtered, and concentrated. Thioguanidine 104 was then purified by column chromatography on silica gel (DCM:MeOH:$NH_4$OH; 79:20:1) and isolated (2.0 g) as a white solid in 68% yield.

$^1$H NMR ($CDCl_3$, 300 MHz); δ 8.19 (d, J=9.3 Hz, 2H), 7.55 (d, J=7.8 Hz, 2H), 5.20 (s, 2H), 3.03 (t, J=5.1 Hz, 2H), 2.77 (J=5.1 Hz, 2H), 2.32 (s, 6H).

Synthesis of the mono-PNB-Protected N,N-Dimethyethylamine Sidechain 105

105

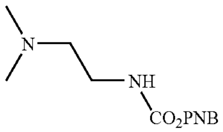

N,N-Dimethylethylamine (11.3 mmol, 1 g) was dissolved in dry DCM (100 mL) and cooled to 0° C. under $N_2$ atm. DIEA (17.0 mmol, 2.2 g) was then added in one portion and the mixture stirred for 5 min. A solution of 4-nitrobenzyl chloroformate (12.5 mmol, 2.7 g) in dry DCM (20 mL) was then added dropwise over 10 minutes and the resulting mixture was allowed to age while warming to rt overnight. The crude reaction mixture was then washed with DI water, 50% brine, dried over anhydrous $Na_2SO_4$, filtered, and concentrated. The crude residue was then purified by column chromatography on silica gel eluted with 9:1 ACN:DI water to produce 2.2 g of the desired product (105, 72% yield) as a white solid.

$^1$H NMR ($CDCl_3$, 300 MHz); δ 8.20 (d, J=8.1 Hz, 2H), 7.51 (d, J=7.5 Hz, 2H), 5.53 (bs, 1H), 5.18 (s, 2H), 3.29 (q, J=5.5 Hz, 2H), 2.44 (t, J=5.5 Hz, 2H), 2.21 (s, 6H).

Synthesis of bis-PNB-Protected N,N-Dimethylpropylthioguanidine Nucleophile 106

106

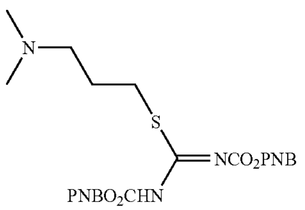

N,N-Dimethylaminopropyl thioguanidine dihydrochloride (1.71 mmol, 400 mg) was suspended in dry DCM and cooled to 0° C. under $N_2$ atm. DIEA (6.0 mmol, 775 mg) was then added over 5 min. and the mixture stirred until it became homogeneous (5-10 min). A solution of 4-nitrobenzylchloroformate (2.05 mmol, 445 mg) in dry DCM (10 mL) was then added via syringe over 15 minutes and the resulting mixture was allowed to warm to rt overnight. The crude reaction mixture was then washed with DI water and 50% brine, dried over anhydrous $Na_2SO_4$, filtered, and concentrated. Purification of the resulting residue by column chromatography on silica get with 9:1 ACN:DI water afforded the desired product (106, 350 mg, 40% yield) as a white foamy solid.

$^1$H NMR ($CDCl_3$, 300 MHz); δ 8.22 (d, J=8.7 Hz, 4H), 7.55 (d, J=7.5 Hz, 4H), 5.27 (s, 4H), 3.10 (t, J=7.5 Hz, 2H), 2.40 (t, J=7.5 Hz, 2H), 2.22 (s, 6H), 1.86 (q, J=7.5 Hz, 2H).

Synthesis of the PNB-Protected Amidine 107

107

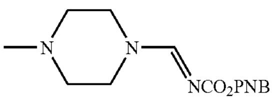

Methypiperazine (134 μL, 1.21 mmol) and triethylamine (337 μL, 2.42 mmol) were dissolved in dry EtOH (20 mL) and stirred at rt. Isopropylformimidate (180 mg, 1.45 mmol) was then added and the reaction was aged for 3 h. 4-Nitrobenzylchloroformate (313 mg, 1.45 mmol) was added and the mixture aged for 12 h. The solvent was removed under reduced pressure and the crude residue was purified by flash column chromatography 5% methanol in dichloromethane to afford the desired product 107 as a white solid (200 mg, 52% yield).

$^1$H NMR ($CDCl_3$, 300 MHz): δ 2.30 (s, 3H), 2.50 (m, 4H), 3.55 (m, 2H), 3.80 (m, 2H), 5.25 (s, 2H), 7.60 (d, 2H), 8.20 (d, 2H), 8.45 (s, 1H).

N-PNB-Protected Pyrrolidine 108

108

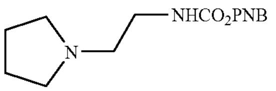

1-(2-Aminoethyl)pyrrolidine (100 μg, 0.80 mmol) was dissolved in dry DCM (15 mL) cooled to 0° C. 4-Nitrobenzylchloroformate (172 mg, 0.8 mmol) was then added and the resulting mixture was aged for 1 hour at 0° C., quenched with saturated $NaHCO_3$ solution (aq., 15 mL), extracted with dichloromethane (10 mL) and dried over anhydrous $MgSO_4$. The crude product 108 (220 mg, 94% yield) was used directly in the next step without purification.

$^1$H NMR ($CDCL_3$, 300 MHz) δ: 1.75 (m, 4H), 2.50 (m, 4H), 2.60 (q, 2H), 3.30 (q, 2H), 5.20 (s, 2H), 7.55 (brs, 1H), 7.55 (d, 2H), 8.25 (d, 2H).

Synthesis of the Nucleophile Intermediates and Supporting Reagents

Part II:

The following procedure was used to make the neutral amine, amidine, guanidine, and sulfonamide analogs 59, 61, 63, 65, 89, 97, and 100.

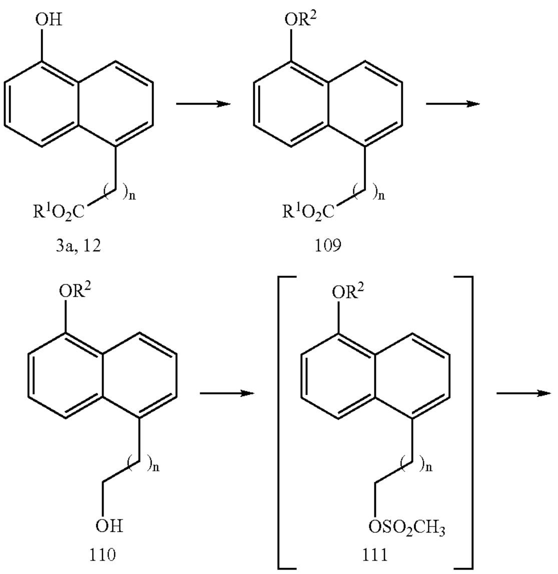

3a, 12

109

110

111

-continued

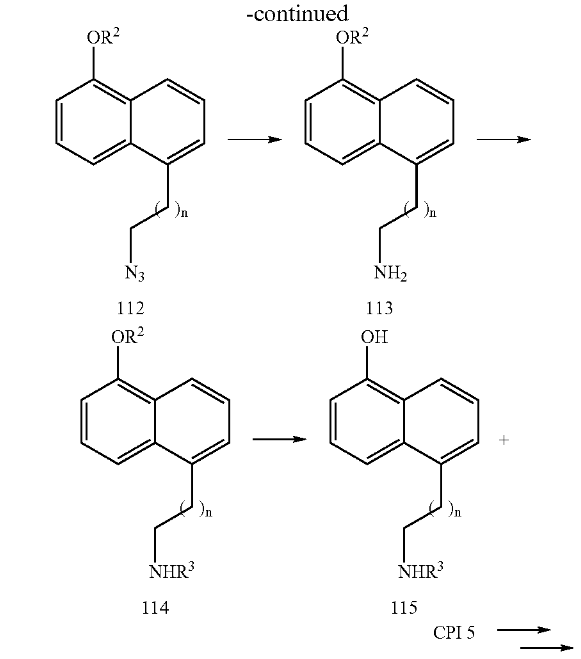

112 113 114 115 CPI 5

$R_1$ = Me or Et
$R_2$ = TBDMS or TBDPS
$R_3$ = $CO_2PNB$, Amidine, Guanidine, and Sulfonamde
n = 0, 1

Discussion

The reaction sequence begins by first protecting the naphthol hydroxyl group of the 1- and 2-carbon naphthol intermediates 3a and 12 with either a TBDMS or a TBDPS group. The ester groups of each series were then reduced with LAH to produce the monoprotected alcohol intermediates 110. Activation of the hydroxyl group with mesyl chloride followed by nucleophilic displacement with sodium azide produced the corresponding azides 112, which were reduced to their corresponding amines 114 with zinc dust/ammonium chloride in refluxing ethanol/DI water (Lin, W., Zhang, Ze, H., Jin, Y., Gong, L., and Mi, A., *Synthetic Communications,* 2002, 32, 3279). Amines 113 were then either PNB protected or further functionalized to their protected amidine or guanidine intermediates 114, desilylated with TBAF/AcOH to naphthols 115, and then coupled to CPI 5 using similar conditions as previously described for 6 and 14. Deprotection of the TES-protected intermediates using the tandem 2-step, 1-pot procedure described above yielded the final analogs 59, 61, 63, 65, 89, 97, and 100.

Experimental

General Procedure for the Synthesis of the Naphthol Silyl Ether Intermediates 109

Naphthols 3a, 12 (18.7 mmol) was dissolved in dry DCM (100 mL) and cooled to 0° C. under $N_2$ atm. Either TBDMS chloride or TBDPS chloride (20.5 mmol) was then added and the mixture stirred 5 minutes at 0° C. (Note: ACN, THF, and DMF can also be used as solvents or co-solvents). DIEA (28.0 mmol) was then added by syringe over 15 minutes and the resulting mixture was allowed to warm to rt overnight. (Note: Heat was required to drive the reaction when TBDPS chloride was used; reactions were monitored by TLC). Upon completion, the crude reaction mixture was washed with DI water and the organics dried over anhydrous $Na_2SO_4$, filtered, and the solvent removed under vacuum. Purification of the resulting residue by column chromatography on silica gel with 9:1 hexanes:EtOAc afforded silyl ether 109 in 76-96% yield.

General Procedure for the LAH Reduction

A solution of ester 109 (16.5 mmol) in dry THF (200 mL) was stirred and cooled to 0° C. under $N_2$ atm. Solid LAH was then added portionwise and the resulting mixture was aged for 2 hrs at 0° C. (monitored by TLC). Upon completion, the reaction mixture was quenched with cold EtOAc (10 mL) and, after stirring for 5 min., DI water (5 mL) was added. The resulting mixture was stirred until homogeneous, dried with anhydrous $Na_2SO_4$, filtered over celite, and concentrated. Purification was done by column chromatography with 5-20% EtOAc in hexanes to yield alcohols 110 in 68-80% yield.

General Procedure for the Synthesis of Azides 112

Both 1- and 2-carbon naphthols were converted to their corresponding mesylate intermediates 111 using the reaction conditions previously described (see 15) and used immediately after formation. The crude mesylate (6.6 mmol) and sodium azide (19.8 mmol) were then added to dry DMF (100 mL) and the resulting mixture was stirred at 60° C. for 18 h (until complete by TLC). The reaction mixture was then allowed to cool to rt, concentrated under vacuum, and purified by column chromatography with 10-20% EtOAc in hexanes (percent yields, 60-70%).

General Procedure for the Synthesis of Amines 113

To a solution of azide 112 (4.6 mmol) in THF/EtOH (10 mL/25 mL) was added DI water (7 mL), zinc dust (5.7 mmol), and solid ammonium chloride (9.6 mmol) and the resulting mixture was refluxed for 1-2 hrs (monitored by TLC). After cooling to rt, the reaction mixture was basified with 5% $NH_4OH$ solution to pH 9-11, diluted with EtOAc (50 mL), filtered over a pad of celite, and the filter cake washed with EtOAc (2×25 mL). The filtrate was then washed with brine, dried over anhydrous $Na_2SO_4$, filtered, and concentrated. Purification on silica gel with DCM:MeOH:$NH_4OH$ (79:20:1) afforded amine 113 as a colorless waxy solid in 65-75% yield.

General Procedure for the Deprotection of TBDMS or TBDPS Ethers

To a solution of silylether 114 (0.68 mmol) in dry THF (20 mL) at 0° C. under $N_2$ atm were added glacial acetic acid (neat, 2.0 mmol), and TBAF solution (1.0M solution in THF, 1.35 mmol) and the resulting mixture was maintained at 0° C. for 2-4 hrs (monitored by TLC). Upon completion, the reaction mixture was quenched with 0.25M sodium phosphate buffer (pH=7.0, 25 mL), stirred for several minutes, diluted with EtOAc (50 mL), and washed with 50% brine. The organics were then dried over anhydrous $Na_2SO_4$, filtered, and concentrated. The crude products were purified by column chromatography on silica gel using 10-50% EtOAc in hexanes to produce naphthols 115 in 60-88% yield.

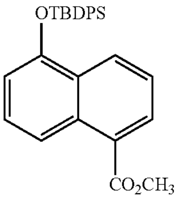

116

Percent yield: 76%; $^{1}$H NMR ($CDCl_3$, 300 MHz); δ 8.77 (d, J=8.1 Hz, 1H), 8.37 (d, J=8.1 Hz, 1H), 8.20 (dd, J=8.1, 1.5 Hz, 1H), 7.76 (d, J=7.5 Hz, 4H), 7.58 (t, J=7.5 Hz, 1H), 7.41 (m, 6H), 7.15 (t, J=8.5 Hz, 1H), 6.51 (d, J=8.1 Hz, 1H), 4.00 (s, 3H), 1.20 (s, 9H).

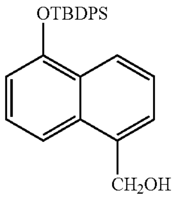

117

Percent yield: 88%; $^{1}$H NMR ($CDCl_3$, 300 MHz); δ 8.54 (d, J=8.4 Hz, 1H), 7.78 (dd, J=7.5, 1.8 Hz, 4H), 7.73 (d, J=8.1 Hz, 1H), 7.56 (m, 3H), 7.41 (m, 6H), 7.09 (t, J=8.1 Hz, 1H), 6.49 (d, J=7.8 Hz, 1H), 5.14 (s, 2H), 1.20 (s, 9H).

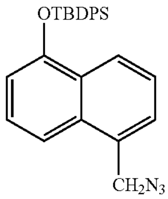

118

Percent yield: 78%; $^{1}$H NMR ($CDCl_3$, 300 MHz); δ 8.58 (dd, J=7.5, 3.0 Hz, 1H), 7.77 (dd, J=7.7, 2.0 Hz, 4H), 7.54 (m, 3H), 7.41 (m, 6H), 7.11 (t, J=7.8 Hz, 1H), 6.50 (d, J=6.6 Hz, 1H), 4.76 (s, 2H), 1.20 (s, 9H).

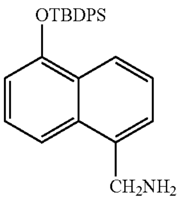

119

Percent yield: 98%; $^{1}$H NMR ($CDCl_3$, 300 MHz); δ 8.50 (t, J=5.0 Hz, 1H), 7.78 (d, J=7.8 Hz, 4H), 7.58 (d, J=9.3 Hz, 1H), 7.53 (d, J=6.3 Hz, 3H), 7.41 (m, 6H), 7.08 (t, J=8.1 Hz, 1H), 6.48 (d, J=6.9 Hz, 1H), 4.31 (s, 2H), 1.20 (s, 9H).

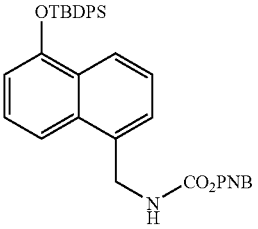

120

Percent yield: 98%; $^{1}$H NMR ($CDCl_3$, 300 MHz); δ 8.55 (dd, J=6.6, 3.3 Hz, 1H), 8.20 (d, J=8.7 Hz, 2H), 7.77 (d, J=6.6 Hz, 4H), 7.51 (m, 4H), 7.40 (m, 8H), 7.08 (t, J=8.1 Hz, 1H), 6.50 (d, J=7.8 Hz, 1H), 5.23 (bs, 2H), 5.16 (m, 1H), 4.84 (d, 2H), 1.20 (s, 9H).

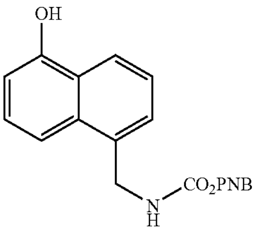

121

Percent yield: 83%; $^{1}$H NMR ($CDCl_3$+MeOD-d6, 300 MHz); δ 8.16 (t, J=9.5 Hz, 2H), 7.45 (t, J=9.5 Hz, 2H), 7.32 (m, 4H), 6.82 (d, J=7.5 Hz, 1H), 5.18 (s, 2H), 4.72 (s, 2H).

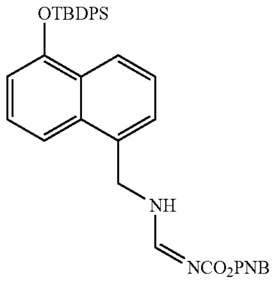

122

Percent yield: 48%; $^{1}$H NMR ($CDCl_3$, 300 MHz); δ 8.54 (dd, J=7.2, 2.7 Hz, 1H), 8.19 (d, J=13.8 Hz, 2H), 7.76 (d, J=7.80 Hz, 4H), 7.51 (m, 6H), 7.40 (m, 6H), 7.08 (t, J=7.2 Hz, 1H), 6.50 (d, J=4.8 Hz, 1H), 5.29 (bs, 1H), 5.24 (s, 2H), 5.15 (m, 1H), 4.84 (d, J=4.8 Hz, 2H), 1.20 (s, 9H).

123

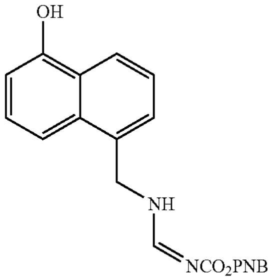

Percent yield: 76%; $^1$H NMR ($CDCl_3$+MeOD-d6, 300 MHz); δ 8.16 (t, J=8.4 Hz, 3H), 7.38 (m, 8H), 6.83 (d, J=6.9 Hz, 1H), 5.19 (s, 2H), 4.73 (s, 2H).

124

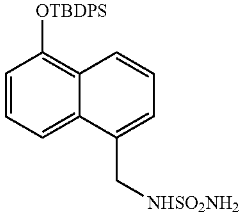

To a solution of TPS-protected amine 119 (440 mg, 1.06 mmol) in dry dioxane (20 mL) was added sulfamide (193 mg, 2.12 mol) and the resulting mixture heated to 90° C. for 12 h. The solvent was removed under reduced pressure and the organic residue was purified by flash column 5% methanol in dichloromethane to afford the desired protected naphtholaminesulfamide 124 as a brown solid (0.450 g, 55% yield).

$^1$H NMR ($CDCl_3$, 300 MHz) δ: 1.15 (s, 9H), 4.40 (bs, 2H), 4.75 (s, 2H), 6.30 (d, 1H), 7.15 (t, 2H), 7.20 (m, 8H), 7.55 (m, 4H), 7.75 (m, 5H), 8.55 (d, 1H).

125

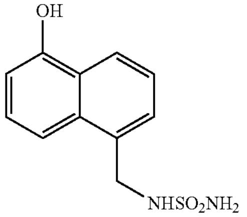

Percent yield: 79%; $^1$H NMR ($CDCl_3$, 300 MHz): δ 3.10 (brs, 2H), 4.55 (s, 2H), 6.75 (d, 1H), 7.15 (m, 2H) 7.40 (d, 1H), 7.50 (d, 1H), 8.05 (d, 1H).

126

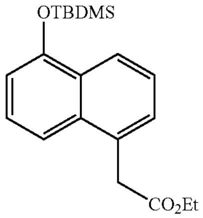

Percent yield: 89%; $^1$H NMR ($CDCl_3$, 300 MHz); δ 8.19 (d, J=7.5 Hz, 1H), 7.60 (d, J=8.4 Hz, 1H), 7.43 (m, 2H), 7.37 (d, J=8.4 Hz, 4H), 6.89 (d, J=7.5 Hz, 1H), 4.16 (q, J=7.6 Hz, 2H), 4.04 (s, 2H), 1.24 (t, J=7.6 Hz, 3H), 1.11 (s, 9H), 0.30 (s, 6H)

127

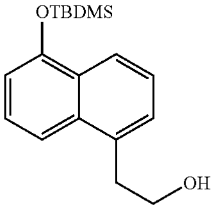

Percent yield: 83%; $^1$H NMR ($CDCl_3$, 300 MHz); δ 8.16 (dd, J=7.2, 1.5 Hz, 1H), 7.66 (d, J=8.7 Hz, 3H), 7.40 (m, 3H), 6.89 (d, J=6.6 Hz, 1H), 4.00 (t, J=6.6 Hz, 2H), 3.34 (t, J=6.6 Hz, 2H), 1.11 (s, 9H), 0.30 (s, 6H).

128

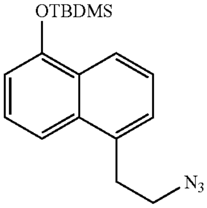

Percent yield: 70%; $^1$H NMR ($CDCl_3$, 300 MHz); δ 8.18 (dd, J=8.2, 1.4 Hz, 1H), 7.60 (d, J=8.4 Hz, 1H), 7.40 (m, 3H), 6.89 (d, J=7.2 Hz, 1H), 3.64 (t, J=7.5 Hz, 2H), 3.35 (t, J=7.5 Hz, 2H), 1.11 (s, 9H), 0.30 (s, 6H).

129

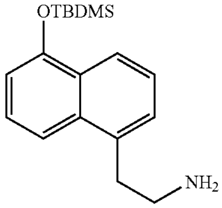

Percent yield: 72%; $^1$H NMR ($CDCl_3$, 300 MHz); δ 8.14 (d, J=8.1 Hz, 1H), 7.65 (d, J=8.4 Hz, 1H), 7.38 (m, 3H), 6.88 (d, J=7.8 Hz, 1H), 3.23 (t, J=7.0 Hz, 2H), 3.12 (t, J=7.0 Hz, 2H), 1.11 (s, 9H), 0.30 (s, 6H).

130

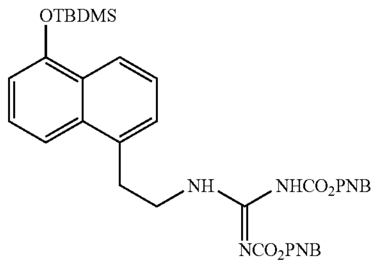

Percent yield: 90%; $^1$H NMR ($CDCl_3$, 300 MHz); δ 11.75 (s, 1H), 8.36 (m, 1H), 8.23 (t, J=8.7 Hz, 4H), 8.16 (d, J=8.4 Hz, 1H), 7.75 (d, J=7.8 Hz, 1H), 7.56 (d, J=8.4 Hz, 2H), 7.51 (d, J=9.3 Hz, 2H), 7.37 (m, 4H), 6.88 (J=7.0 Hz, 1H), 3.83 (q, J=6.8 Hz, 2H), 3.36 (t, J=6.8 Hz, 2H), 1.10 (s, 9H), 0.29 (s, 6H).

131

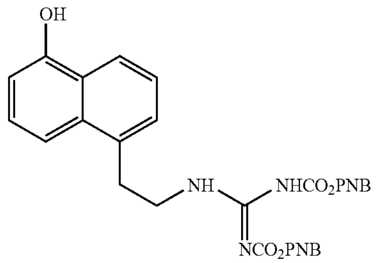

Percent yield: 88%; $^1$H NMR ($CDCl_3$, 300 MHz); δ 11.74 (bs, 1H), 8.36 (m, 1H), 8.22 (dd, J=8.7, 10.0 Hz, 4H), 8.16 (d, J=8.1 Hz, 1H), 7.71 (d, J=8.4 Hz, 1H), 7.66 (bs, 1H), 7.53 (dd, J=8.6, 11.5 Hz, 4H), 7.37 (m, 5H), 6.82 (d, J=7.5 Hz, 1H), 5.24 (s, 2H), 5.23 (s, 2H), 3.83 (q, J=7.6 Hz, 2H), 3.36 (t, J=7.6 Hz, 2H).

Synthesis of the Nucleophile Intermediates and Supporting Reagents

Part III:

The following procedures were used to synthesize the nucleophilic intermediates for the S- and N-alkylated guanidine and thioguanidine analogs 30 and 32.

132

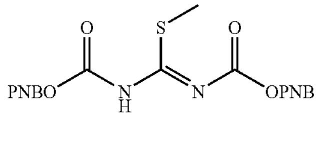

N,N'-bis(p-nitrobenzyloxycarbonyl)-S-methylisothiourea 132

To a clean 3-necked round bottom flask equipped with two addition funnels were added DCM (60 mL), S-methylisothiourea (1 g, 7.18 mmol), and 6.25N NaOH solution (aq, 570 uL). After cooling the resulting mixture to 0° C., a solution of 4-nitrobenzyl chloroformate (3.17 g, 14.73 mmol) in DCM (20 mL) and a solution of sodium hydroxide (aq, 1N, 15 mL)

were simultaneously added dropwise using the two addition funnels while maintaining pH 11. The mixture was aged for 16 h with gradual warming to rt. The layers were separated and the organic phase was washed with brine (20 mL) and dried over sodium sulfate. Solvent was removed under vacuum and the resulting white solid recrystallized from ethyl acetate and hexanes to give 132 (2.7 g, 84%) as a white powder.

$^1$H NMR ($CDCl_3$, 300 MHz): δ 11.92 (s, 1H), 8.23 (d, J=9.2 Hz, 4H), 7.55 (d, J=8.4 Hz, 4H), 5.29 (s, 4H), 2.46(s, 3H).

133

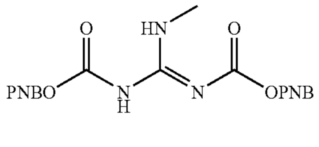

N,N'-bis(p-Nitrobenzyloxycarbonyl)-N-Methylguanidine Intermediate 133

To a solution of 132 (0.5 g, 1.11 mmol) in dry THF (35 mL) was added methylamine (1.12 mL of 2.0 M in THF, 2.23 mmol). The mixture was aged for 8 h at rt and then concentrated under vacuum. The crude light yellow solid was purified by recrystallization from ethyl acetate and hexanes to give 133 (370 mg, 76%) as a white solid.

$^1$H NMR ($CDCl_3$, 300 MHz): δ 11.77 (s, 1H), 8.24 (d, J=9.0 Hz, 2H), 8.23 (d, J=8 Hz, 2H), 7.55 (m, 4H), 5.31 (s, 2H), 5.28 (s, 2H), 3.00 (d, J=4.6 Hz, 3H).

N,N'-bis(p-Nitrobenzyloxycarbonyl)-N,N-Dimethylamino Intermediate 134

134

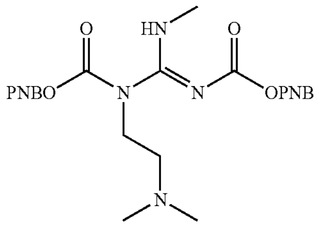

A clean round-bottomed flask was charged with 133 (266 mg, 0.62 mmol), N,N-dimethylethanolamine (55 mg, 0.62 mmol), triphenylphosphine (356 mg, 1.36 mmol) and dry THF (10 mL). After cooling to 0° C., the mixture was treated dropwise over a 20 min. period with a solution of diisopropylazodicarboxylate (247 mg, 1.36 mmol) in THF (1 mL). The mixture was aged for 16 h with gradual warming to rt and then concentrated under vacuum. The resulting orange gum was purified by column chromatography on silica gel with 5% water in acetonitrile to give 134 (145 mg, 50%) as a white solid.

$^1$H NMR (acetone-$d_6$+$CDCl_3$, 300 MHz): δ 9.67 (s, 1H), 8.06 (m, 4H), 7.49 (m, 4H), 5.13 (s, 2H), 5.02 (s, 2H), 3.63 (m, 2H), 2.86 (s, 3H), 2.51 (m, 2H), 2.29 (s, 6H).

N,N'-bis(p-Nitrobenzyloxycarbonyl)-N,N-Dimethylamino Intermediate 135

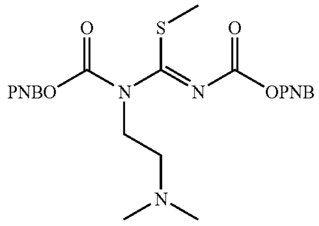

135

A clean round-bottomed flask was charged with 132 (320 mg, 0.71 mmol), N,N-dimethylethanolamine (64 mg, 0.71 mmol), triphenylphosphine (375 mg, 1.43 mmol) and dry THF (10 mL). After cooled to 0° C., the mixture was treated dropwise over a 1 h period with a solution of diisopropylazodicarboxylate (289 mg, 1.43 mmol) in THF (4 mL). The mixture was aged for 16 h with gradual warming to rt and then concentrated under vacuum. The resulting orange gum was purified by chromatography over silica gel with 5% water in acetonitrile to give 135 (185 mg, 50%) as a white solid.

$^1$H NMR ($CDCl_3$, 300 MHz): δ 8.19 (d, J=9.0 Hz, 4H), 7.53 (d, J=9.0 Hz, 2H), 7.50 (d, J=9.0 Hz, 2H), 5.21 (s, 2H), 5.19 (s, 2H), 3.87 (t, J=6.3 Hz, 2H), 2.33 (m, 2H), 2.45 (s, 3H), 2.34 (s, 6H).

Synthesis of the Nucleophile Intermediates and Supporting Reagents

Part IV:

The following sequence was used to synthesize the nucleophilic intermediates for the S-attached guanidine analog 57.

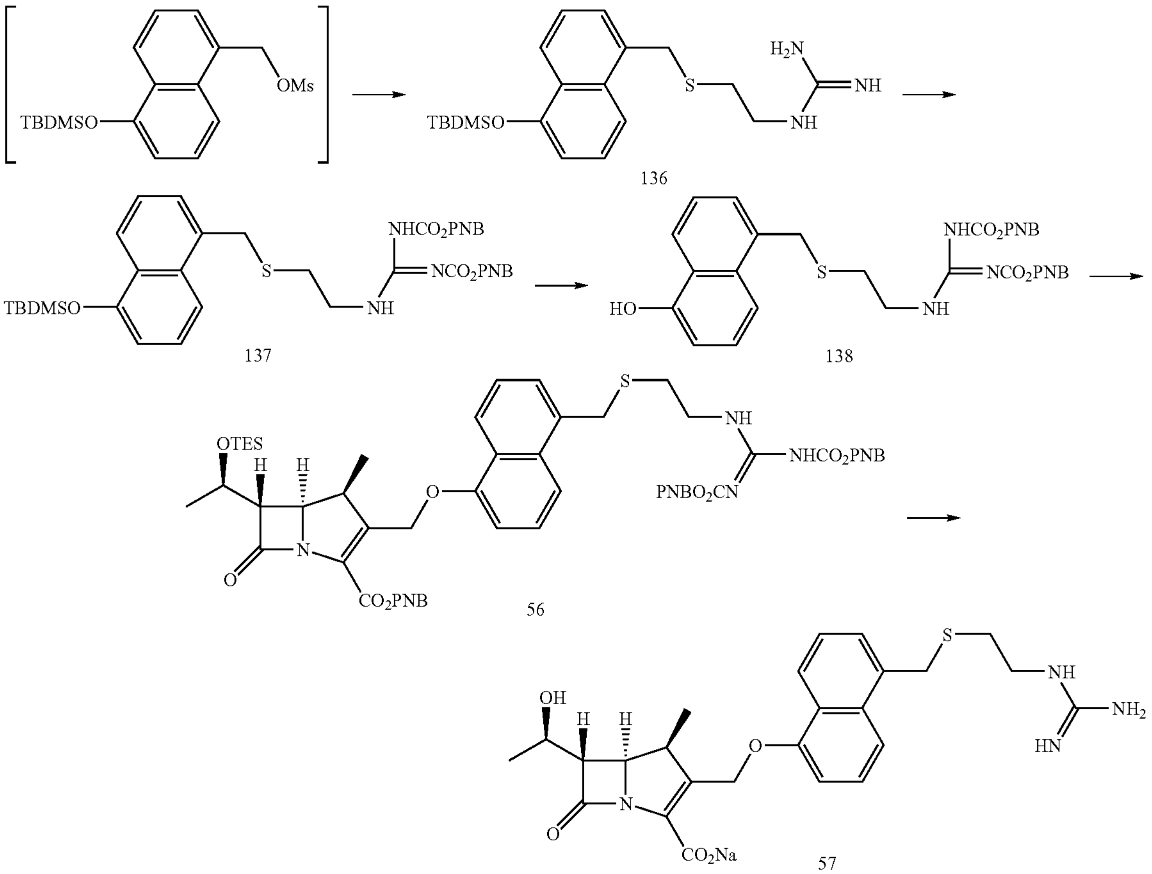

136 137 138 56 57

Percent yield: 76%; $^1$H NMR ($CDCl_3$, 300 MHz); δ 8.17 (dd, J=2.7, 6.3 Hz, 1H), 7.68 (d, J=8.7 Hz, 1H), 7.56 (t, J=5.7 Hz, 1H), 7.43-7.31 (m, 2H), 6.88 (d, J=6.9 Hz, 1H), 7.40-6.40 (bs, 3H), 4.16 (s, 2H), 3.14 (m, 2H), 2.65 (m, 2H), 1.08 (s, 9H), 0.27 (s, 6H).

137

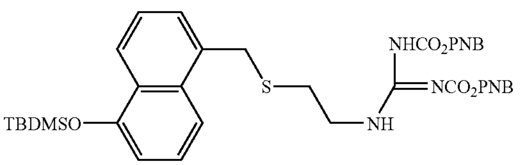

Percent yield; 81%: $^1$H NMR ($CDCl_3$, 300 MHz); δ 9.39 (bs, 1H), 9.19 (bs, 1H), 8.27-8.11 (m, 5H), 7.66 (d, J=6.3 Hz, 1H), 7.58 (d, J=9.0 Hz, 2H), 7.55-7.44 (m, 3H), 7.37 (t, J=7.8 Hz, 1H), 7.27 (t, J=7.8 Hz, 1H), 6.87 (d, J=7.1 Hz, 1H), 5.26 (s, 2H), 5.23 (s, 2H), 4.26 (t, J=7.5 Hz, 2H), 4.20 (s, 2H), 2.74 (t, J=7.8 Hz, 2H), 1.17 (s, 9H), 0.28 (s, 6H).

138

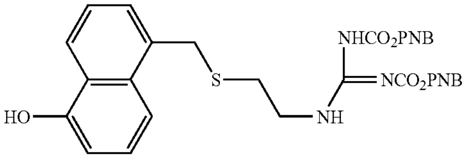

Percent yield; 87%: $^1$H NMR ($CDCl_3$, 300 MHz); δ 9.40 (bs, 1H), 9.19 (bs, 1H), 8.17 (d, J=8.4 Hz, 2H), 8.16 (d, J=8.1 Hz, 1H), 8.10 (d, J=9.0 Hz, 2H), 7.62 (d, J=7.5 Hz, 1H), 7.48 (d, J=8.7 Hz, 2H), 7.46 (d, J=8.4 Hz, 1H), 7.44 (d, J=8.4 Hz, 2H), 7.33-7.26 (m, 2H), 6.83 (d, J=6.9 Hz, 1H), 5.47 (bs, 1H), 5.26 (s, 2H), 5.23 (s, 2H), 4.26 (t, J=6.9 Hz, 2H), 4.20 (s, 2H), 2.74 (t, J=8.4 Hz, 2H).

Synthesis of the Nucleophile Intermediates and Supporting Reagents

Part V: Preparation of Other Nucleophile Intermediates

The following procedure was used to synthesize the nucleophilic intermediate for the N,N-Dimethylaminoacetamide analog 34.

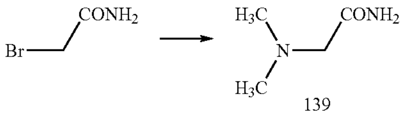

139

A mixture of bromoacetamide (1.37 g, 10 mmole) and dimethylamine (6 mL, 2M in THF) in acetonitrile (15 mL) was stirred for 3 h at rt, and the mixture was concentrated under vacuum and re-dissolved in THF (20 mL). The mixture was treated with $Na_2CO_3$ for neutralization overnight and filtered through celite to afford 139 as a white solid (800 mg, 78%).

$^1$H NMR ($D_2O$, 300 MHz); δ 3.03 (s, 2H), 2.21 (s, 6H).

The following procedure was used to synthesize the nucleophilic intermediate for the N,N-Dimethylamino thioguanidine analog 36.

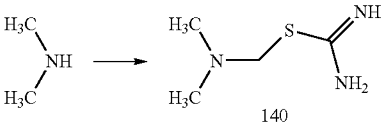

140

Formaldehyde (1.5 mL, 54.5 mmole) was added to a suspension of dimethylamine (5 mL, 2M in THF) and activated molecular sieve (3.5 g) in methanol (12 mL) at 0° C. After 3 h, thiourea (760 mg, 10 mmole) was added and the mixture was gradually warmed up to rt overnight. The mixture was filtered through Celite and concentrate to afford 140 as a white solid (1.3 g, 98%).

$^1$H NMR ($CD_3OD$, 300 MHz); δ 4.88 (bs, 3H), 3.33 (s, 2H), 2.27 (bs, 6H).

141

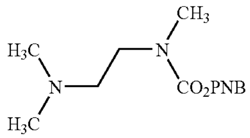

Percent yield; 78; $^1$H NMR ($CDCl_3$, 300 MHz); δ 8.22 (d, J=8.7 Hz, 2H), 7.52 (d, J=8.4 Hz, 2H), 5.23 (s, 2H), 3.42 (q, J=7.2 Hz, 2H), 3.0 (s, 1.6H), 2.97 (s, 1.4H), 2.47 (m, 2H), 2.30 (s, 3.2H), 2.25 (s, 2.8H).

Examples of Amino-Substituted Naphthol CP Analogs

Preparation of the 5-Amino-1-Naphthol Sidechains

Discussion

The following experimental procedures serve as examples of the aminonaphthol series of carbapenem analogs prepared in our labs. In general, these analogs were prepared by first synthesizing the functionalized aminonaphthol sidechains, coupling these sidechains to CPI 5 with palladium catalyst, and, lastly, deprotecting the resulting TES- and PNB-protected intermediates in two synthetic steps.

Experimental

Synthesis of Silylether 142

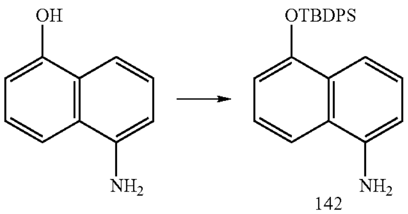

142

To a suspension of 5-Amino-1-naphthol (15.92 g, 100 mmol) in dry chloroform (500 mL) were added TEA (28 mL, 200 mmol) and TBDPS chloride (44 mL, 170 mmol) and heated at reflux until TLC indicated the absence of starting material (3 days). The cooled mixture was quenched with 300 mL ice/water, diluted with DCM (100 mL) and washed with water. The solvent was evaporated under reduced pressure and the residue was purified on a flash column (5%-12% EtOAc/Hexanes) to afford the desired protected naphthol 142 (22.5 g, 57% yield) as a pink foam.

$^1$H NMR ($CDCl_3$, 300 MHz); δ 1.17 (s, 9H), 6.43 (d, J=7.2 Hz, 1H), 6.86 (d, J=7.2 Hz, 1H), 6.98 (t, J=9.0, 7.2 Hz, 1H), 7.38 (m, 8H), 7.76 (dd, J=1.3, 1.3 Hz, 4H), 8.01 (d, J=7.8 Hz, 1H).

Example 40

Preparation of Side chain 145

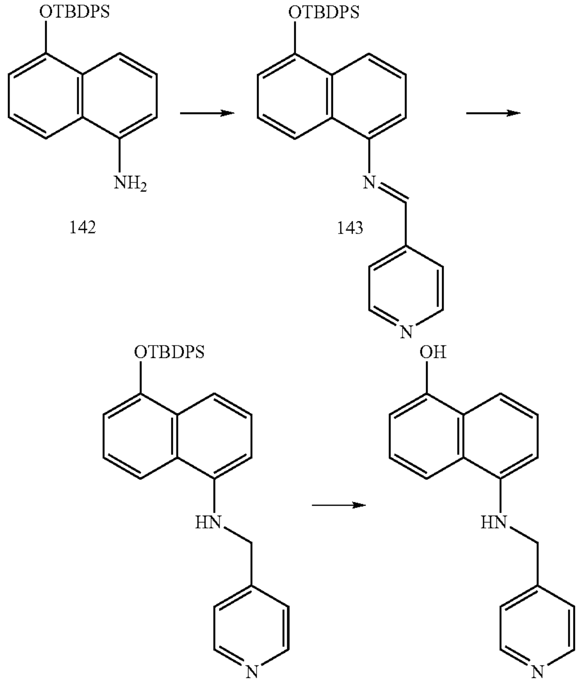

142 143 144 145

To a solution of naphthol 142 (0.25 g, 0.63 mmol) in dry DCE (10 mL) were added sodium sulfate (0.13 g, 0.94 mmol) and pyridine-4-carboxaldehyde (0.075 mL, 0.82 mmol) and the mixture was heated at 60° C. until TLC indicated the absence of starting material (2 days). The sodium sulfate was filtered off and dichloroethane was evaporated under reduced pressure to afford crude desired imine 143 (0.30 g, 100% yield)

$^1$H NMR ($CDCl_3$, 300 MHz); δ 1.20 (s, 9H), 6.51 (d, J=8.4 Hz, 1H), 7.06 (t, J=8.4 Hz, 1H), 7.13 (d, J=7.2 Hz, 1H), 7.39 (m, 6H), 7.54 (t, J=7.2 Hz, 1H), 7.80 (m, 5H), 7.89 (d, J=5.5 Hz, 2H), 8.46 (d, J=8.1 Hz, 1H), 8.57 (s, 1H), 8.80 (d, J=5.5 Hz, 2H).

To a solution of imine 143 (1.28 g, 2.6 mmol) in absolute ethanol (25 mL) was added sodium borohydride (0.15 g, 3.9 mmol) and the mixture was aged overnight at room temperature. The mixture was then quenched with water and solvent evaporated under reduced pressure. The residue was then taken up in dichloromethane and washed with brine, then the organic layer was dried over $MgSO_4$, filtered and the solvent was concentrated to afford desired amine 144 (1.13 g, 89% yield).

$^1$H NMR ($CDCl_3$, 300 MHz); δ 1.17 (s, 9H), 4.60 (d, J=3.9 Hz, 2H), 6.48 (t, J=8.1 Hz, 2H), 7.01 (t, J=8.1 Hz, 1H), 7.39 (m, 10H), 7.74 (m, 5H), 7.98 (d, J=8.1 Hz, 1H), 8.58 (d, J=6.6 Hz, 1H).

To a solution of amine 144 (1.44 g, 3.0 mmol) in dry THF (25 mL) at 0° C. was added 1M solution TBAF in THF (5.91 mL, 3.9 mmol) and the mixture was aged 45 minutes at room temperature. THF was removed under reduced pressure and the residue was taken up in dichloromethane and washed with brine, dried over $MgSO_4$, filtered, and the solvent was concentrated to afford the desired naphtholamine 145 (0.316 g, 43% yield) as a light brown solid.

$^1$H NMR (DMSO-$d_6$, 300 MHz); δ 4.49 (d, J=5.5 Hz, 2H), 6.22 (d, J=7.2 Hz, 1H), 6.83 (m, 2H), 7.06 (t, J=7.2 Hz, 1H), 7.22 (t, J=8.1 Hz, 1H), 7.34 (m, 3H), 7.64 (d, J=8.1 Hz, 1H), 8.45 (d, J=5.5 Hz, 1H).

TES-Protected Aminonaphthol Intermediate 146

146

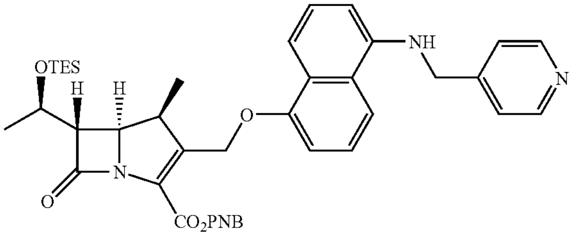

To dry DMF (60 mL) were added $Pd_2$ $dba_3$-$CHCl_3$ (0.04 g, 0.038 mmol), and triethyl phosphite (0.04 mL, 0.229 mmol), and the solution was aged for 5 minutes at room temperature. The mixture was degassed with 3 nitrogen/vacuum cycles and stirred for 30 minutes until solution became yellow. Then the naphtholamine 145 (0.20 g, 0.80 mmol), CPI 5 (0.52 g, 0.88 mmol), and 2,6-lutidine (0.046 mL, 0.4 mmole) were added to the reaction solution and the resulting mixture was aged for 3 hours. Solvent was removed under reduced pressure and crude residue was purified by flash column chromatography with 97:3 $CH_2Cl_2$/MeOH to afford the desired couple product 146 as a yellow oil (0.47 g, 82% yield).

$^1$H NMR ($CDCL_3$, 300 MHz) δ: 0.60 (q, J=7.8 Hz, 6H), 0.90 (t, J=7.8 Hz, 9H), 1.15 (d, J=6.1 Hz, 3H), 1.18 (d, J=7.4 Hz, 4H), 3.30 (m, 1H), 3.55 (m, 1H), 4.30 (m, 2H), 4.65 (s, 2H), 4.85 (d, J=13.5 Hz, 1H), 5.30 (d, J=17.1 Hz, 1H), 5.50 (d, J=17.1 Hz, 1H), 5.60 (d, J=13.5 Hz, 1H), 6.50 (d, J=7.2 Hz,

1H), 6.85 (d, J=7.5 Hz, 1H), 7.25 (m, 6H), 7.65 (d, J=7.5 Hz, 2H), 8.10 (d, J=7.5 Hz, 2H), 8.60 (d, J=5.5 Hz, 1H).

PNB-Protected Aminonaphthol Intermediate 147

147

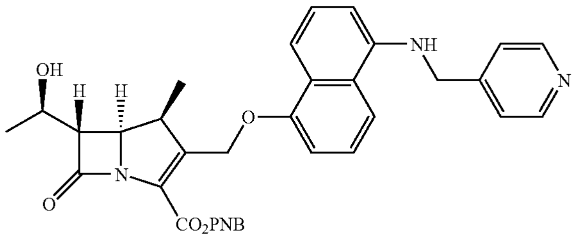

To a solution of 146 (0.47 g, 0.65 mmol) in dry THF (30 mL) at 0° C., were added acetic acid (0.18 mL, 1.35 mmol) and 1M solution of TBAF in THF (2.06 mL, 2.06 mmol). The reaction mixture was aged for 4 hours at 0° C., quenched with 0.25M sodium phosphate buffer (pH 7.0, 30 mL), stirred for several minutes. The mixture was then extracted with EtOAc (90 mL), dried over $MgSO_4$, filtered, and concentrated to give a yellow oil. The oil was purified by flash column chromatography with 9:1 $CH_2Cl_2$/MeOH to afford alcohol 147 as a yellow solid (0.32 g, 80% yield).

$^1$H NMR ($CDCl_3$, 300 MHz): δ 1.20 (d, J=7.4 Hz, 3H), 1.25 (d, J=7.5 Hz, 3H), 3.38 (m, 1H), 3.58 (m, 1H), 4.22 (m, 2H), 4.50 (s, 2H), 4.90 (d, J=13.5 Hz, 1H), 5.20 (d, J=17.0 Hz, 1H), 5.50 (d, J=17.1 Hz, 1H), 5.8 (d, J=13.5 Hz, 1H), 6.40 (d, J=7.2 Hz, 1H), 6.80 (d, J=7.2 Hz, 1H), 7.30 (m, 6H) 7.60 (d, J=7.5 Hz, 2H), 8.05 (d, J=7.5 Hz, 2H), 8.30 (s, 2H).

1,5-Aminonaphthol Analog 148

148

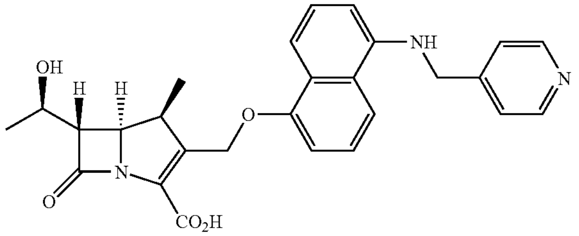

In a round bottom flask equipped with a side arm, compound 147 (60 mg, 0.098 mmol) was dissolved in THF/IPA (2 mL/4 mL). 0.25M Sodium phosphate buffer solution (pH 7.0, 6 mL) was added in 1 mL increments so as to maintain a homogeneous system and the resulting mixture was cooled down to 0° C. 5% Pt/C (50 mg) was added and the reaction flask was purged with $H_2$, and the resulting mixture was aged for 6 h at 0° C. (monitored by TLC). Ethyl acetate (15 ml) and DI $H_2O$ (15 mL) were then added and the resulting mixture was stirred for several minutes at 0° C., filtered over celite, and the celite pad was washed well with DI $H_2O$ (20 mL) and EtOAc (20 mL). The aqueous phase was then lyophilized and the crude product was purified on SP207 resin column with water/IPA. Lyophilization of the column fractions produced CP 148 (20 mg, 46% yield) as an off-white solid.

$^1$H NMR ($D_2O$, 400 MHz) δ: 0.65 (d, J=7.3 Hz, 3H), 0.85 (d, J=7.7 Hz, 3H), 2.78 (m, 1H), 2.98 (m, 1H), 3.49 (m, 1H), 3.86 (m, 3H), 4.65 (d, 1H), 5.39 (d, 1H), 5.78 (s, 1H), 6.78 (m, 3H), 7.15 (m, 3H), 7.29 (m, 2H), 7.09 (m, 2H).

Example 41

Thiazole Sidechain 149

149

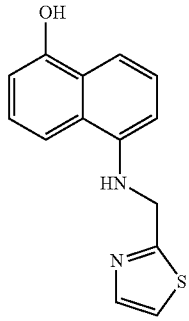

Percent yield: 73%; $^1$H NMR ($CDCl_3$, 300 MHz): δ 4.75 (s, 2H), 6.20 (d, J=7.2 Hz, 1H), 6.80 (d, J=7.2 Hz, 1H), 7.15 (t, J=8.5 Hz, 1H), 7.23 (t, J=8.5 Hz, 1H), 7.38 (d, J=5.5 Hz, 1H), 7.57 (t, J=8.5 Hz, 2H), 7.60 (d, J=5.5 Hz, 1H).

TES-Protected Aminonaphthol Intermediate 150

150

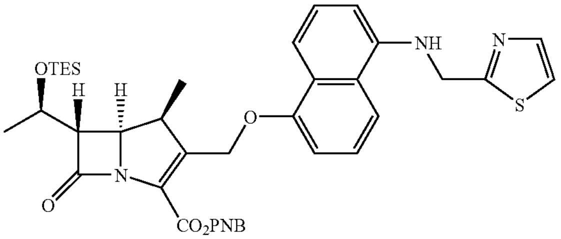

Percent yield: 66%; $^1$H NMR ($CDCl_3$, 300 MHz): δ 0.62 (q, J=7.8 Hz, 6H), 0.95 (t, J=7.8 Hz, 9H), 1.24 (d, J=6.1 Hz, 3H), 1.33 (d, J=7.4 Hz, 4H), 3.25 (m, 1H), 3.55 (m, 1H), 4.3 (m, 2H), 4.80 (s, 2H), 4.90 (d, J=13.5 Hz, 1H), 5.30 (d, J=17.1 Hz, 1H), 5.50 (d, J=17.1 Hz, 1H), 5.85 (d, J=13.5 Hz, 1H), 6.65 (d, J=7.2 Hz, 1H), 6.85 (d, J=7.2 Hz, 1H), 7.15 (m, 4H), 7.25 (t, J=8.5 Hz, 2H), 7.75 (d, J=7.5 Hz, 2H), 8.10 (d, J=7.5 Hz, 2H).

PNB-Protected Aminonaphthol Intermediate 151

151

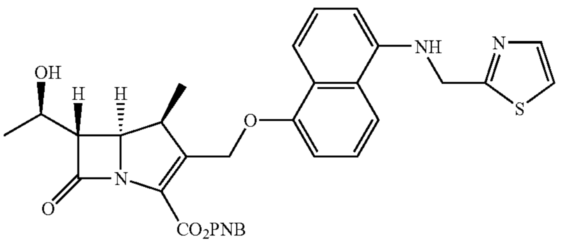

Percent yield: 73%; $^1$H NMR ($CDCl_3$, 300 MHz): δ 1.10 (d, J=7.4 Hz, 3H), 1.17 (d, J=7.5 Hz, 3H), 3.15 (m, 1H), 3.55 (m, 1H), 4.25 (m, 1H), 4.80 (s, 2H), 4.85 (d, J=13.5 Hz, 1H), 5.21 (d, J=17.1 Hz, 1H), 5.45 (d, J=17.1 Hz, 1H), 5.49 (d, J=13.5 Hz, 1H), 6.65 (d, J=7.2 Hz, 1H), 6.80 (d, J=7.2 Hz, 1H), 7.15 (m, 4H), 7.60 (t, J=8.5 Hz, 2H), 7.75 (d, J=7.5 Hz, 2H), 8.10 (d, J=7.5 Hz, 2H).

1,5-Aminonaphthol Analog 152

152

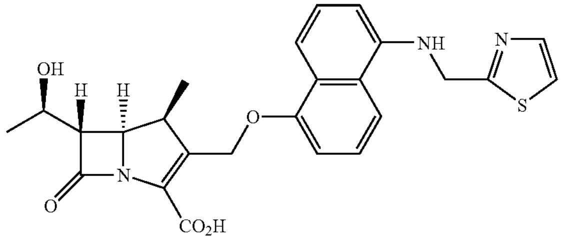

Percent yield: 22%; $^1$H NMR ($D_2O$, 400 MHz): δ 0.58 (d, J=7.3 Hz, 3H), 0.77 (d, J=7.7 Hz, 3H), 2.70 (m, 1H), 2.89 (m, 1H), 3.41 (d, J=6.0 Hz, 1H), 3.75 (m, 1H), 4.32 (s, 2H), 4.49 (d, J=9.6 Hz, 1H), 5.20 (d, J=9.6 Hz, 1H), 6.03 (s, 1H), 6.62 (t, J=4.0 Hz, 2H), 6.76 (s, 1H), 7.04 (s, 1H), 7.19 (m, 2H), 7.30 (s, 1H): MS 518.2.

Example 42

Aminonaphthol Sidechain 153

153

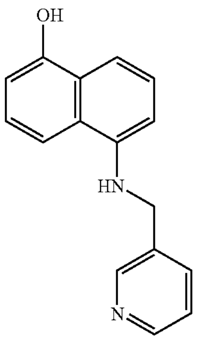

Percent yield: quantitative; $^1$H NMR (DMSO-$d_6$, 300 MHz); δ 4.49 (d, J=6.0 Hz, 2H), 6.35 (d, J=8.4 Hz, 1H), 6.81 (d, J=7.5 Hz, 2H), 7.08 (t, J=7.5 Hz, 1H), 7.20 (t, J=8.7 Hz, 1H), 7.32 (m, 2H), 7.62 (d, J=9.0 Hz, 1H), 7.75 (d, J=8.4 Hz, 1H) 8.41 (d, J=3.3 Hz, 1H), 8.61 (s, 1H).

TES-Protected Aminonaphthol Intermediate 154

154

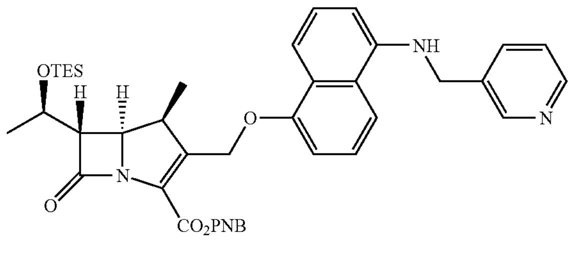

Percent yield: 36%; $^1$H NMR ($CDCL_3$, 300 MHz): δ 0.60 (q, J=7.8 Hz, 6H), 0.95 (t, J=7.8 Hz, 9H), 1.14 (d, J=6.1 Hz, 3H), 1.20 (d, J=7.4 Hz, 4H), 3.25 (m, 1H), 3.50 (m, 1H), 4.25 (m, 2H), 4.50 (s, 2H), 4.90 (d, J=13.5 Hz, 1H), 5.20 (d, J=17.1 Hz, 1H), 5.40 (d, J=17.1 Hz, 1H), 5.65 (d, J=13.5 Hz, 1H), 6.60 (d, J=7.2 Hz, 1H), 6.80 (d, J=7.5 Hz, 1H), 7.15 (m, 4H), 7.45 (d, J=7.6 Hz, 2H), 7.65 (d, J=7.5 Hz, 2H), 8.10 (d, J=7.5 Hz, 2H), 8.55 (d, J=5.5 Hz, 1H), 8.70 (s, 1H).

PNB-Protected Aminonaphthol Intermediate 155

155

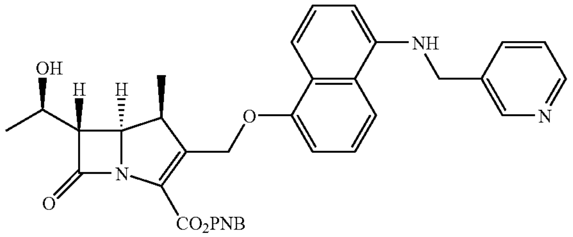

Percent yield: 45%; $^1$H NMR ($CDCl_3$, 300 MHz): δ 1.15 (d, J=7.4 Hz, 3H), 1.19 (d, J=7.5 Hz, 3H), 3.35 (m, 1H), 3.60 (m, 1H), 4.25 (m, 2H), 4.50 (s, 2H), 4.90 (d, J=13.5 Hz, 1H), 5.25 (d, J=17.0 Hz, 1H), 5.50 (d, J=17.1 Hz, 1H), 5.80 (d, J=13.5 Hz, 1H), 6.60 (d, J=7.2 Hz, 1H), 6.80 (d, J=7.2 Hz, 1H), 7.25 (m, 3H), 7.42 (d, J=7.5 Hz, 1H), 7.50 (d, J=7.5 Hz, 1H), 7.64 (d, J=7.5 Hz, 2H), 7.80 (d, J=7.5 Hz, 1H), 8.20 (d, J=7.5 Hz, 2H), 8.58 (d, J=5.5 Hz, 1H), 8.70 (s, 1H).

1,5-Aminonaphthol Analog 156

157

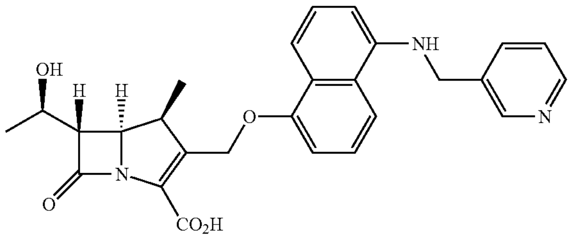

Percent yield: 53%; $^1$H NMR ($D_2O$, 400 MHz): δ 0.75 (d, J=7.3 Hz, 3H), 0.90 (d, J=7.7 Hz, 3H), 2.80 (m, 1H), 2.95 (m, 1H), 3.51 (m, 1H), 3.92 (m, 3H), 4.70 (d, 1H), 5.38 (d, 1H), 5.95 (s, 1H), 6.70 (m, 3H), 7.15 (m, 3H), 7.20 (m, 2H), 8.05 (m, 2H).

Example 43

Aminonaphthol Sidechain 159

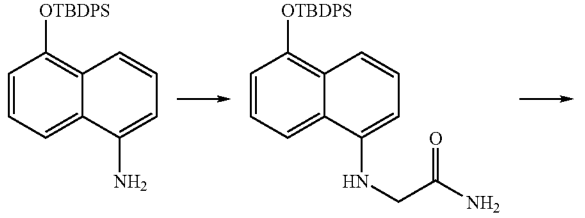

142 158

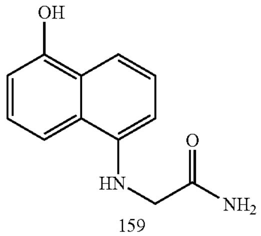

159

To a clean, dry round bottom flask were added dry ACN (40 mL) and naphthylamine 142 (3 mmol, 1.2 g), and the resulting solution stirred under $N_2$ atmosphere at room temperature (rt). α-Bromoacetamide (3 mmol, 420 mg), and sodium carbonate (3.3 mmol, 350 mg) were then added and the resulting mixture heated at reflux for 48 hr (additional sodium carbonate (3.3 mmol, 350 mg) was added after 24 hr). Upon completion (monitored by TLC, $R_f$=0.2 in 1:1 EtOAc:hexanes), the mixture was quenched with water (50 mL), extracted with EtOAc (50 mL) and concentrated under vacuum. The crude product was purified by column chromatography with 50-80% EtOAc in hexanes to give naphtholamide 158 (0.9 g, 66% yield).

$^1$H NMR ($CDCl_3$, 300 MHz): δ 8.05 (d, J=8.4 Hz, 1H), δ 7.76 (dd, J=1.4, 9.0 Hz, 4H), δ 7.40 (m, 8H), δ 7.03 (t, J=8.2 Hz, 1H), δ 6.64 (d, J=7.2 Hz, 1H),), δ 6.55 (m, 1H), δ 6.47 (d, J=7.2 Hz, 1H), δ 5.46 (m, 1H), δ 4.02 (s, 2H), δ 1.18 (s, 9H).

To a clean, dry round bottom flask were added dry THF (40 mL) and silylether 158 (2 mmol, 0.9 g), and the resulting solution cooled to 0° C. under $N_2$ atmosphere. TBAF (1.0M solution in THF, 2.5 mmol, 2.5 mL) was then added dropwise, the resulting mixture aged for 30 minutes (monitored by TLC, $R_{f=0.25}$ in EtOAc) and quenched with water (20 mL) and 0.5M phosphate buffer solution (pH=7.0, 20 mL). The resulting heterogeneous mixture was partitioned between EtOAc (50 mL) and brine (20 mL) and the organic layer concentrated to dryness. Crystallization of the crude product from DCM produced naphthol 159 (350 mg, 87% yield).

$^1$H NMR (DMSO-$d^6$, 300 MHz): δ 9.85 (bs, 1H), δ 7.42 (m, 2H), δ 7.16 (m, 2H), δ 6.79 (d, J=7.5 Hz, 1H), δ 6.28 (m, 2H), δ 3.70 (d, J=5.4 Hz, 2H).

TES-Protected Aminonaphthol Intermediate 160

160

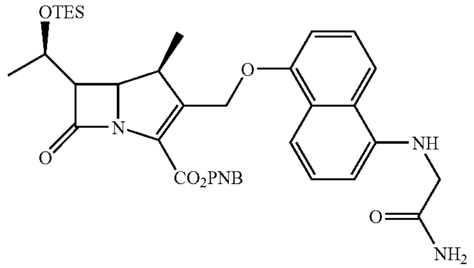

Percent yield: 62%; $^1$H NMR ($CDCl_3$, 300 MHz): δ 8.17 (d, J=9.0 Hz, 1H), δ 8.04 (m, 1H), δ 7.68 (m, 2H), δ 7.38 (m, 4H), δ 6.85 (d, J=7.8 Hz, 1H), δ 6.62 (d, J=7.8 Hz, 1H), δ 6.53 (m, 2H), δ 5.62 (d, J=14.1 Hz, 1H), δ 5.39 (m, 2H), δ 4.91 (d, J=14.1 Hz, 1H), δ 4.29 (m, 2H), δ 3.99 (m, 2H), δ 3.47 (m, 1H), δ 3.30 (m, 1H), δ 1.30 (m, 6H), □ 0.95 (m, 9H), δ 0.64 (m, 6H).

PNB-Protected Aminonaphthol Intermediate 161

161

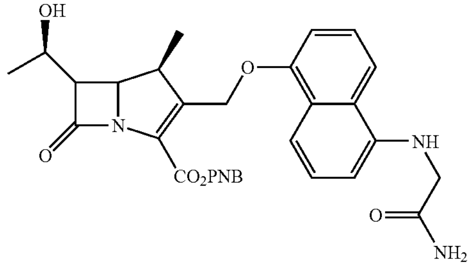

Percent yield: 20%; $^1$H NMR ($CDCl_3$, 300 MHz): δ 8.18 (d, J=9.0 Hz, 2H), δ 7.71 (m, 2H), δ 7.64 (d, J=9.0 Hz, 2H), δ 7.44 (m, 3H), δ 6.83 (d, J=6.9 Hz, 1H), δ 6.62 (d, J=7.8 Hz, 1H), δ 5.61 (d, J=14.7 Hz, δ 5.52 (d, J=14.7 Hz, 1H), δ 5.28 (d, J=14.7 Hz, 1H), δ 4.92 (d, J=14.7 Hz, 1H), δ 4.31 (m, 2H), δ 4.01 (m, 2H), δ 3.62 (m, 1H), δ 3.38 (dd, J=2.7, 7.5 Hz, 1H), δ 1.32 (m, 6H).

Aminonaphthol Analog 162

162

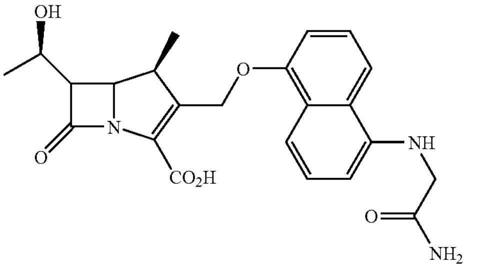

Percent yield: 13%; $^{1}$H NMR ($D_2O$, 400 MHz): δ 7.65 (dd, J=8.4, 26.0 Hz, 2H), δ 7.44 (t, J=8.4 Hz, 1H), δ 7.38 (t, J=8.4 Hz, 1H), δ 7.00 (d, J=7.6 Hz, 1H), δ 6.55 (d, J=7.6 Hz, 1H), δ 5.59 (d, J=14.0 Hz, 1H), δ 4.90 (d, J=14.0 Hz, 1H), δ 4.08 (m, 1H), δ 3.98 (s, 2H), δ 3.92 (d, J=9.2 Hz, 1H), δ 3.35 (m, 1H), δ 3.23 (m, 1H), δ 1.19 (d, J=6.0 Hz, 3H), δ 1.14 (d, J=7.2 Hz, 3H).

Example 44

Aminonaphthol Sidechain 164

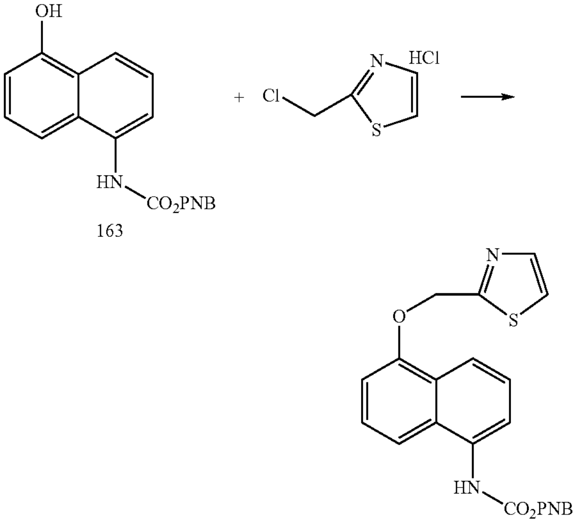

163

164

163: $^{1}$H NMR (DMSO-$d^6$, 300 MHz): δ 9.75 (bs, 1H), δ 9.14 (d, J=2.4 Hz, 1H), δ 8.25 (d, J=9.3 Hz, 2H), δ 7.95 (d, J=7.8 Hz, 1H), δ 7.68 (d, J=7.8 Hz, 2H), δ 7.55 (d, J=7.2 Hz, 1H), δ 7.48 (d, J=8.7 Hz, 1H), δ 7.37 (t, J=7.8 Hz, 1H), δ 7.29 (t, J=7.8 Hz, 1H), δ 6.85 (d, J=7.2 Hz, 1H).

To a clean, dry round bottom flask was added dry DMF (40 mL) and naphthol 163 (1.2 g, 3.5 mmol) and the resulting mixture stirred under $N_2$ atmosphere at rt. 2-Chloromethylthiazole hydrochloride (595 mg, 3.5 mmol) and sodium carbonate (740 mg, 7 mmol) were then added at rt and the resulting mixture aged at 80° C. for 48 hr. Additional $Na_2CO_3$ (2 mmol, 320 mg) and 2-chloromethylthiazole hydrochloride (350 mg, 2 mmol) were added to the reaction mixture after 24 hr and the mixture aged for 5 h. Upon completion (monitored by TLC, $R_f$=0.6 in 1:1 EtOAc:hexanes), the reaction mixture was allowed to cool to rt, concentrated to dryness, and purified by column chromatography (2:3 EtOAc:hexanes) to give thiazole ether 164 as a brown solid (340 mg, 24% yield).

164: $^{1}$H NMR (DMSO-$d^6$, 300 MHz): δ 9.75 (bs, 1H), δ 9.14 (d, J=2.4 Hz, 1H), δ 8.25 (d, J=8.7 Hz, 2H), δ 8.03 (d, J=8.7 Hz, 1H), δ 7.90 (s, 1H), δ 7.65 (m, 4H), δ 7.44 (m, 2H), δ 7.16 (d, J=8.1 Hz, 1H), δ 6.40 (s, 2H), δ 5.31 (s, 2H).

TES-Protected Aminonaphthol Intermediate 165

165

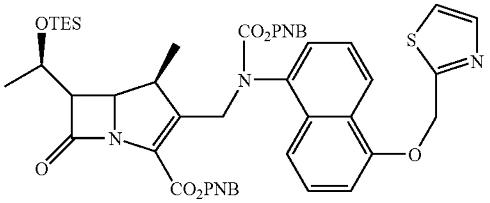

To a clean, dry round bottom flask was added dry DMF (50 mL) and the solvent degassed under vacuum for 10 min. $Pd_2dba_3$-$CHCl_3$ (40 mg, 40 μmol) and triethyl phosphite (45 μl, 260 μmol) were added and the mixture degassed for 10 min. CPI 5 (300 mg, 0.5 mmol), 164 (230 mg, 0.5 mmol), and DMAP (30 mg, 0.25 mmol) were added at once and the mixture degassed for 10 min under vacuum. The resulting mixture was aged at rt for 3 hr (monitored by TLC, $R_f$=0.4 in 1:1 EtOAc:hexanes) and concentrated in vacuo, The crude product was purified by column chromatography with 2:3 EtOAc:hexanes to give the desired product 165 (265 mg, 58% yield).

165: $^{1}$H NMR ($CDCl_3$, 300 MHz): δ 8.90 (m, 1H), δ 8.29 (m, 3H), δ 8.09 (m, 2H), δ 7.50 (m, 6H), δ 7.10 (m, 4H), δ 5.17 (m, 8H),δ 4.14 (m, 2H), δ 3.24 (m, 2H), δ 1.25 (m, 6H), δ 0.94 (m, 9H), δ 0.61 (m, 6H).

PNB-Protected Aminonaphthol Intermediate 166

166

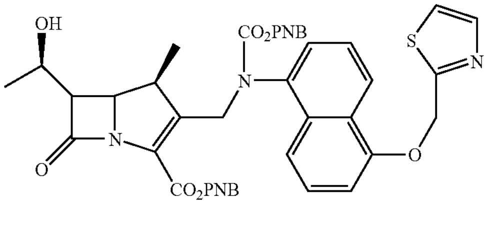

Percent yield: 49%; $^{1}$H NMR ($CDCl_3$, 300 MHz): δ 8.91 (d, J=2.4 Hz, 1H), δ 8.35 (t, J=8.1 Hz, 1H), δ 8.16 (d, J=9.0

Hz, 1H), δ 8.02 (m, 2H), δ 7.43 (m, 6H), δ 7.09 (m, 4H), δ 5.19 (m, 8H), δ 4.27 (m, 2H), δ 3.35 (m, 2H), δ 1.31 (m, 6H).

1,5-Aminonaphthol Analog 167

167

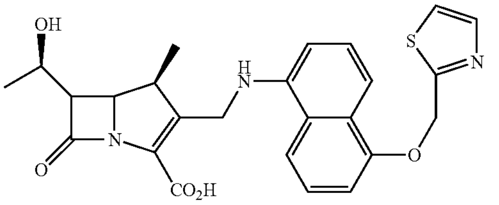

Percent yield: 21%; $^1$H NMR ($D_2O$, 400 MHz): δ 8.98 (s, 1H), δ 7.64 (bs, 3H), δ 7.40 (m, 2H), δ 7.11 (d, J=7.6 Hz, 1H), δ 6.75 (d, J=7.2 Hz, 1H), δ 5.41 (s, 2H), δ 4.69 (m, 1H), δ 4.07 (m, 1H), δ 3.88 (m, 1H), 3.72 (m, 1H), δ 3.30 (m, 1H), δ 2.98 (m, 1H), δ 1.14 (m, 6H).

Example 45

1,4-Aminonitrile Sidechain 168

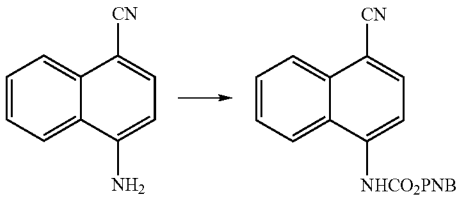

168

Percent yield: 91%; $^1$H NMR ($CDCl_3$, 300 MHz): δ 8.27 (d, J=8.4 Hz, 2H), 8.32-8.17 (m, 2H), 7.94 (d, J=8.1 Hz, 1H) 7.92 (d, J=7.2 Hz, 1H), 7.62 (d, J=8.4 Hz, 2H), 7.75-7.54 (m, 2H), 7.45 (br s, 1H), 5.39 (s, 2H).

TES-Protected Naphthylamine Intermediate 169

169

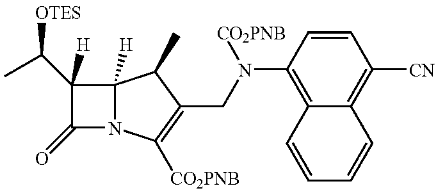

Percent yield: 93%; $^1$H NMR ($CDCl_3$, 300 MHz): δ 8.35-7.20 (m, 14H), 5.30-4.75 (m, 6H), 4.27 (t, J=6.0 Hz, 1H), 3.99 (dd, J=3.0, 10.2 Hz, 1H), 3.29 (br s, 1H), 3.21 (dd, J=3.0, 12.3 Hz, 1H), 1.29-1.22 (m, 6H), 0.98-0.88 (m, 9H), 0.65-0.51 (m, 6H).

PNB-Protected Naphthylamine Intermediate 170

170

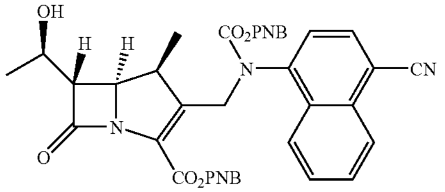

Percent yield: 78%; $^1$H NMR ($CDCl_3$ at 50° C., 400 MHz): δ 8.30-8.27 (2 d, J=5.6 Hz, 1H), 8.15 (d, J=5.6 Hz, 1H), 8.08 (d, J=5.6 Hz, 1H), 8.04 (d, J=4.8 Hz, 2H), 7.87-7.70 (m, 4H), 7.64-7.57 (2 t, J=4.2 Hz, 1H), 7.47-7.42 (2 d, J=5.6 Hz, 1H), 7.33 (d, J=5.6 Hz, 1H), 7.17 (d, J=4.2 Hz, 1H), 7.10 (br s, 1H), 5.44-4.68 (m, 6H), 4.28 (dd, J=1.6, 6.4 Hz, 0.6H), 4.24 (q, J=4.0 Hz, 0.6H), 4.16 (p, J=4.0 Hz, 0.4H), 4.01 (dd, J=1.6, 6.4 Hz, 0.4H), 3.33 (p, J=6.4 Hz, 1H), 3.29 (dd, J=2.0, 4.4 Hz, 0.6H), 3.22 (dd, J=2.0, 4.4 Hz, 0.4H), 1.33 (d, J=4.0 Hz, 1.8H), 1.29 (d, J=4.4 Hz, 1.8H), 1.27 (d, J=2.4 Hz, 1.2H), 1.20 (br s, 1.2H).

1,4-Naphthylamine Analog 171

171

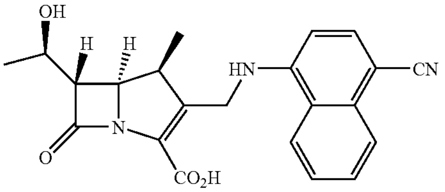

Percent yield: 28%; $^1$H NMR ($D_2O$, 400 MHz): δ 7.86 (d, J=9.2 Hz, 1H), 7.79 (d, J=8.8 Hz, 1H), 7.56 (d, J=8.0 Hz, 1H), 7.49 (m, 1H), 7.39 (t, J=8.0 Hz, 1H), 6.32 (d, J=5.6 Hz, 1H), 4.75 (d, J=10.4 Hz, 1H), 3.95 (m, 2H), 3.76 (d, J=10.4 Hz, 1H), 3.14 (m, 1H), 2.80 (m, 1H), 1.02 (d, J=4.4 Hz, 3H), 0.94 (d, J=4.0 Hz, 3H).

Example 46

1,5-Aminonaphthol Sidechain 172

172

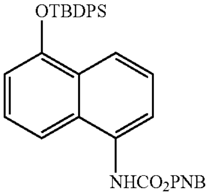

Percent yield: 90%; $^1$H NMR ($CDCl_3$, 300 MHz): δ 8.39 (d, J=8.4 Hz, 1H), 8.25 (d, J=9.0 Hz, 2H), 7.92 (br s, 1H), 7.75

(dd, J=1.5, 7.8 Hz, 4H), 7.56 (m, 3H), 7.47-7.27 (m, 7H), 7.07 (t, J=8.1 Hz, 2H), 6.49 (d, J=7.8 Hz, 1H), 5.35 (s, 2H), 1.19 (s, 9H).

TES-Protected Aminonaphthol Intermediate 173

173

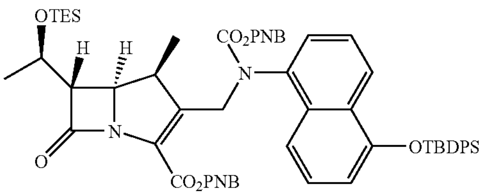

Percent yield: 65%; $^1$H NMR ($CDCl_3$, 300 MHz): δ 8.55 (t, J=10.8 Hz, 1H), 8.17 (d, J=8.4 Hz, 1H), 8.04 (d, J=9.0 Hz, 1H), 7.98 (t, J=7.8 Hz, 2H), 7.77 (m, 4H), 7.55-7.32 (m, 8H), 7.20 (d, J=8.1 Hz, 3H), 7.06-6.97 (m, 3H), 6.54 (dd, J=7.5, 17.1 Hz, 1H), 5.27 (d, J=12.6 Hz, 1H), 5.49-4.88 (m, 4H), 4.69 (d, J=12.6 Hz, 1H), 4.28 (m, 1H), 4.19-3.96 (m, 1H), 3.42-3.19 (m, 2H), 1.29-1.21 (m, 6H), 1.22 (br s, 9H), 0.97 (t, J=7.8 Hz, 6H), 0.89 (t, J=7.8 Hz, 3H), 0.67 (q, J=8.4 Hz, 4H), 0.53 (q, J=8.1 Hz, 2H).

PNB-Protected Aminonaphthol Intermediate 174

174

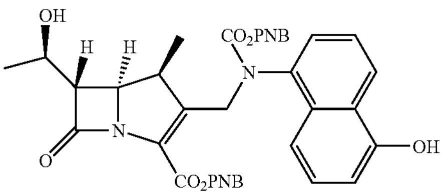

Percent yield: 84%; $^1$H NMR ($CDCl_3$, 300 MHz): δ 8.22 (d, J=8.4 Hz, 1H), 8.14 (d, J=9.0 Hz, 1H), 8.03 (s, 1H), 7.99 (d, J=8.4 Hz, 2H), 7.44-6.76 (m, 10H), 5.40-4.69 (m, 6H), 4.37-4.02 (m, 2H), 3.49-3.26 (m, 2H), 1.38-1.32 (m, 6H).

1.5-Aminonaphthol Analog 175

175

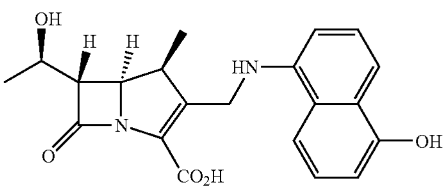

Percent yield: 17%; $^1$H NMR ($D_2O$, 600 MHz): δ 7.42 (t, J=8.4 Hz, 2H), 7.23 (q, J=7.8 Hz, 2H), 6.82 (d, J=7.8 Hz, 1H), 6.58 (d, J=7.2 Hz, 1H), 4.55 (d, J=16.2 Hz, 1H), 3.96 (p, J=6.6 Hz, 1H), 3.89 (d, J=16.2 Hz, 1H), 3.75 (d, J=10.2 Hz, 1H), 3.15 (dd, J=2.4, 6.0 Hz, 1H), 2.87 (p, J=7.2 Hz, 1H), 1.02 (d, J=6.0 Hz, 3H), 0.94 (d, J=7.8 Hz, 3H).

Example 47

1,5-Aminonaphthol Sidechain 177

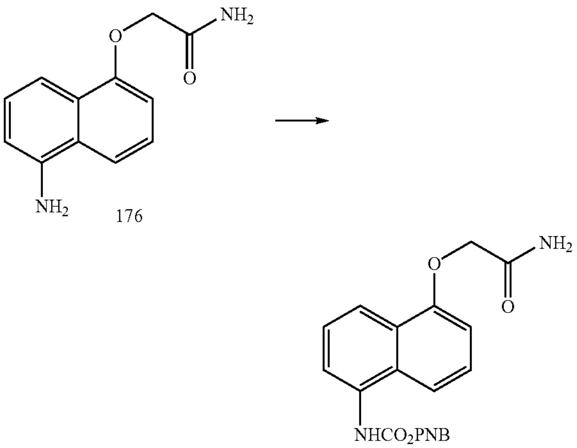

176

177

Preparation on Intermediate 176

To a solution of 5-amino-1-naphthol (1.24 mmol, 208 mg) in dry DMF (10 mL) was added 1.3 mL of LHMDS (1 M in Hexane) at −40° C. and the resulting solution was stirred for 1 h under $N_2$ atmosphere. α-Chloroacetamide (116 mg, 1.24 mmole) was added, and the solution was warmed slowly to rt over 2 h. The mixture was concentrated and purified by a flash chromatography with mixtures of $CH_2Cl_2$/EtOH/EtOAc (85/10/5) to afford aminonaphthalene 176 (165 mg, 62% yield). $^1$H NMR ($CDCl_3$, 300 MHz): δ 7.62 (d, J=8.3 Hz, 1H), 7.50 (d, J=7.5 Hz, 1H), 7.46 (d, J=16.7 Hz, 2H), 7.21 (t, J=8.4 Hz, 1H), 7.16 (t, J=8.0 Hz, 1H), 6.77 (d, J=8.5 Hz, 1H), 6.67 (d, J=7.4 Hz, 1H), 5.62 (s, 2H), 4.53 (s, 2H).

Sidechain 177

$^1$H NMR ($CDCl_3$, 300 MHz): δ 9.74 (br s, 1H), 8.25 (d, J=9.0 Hz, 2H), 8.21 (d, J=8.7 Hz, 1H), 7.70-7.61 (m, 5H), 7.49-7.38 (m, 3H), 6.89 (d, J=8.1 Hz, 1H), 5.30 (s, 2H), 4.60 (s, 2H).

TES-Protected Aminonaphthol Intermediate 178

178

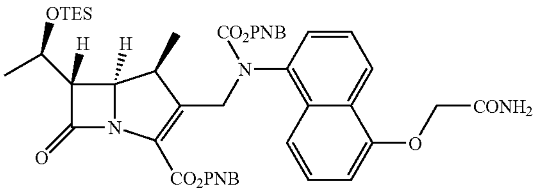

Percent yield: 16%; $^1$H NMR ($CDCl_3$, 300 MHz): δ 8.22 (t, J=7.8 Hz, 1H), 8.15 (d, J=9.0 Hz, 1H), 8.02 (d, J=9.0 Hz, 3H), 7.49-7.35 (m, 4H), 7.21 (t, J=8.4 Hz, 2H), 7.06 (d, J=8.1 Hz, 2H), 6.90 (m, 1H), 6.62 (br s, 1H), 6.20 (br s, 1H), 5.44-4.69 (m, 8H), 4.28 (m, 1H), 4.19-3.99 (m, 1H), 3.40-3.19 (m, 2H), 1.25 (m, 6H), 0.98-0.87 (m, 9H), 0.65-0.54 (m, 6H).

PNB-Protected Aminonaphthol Intermediate 179

179

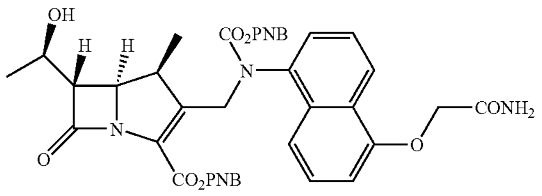

Percent yield: 63%; $^1$H NMR ($CDCl_3$, 300 MHz): δ 8.24-7.96 (m, 5H), 7.47-7.33 (m, 4H), 7.17 (d, J=7.5 Hz, 1H), 7.13 (d, J=9.3 Hz, 1H), 7.05 (d, J=7.8 Hz, 2H), 6.87 (dd, J=8.4, 9.0 Hz, 1H), 6.65 (d, J=13.5 Hz, 1H), 6.29 (br s, 1H), 5.20-4.66 (m, 8H), 4.37-4.25 (m, 2H), 3.45-3.24 (m, 2H), 1.23 (d, J=6.0 Hz, 3H), 1.21 (d, J=5.7 Hz, 3H).

1,5-Aminonaphthol Analog 180

180

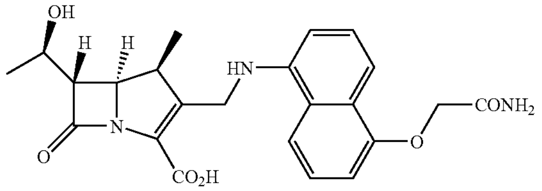

Percent yield: 38%; $^1$H NMR ($D_2O$, 600 MHz): δ 7.57 (d, J=7.8 Hz, 1H), 7.50 (d, J=8.4 Hz, 1H), 7.26 (q, J=7.8 Hz, 2H), 6.77 (d, J=7.2 Hz, 1H), 6.61 (d, J=8.4 Hz, 1H), 4.57 (s, 2H), 4.54 (d, J=16.2 Hz, 1H), 3.95 (p, J=6.0 Hz, 1H), 3.88 (d, J=16.2 Hz, 1H), 3.75 (dd, J=3.0, 9.6 Hz, 1H), 3.15 (dd, J=2.4, 6.0 Hz, 1H), 2.88 (p, J=7.8 Hz, 1H), 1.02 (d, J=6.0 Hz, 3H), 0.94 (d, J=7.2 Hz, 3H).

Example 48

TES-Protected Aminonaphthol Intermediate 181

181

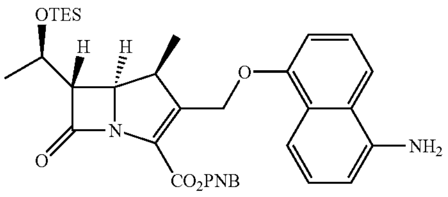

Percent yield: 82%; $^1$H NMR ($CDCl_3$, 300 MHz): δ 8.20 (d, J=5.4 Hz, 2H), 7.69 (d, J=6.3 Hz, 1H), 7.67 (d, J=8.4 Hz, 2H), 7.44 (d, J=6.6 Hz, 1H), 7.32 (q, J=8.1 Hz, 2H), 6.85 (d, J=8.4 Hz, 1H), 6.73 (d, J=7.2 Hz, 1H), 5.63 (d, J=14.7 Hz, 1H), 5.49 (d, J=13.8 Hz, 1H), 5.28 (d, J=14.8 Hz, 1H), 4.92 (d, J=14.7 Hz, 1H), 4.30 (m, 2H), 3.57 (dq, J=7.2, 3.3, Hz, 1H), 3.32 (dd, J=3.9, 5.1 Hz, 1H), 1.30 (d, J=7.5 Hz, 3H), 1.26 (d, J=6.0 Hz, 3H), 0.95 (t, J=8.4 Hz, 9H), 0.62 (q, J=8.1 Hz, 6H).

TES-Protected Aminonaphthol Intermediate 182

182

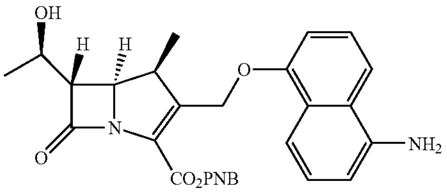

Percent yield: 63%; $^1$H NMR ($CDCl_3$, 300 MHz): δ 8.21 (d, J=9.0 Hz, 2H), 7.67 (d, J=9.0 Hz, 1H), 7.66 (d, J=8.1 Hz, 2H), 7.43 (d, J=8.1 Hz, 1H), 7.32 (m, 2H), 6.83 (d, J=7.5 Hz, 1H), 6.79 (d, J=8.1 Hz, 1H), 5.63 (d, J=15.3 Hz, 1H), 5.54 (d, J=12.9 Hz, 1H), 5.29 (d, J=14.4 Hz, 1H), 4.92 (d, J=14.7 Hz, 1H), 4.29 (dd, J=3.0, 10.8 Hz, 2H), 3.62 (dq, J=7.2, 3.3 Hz, 1H), 3.37 (dd, J=3.0, 6.3 Hz, 1H), 1.36 (d, J=6.6 Hz, 3H), 1.32 (d, J=7.2 Hz, 3H).

1,5-Aminonaphthol Analog 183

183

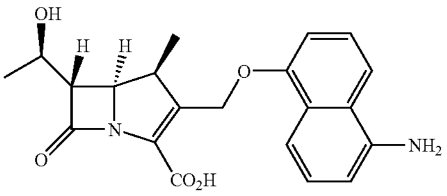

Percent yield: 28%; $^1$H NMR ($D_2O$, 400 MHz): δ 7.58 (d, J=8.4 Hz, 1H), 7.39 (d, J=8.4 Hz, 1H), 7.26 (t, J=8.0 Hz, 1H), 7.19 (t, J=8.0 Hz, 1H), 6.80 (d, J=7.6 Hz, 2H), 5.42 (d, J=14.0 Hz, 1H), 4.73 (d, J=13.6 Hz, 1H), 3.98 (p, J=6.4 Hz, 1H), 3.83 (dd, J=2.8, 10.0 Hz, 1H), 3.21 (dd, J=2.8, 6.0 Hz, 1H), 3.12 (m, 1H), 1.04 (d, J=6.4 Hz, 3H), 0.99 (d, J=7.6 Hz, 3H).

Example 49

1,5-Aminonaphthol Sidechains 184 and 185

184

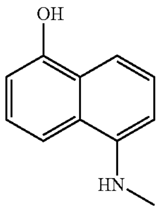

-continued

185

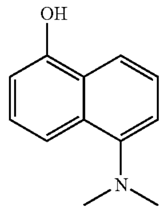

To a solution of 5-amino-1-naphthol (320 mg, 2 mmole) in ACN (10 mL) was added MeI (125 µL, 2 mmole) at rt and the solution was stirred overnight in the dark. The mixture was quenched with a saturated aqueous $NaHCO_3$, extracted with DCM, and the organic layer was concentrated. The crude mixture were purified with 20% ethyl acetate in hexane to afford 5-(methylamino)-1-naphthol 184 (179 mg, 52% yield) & 5-(dimethylamino)-1-naphthol 185 (85 mg, 23% yield).

184 $^1$H NMR ($CDCl_3$, 300 MHz): δ 7.55 (d, J=7.5 Hz, 1H), 7.41 (m, 2H), 7.27 (m, 2H), 6.84 (d, J=7.5 Hz, 1H), 6.65 (d, J=7.2 Hz, 1H), 5.4 (br s, 1H), 3.03 (s, 3H).

185 $^1$H NMR ($CDCl_3$, 400 MHz): δ 7.91 (d, J=8.4 Hz, 1H), 7.83 (d, J=8.4 Hz, 1H), 7.42 (dd, J=7.8, 8.7 Hz, 1H), 7.30 (dd, J=7.5, 8.4 Hz, 1H), 7.13 (d, J=7.5 Hz, 1H), 6.77 (d, J=7.5 Hz, 1H), 5.78 (br s, 1H), 2.92 (s, 6H).

TES-Protected Aminonaphthol Intermediate 186

186

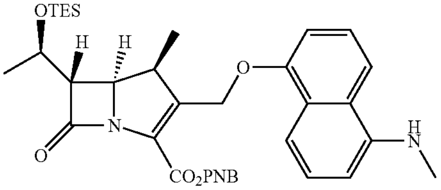

Percent yield: 55%; $^1$H NMR ($CDCl_3$, 300 MHz): δ 8.19 (d, J=9.3 Hz, 2H), 8.06 (d, J=9.0 Hz, 1H), 7.65 (d, J=8.1 Hz, 2H), 7.39 (m, 4H), 6.83 (d, J=7.5 Hz, 1H), 6.67 (d, J=6.3 Hz, 1H), 5.64 (d, J=14.7 Hz, 1H), 5.48 (d, J=13.8 Hz, 1H), 5.29 (d, J=14.1 Hz, 1H), 4.91 (d, J=15.0 Hz, 1H), 4.30 (m, 2H), 3.58 (m, 1H), 3.32 (dd, J=3.0, 5.7 Hz, 1H), 3.03 (s, 3H), 1.31 (d, J=7.2 Hz, 3H), 1.26 (d, J=6.0 Hz, 3H), 0.96 (t, J=8.1 Hz, 9H), 0.62 (q, J=8.1 Hz, 6H).

PNB-Protected Aminonaphthol Intermediate 187

187

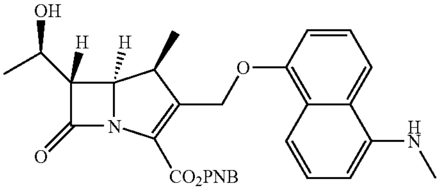

Percent yield: 57%; $^1$H NMR ($CDCl_3$, 300 MHz): δ 8.21 (d, J=8.7 Hz, 2H), 7.65 (d, J=8.7 Hz, 2H), 7.60 (d, J=7.8 Hz, 1H), 7.39 (m, 3H), 7.29 (m, 1H), 6.79 (d, J=7.5 Hz, 1H), 6.65 (d, J=7.8 Hz, 1H), 5.62 (d, J=15.0 Hz, 1H), 5.53 (d, J=13.5 Hz, 1H), 5.28 (d, J=14.1 Hz, 1H), 4.92 (d, J=15.0 Hz, 1H), 4.29 (m, 2H), 3.61 (p, J=7.2 Hz, 1H), 3.32 (dd, J=3.0, 6.6 Hz, 1H), 3.02 (s, 3H), 1.35 (d, J=6.6 Hz, 3H), 1.32 (d, J=7.5 Hz, 3H).

1,5-Aminonaphthol Analog 188

188

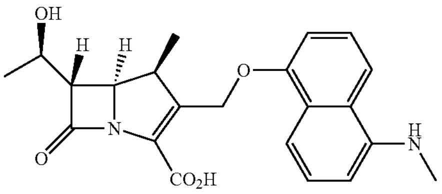

Percent yield: 27%; $^1$H NMR ($D_2O$, 400 MHz): δ 7.57 (d, J=8.4 Hz, 1H), 7.41 (d, J=8.4 Hz, 1H), 7.32-7.25 (m, 2H) 6.84 (d, J=7.6 Hz, 1H), 6.68 (d, J=7.2 Hz, 1H), 5.44 (d, J=14.4 Hz, 1H), 4.75 (d, J=14.8 Hz, 1H), 3.97 (m, 1H), 3.82 (m, 1H), 3.23 (m, 1H), 3.13 (m, 1H), 2.73 (s, 3H), 1.04 (d, J=6.4 Hz, 3H), 1.01 (d, J=7.2 Hz, 3H).

Example 50

TES-Protected Aminonaphthol Intermediate 189

189

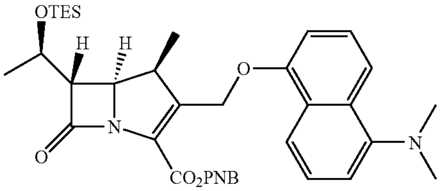

Percent yield, 61%; $^1$H NMR ($CDCl_3$, 300 MHz): δ 8.21 (d, J=8.1 Hz, 2H), 7.91 (d, J=8.4 Hz, 1H), 7.67 (d, J=9.3 Hz, 2H), 7.39 (m, 4H), 7.13 (d, J=7.5 Hz, 1H), 6.82 (d, J=7.5 Hz, 1H), 5.65 (d, J=14.7 Hz, 1H), 5.49 (d, J=14.1 Hz, 1H), 5.30 (d, J=13.8 Hz, 1H), 4.93 (d, J=14.7 Hz, 1H), 4.31 (m, 2H), 3.58 (m, 1H), 3.32 (m, 1H), 2.90 (s, 6H), 1.31 (d, J=7.2 Hz, 3H), 1.26 (d, J=6.3 Hz, 3H), 0.96 (t, J=8.4 Hz, 9H), 0.62 (q, J=8.4 Hz, 6H).

TES-Protected Aminonaphthol Intermediate 190

190

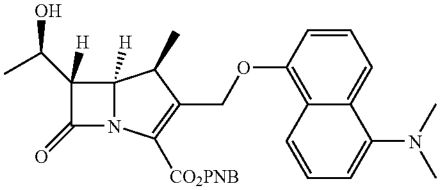

Percent yield; 46%; $^1$H NMR ($CDCl_3$, 300 MHz): δ 8.23 (d, J=9.0 Hz, 2H), 7.90 (d, J=8.7 Hz, 1H), 7.67 (d, J=8.1 Hz, 2H), 7.34 (m, 3H), 7.18 (d, J=7.5 Hz, 1H), 6.80 (d, J=7.8 Hz, 1H), 5.64 (d, J=15.6 Hz, 1H), 5.55 (d, J=12.9 Hz, 1H), 5.29 (d, J=13.5 Hz, 1H), 4.93 (d, J=15.6 Hz, 1H), 4.29 (dd, J=2.7, 9.3 Hz, 2H), 3.62 (m, 1H), 3.36 (dd, J=2.7, 5.4 Hz, 1H), 2.88 (s, 6H), 1.38 (d, J=7.8 Hz, 3H), 1.32 (d, J=7.2 Hz, 3H).

1,5-Aminonaphthol Analog 191

191

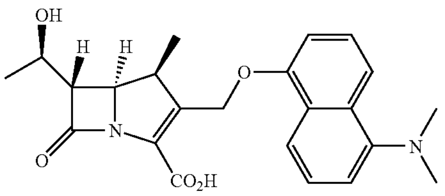

Percent yield: 27%; $^1$H NMR ($D_2O$, 400 MHz): δ 7.86 (d, J=8.8 Hz, 1H), 7.54 (d, J=8.8 Hz, 1H), 7.32 (t, J=7.6 Hz, 2H), 7.14 (d, J=7.2 Hz, 1H), 6.83 (d, J=7.6 Hz, 1H), 5.44 (d, J=14.0 Hz, 1H), 4.76 (d, J=14.0 Hz, 1H), 4.02 (p, J=6.0 Hz, 1H), 3.87 (d, J=8.4 Hz, 1H), 3.24 (m, 1H), 3.14 (p, J=8.0 Hz, 1H), 2.67 (s, 6H), 1.04 (d, J=6.0 Hz, 3H), 1.01 (d, J=7.6 Hz, 3H).

Example 51

TES-Protected Aminophenol Intermediate 192

192

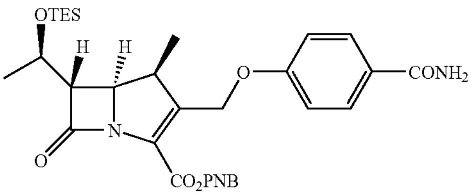

Percent yield: 23%; $^1$H NMR ($CDCl_3$, 300 MHz): δ 8.23 (d, J=8.1 Hz, 2H), 7.78 (d, J=9.0 Hz, 2H), 7.68 (d, J=8.4 Hz, 2H), 6.95 (d, J=9.0 Hz, 2H), 5.70 (br s, 2H), 5.53 (d, J=15.3 Hz, 1H), 5.49 (d, J=13.8 Hz, 1H), 5.28 (d, J=13.5 Hz, 1H), 4.77 (d, J=14.7 Hz, 1H), 4.28 (m, 2H), 3.45 (m, 1H), 3.31 (dd, J=2.7, 4.5 Hz, 1H), 1.26 (d, J=6.3 Hz, 3H), 1.24 (d, J=7.5 Hz, 3H), 0.95 (t, J=7.6 Hz, 9H), 0.60 (q, J=7.6 Hz, 6H).

PNB-Protected Aminophenol Intermediate 193

193

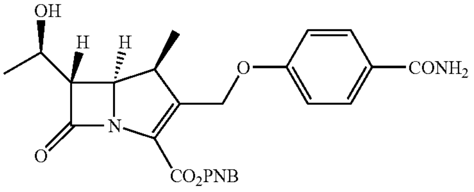

Percent yield: 86%; $^1$H NMR ($CDCl_3$, 300 MHz): δ 8.21 (d, J=8.7 Hz, 2H), 7.76 (d, J=9.0 Hz, 2H), 7.66 (d, J=8.4 Hz, 2H), 6.92 (d, J=9.0 Hz, 2H), 6.12 (br s, 3H), 5.51 (d, J=13.5 Hz, 1H), 5.50 (d, J=15.0 Hz, 1H), 5.25 (d, J=14.4 Hz, 1H), 4.77 (d, J=14.7 Hz, 1H), 4.28 (m, 2H), 3.49 (m, 1H), 3.31 (dd, J=2.7, 6.0 Hz, 1H), 1.26 (d, J=6.3 Hz, 3H), 1.24 (d, J=7.5 Hz, 3H).

1,4-Aminophenol Analog 194

194

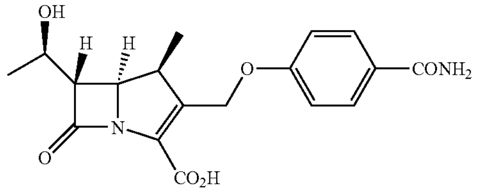

Percent yield: 51%; $^1$H NMR ($D_2O$, 400 MHz): δ 7.60 (d, J=8.4 Hz, 2H), 6.87 (d, J=8.4 Hz, 2H), 5.32 (d, J=13.6 Hz, 1H), 4.60 (d, J=12.8 Hz, 1H), 4.03 (p, J=4.5 Hz, 1H), 3.92 (dd, J=2.4, 10.0 Hz, 1H), 3.25 (dd, J=2.4, 6.4 Hz, 1H), 3.08 (m, 1H), 1.07 (d, J=6.4 Hz, 3H), 0.98 (d, J=7.2 Hz, 3H).

Example 52

TES-Protected Aminophenol Intermediate 195

195

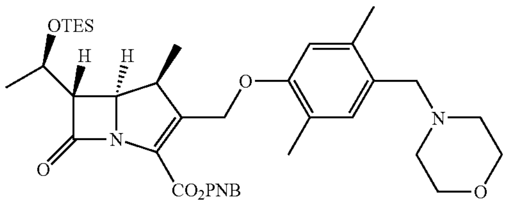

Percent yield: 22%; $^1$H NMR ($CDCl_3$, 300 MHz): δ 8.23 (d, J=9.0 Hz, 2H), 7.68 (d, J=9.3 Hz, 2H), 7.01 (s, 1H), 6.62 (s, 1H), 5.49 (d, J=14.1 Hz, 1H), 5.42 (d, J=14.7 Hz, 1H), 5.28 (d, J=14.1 Hz, 1H), 4.70 (d, J=15.3 Hz, 1H), 4.29 (m, 2H), 3.68 (m, 4H), 3.52 (m, 1H), 3.37 (s, 2H), 3.31 (m, 1H), 2.42 (br s, 4H), 2.30 (s, 3H), 2.19 (s, 3H), 1.27 (d, J=6.0 Hz, 3H), 1.26 (d, J=7.2 Hz, 3H), 0.96 (t, J=8.1 Hz, 9H), 0.61 (q, J=7.8 Hz, 6H).

PNB-Protected Aminophenol Intermediate 196

196

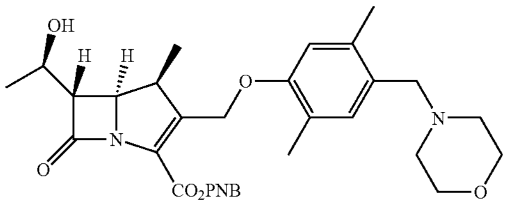

Percent yield: 52%; $^1$H NMR ($CDCl_3$, 300 MHz): δ 8.22 (d, J=8.4 Hz, 2H), 7.66 (d, J=8.1 Hz, 2H), 7.00 (s, 1H), 6.59 (s, 1H), 5.51 (d, J=12.9 Hz, 1H), 5.40 (d, J=15.3 Hz, 1H), 5.26 (d, J=13.5 Hz, 1H), 4.71 (d, J=15.9 Hz, 1H), 4.26 (m, 2H), 3.67 (m, 4H), 3.58 (m, 1H), 3.36 (s, 2H), 3.32 (m, 1H), 2.42 (br s, 4H), 2.28 (s, 3H), 2.17 (s, 3H), 1.34 (d, J=6.9 Hz, 3H), 1.26 (d, J=7.5 Hz, 3H).

1,4-Aminophenol Analog 197

197

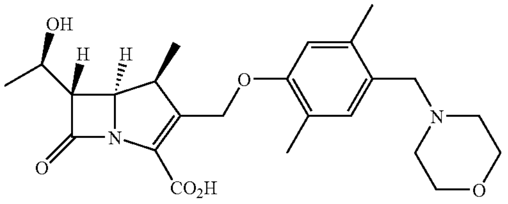

Percent yield: 24%; $^1$H NMR ($D_2O$, 400 MHz): δ 7.03 (s, 1H), 6.67 (s, 1H), 5.32 (d, J=13.6 Hz, 1H), 4.60 (d, J=12.8 Hz, 1H), 4.03 (p, J=4.5 Hz, 1H), 3.93 (s, 2H), 3.90 (dd, J=2.4, 10.0 Hz, 1H), 3.70 (br s, 4H), 3.25 (dd, J=2.4, 6.4 Hz, 1H), 3.07 (m, 1H), 2.97 (br s, 4H), 2.13 (s, 3H), 2.00 (s, 3H), 1.07 (d, J=6.4 Hz, 3H), 0.98 (d, J=7.2 Hz, 3H).

Dilution Antimicrobial Susceptibility Tests

The agar dilution method for determining the antimicrobial susceptibility was carried out using an agar dilution method with Mueller-Hinton agar (see, M7-A5, Vol. 20 (2), 2000). A final inoculum of 104 CFU was applied with a replicating device. Broth dilution tests wre performed with 5x105 CFU in tubes containing 1 mL of broth. Incubation of test tubes containing agar and broth was done at 35 C for 18 h. The susceptibilities of streptococci were determined by Mueller-Hinton agar supplemented with 5% sheep blood, and the susceptibility of anaerobic species was determined with brucella agar supplemented with 5% sheep blood, hemin, and vitamin K. Incubation of anaerobic cultures was done for 48 h in jars. The susceptibilities of methicillin-resistant staphylococci were determined on Mueller-Hinton agar or in broth supplemented with 3% NaCl. All assays were run with the indicated control strains, available from the American Type Culture Collection, Rockville, Md.). Results of the antimicrobial susceptibility tests of compounds 22-197 against Gram-positive organisms are shown in Tables 1 and 2.

All of the compositions, methods and/or processes disclosed and claimed herein can be made and executed without undue experimentation in light of the present disclosure. While the compositions and methods of this invention have been described in terms of certain embodiments, it will be apparent to those of skill in the art that variations may be applied to the compositions, methods and/or processes and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

The invention claimed is:

1. A carbapenem compound of the formula (I) or (III):

(I)

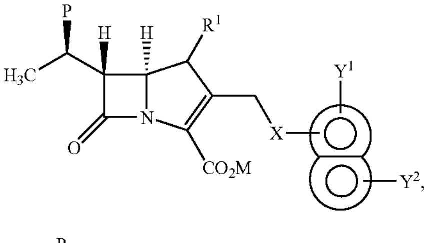

(III)

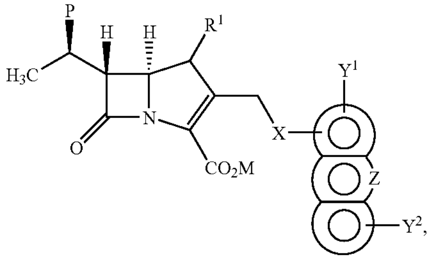

or a pharmaceutically acceptable salt or prodrug thereof, wherein:

$R^1$ is either H or alkyl;

$CO_2M$ is independently a carboxylic acid, a carboxylate anion, a pharmaceutically acceptable ester group or a carboxylic acid protected by a protecting group;

P is independently hydrogen, hydroxyl, F or hydroxyl protected by a hydroxyl-protecting group;

X is independently O, S, C(O), C(O)O, OC(O), C(O)NH, C(O)NR, NHC(O), NRC(O), NH, or NR;

each R is independently H or alkyl;

each

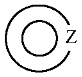 and 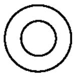

is independently a substituted or unsubstituted phenyl;

each $Y^1$ and $Y^2$ is independently selected from the group consisting of hydrogen; halo; —CN; —$NO_2$; —$NR^aR^b$; —$OR^c$; —$SR^c$; —$C(O)OR^h$; $S(O)R^c$; —$SO_2R^c$; —$SO_2NR^aR^b$; —$NR^aSO_2R^b$; —$C(O)R^a$; —$OC(O)R^a$; $OC(O)NR^aR^b$; —$NR^aC(O)NR^bR^c$; —$NR^aCO_2R^h$; —$OCO_2R^h$; $NR^aC(O)R^b$; —$C_{1-6}$ straight- or branched-chain alkyl, —$C_{2-6}$ straight- or branched-chain alkenyl, or —$C_{2-6}$ straight- or branched-chain alkynyl, unsubstituted or substituted with 1 to 4 $R^d$ groups; —A—$(CH_2)_n$-Q; —$(CH_2)_n$A-Q; —$[(CH_2)_nA]_m(CH_2)_p$-Q; $(CH_2)_n$-Q; and —$C_{3-7}$ cycloalkyl, unsubstituted or substituted with one to four $R^d$ groups;

wherein at least one of $Y^1$ and $Y^2$ is not hydrogen;

A is O, S, NH, $NCH_3$, NR, or —$CH_2$—;

each m, n, and p is independently 0, 1, 2 or 3;

each $R^a$, $R^b$ and $R^c$ is independently selected from hydrogen, —$C_{1-6}$ straight- or branched-chain alkyl, unsubstituted or substituted with one to four $R^d$ groups, or -$C_{3-7}$ cycloalkyl, unsubstituted or substituted with one to four $R^d$ groups;

or $R^a$ and $R^b$ taken together with any intervening atoms form a 4-6 membered saturated heterocycloalkyl ring interrupted by one to three of O, S, $NR^c$, or —C(O)—, said ring being unsubstituted or substituted with one to four $R^i$ groups;

or $R^b$ and $R^c$ taken together with any intervening atoms form a 4-6 membered saturated heterocycloalkyl ring optionally interrupted by one to three of O, S, $NR^a$, or —C(O)—, said ring being unsubstituted or substituted with one to four $R^i$ groups;

each $R^d$ is independently selected from the group consisting of halo; —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; $NR^eCONR^fR^g$; —$NR^eCO_2R^h$; —$OCO_2R^h$; —$C(NR^e)NR^fR^g$; $NR^eC(NH)NR^fR^g$ or —$NR^eC(NR^f)R^g$;

each $R^e$, $R^f$ and $R^g$ is independently selected from hydrogen; —R; —$C_{1-6}$ straight- or branched-chain alkyl unsubstituted or substituted with one to four $R^i$ groups;

or $R^e$ and $R^f$ taken together with any intervening atoms form a 4-6 membered saturated heterocycloalkyl ring interrupted by one to three of O, S, —C(O)— or $NR^g$, said ring being unsubstituted or substituted with one to four $R^i$ groups;

each $R^i$ is independently selected from halo; —CN; —$NO_2$; phenyl; —$NHSO_2R^h$; —$OR^h$, —$SR^h$; —$N(R^h)_2$; —$N^+(R^h)3$; —$C(O)N(R^h)_2$; $SO_2N(R^h)2$; heteroaryl; heteroarylium; —$CO_2R^h$; —$C(O)R^h$; —$OCOR^h$; $NHCOR^h$; guanidinyl; carbamimidoyl or ureido;

each $R^h$ is independently selected from hydrogen, a —$C_{1-6}$ straight or branched-chain alkyl group, a —$C_3$-$C_6$ cycloalkyl group or phenyl, or when two $R^h$ groups are present, said $R^h$ groups can form a 4-6 membered saturated heterocycloalkyl ring, optionally interrupted by one or two of O, S, $SO_2$, —C(O)—, NH and $NCH_3$;

each Q is selected from the group consisting of:

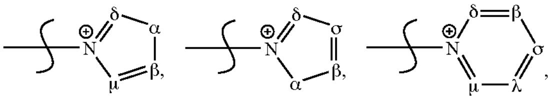

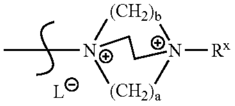 and 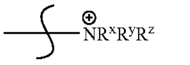

wherein:

a and b are 1, 2 or 3;

$L^-$ is a pharmaceutically acceptable counterion;

α is O, S or $NR^s$;

β, δ, λ, μ, and σ are independently selected from $CR^t$, or N;

each $R^s$ is independently selected from hydrogen; phenyl or $C_{1-6}$ straight- or branched-chain alkyl, unsubstituted or substituted with one to four $R^i$ groups;

each $R^t$ is independently selected from hydrogen; halo; phenyl; —CN; —$NO_2$; —$NR^uR^v$; —$OR^u$; —$SR^u$; —$CONR^uR^v$; —$COOR^h$; —$SOR^u$; —$SO_2R^u$; —$SO_2NR^uR^v$; —$NR^uSO_2R^v$; —$COR^u$; —$NR^uCOR^v$; —$OCOR^u$; —$OCONR^uR^v$; —$NR^uCO_2R^v$; —$NR^uCONR^vR^w$; —$OCO_2R^v$; —$C_{1-6}$ straight- or branched-chain alkyl, unsubstituted or substituted with one to four $R^i$ groups;

each $R^u$ and $R^v$ is independently hydrogen or —$C_{1-6}$ straight- or branched-chain alkyl, unsubstituted or substituted with one to four $R^i$ groups;

or $R^u$ and $R^v$ taken together with any intervening atoms form a 4-6 membered saturated heterocycloalkyl ring interrupted by one or more of O, S, $NR^w$ or —C(O)—, said ring being unsubstituted or substituted with one to four $R^i$ groups;

each $R^w$ is independently hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1-4 $R^i$ groups; or $R^h$ and $R^w$ taken together with any intervening atoms represent a 5-6 membered saturated heterocycloalkyl ring, optionally interrupted by one or two of O, S, $SO_2$, NH or $NCH_3$;

$R^x$ is independently hydrogen or a $C_{1-8}$ straight- or branched chain alkyl, optionally interrupted by one or two of O, S, SO, $SO_2$, $NR^w$, or —C(O)—, said chain being unsubstituted or substituted with one to four of halo, CN, $NO_2$, $OR^w$, $SR^w$, $SOR^w$, $SO_2R^w$, $NR^hR^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched- chain alkyl groups, said alkyl groups being unsubstituted or substituted with one to four $R^i$ groups;

$R^y$ and $R^z$ are independently hydrogen; phenyl; —$C_{1-6}$ straight or branched chain alkyl, unsubstituted or substituted with one to four $R^i$ groups, and optionally interrupted by O, S, $NR^w$, or —C(O)—;

or $R^x$ and $R^y$ together with any intervening atoms form a 4-6 membered saturated heterocycloalkyl ring interrupted by O, S, $SO_2$, $NR^w$, or —C(O)—, unsubstituted or substituted with 1-4 $R^i$ groups, and when $R^x$ and $R^y$ together form a 4-6 membered heterocycloalkyl ring, $R^z$ is as defined above or $R^z$ represents an additional saturated 4-6 membered heterocycloalkyl ring fused to the ring represented by $R^x$ and $R^y$ taken together, optionally interrupted by O, S, $NR^w$ or —C(O)—, said rings being unsubstituted or substituted with one to four $R^i$ groups.

2. The compound of claim 1 wherein the compound is of the formula (Va):

(Va)

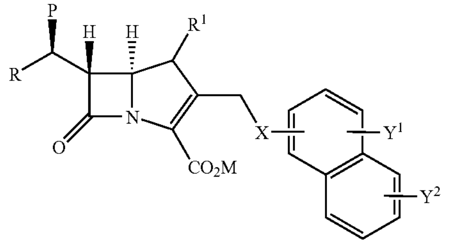

or a pharmaceutically acceptable salt thereof wherein X is O or NH.

3. The compound of claim 2 wherein P is hydrogen or hydroxyl and $R^1$ is hydrogen or methyl.

4. The compound of claim 3 wherein X is O.

5. The compound of claim 3 wherein X is NH.

6. The compound of claim 3 wherein P is hydroxyl and $R^1$ is methyl.

7. A carbapenem compound of the formula (Vb) or (Vd):

(Vb) or (Vd)

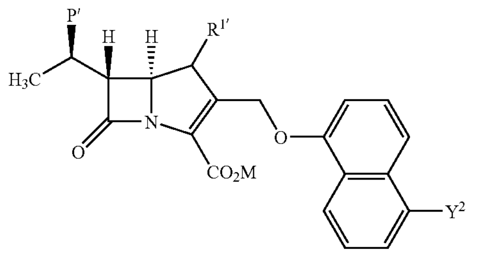

or a pharmaceutically acceptable salt thereof; wherein

P' is hydrogen or hydroxyl, $R^{1'}$ is hydrogen or methyl, and $CO_2M$ is independently a carboxylic acid, a pharmaceutically acceptable ester group or a carboxylic acid protected by a protecting group;

$Y^2$ is $-(CH_2)_{n1}$-A-$(CH_2)_{n2}$-Q wherein $n_1$ and $n_2$ are independently 0-4, or $-(CH_2)_n$-Q wherein n is 0-4;

A is selected from the group consisting of O, S, NH, and $NR^2$ wherein each $R^2$ is independently $C_1$-$C_4$ alkyl, and Q is $-NH-C(=NR^3)-N(R^3)_2$, $-S-C(=NR^3)-N(R^3)_2$, or $-NR^3-SO_2-N(R^3)_2$, wherein each $R^3$ independently $C_1$-$C_4$ alkyl or H.

8. A carbapenem compound of the formula (Vc):

(Vc)

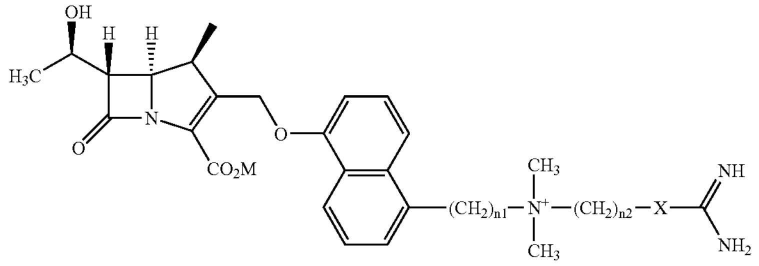

or a pharmaceutically acceptable salt thereof wherein, independently, $n_1$=1 or 2, $n_2$=1, 2, or 3, $CO_2M$ is a carboxylate anion;

and X is either S or NH.

9. A carbapenem compound of the formula (Ve) or (Vf):

(Ve) or (Vf)

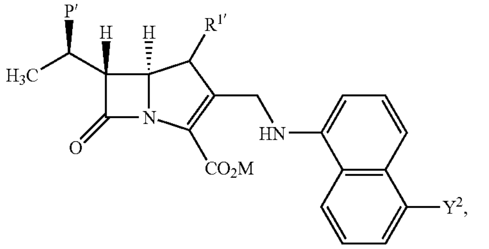

or a pharmaceutically acceptable salt thereof; wherein

P' is hydrogen or hydroxyl, $R^{1'}$ is hydrogen or methyl, and $CO_2M$ is independently a carboxylic acid, a pharmaceutically acceptable ester group or a carboxylic acid protected by a protecting group;

$Y^2$ is $-(CH_2)_{n1}$-A-$(CH_2)_{n2}$-Q wherein $n_1$ and $n_2$ are independently 0-4, or $-(CH_2)_n$-Q wherein n=0-4

A is selected from the group consisting of O, S, NH, and $NR^2$ wherein each $R^2$is independently $C_1$-$C_4$ alkyl, and Q is $-NH-C(=NR^3)-N(R^3)_2$ or $-S-C(=NR^3)-N(R^3)_2$, wherein each $R^3$ is independently $C_1$-$C_4$ alkyl or H.

10. A carbapenem compound:

30

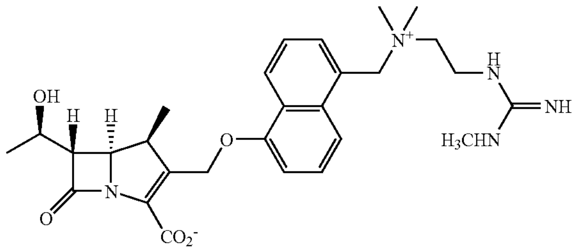

or a pharmaceutically acceptable salt thereof.

11. A carbapenem compound:

32

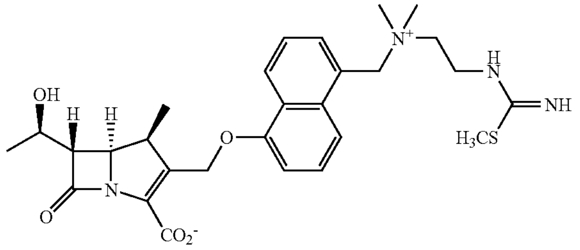

or a pharmaceutically acceptable salt thereof.

12. A carbapenem compound:

197

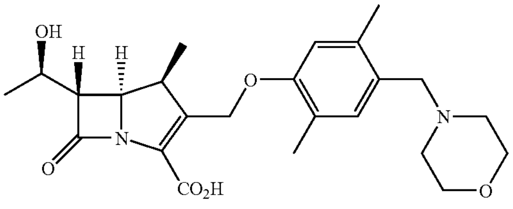

or a pharmaceutically acceptable salt thereof.

13. A carbapenem compound of the formula (IV):

(IV)

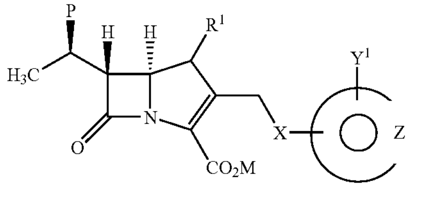

or a pharmaceutically acceptable salt or prodrug thereof, wherein:

$R^1$ is either H or alkyl;

$CO_2M$ is independently a carboxylic acid, a carboxylate anion, a pharmaceutically acceptable ester group or a carboxylic acid protected by a protecting group;

P is independently hydrogen, hydroxyl, F or hydroxyl protected by a hydroxyl-protecting group;

X is independently O, C(O)O, OC(O), C(O)NH, C(O)NR, NHC(O), NRC(O), NH, or NR;

each R is independently H or alkyl;

each

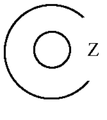

is unsubstituted phenyl;

$Y^1$ is independently from the group consisting of chloro; bromo; iodo; $—NO_2$; $—NR^aR^b$; $—OR^c$; $—SR^c$; $—C(O)NR^aR^b$, $—C(O)OR^h$; $—S(O)R^c$; $SO_2R^c$; $SO_2NR^aR^b$; $—NR^aSO_2R^b$; $—C(O)R^a$; $—OC(O)R^a$; $OC(O)NR^aR^b$; $—NR^aC(O)NR^bR^c$; $—NR^aCO_2R^h$; $—OCO_2R^h$; $—NR^aC(O)R^b$; $—C_{1-6}$ straight- or branched-chain alkyl, $—C_{2-6}$ straight- or branched-chain alkenyl, or $—C_{2-6}$ straight- or branched-chain alkynyl, unsubstituted or substituted with 1 to 4 $R^d$ groups; A $(CH_2)_n$-Q; $—(CH_2)_n$A-Q; $—[(CH_2)_nA]_m(CH_2)_p$-Q; $(CH_2)_n$-Q; and $—C_{3-7}$ cycloalkyl, unsubstituted or substituted with one to four $R^d$ groups;

A is O, S, NH, $NCH_3$, NR, or $—CH_2—$;

each m, n, and p is independently 0, 1, 2 or 3;

each $R^a$, $R^b$ and $R^c$ is independently selected from hydrogen, $—C_{1-6}$ straight- or branched-chain alkyl, unsubstituted or substituted with one to four $R^d$ groups, or $—C_{3-7}$ cycloalkyl, unsubstituted or substituted with one to four $R^d$ groups;

or $R^a$ and $R^b$ taken together with any intervening atoms form a 4-6 membered saturated heterocycloalkyl ring interrupted by one to three of O, S, $NR^c$, or —C(O)—, said ring being unsubstituted or substituted with one to four $R^i$ groups;

or $R^b$ and $R^c$ taken together with any intervening atoms form a 4-6 membered saturated heterocycloalkyl ring optionally interrupted by one to three of O, S, $NR^a$ or —C(O)—, said ring being unsubstituted or substituted with one to four $R^i$ groups;

each $R^d$ is independently selected from the group consisting of halo; —CN; $—NO_2$; $—NR^eR^f$; $—OR^g$; $—SR^g$; $—CONR^eR^f$; $—COOR^g$; $—SOR^g$; $—SO_2R^g$; $—SO_2NR^eR^f$; $—NR^eSO_2R^f$; $—COR^e$; $—NR^eCOR^f$; $—OCOR^e$; $—OCONR^eR^f$; $NR^eCONR^fR^g$; $—NR^eCO_2R^h$; $—OCO_2R^h$; $—C(NR^e)NR^fR^g$; $NR^eC(NH)NR^fR^g$ or $—NR^eC(NR^f)R^g$;

each $R^e$, $R^f$ and $R^g$ is independently selected from hydrogen; —R; $—C_{1-6}$ straight- or branched-chain alkyl unsubstituted or substituted with one to four $R^i$ groups;

or $R^e$ and $R^f$ taken together with any intervening atoms form a 4-6 membered saturated heterocycloalkyl ring interrupted by one to three of O, S, —C(O)— or said ring being unsubstituted or substituted with one to four $R^i$ groups;

each $R^i$ is independently selected from halo; —CN; $—NO_2$, phenyl; $—NHSO_2R^h$; $—OR^h$, $—SR^h$; $—N(R^h)_2$; $-N^+(R^h)3$; $—C(O)N(R^h)_2$; $SO_2N(R^h)2$; heteroaryl; heteroarylium; $—CO_2R^h$; $—C(O)R^h$; $—OCOR^h$; $NHCOR^h$; guanidinyl; carbamimidoyl or ureido;

each $R^h$ is independently selected from hydrogen, a $—C_{1-6}$ straight or branched-chain alkyl group, a $—C_3$-$C_6$ cycloalkyl group or phenyl, or when two $R^h$ groups are present, said $R^h$ groups can form a 4-6 membered saturated ring, optionally interrupted by one or two of O, S, $SO_2$, —C(O)—, NH and $NCH_3$;

each Q is selected from the group consisting of:

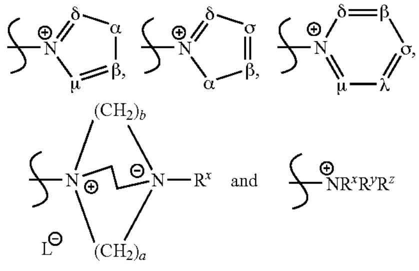

wherein:

a and b are 1, 2or 3;

$L^-$ is a pharmaceutically acceptable counterion;

α is O, S or $NR^s$;

β, δ, λ, μ and σ are independently selected from $CR^t$ or N;

each $R^s$ is independently selected from hydrogen; phenyl or $C_{1-6}$ straight- or branched-chain alkyl, unsubstituted or substituted with one to four $R^i$ groups;

each $R^t$ is independently selected from hydrogen; halo; phenyl; —CN; $—NO_2$; $—NR^uR^v$; $—OR^u$; $—SR^u$; $—CONR^uR^v$; $—COOR^h$; $—SOR^u$; $—SO_2R^u$; $—SO_2NR^uR^v$; $—NR^uSO_2R^v$; $—COR^u$; $—NR^uCOR^v$; $—OCOR^u$; $—OCONR^uR^v$; $—NR^uCO_2R^v$; $—NR^u$-

CONR$^v$R$^w$; —OCO$_2$R$^v$; —C$_{1-6}$ straight- or branched-chain alkyl, unsubstituted or substituted with one to four R$^i$ groups;

each R$^u$ and R$^v$ is independently hydrogen or —C$_{1-6}$ straight- or branched-chain alkyl, unsubstituted or substituted with one to four R$^i$ groups;

or R$^u$ and R$^v$ together with any intervening atoms form a 4-6 membered saturated heterocycloalkyl ring interrupted by one or more of O, S, NR$^w$ or —C(O)—, said ring being unsubstituted or substituted with one to four R$^i$ groups;

each R$^w$ is independently hydrogen; —C$_{1-6}$ straight- or branched-chain alkyl, unsubstituted or substituted with one to four R$^i$ groups; C$_{3-6}$ cycloalkyl optionally substituted with one to four R$^i$ groups; phenyl optionally substituted with one to four R$^i$ groups, or heteroaryl optionally substituted with 1-4 R$^i$ groups; or R$^h$ and R$^w$ taken together with any intervening atoms represent a 5-6 membered saturated heterocycloalkyl ring, optionally interrupted by one or two of O, S, SO$_2$, NH or NCH$_3$;

R$^x$ is independently hydrogen or a C$_{1-8}$ straight- or branched chain alkyl, optionally interrupted by one or two of O, S, SO, SO$_2$, NR$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two C$_{1-3}$ straight- or branched- chain alkyl groups, said alkyl groups being unsubstituted or substituted with one to four R$^i$ groups;

R$^y$ and R$^z$ are independently hydrogen; phenyl; —C$_{1-6}$ straight or branched chain alkyl, unsubstituted or substituted with one to four R$^i$ groups, and optionally interrupted by O, S, NR$^w$, or —C(O)—;

or R$^x$ and R$^y$ together with any intervening atoms form a 4-6 membered saturated heterocycloalkyl ring interrupted by O, S, SO$_2$, NR$^w$, or —C(O)—, unsubstituted or substituted with 1-4 R$^i$ groups, and when R$^x$ and R$^y$ together form a 4-6 membered ring, R$^z$ is as defined above or R$^z$ represents an additional saturated 4-6 membered heterocycloalkyl ring fused to the ring represented by R$^x$ and R$^y$ taken together, optionally interrupted by O, S, NR$^w$ or —C(O)—, said rings being unsubstituted or substituted with one to four R$^i$ groups.

14. The compound of claim 2 wherein Y$^1$ is hydrogen and Y$^2$ is not hydrogen.

15. The compound of claim 8, wherein the carbapenem is compound 24:

24

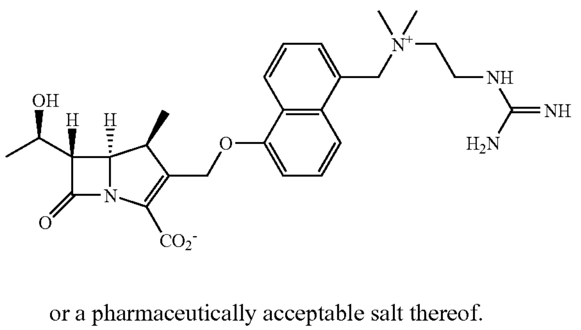

or a pharmaceutically acceptable salt thereof.

16. A method of preventing or treating an infection by a gram positive bacteria, in a host comprising administering to the host a therapeutic amount of a compound of claim 1, optionally in a pharmaceutically acceptable carrier.

17. The method of claim 16 wherein X is O.

18. A pharmaceutical composition comprising a compound of claim 1 and a pharmaceutically acceptable carrier.

19. The composition of claim 18 wherein X is O.

20. A pharmaceutical composition comprising a compound of claim 7 and a pharmaceutically acceptable carrier.

21. A pharmaceutical composition comprising a compound of claim 8 and a pharmaceutically acceptable carrier.

22. A pharmaceutical composition comprising a compound of claim 9 and a pharmaceutically acceptable carrier.

23. A pharmaceutical composition comprising a compound of claim 10 and a pharmaceutically acceptable carrier.

24. A pharmaceutical composition comprising a compound of claim 11 and a pharmaceutically acceptable carrier.

25. A pharmaceutical composition comprising a compound of claim 12 and a pharmaceutically acceptable carrier.

26. A pharmaceutical composition comprising a compound of claim 13 and a pharmaceutically acceptable carrier.

27. The composition of any one of claims 18, 20, 21, 22, 23, 24, 25 or 26 wherein the composition is suitable for intravenous administration.

28. The composition of any one of claims 18, 20, 21, 22, 23, 24, 25 or 26 wherein the composition further comprises at least one additional antibacterial agent.

29. A method of preventing or treating an infection by a gram positive bacteria, in a host comprising administering to the host a therapeutic amount of a compound of claim 7, optionally in a pharmaceutically acceptable carrier.

30. A method of preventing or treating an infection by a gram positive bacteria, in a host comprising administering to the host a therapeutic amount of a compound of claim 8, optionally in a pharmaceutically acceptable carrier.

31. A method of preventing or treating an infection by a gram positive bacteria, in a host comprising administering to the host a therapeutic amount of a compound of claim 9, optionally in a pharmaceutically acceptable carrier.

32. A method of preventing or treating an infection by a gram positive bacteria, in a host comprising administering to the host a therapeutic amount of a compound of claim 10, optionally in a pharmaceutically acceptable carrier.

33. A method of preventing or treating an infection by a gram positive bacteria, in a host comprising administering to the host a therapeutic amount of a compound of claim 11, optionally in a pharmaceutically acceptable carrier.

34. A method of preventing or treating an infection by a gram positive bacteria, in a host comprising administering to the host a therapeutic amount of a compound of claim 12, optionally in a pharmaceutically acceptable carrier.

35. The method of any of one of claims 16, 29, 30, 31, 32, 33, or 34 wherein the host is a human.

36. The method of claim 16 wherein the infection is by a drug resistant bacterial strain.

37. The method of claim 16 wherein the infection is by a multiple-drug resistant strain.

38. The method of claim 36 or 37 wherein the strain is selected from a methicillin resistant *Staphylococcus aureus* (MRSA), a methicillin resistant *Staphylococcus epidermidis* (MRSE), a methicillin resistant coagulase negative *Staphylococci* (MRCNS), a vancomycin resistant *Enterococcus faecalis*, and vancomycin resistant *Enterococcus faecium*.

39. The method of any of one of claims 16, 29, 30, 31, 32, 33 or 34 wherein the compound is administered in combination or alternation with at least one other antimicrobial agent.

40. The method of any of one of claims 16, 29, 30, 31, 32, 33 or 34 wherein the compound is administered in combination with a β-lactamase inhibiting agent.

41. The compound of claim 8, wherein the carbapenem is compound 69:

69

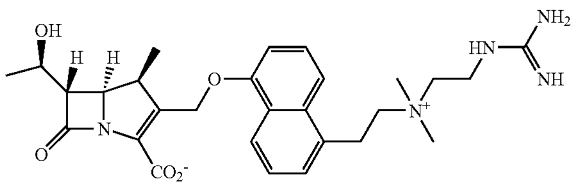

or a pharmaceutically acceptable salt thereof.

42. The compound of claim 8, wherein the carbapenem is compound 26:

26

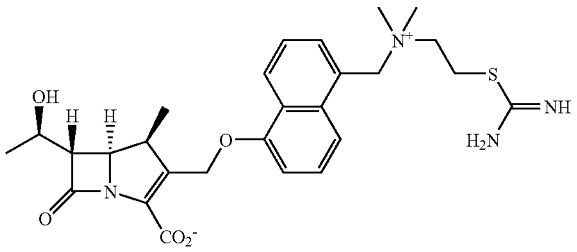

or a pharmaceutically acceptable salt thereof.

43. The compound of claim 8, wherein the carbapenem is compound 28:

28

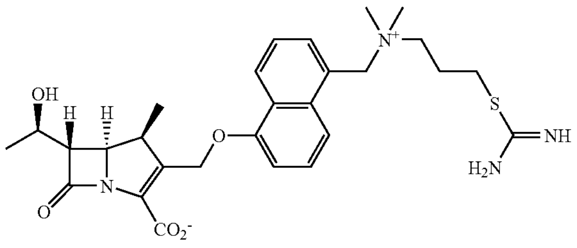

or a pharmaceutically acceptable salt thereof.

44. The compound of claim 8, wherein the carbapenem is compound 43:

43

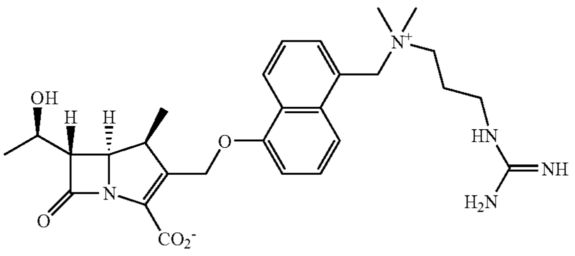

or a pharmaceutically acceptable salt thereof.

45. The compound of claim 7, wherein the carbapenem is compound 53:

53a

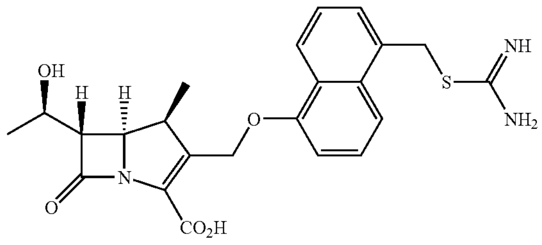

or a pharmaceutically acceptable salt thereof.

46. The compound of claim 7, wherein the carbapenem is compound 63:

63

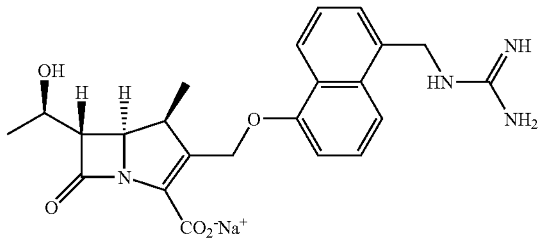

or a pharmaceutically acceptable salt thereof.

47. The compound of claim 1 wherein the carbapenem is compound 79:

79

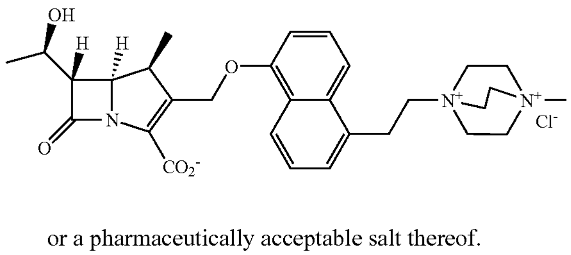

or a pharmaceutically acceptable salt thereof.

48. The compound of claim 13 wherein the compound is compound 194:

194
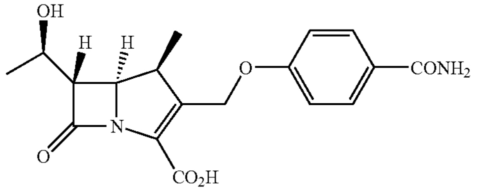
or a pharmaceutically acceptable salt or prodrug thereof.
49. The method of claim 30 wherein the carbapenem is selected from the group consisting of:
24
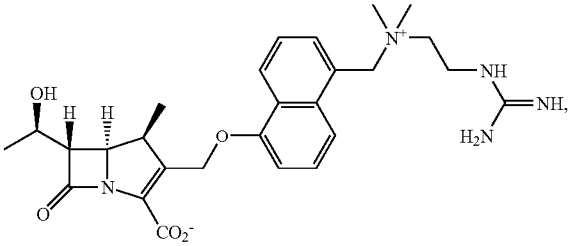
69
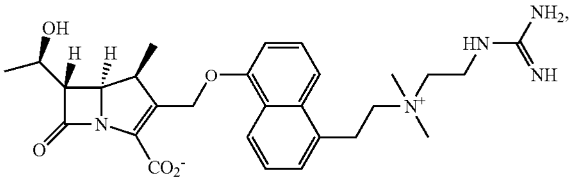
26
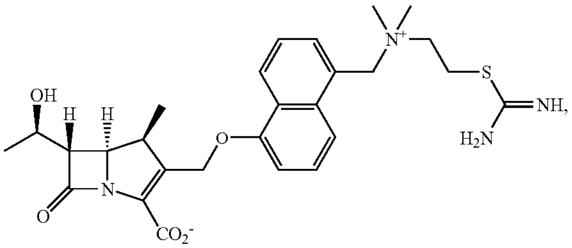
28
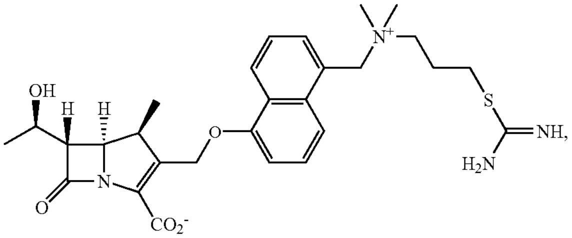
-continued
43
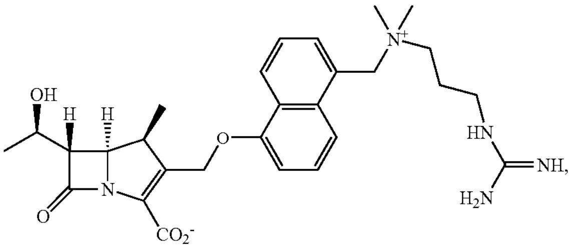
53a
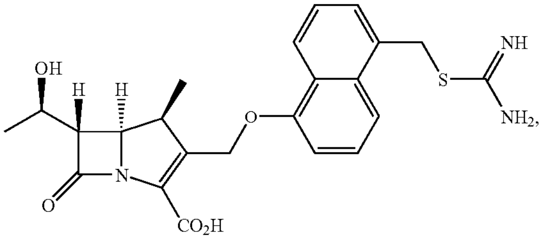
30
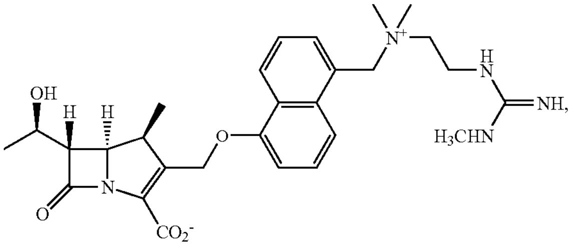
32
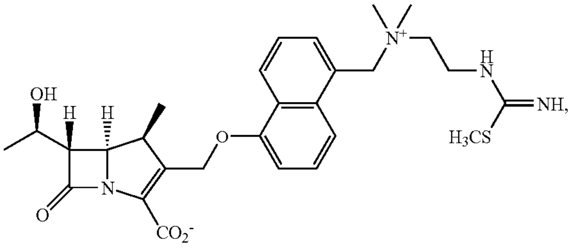
63
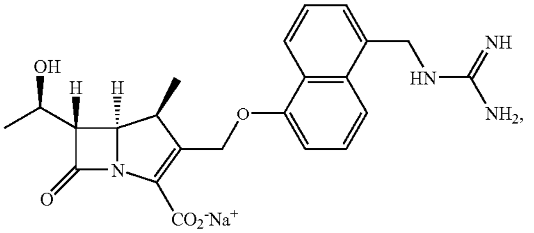
and
79
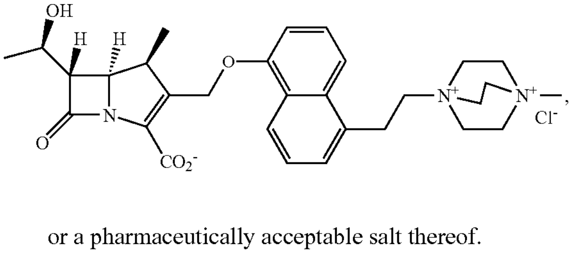
or a pharmaceutically acceptable salt thereof.

50. The composition of claim 21 wherein the carbapenem is selected from the group consisting of:

24

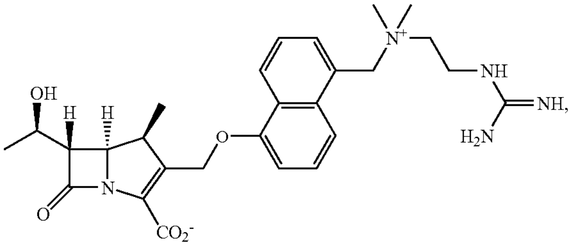

69

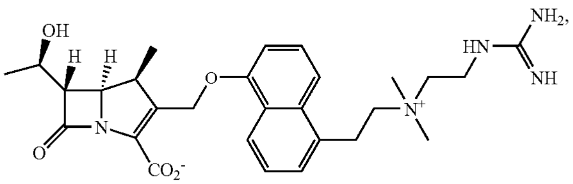

26

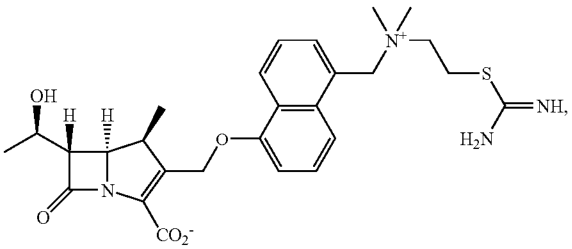

28

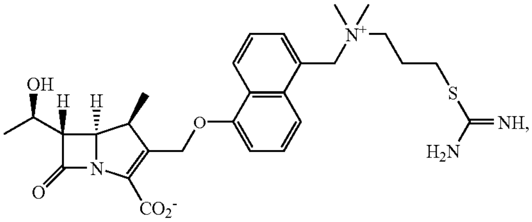

and

43

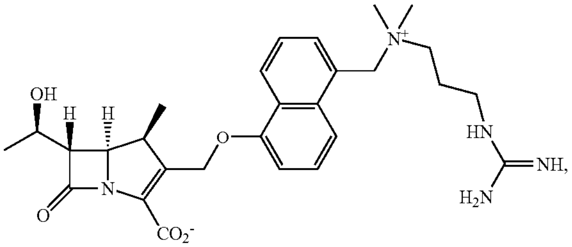

or a pharmaceutically acceptable salt thereof.

51. A compound of claim 8, wherein $n_2$ is 3.

52. A method of preventing or treating an infection by a gram positive bacteria, in a host comprising administering to the host a therapeutic amount of a compound of claim 13, optionally in a pharmaceutically acceptable carrier.

53. The method of claim 52 wherein the infection is by a drug resistant bacterial strain.

54. The method of claim 52 wherein the infection is by a multiple-drug resistant strain.

55. The method of claim 53 or 54 wherein the strain is selected from a methicillin resistant *Staphylococcus aureus* (MRSA), a methicillin resistant *Staphylococcus epidermidis* (MRSE), a methicillin resistant coagulase negative *Staphylococci* (MRCNS), a vancomycin resistant *Enterococcus faecalis*, and vancomycin resistant *Enterococcus faecium*.

56. The composition of claim 20 wherein the carbapenem is selected from the group consisting of:

53a

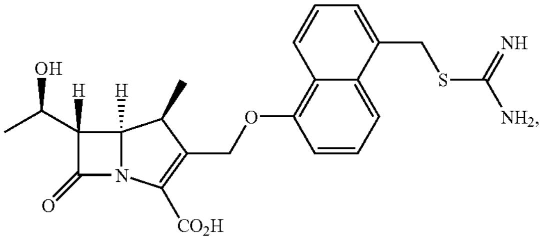

63

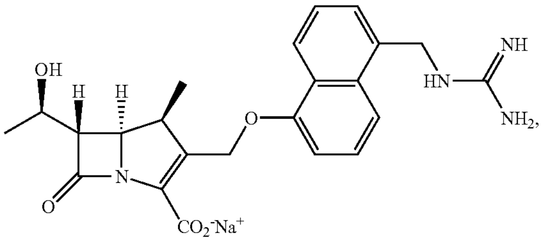

or a pharmaceutically acceptable salt thereof.

57. The composition of claim 18 wherein the carbapenem is selected from the group consisting of:

79

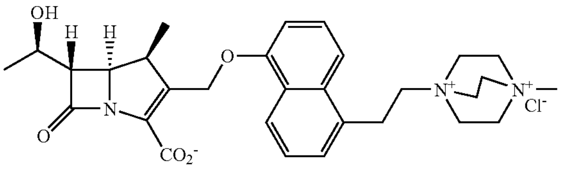

or a pharmaceutically acceptable salt thereof.

58. The method of claim 29 wherein the carbapenem is selected from the group consisting of:

53a

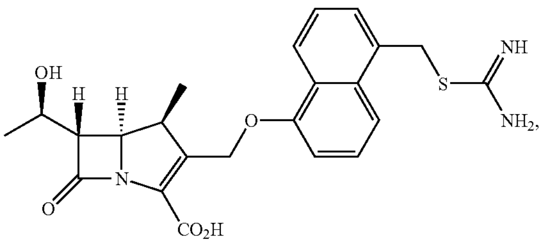

-continued

63

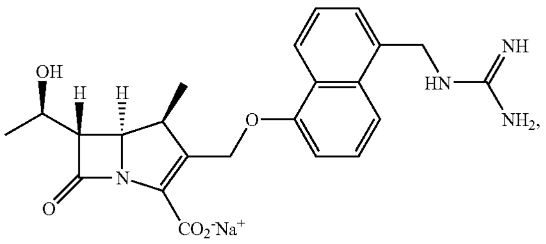

or a pharmaceutically acceptable salt thereof.

59. The method of claim 16 wherein the carbapenem is selected from the group consisting of:

79

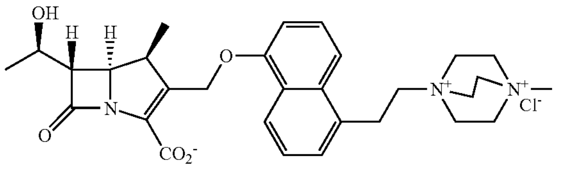

or a pharmaceutically acceptable salt thereof.

60. The method of claim 29 wherein the infection is by a drug resistant bacterial strain.

61. The method of claim 29 wherein the infection is by a multiple-drug resistant strain.

62. The method of claim 60 or 61 wherein the strain is selected from a methicillin resistant *Staphylococcus aureus* (MRSA), a methicillin resistant *Staphylococcus epidermidis* (MRSE), a methicillin resistant coagulase negative *Staphylococci* (MRCNS), a vancomycin resistant *Enterococcus faecalis*, and vancomycin resistant *Enterococcus faecium*.

63. The method of claim 30 wherein the infection is by a drug resistant bacterial strain.

64. The method of claim 30 wherein the infection is by a multiple-drug resistant strain.

65. The method of claim 63 or 64 wherein the strain is selected from a methicillin resistant *Staphylococcus aureus* (MRSA), a methicillin resistant *Staphylococcus epidermidis* (MRSE), a methicillin resistant coagulase negative *Staphylococci* (MRCNS), a vancomycin resistant *Enterococcus faecalis*, and vancomycin resistant *Enterococcus faecium*.

66. The method of claim 31 wherein the infection is by a drug resistant bacterial strain.

67. The method of claim 31 wherein the infection is by a multiple-drug resistant strain.

68. The method of claim 66 or 67 wherein the strain is selected from a methicillin resistant *Staphylococcus aureus* (MRSA), a methicillin resistant *Staphylococcus epidermidis* (MRSE), a methicillin resistant coagulase negative *Staphylococci* (MRCNS), a vancomycin resistant *Enterococcus faecalis*, and vancomycin resistant *Enterococcus faecium*.

69. The method of claim 34 wherein the infection is by a drug resistant bacterial strain.

70. The method of claim 34 wherein the infection is by a multiple-drug resistant strain.

71. The method of claim 69 or 70 wherein the strain is selected from a methicillin resistant *Staphylococcus aureus* (MRSA), a methicillin resistant *Staphylococcus epidermidis* (MRSE), a methicillin resistant coagulase negative *Staphylococci* (MRCNS), a vancomycin resistant *Enterococcus faecalis*, and vancomycin resistant *Enterococcus faecium*.

72. A compound of claim 7, wherein $Y^2$ is $—(CH_2)_{n1}$-A-$(CH_2)_{n2}$-Q and wherein $n_1$ is 1 and $n_2$ is 1, 2 or 3.

73. A compound of claim 7, wherein $Y^2$ is $—(CH_2)_{n1}$-A-$(CH_2)_{n2}$-Q and wherein $n_1$ is 2 and $n_2$ is 1, 2 or 3.

74. A compound of claim 7, wherein $Y^2$ is $—(CH_2)_n$-Q and wherein n is 1.

75. A compound of claim 7, wherein $Y^2$ is $—(CH_2)_n$-Q and wherein n is 2.

76. A compound of claim 9, wherein $Y^2$ is $—(CH_2)_{n1}$-A-$(CH_2)_{n2}$-Q and wherein $n_1$ is 1 and $n_2$ is 1, 2 or 3.

77. A compound of claim 9, wherein $Y^2$ is $—(CH_2)_{n1}$-A-$(CH_2)_{n2}$-Q and wherein $n_1$ is 2 and $n_2$ is 1, 2 or 3.

78. A compound of claim 9, wherein $Y^2$ is $—(CH_2)_n$-Q and wherein n is 1.

79. A compound of claim 9, wherein $Y^2$ is $—(CH_2)_n$-Q and wherein n is 2.

80. A compound of claim 8, wherein X is S.

81. A compound of claim 8, wherein X is NH.

82. A compound of claim 8, wherein $n_1$ is 1.

83. A compound of claim 8, wherein $n_1$ is 2.

84. A compound of claim 8, wherein $n_2$ is 1.

85. A compound of claim 8, wherein $n_2$ is 2.

* * * * *